(12) United States Patent
Rui et al.

(10) Patent No.: US 10,000,775 B2
(45) Date of Patent: Jun. 19, 2018

(54) BIOSYNTHESIS OF 1-UNDECENE AND RELATED TERMINAL OLEFINS

(71) Applicant: The Regents of the University of California, Oakland, CA (US)

(72) Inventors: Zhe Rui, Berkeley, CA (US); Wenjun Zhang, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days. days.

(21) Appl. No.: 15/184,053

(22) Filed: Jun. 16, 2016

(65) Prior Publication Data

US 2016/0289701 A1 Oct. 6, 2016

Related U.S. Application Data

(63) Continuation of application No. PCT/US2014/070683, filed on Dec. 16, 2014.

(60) Provisional application No. 61/919,680, filed on Dec. 20, 2013.

(51) Int. Cl.
*C12P 5/02* (2006.01)

(52) U.S. Cl.
CPC .................................. *C12P 5/026* (2013.01)

(58) Field of Classification Search
CPC ............ C12P 7/64; C12P 7/6409; C12P 5/026
See application file for complete search history.

(56) References Cited

U.S. PATENT DOCUMENTS 8,183,028 B2 * 5/2012 Alibhai .................... C10G 3/00
435/167

FOREIGN PATENT DOCUMENTS

KR              113760        * 10/2013

OTHER PUBLICATIONS

Copeland et al., Uniprot database, accession No. A5W7G6, Jul. 2007.*
Rui et al., PNAS USA, 111(51), 18237-18242, 2014.*
Zechman et al., Ca. J. Microbiol., 31, 232-236, 1985.*
Schulz et al., Nat. Prod. rep, 24, 814-842, 2007.*

* cited by examiner

*Primary Examiner* — Maryam Monshipouri
(74) *Attorney, Agent, or Firm* — Richard Aron Osman

(57) ABSTRACT

The present disclosure relates to the biosynthesis of 1-undecene and related terminal olefins. Specifically, the present disclosure relates to methods of using proteins to produce 1-undecene and related terminal olefins.

20 Claims, 36 Drawing Sheets
(18 of 36 Drawing Sheet(s) Filed in Color)

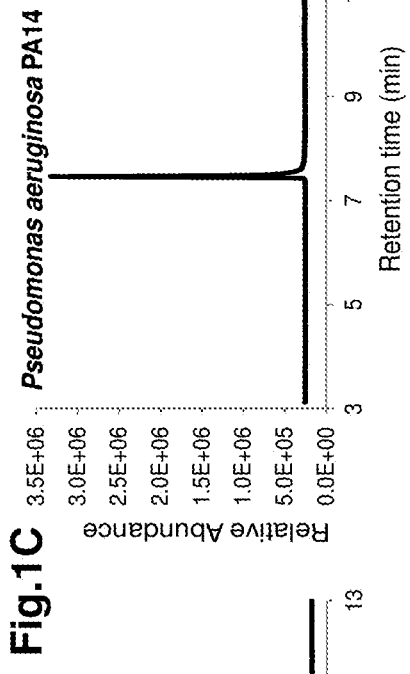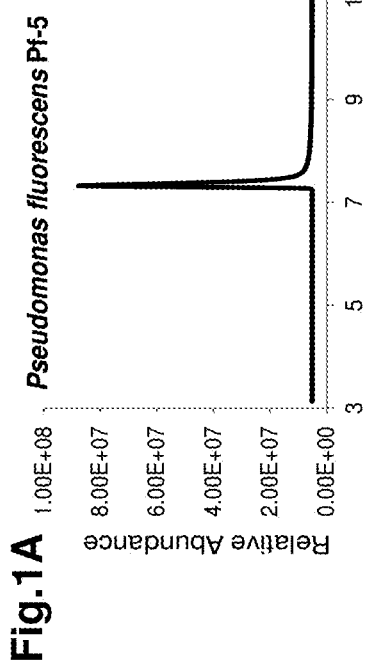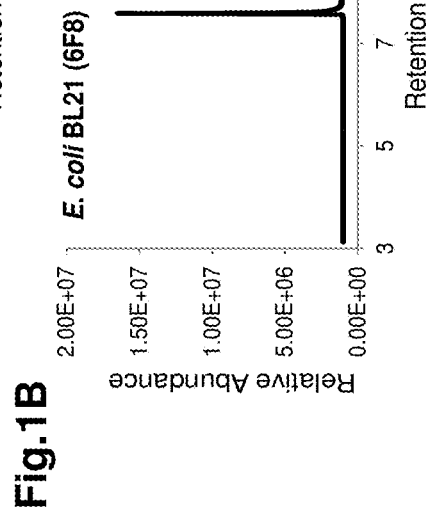

FIG. 2
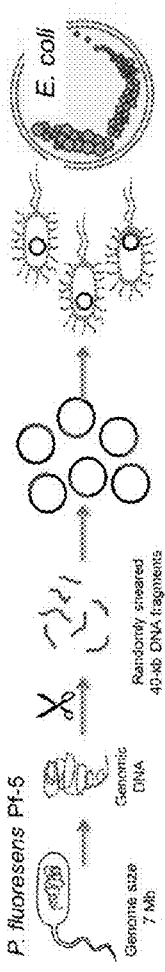
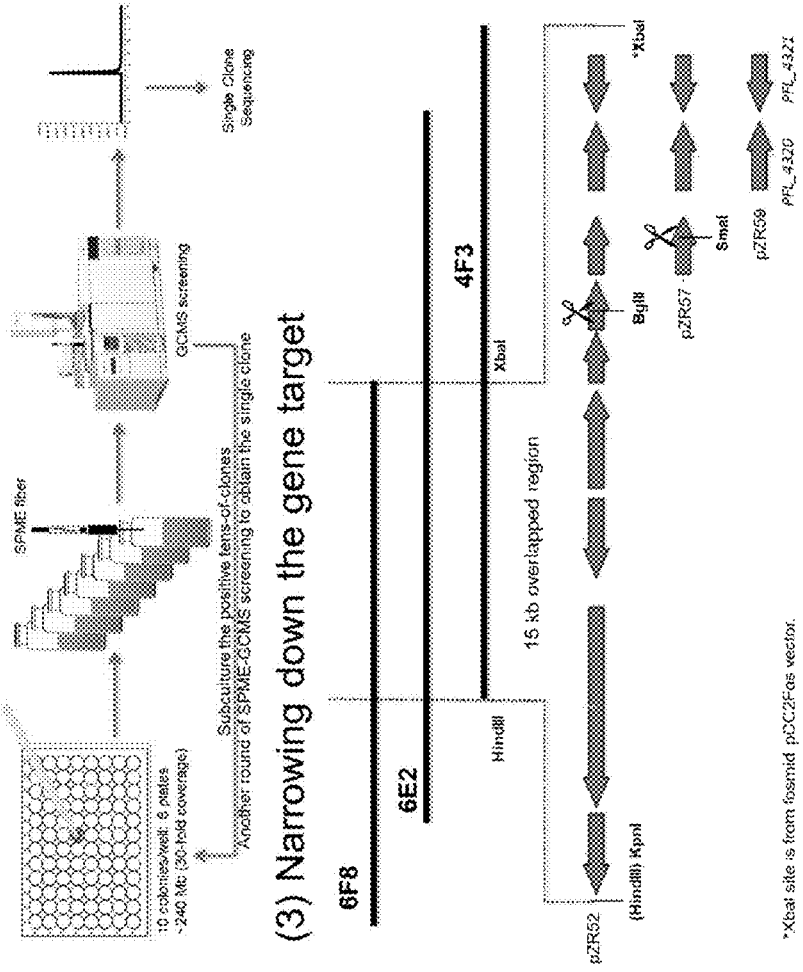

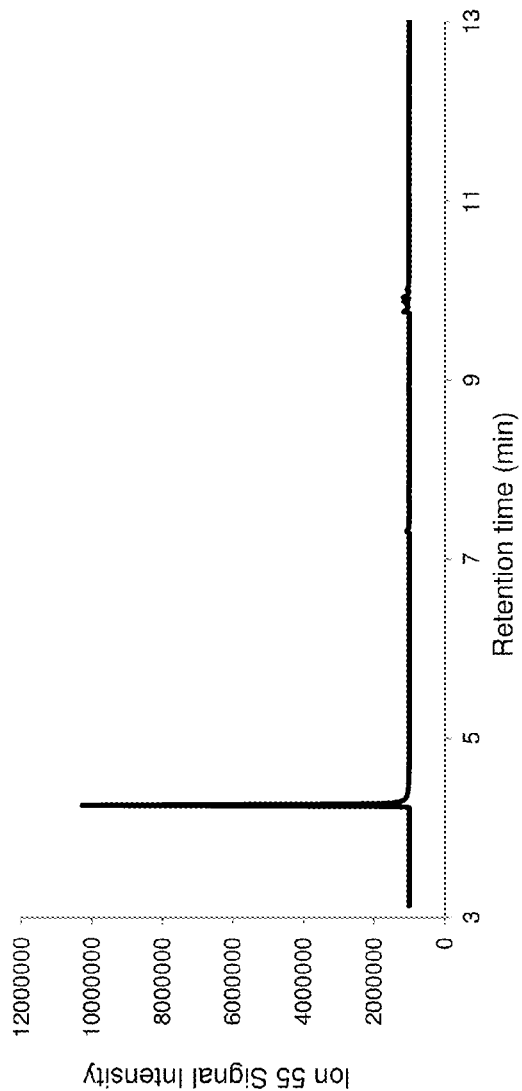
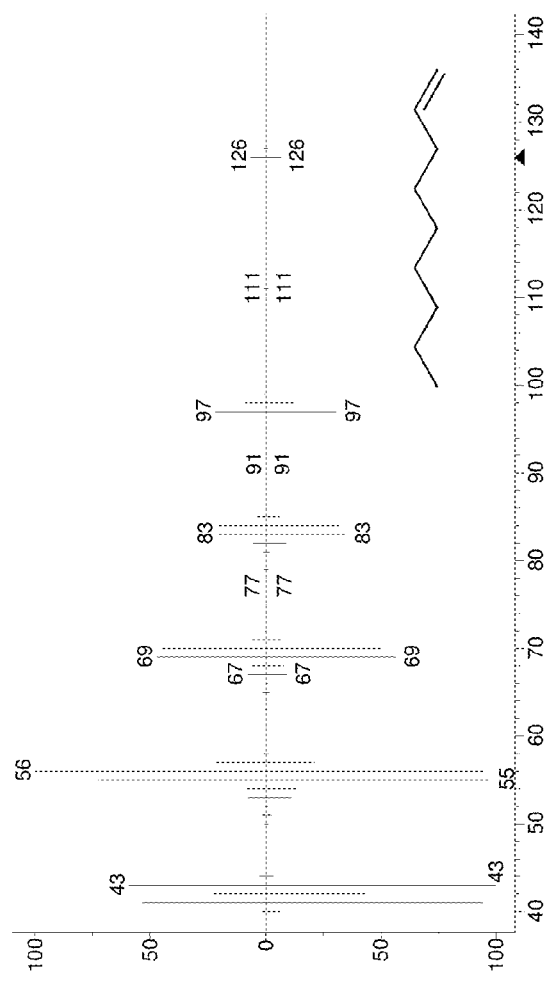
Fig.9A
Fig.9B

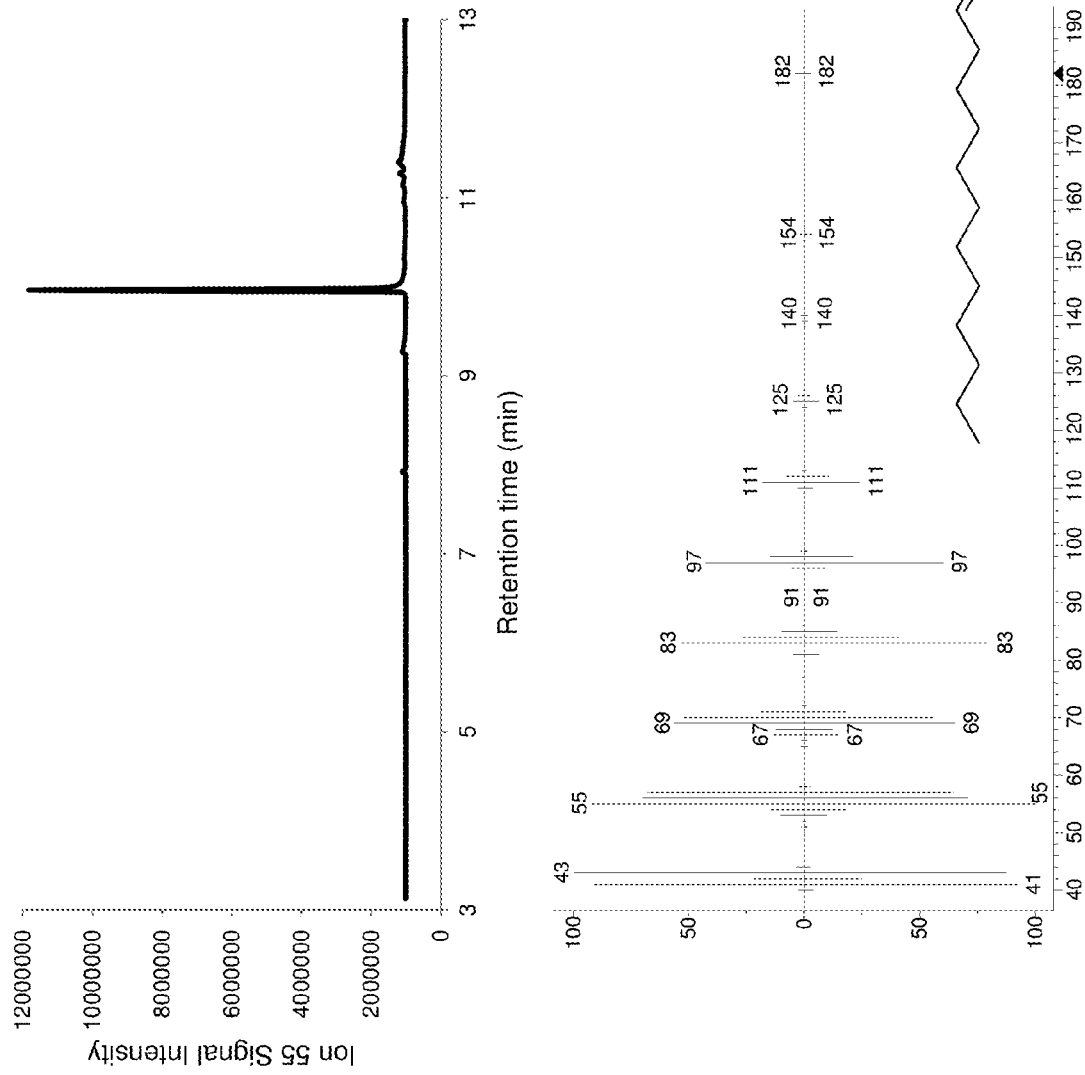

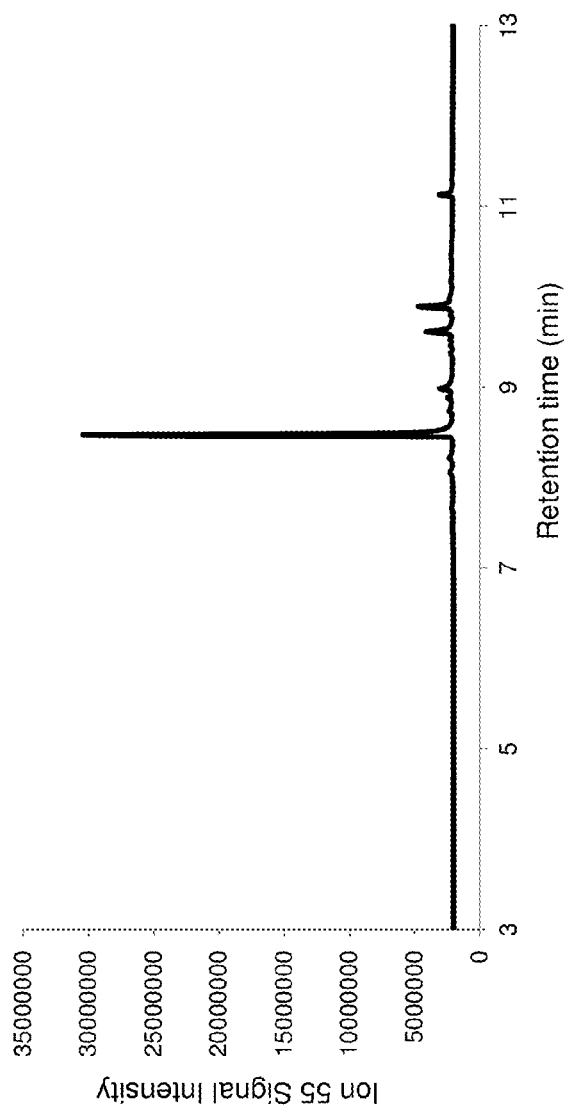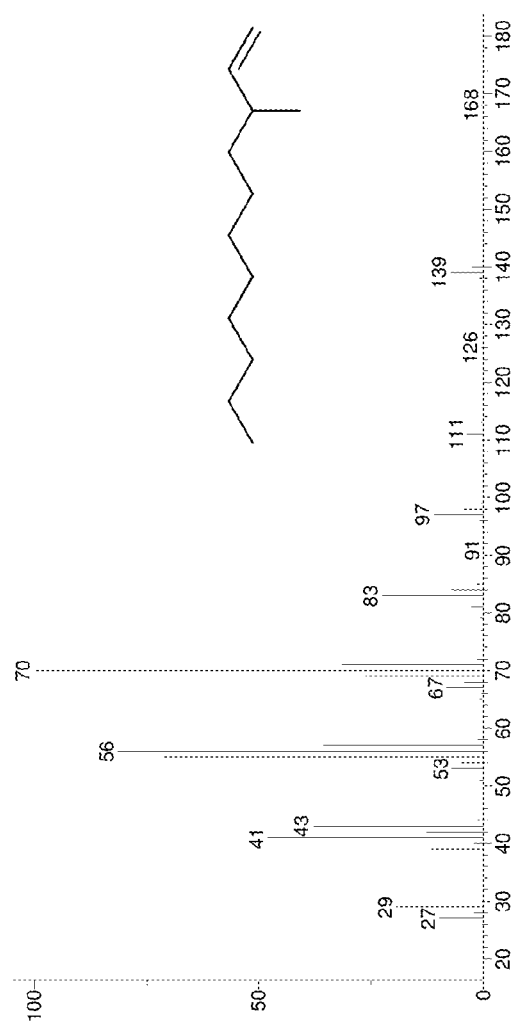
Fig.17A
Fig.17B

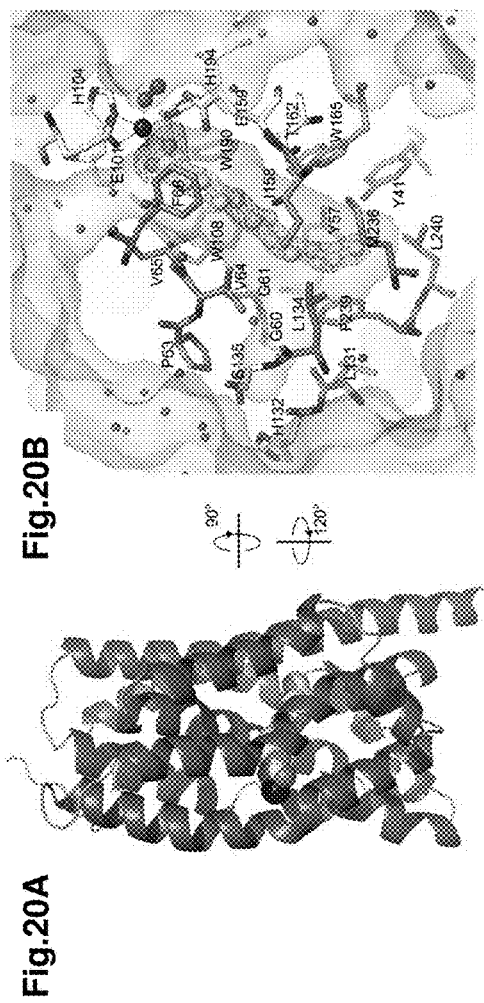

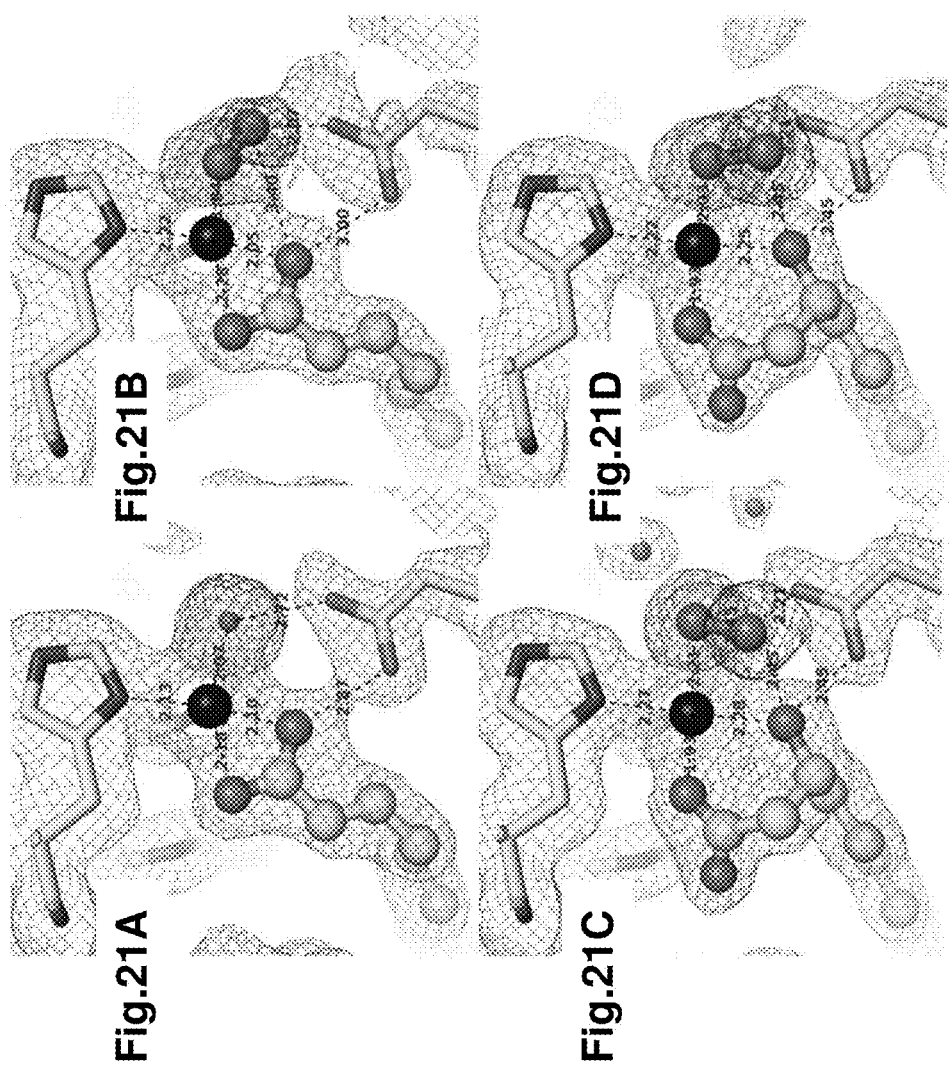

SEQUENCE LISTING

<160> NUMBER OF SEQ ID NOS: 75

<210> SEQ ID NO 1
<211> LENGTH: 261
<212> TYPE: PRT
<213> ORGANISM: Pseudomonas fluorescens

<400> SEQUENCE: 1

```
Met Ile Asp Thr Phe Ser Arg Thr Gly Pro Leu Met Glu Ala Ala Ser
1               5                   10                  15

Tyr Pro Ala Trp Thr Gln Gln Leu Ile Gln Asp Cys Ser Glu Ser Lys
            20                  25                  30

Arg Arg Val Val Glu His Glu Leu Tyr Gln Arg Met Arg Asp Asn Lys
        35                  40                  45
```

```
Leu Ser Ala Lys Val Met Arg Gln Tyr Leu Ile Gly Gly Trp Pro Val
 50                  55                  60

Val Glu Gln Phe Ala Leu Tyr Met Ala Gln Asn Leu Thr Lys Thr Arg
 65                  70                  75                  80

Phe Ala Arg His Pro Gly Glu Asp Met Ala Arg Arg Trp Leu Met Arg
                 85                  90                  95

Asn Ile Arg Val Glu Leu Asn His Ala Asp Tyr Trp Val His Trp Ser
                100                 105                 110

Arg Ala His Gly Val Thr Leu Glu Asp Leu Gln Ala Gln Gln Val Pro
                115                 120                 125

Pro Glu Leu His Ala Leu Ser His Trp Cys Trp His Thr Ser Ser Ala
130                 135                 140

Asp Ser Leu Ile Val Ala Ile Ala Ala Thr Asn Tyr Ala Ile Glu Gly
145                 150                 155                 160

Ala Thr Gly Glu Trp Ser Ala Leu Val Cys Ser Asn Gly Ile Tyr Ala
                165                 170                 175

Ala Ala Phe Pro Glu Glu Asp Arg Lys Arg Ala Met Lys Trp Leu Lys
                180                 185                 190

Met His Ala Gln Tyr Asp Asp Ala His Pro Trp Glu Ala Leu Glu Ile
                195                 200                 205

Ile Val Thr Leu Ala Gly Leu Asn Pro Thr Lys Ala Leu Gln Ala Glu
                210                 215                 220

Leu Arg Gln Ala Ile Cys Lys Ser Tyr Asp Tyr Met Tyr Leu Phe Leu
225                 230                 235                 240

Glu Arg Cys Met Gln Gln Glu Lys Thr Ala Val Thr Arg Glu Arg Leu
                245                 250                 255

Ala Leu Ala Glu Gly
                260

<210> SEQ ID NO 2
<211> LENGTH: 271
<212> TYPE: PRT
<213> ORGANISM: Pseudomonas putida

<400> SEQUENCE: 2

Met Glu Ile Thr Arg Ile Lys Glu Leu Lys Val Ile Asp Ala Phe Val
 1               5                  10                  15

Arg Ile Gly Pro Leu Met Asp Pro Ala Ser Tyr Pro Gln Trp Ala Gln
                20                  25                  30

Gln Leu Ile Glu Asp Cys Arg Glu Ser Lys Arg Val Val Glu His
             35                  40                  45

Glu Phe Tyr Ala Arg Leu Arg Asp Gly Gln Leu Lys Gln Ser Thr Ile
 50                  55                  60

Arg Gln Tyr Leu Ile Gly Gly Trp Pro Val Val Glu Gln Phe Ser Leu
 65                  70                  75                  80

Tyr Met Ala His Asn Leu Thr Lys Thr Arg Tyr Gly Arg His Gln Gly
                 85                  90                  95

Glu Asp Met Ala Arg Arg Trp Leu Met Arg Asn Ile Arg Val Glu Leu
                100                 105                 110

Asn His Ala Asp Tyr Trp Val Asn Trp Cys Gln Ala His Gly Val His
                115                 120                 125

Leu His Glu Leu Gln Ala Gln Glu Val Pro Pro Glu Leu Asn Gly Leu
130                 135                 140

Asn Asp Trp Cys Trp Arg Val Cys Ala Thr Glu Asn Leu Ala Ile Ser
145                 150                 155                 160
```

```
Met Ala Ala Thr Asn Tyr Ala Ile Glu Gly Ala Thr Gly Glu Trp Ser
                165                 170                 175

Ala Val Val Cys Ser Thr Asp Thr Tyr Ala Gln Gly Phe Pro Glu Glu
            180                 185                 190

Gly Arg Lys Arg Ala Met Lys Trp Leu Lys Met His Ala Gln Tyr Asp
        195                 200                 205

Asp Ala His Pro Trp Glu Ala Leu Glu Ile Ile Cys Thr Leu Ala Gly
    210                 215                 220

Glu Asn Pro Thr Leu Gly Leu Arg Thr Glu Leu Arg Arg Ala Ile Cys
225                 230                 235                 240

Lys Ser Tyr Asp Cys Met Phe Leu Phe Leu Glu Arg Cys Met Gln Leu
                245                 250                 255

Glu Gly Arg Gln Gln Gly Arg Met Arg Pro Ala Leu Ala Ala Gly
            260                 265                 270

<210> SEQ ID NO 3
<211> LENGTH: 260
<212> TYPE: PRT
<213> ORGANISM: Pseudomonas aeruginosa

<400> SEQUENCE: 3

Met Ser Glu Phe Phe Asp Arg Thr Gly Pro Leu Gln Glu Ala Gly Ser
1               5                   10                  15

Tyr Pro Gln Trp Ala Gln Gln Leu Ile Val Asp Cys Gln Ala Ser Lys
            20                  25                  30

Asp Arg Val Ser Gly His Glu Leu Tyr Arg Arg Met Arg Asp Ala Glu
        35                  40                  45

Leu Ser Pro Ala Leu Met Arg Leu Tyr Leu Ile Gly Gly Trp Pro Val
    50                  55                  60

Val Glu Gln Phe Pro Leu Tyr Met Ser Gln Asn Leu Leu Lys Thr Arg
65                  70                  75                  80

Phe Ala Arg His Pro Gly Glu Asp Met Ala Arg Arg Trp Leu Met Arg
                85                  90                  95

Asn Ile Arg Val Glu Leu Asn His Ala Asp Tyr Trp Leu His Trp Ala
            100                 105                 110

Glu Ala His Gly Val Ser Leu Ala Glu Ile Gln Ala Gln Asp Val Pro
        115                 120                 125

Ala Glu Leu His Ala Leu Ser His Trp Cys Trp His Thr Cys Ala Ser
    130                 135                 140

Asp Ser Leu Pro Val Ala Met Ala Ala Thr Asn Tyr Ala Ile Glu Gly
145                 150                 155                 160

Val Thr Gly Glu Trp Ser Ala Leu Val Cys Ser Asn Gly Val Tyr Glu
                165                 170                 175

Asn Ala Phe Pro Lys Glu Gly Arg Lys Arg Ala Met Lys Trp Leu Lys
            180                 185                 190

Leu His Ala Gln Tyr Asp Asp Ala His Pro Trp Glu Ala Leu Glu Ile
        195                 200                 205

Ile Cys Thr Leu Ala Gly Thr Asn Pro Ser Ala Glu Leu Arg Arg Gln
    210                 215                 220

Leu Arg Asp Ala Ile Cys Lys Ser Tyr Asp Tyr Met Tyr Leu Phe Leu
225                 230                 235                 240

Glu Arg Cys Met Gln Leu Glu Glu Ala Arg Ser Ala Arg Lys Leu Ala
                245                 250                 255

Val Gly Ala Glu
```

260

<210> SEQ ID NO 4
<211> LENGTH: 255
<212> TYPE: PRT
<213> ORGANISM: Acinetobacter baylyi

<400> SEQUENCE: 4

Met Phe Glu Ser Asn Ser Tyr Arg Ile Ile Ala Met Ser Ala Leu Leu
1               5                   10                  15

Glu Gly Thr Asp Leu Lys Ile Thr Pro His Ser Pro Trp Ala Gln Gln
            20                  25                  30

Phe Trp Asp Glu Leu Ile Pro Ala Lys Asp Arg Val Gly Gln His Pro
        35                  40                  45

Leu Phe Gln Asp Met Ala Asn Gly Arg Leu Asn Leu Lys Cys Phe Arg
    50                  55                  60

Ser Ala Leu Leu Asn Phe Tyr Pro Leu Val Ala His Phe Pro Ser Tyr
65                  70                  75                  80

Met Ala Leu Ala Leu Ser Lys Ala Thr Asp Phe Thr Glu Ala Gly Val
                85                  90                  95

Thr Glu Thr Arg Asn Trp Leu Ile Gln Asn Ile Lys Val Glu Glu Arg
            100                 105                 110

His Leu Asn Trp Tyr Arg Asp Trp Ala Gly Phe Gly Leu Thr Val
        115                 120                 125

Glu Glu Leu Asp Arg Val Arg Pro Pro Val Ala Met Asp Ala Val Asn
130                 135                 140

His Phe Leu Trp Asn Ile Asn Thr Lys Gly Ser Leu Ala Glu Cys Leu
145                 150                 155                 160

Ala Ala Thr Asn Leu Ala Ile Glu Trp Ala Thr Gly Asp Trp Ser Ile
                165                 170                 175

Gln Val Tyr Lys Gly Ile Asn Ala Tyr Ile Asp His Pro Glu Val Ser
            180                 185                 190

Ile Asn Lys Arg Ser Leu Ala Trp Leu Arg Ala His Ala His Tyr Asp
        195                 200                 205

Asp Ile His Pro Tyr Glu Ala Met Glu Leu Ile Lys Arg Leu Gly Glu
    210                 215                 220

Gly Lys Pro Glu Ile Gln Glu Lys Ala Phe Gln Ala Ala Gln Asp Gly
225                 230                 235                 240

Leu Ala Tyr Tyr Glu Leu Ala Leu Asp Glu Cys Tyr Lys His Gln
                245                 250                 255

<210> SEQ ID NO 5
<211> LENGTH: 261
<212> TYPE: PRT
<213> ORGANISM: Pseudomonas syringae

<400> SEQUENCE: 5

Met Ile Asp Thr Phe Glu Arg Thr Gly Pro Leu Met Glu Ala Ser Ser
1               5                   10                  15

Tyr Pro Ala Trp Ala Gln Gln Leu Ile Asn Asp Cys Ser Pro Ala Lys
            20                  25                  30

Ala Arg Val Val Glu His Glu Leu Tyr Gln Gln Met Arg Asp Ala Lys
        35                  40                  45

Leu Ser Pro Gln Ile Met Arg Gln Tyr Leu Ile Gly Gly Trp Pro Val
    50                  55                  60

Val Glu Gln Phe Ala Val Tyr Met Ala Lys Asn Leu Thr Lys Thr Arg

```
                65                  70                  75                  80

Phe Gly Arg His Pro Gly Glu Asp Met Ala Arg Arg Trp Leu Met Arg
                85                  90                  95

Asn Ile Arg Val Glu Leu Asn His Ala Asp Tyr Trp Val Asn Trp Cys
                100                 105                 110

Ala Ala His Asp Val Thr Leu Glu Asp Leu His Asp Gln Arg Val Ala
                115                 120                 125

Pro Glu Leu His Ala Leu Ser His Trp Cys Trp Gln Thr Ser Ser Ser
            130                 135                 140

Asp Ser Leu Ala Val Ala Met Ala Ala Thr Asn Tyr Ala Ile Glu Gly
145                 150                 155                 160

Ala Thr Gly Glu Trp Ser Ala Val Val Cys Ser Thr Gly Val Tyr Ala
                165                 170                 175

Glu Ala Phe Ala Glu Thr Arg Lys Lys Ser Met Lys Trp Leu Lys
            180                 185                 190

Met His Ala Gln Tyr Asp Asp Ala His Pro Trp Glu Ala Leu Glu Ile
            195                 200                 205

Ile Cys Thr Leu Val Gly Asn Lys Pro Ser Leu Gln Leu Gln Ala Glu
            210                 215                 220

Leu Arg Gln Ala Val Thr Lys Ser Tyr Asp Tyr Met Tyr Leu Phe Leu
225                 230                 235                 240

Glu Arg Cys Ile Gln Leu Asp Lys Val Lys Ser Pro Arg Gly Arg Val
                245                 250                 255

Ala Ala Leu Glu Met
            260

<210> SEQ ID NO 6
<211> LENGTH: 264
<212> TYPE: PRT
<213> ORGANISM: Pseudomonas fluorescens

<400> SEQUENCE: 6

Met Ile Asp Thr Phe Asn Arg Thr Gly Pro Leu Met Glu Ala Ala Ser
1               5                   10                  15

Tyr Pro Ala Trp Ala Gln Gln Leu Ile Gln Asp Cys Ser Glu Ser Lys
                20                  25                  30

Arg Arg Val Val Glu His Glu Leu Tyr Leu Arg Leu Arg Asp Asn Lys
            35                  40                  45

Leu Ser Ala Lys Thr Met Arg Gln Tyr Leu Ile Gly Gly Trp Pro Val
50                  55                  60

Val Glu Gln Phe Ala Leu Tyr Met Ala Gln Asn Leu Thr Lys Thr Lys
65                  70                  75                  80

Phe Ala Arg His Pro Gly Glu Asp Met Ala Arg Arg Trp Leu Met Arg
                85                  90                  95

Asn Ile Arg Val Glu Leu Asn His Ala Asp Tyr Trp Leu His Trp Ser
                100                 105                 110

Arg Ala His Gly Val Ser Leu Glu Asp Leu Gln Ala Gln Gln Val Pro
            115                 120                 125

Pro Glu Leu His Ala Leu Ser His Trp Cys Trp His Thr Ser Ser Ala
            130                 135                 140

Asp Ser Leu Ile Val Ala Ile Ala Ala Thr Asn Tyr Ala Ile Glu Gly
145                 150                 155                 160

Ala Thr Gly Glu Trp Ser Ala Leu Val Cys Ser Thr Gly Val Tyr Ala
                165                 170                 175
```

Ala Ala Phe Pro Glu Glu Asp Arg Lys Arg Ala Met Lys Trp Leu Lys
            180                 185                 190

Met His Ala Gln Tyr Asp Asp Ala His Pro Trp Glu Ala Leu Glu Ile
        195                 200                 205

Ile Cys Thr Leu Ala Gly Met Asn Pro Ser Lys Ala Leu Gln Ala Glu
        210                 215                 220

Leu Arg Gln Ala Ile Cys Lys Ser Tyr Asp Tyr Met Tyr Leu Phe Leu
225                 230                 235                 240

Glu Arg Cys Met Gln Leu Glu Leu Ser Glu Arg Val Met Val Gly Arg
                245                 250                 255

Glu Arg Arg Ala Leu Val Glu Ser
            260

<210> SEQ ID NO 7
<211> LENGTH: 267
<212> TYPE: PRT
<213> ORGANISM: Pseudomonas fluorescens

<400> SEQUENCE: 7

Met Ile Asp Thr Phe Asn Arg Thr Gly Pro Leu Met Asp Ala Thr Ser
1               5                   10                  15

Tyr Pro Lys Trp Ala Gln Gln Leu Ile Thr Asp Cys Ser Glu Ser Lys
            20                  25                  30

Arg Arg Val Val Glu His Glu Leu Tyr Gln Arg Met Arg Asp Asn Lys
        35                  40                  45

Leu Ser Ala Arg Thr Met Arg His Tyr Leu Ile Gly Gly Trp Pro Val
    50                  55                  60

Val Glu Gln Phe Ala Leu Tyr Met Ala Gln Asn Leu Thr Lys Thr Arg
65                  70                  75                  80

Phe Ala Arg His Pro Gly Glu Asp Met Ala Arg Arg Trp Leu Met Arg
                85                  90                  95

Asn Ile Arg Val Glu Leu Asn His Ala Asp Tyr Trp Val Asn Trp Ser
            100                 105                 110

Ala Ala His Gly Val Thr Leu Glu Asp Leu Gln Ala Gln His Val Pro
        115                 120                 125

Pro Glu Leu His Ala Leu Ser His Trp Cys Trp His Thr Ser Ser Ser
    130                 135                 140

Asp Ser Leu Ile Val Ala Ile Ala Thr Asn Tyr Ala Ile Glu Gly Gly
145                 150                 155                 160

Ala Thr Gly Glu Trp Ser Ala Leu Val Cys Ser Ser Gly Val Tyr Ala
                165                 170                 175

Ala Ala Phe Ala Glu Glu Asp Arg Lys Arg Ala Met Lys Trp Leu Lys
            180                 185                 190

Met His Ala Gln Tyr Asp Asp Ala His Pro Trp Glu Ala Leu Glu Ile
        195                 200                 205

Ile Cys Thr Leu Ala Gly Met Asn Pro Ser Lys Ala Leu Gln Ala Glu
    210                 215                 220

Leu Arg Gln Ala Val Cys Lys Ser Tyr Asp Tyr Met Tyr Leu Phe Leu
225                 230                 235                 240

Glu Arg Cys Met Gln Leu Glu Gln Ser Glu Thr Val Ser Lys Ser Ser
                245                 250                 255

Ser Thr Arg Glu Arg Leu Ala Leu Ala Gln Ser
            260                 265

<210> SEQ ID NO 8

```
<211> LENGTH: 260
<212> TYPE: PRT
<213> ORGANISM: Pseudomonas aeruginosa

<400> SEQUENCE: 8

Met Ser Glu Phe Phe Asp Arg Thr Gly Pro Leu Gln Glu Ala Gly Ser
1               5                   10                  15

Tyr Pro Gln Trp Ala Gln Gln Leu Ile Val Asp Cys Gln Ala Ser Lys
            20                  25                  30

Asp Arg Val Ser Gly His Glu Leu Tyr Arg Arg Met Arg Asp Ala Glu
        35                  40                  45

Leu Ser Pro Ala Leu Met Arg Leu Tyr Leu Ile Gly Gly Trp Pro Val
    50                  55                  60

Val Glu Gln Phe Pro Leu Tyr Met Ser Gln Asn Leu Leu Lys Thr Arg
65                  70                  75                  80

Phe Ala Arg His Pro Gly Glu Asp Met Ala Arg Arg Trp Leu Met Arg
                85                  90                  95

Asn Ile Arg Val Glu Leu Asn His Ala Asp Tyr Trp Leu His Trp Ala
            100                 105                 110

Glu Ala His Gly Val Ser Leu Ala Glu Ile Gln Ala Gln Asp Val Pro
        115                 120                 125

Ala Glu Leu His Ala Leu Ser His Trp Cys Trp His Thr Cys Ala Ser
    130                 135                 140

Asp Ser Leu Ala Val Ala Met Ala Ala Thr Asn Tyr Ala Ile Glu Gly
145                 150                 155                 160

Val Thr Gly Glu Trp Ser Ala Leu Val Cys Ser Asn Gly Val Tyr Glu
                165                 170                 175

Asn Ala Phe Pro Lys Glu Gly Arg Lys Arg Ala Met Lys Trp Leu Lys
            180                 185                 190

Leu His Ala Gln Tyr Asp Asp Ala His Pro Trp Glu Ala Leu Glu Ile
        195                 200                 205

Ile Cys Thr Leu Ala Gly Thr Asn Pro Ser Ala Glu Leu Arg Arg Gln
    210                 215                 220

Leu Arg Asp Ala Ile Cys Lys Ser Tyr Asp Tyr Met Tyr Leu Phe Leu
225                 230                 235                 240

Glu Arg Cys Met Gln Leu Glu Glu Ala Arg Ser Ala Arg Lys Leu Ala
                245                 250                 255

Val Gly Ala Glu
            260

<210> SEQ ID NO 9
<211> LENGTH: 260
<212> TYPE: PRT
<213> ORGANISM: Pseudomonas aeruginosa

<400> SEQUENCE: 9

Met Ser Glu Phe Phe Asp Arg Thr Gly Pro Leu Gln Glu Ala Gly Ser
1               5                   10                  15

Tyr Pro Gln Trp Ala Gln Gln Leu Ile Val Asp Cys Gln Ala Ser Lys
            20                  25                  30

Asp Arg Val Ser Gly His Glu Leu Tyr Arg Arg Met Arg Asp Ala Glu
        35                  40                  45

Leu Ser Pro Ala Leu Met Arg Leu Tyr Leu Ile Gly Gly Trp Pro Val
    50                  55                  60

Val Glu Gln Phe Pro Leu Tyr Met Ser Gln Asn Leu Leu Lys Thr Arg
65                  70                  75                  80
```

```
Phe Ala Arg His Pro Gly Glu Asp Met Ala Arg Arg Trp Leu Met Arg
                85                  90                  95

Asn Ile Arg Val Glu Leu Asn His Ala Asp Tyr Trp Leu His Trp Ala
            100                 105                 110

Glu Ala His Gly Val Ser Leu Ala Glu Ile Gln Ser Gln Asp Val Pro
        115                 120                 125

Ala Glu Leu His Ala Leu Ser His Trp Cys Trp His Thr Cys Ala Ser
    130                 135                 140

Asp Ser Leu Ala Val Ala Met Ala Ala Thr Asn Tyr Ala Ile Glu Gly
145                 150                 155                 160

Val Thr Gly Glu Trp Ser Ala Leu Val Cys Ser Asn Gly Val Tyr Glu
                165                 170                 175

Asn Ala Phe Pro Lys Glu Gly Arg Lys Arg Ala Met Lys Trp Leu Lys
            180                 185                 190

Leu His Ala Gln Tyr Asp Asp Ala His Pro Trp Glu Ala Leu Glu Ile
        195                 200                 205

Ile Cys Thr Leu Ala Gly Thr Asn Pro Ser Ala Glu Leu Arg Arg Gln
    210                 215                 220

Leu Arg Asp Ala Ile Cys Lys Ser Tyr Asp Tyr Met Tyr Leu Phe Leu
225                 230                 235                 240

Glu Arg Cys Met Gln Leu Glu Glu Ala Arg Ser Ala Arg Lys Leu Ala
                245                 250                 255

Val Gly Ala Glu
            260

<210> SEQ ID NO 10
<211> LENGTH: 261
<212> TYPE: PRT
<213> ORGANISM: Pseudomonas putida

<400> SEQUENCE: 10

Met Ile Asp Ala Phe Val Arg Ile Gly Pro Leu Met Asp Pro Ala Ser
  1               5                  10                  15

Tyr Pro Gln Trp Ala Gln Gln Leu Ile Glu Asp Cys Arg Glu Ser Lys
                20                  25                  30

Arg Arg Val Val Glu His Glu Phe Tyr Ala Arg Leu Arg Asp Gly Gln
            35                  40                  45

Leu Lys Gln Ser Thr Ile Arg Gln Tyr Leu Ile Gly Gly Trp Pro Val
        50                  55                  60

Val Glu Gln Phe Ser Leu Tyr Met Ala His Asn Leu Thr Lys Thr Arg
65                  70                  75                  80

Tyr Gly Arg His Gln Gly Glu Asp Met Ala Arg Arg Trp Leu Met Arg
                85                  90                  95

Asn Ile Arg Val Glu Leu Asn His Ala Asp Tyr Trp Val Asn Trp Cys
            100                 105                 110

Gln Ala His Gly Val His Leu His Glu Leu Gln Ala Gln Glu Val Pro
        115                 120                 125

Pro Glu Leu Asn Gly Leu Asn Asp Trp Cys Trp Arg Val Cys Ala Thr
    130                 135                 140

Glu Asn Leu Ala Ile Ser Met Ala Thr Asn Tyr Ala Ile Glu Gly
145                 150                 155                 160

Ala Thr Gly Glu Trp Ser Ala Val Val Cys Ser Thr Asp Thr Tyr Ala
                165                 170                 175

Gln Gly Phe Pro Glu Glu Gly Arg Lys Arg Ala Met Lys Trp Leu Lys
```

```
                    180                 185                 190
Met His Ala Gln Tyr Asp Asp Ala His Pro Trp Glu Ala Leu Glu Ile
                195                 200                 205

Ile Cys Thr Leu Ala Gly Glu Asn Pro Thr Leu Gly Leu Arg Thr Glu
    210                 215                 220

Leu Arg Arg Ala Ile Cys Lys Ser Tyr Asp Cys Met Phe Leu Phe Leu
225                 230                 235                 240

Glu Arg Cys Met Gln Leu Glu Gly Arg Gln Gln Gly Arg Met Arg Pro
                245                 250                 255

Ala Leu Ala Ala Gly
            260

<210> SEQ ID NO 11
<211> LENGTH: 250
<212> TYPE: PRT
<213> ORGANISM: Pseudomonas putida

<400> SEQUENCE: 11

Met Asp Pro Ala Ser Tyr Pro Gln Trp Ala Gln Gln Leu Ile Glu Asp
1               5                   10                  15

Cys Arg Glu Ser Lys Arg Arg Val Val Glu His Glu Phe Tyr Ala Arg
                20                  25                  30

Leu Arg Asp Gly Gln Leu Lys Gln Ser Thr Ile Arg Gln Tyr Leu Ile
            35                  40                  45

Gly Gly Trp Pro Val Val Glu Gln Phe Ser Leu Tyr Met Ala His Asn
        50                  55                  60

Leu Thr Lys Thr Arg Tyr Gly Arg His Gln Gly Glu Asp Met Ala Arg
65                  70                  75                  80

Arg Trp Leu Met Arg Asn Ile Arg Val Glu Leu Asn His Ala Asp Tyr
                85                  90                  95

Trp Val Asn Trp Cys Gln Ala His Gly Val His Leu His Glu Leu Gln
                100                 105                 110

Ala Gln Glu Val Pro Pro Glu Leu Asn Gly Leu Asn Asp Trp Cys Trp
            115                 120                 125

Arg Val Cys Ala Thr Glu Asn Leu Ala Ile Ser Met Ala Ala Thr Asn
        130                 135                 140

Tyr Ala Ile Glu Gly Ala Thr Gly Glu Trp Ser Ala Val Val Cys Ser
145                 150                 155                 160

Thr Asp Thr Tyr Ala Leu Gly Phe Pro Glu Asp Gln Arg Lys Arg Ala
                165                 170                 175

Met Lys Trp Leu Lys Met His Ala Gln Tyr Asp Asp Ala His Pro Trp
            180                 185                 190

Glu Ala Leu Glu Ile Ile Cys Thr Leu Ala Gly Glu Asn Pro Thr Leu
        195                 200                 205

Gly Leu Arg Asn Glu Leu Arg Lys Ala Ile Cys Lys Ser Tyr Asp Cys
    210                 215                 220

Met Tyr Leu Phe Leu Glu Arg Cys Met Gln Leu Glu Gly Arg Gln Gln
225                 230                 235                 240

Gly Arg Met Arg Pro Val Leu Ala Ala Gly
                245                 250

<210> SEQ ID NO 12
<211> LENGTH: 261
<212> TYPE: PRT
<213> ORGANISM: Pseudomonas syringae
```

<400> SEQUENCE: 12

Met Ile Asp Thr Phe Glu Arg Thr Gly Pro Leu Met Glu Ala Ser Ser
1               5                   10                  15

Tyr Pro Ala Trp Ala Gln Gln Leu Ile Lys Asp Cys Ser Ala Ala Lys
            20                  25                  30

Ala Arg Val Val Glu His Glu Leu Tyr Gln Gln Met Arg Asp Ala Lys
        35                  40                  45

Leu Ser Pro Gln Ile Met Arg His Tyr Leu Ile Gly Gly Trp Pro Val
    50                  55                  60

Val Glu Gln Phe Ala Val Tyr Met Ala Lys Asn Leu Thr Lys Thr Arg
65                  70                  75                  80

Phe Gly Arg His Pro Gly Glu Asp Met Ala Arg Arg Trp Leu Met Phe
                85                  90                  95

Asn Ile Arg Val Glu Leu Asn His Ala Asp Tyr Trp Val Asn Trp Cys
            100                 105                 110

Ala Ala His Asp Val Thr Leu Glu Asp Leu His Asp Gln Arg Val Ala
        115                 120                 125

Pro Glu Leu His Ala Leu Ser His Trp Cys Trp Gln Thr Ser Ser Ser
    130                 135                 140

Asp Ser Leu Ala Val Ala Met Ala Ala Thr Asn Tyr Ala Ile Glu Gly
145                 150                 155                 160

Ala Thr Gly Glu Trp Ser Ala Val Val Cys Ser Asn Gly Ala Tyr Ala
                165                 170                 175

Glu Ala Phe Pro Glu Glu Thr Arg Lys Lys Ala Met Lys Trp Leu Lys
            180                 185                 190

Met His Ala Gln Tyr Asp Asp Ala His Pro Trp Glu Ala Leu Glu Ile
        195                 200                 205

Ile Cys Thr Leu Val Gly Asp Lys Pro Ser Leu Gln Leu Gln Ala Glu
    210                 215                 220

Leu Arg Gln Ala Val Thr Lys Ser Tyr Asp Tyr Met His Leu Phe Leu
225                 230                 235                 240

Glu Arg Cys Met Gln Leu Asp Lys Val Lys Pro Ala Arg Gly Arg Val
                245                 250                 255

Ala Ala Leu Glu Val
            260

<210> SEQ ID NO 13
<211> LENGTH: 260
<212> TYPE: PRT
<213> ORGANISM: Pseudomonas syringae

<400> SEQUENCE: 13

Met Ile Asp Ala Phe Asp Arg Thr Gly Pro Leu Met Glu Ala Ser Ser
1               5                   10                  15

Tyr Pro Ala Trp Ala Gln Gln Leu Ile Lys Asp Cys Ser Ala Ala Lys
            20                  25                  30

Ala Arg Val Val Glu His Glu Leu Tyr Gln Gln Met Arg Asp Ala Thr
        35                  40                  45

Leu Ser Pro Gln Ile Met Arg His Tyr Leu Ile Gly Gly Trp Pro Val
    50                  55                  60

Val Glu Gln Phe Ala Val Tyr Met Ala Lys Asn Leu Thr Lys Thr Arg
65                  70                  75                  80

Phe Gly Arg His Pro Gly Glu Asp Met Ala Arg Arg Trp Leu Met Arg
                85                  90                  95

-continued

Asn Ile Arg Val Glu Leu Asn His Ala Asp Tyr Trp Val Asn Trp Cys
            100                 105                 110

Ala Ala His Glu Val Thr Leu Glu Asp Leu His Asp Gln Arg Val Ala
        115                 120                 125

Pro Glu Leu His Ala Leu Ser His Trp Cys Trp Gln Thr Ser Ser Ser
    130                 135                 140

Asp Ser Leu Ala Val Ala Met Ala Ala Thr Asn Tyr Ala Ile Glu Gly
145                 150                 155                 160

Ala Thr Gly Glu Trp Ser Ala Val Val Cys Ser Thr Gly Ala Tyr Ala
                165                 170                 175

Glu Ala Phe Pro Glu Thr Arg Lys Lys Ala Met Lys Trp Leu Lys
            180                 185                 190

Met His Ala Gln Tyr Asp Asp Ala His Pro Trp Glu Ala Leu Glu Ile
        195                 200                 205

Ile Cys Thr Leu Val Gly Asn Lys Pro Ser Val Gln Leu Gln Thr Glu
    210                 215                 220

Leu Arg Gln Ala Val Thr Lys Ser Tyr Asp Tyr Met Tyr Leu Phe Leu
225                 230                 235                 240

Glu Arg Cys Met Gln Leu Asp Arg Val Lys Pro Arg Gly Arg Val Ala
                245                 250                 255

Ala Leu Glu Ala
        260

<210> SEQ ID NO 14
<211> LENGTH: 260
<212> TYPE: PRT
<213> ORGANISM: Pseudomonas syringae

<400> SEQUENCE: 14

Met Ile Asp Ala Phe Asp Arg Thr Gly Pro Leu Met Glu Ala Ser Ser
1               5                   10                  15

Tyr Pro Ala Trp Ala Gln Gln Leu Ile Lys Asp Cys Ser Ala Ala Lys
            20                  25                  30

Ala Arg Val Val Glu His Glu Leu Tyr Gln Gln Met Arg Asp Ala Lys
        35                  40                  45

Leu Ser Pro Gln Ile Met Arg His Tyr Leu Ile Gly Gly Trp Pro Val
    50                  55                  60

Val Glu Gln Phe Ala Val Tyr Met Ala Lys Asn Leu Thr Lys Thr Arg
65                  70                  75                  80

Phe Gly Arg His Pro Gly Glu Asp Met Ala Arg Arg Trp Leu Met Arg
                85                  90                  95

Asn Ile Arg Val Glu Leu Asn His Ala Asp Tyr Trp Val Asn Trp Cys
            100                 105                 110

Ala Ala His Gly Val Thr Leu Glu Asp Leu His Asp Gln Arg Val Ala
        115                 120                 125

Pro Glu Leu His Ala Leu Ser His Trp Cys Trp Gln Thr Ser Ser Ser
    130                 135                 140

Asp Ser Leu Ala Val Ala Met Ala Ala Thr Asn Tyr Ala Ile Glu Gly
145                 150                 155                 160

Ala Thr Gly Glu Trp Ser Ala Val Val Cys Ser Ser Gly Val Tyr Ala
                165                 170                 175

Glu Ala Phe Pro Glu Thr Arg Lys Lys Ala Met Lys Trp Leu Lys
            180                 185                 190

Met His Ala Gln Tyr Asp Asp Ala His Pro Trp Glu Ala Leu Glu Ile
        195                 200                 205

Ile Cys Thr Leu Val Gly Asn Lys Pro Ser Val Gln Leu Gln Ala Glu
210                 215                 220

Leu Arg Gln Ala Val Thr Lys Ser Tyr Asp Tyr Met Tyr Leu Phe Leu
225                 230                 235                 240

Glu Arg Cys Met Gln Leu Asp Arg Val Lys Pro Arg Gly Arg Val Ala
                245                 250                 255

Ala Leu Glu Ala
            260

<210> SEQ ID NO 15
<211> LENGTH: 246
<212> TYPE: PRT
<213> ORGANISM: Burkholderia mallei

<400> SEQUENCE: 15

Met His Ile Pro Phe Glu Arg Asp Gly Asp Leu Met Asp Ile Gly Ser
1               5                   10                  15

Tyr Pro His Trp Leu Gln Asp Val Val Gly Thr Val Arg Ala Ala Arg
            20                  25                  30

Asp Arg Val Arg Phe His Glu Val Phe Ser Leu Met Arg Asp Ser Arg
        35                  40                  45

Leu Ala Pro Arg Gln Leu Ala Ala Phe Phe Val Asn Gly Trp Pro Val
    50                  55                  60

Val Glu Gln Phe Pro Lys Tyr Met Ser Met Asn Leu Leu Lys Ala Asn
65                  70                  75                  80

Gly Thr Asn Ser Ser Gly Glu Glu Lys Ala Arg Arg Tyr Leu Ile Arg
                85                  90                  95

Asn Ile Arg Val Glu Leu Asn His Val Glu His Trp Val Asn Trp Ala
            100                 105                 110

Glu Ala Ser Gly Val Pro Arg Arg Gln Leu Thr Asp Gly Asp Ser Pro
        115                 120                 125

Pro Ala Ala Leu Ala Leu Ser His Trp Cys Trp Lys Ser Ser Ser Ala
    130                 135                 140

Asp Thr Leu Ala Ala Ser Ile Ala Ala Thr Asn Tyr Ala Ile Glu Gly
145                 150                 155                 160

Val Thr Gly Glu Trp Ser Ala Asp Leu Cys Arg Ser Asp Val Tyr Glu
                165                 170                 175

Met Gly Phe Pro Glu Ala Val Arg Gly Arg Ala Met Arg Trp Leu Arg
            180                 185                 190

Leu His Ser Ser Tyr Asp Asp Lys His Pro Trp Glu Ala Leu Asp Ile
        195                 200                 205

Val Ala Thr Ile Leu Gly Gln Ser Pro Ser Thr Glu Gln Val Arg Asp
    210                 215                 220

Val Ala Ala Gly Ile Glu Arg Ser Phe Arg Tyr Phe Glu Met Ser Leu
225                 230                 235                 240

Ser Cys Cys Leu Asp Ala
                245

<210> SEQ ID NO 16
<211> LENGTH: 236
<212> TYPE: PRT
<213> ORGANISM: Burkholderia mallei

<400> SEQUENCE: 16

Met Met Asp Ile Gly Ser Tyr Pro His Trp Leu Gln Asp Val Val Gly
1               5                   10                  15

Thr Val Arg Ala Ala Arg Asp Arg Val Arg Phe His Glu Val Phe Ser
            20                  25                  30

Leu Met Arg Asp Ser Arg Leu Ala Pro Arg Gln Leu Ala Ala Phe Phe
            35                  40                  45

Val Asn Gly Trp Pro Val Val Glu Gln Phe Pro Lys Tyr Met Ser Met
 50                  55                  60

Asn Leu Leu Lys Ala Asn Gly Thr Asn Ser Ser Gly Glu Glu Lys Ala
 65                  70                  75                  80

Arg Arg Tyr Leu Ile Arg Asn Ile Arg Val Glu Leu Asn His Val Glu
                 85                  90                  95

His Trp Val Asn Trp Ala Glu Ala Ser Gly Val Pro Arg Arg Gln Leu
            100                 105                 110

Thr Asp Gly Asp Ser Pro Pro Ala Ala Leu Ala Leu Ser His Trp Cys
            115                 120                 125

Trp Lys Ser Ser Ser Ala Asp Thr Leu Ala Ala Ser Ile Ala Ala Thr
130                 135                 140

Asn Tyr Ala Ile Glu Gly Val Thr Gly Glu Trp Ser Ala Asp Leu Cys
145                 150                 155                 160

Arg Ser Asp Val Tyr Glu Met Gly Phe Pro Glu Ala Val Arg Gly Arg
                165                 170                 175

Ala Met Arg Trp Leu Arg Leu His Ser Ser Tyr Asp Asp Lys His Pro
            180                 185                 190

Trp Glu Ala Leu Asp Ile Val Ala Thr Ile Leu Gly Gln Ser Pro Ser
            195                 200                 205

Thr Glu Gln Val Arg Asp Val Ala Ala Gly Ile Glu Arg Ser Phe Arg
            210                 215                 220

Tyr Phe Glu Met Ser Leu Ser Cys Cys Leu Asp Ala
225                 230                 235

<210> SEQ ID NO 17
<211> LENGTH: 235
<212> TYPE: PRT
<213> ORGANISM: Burkholderia mallei

<400> SEQUENCE: 17

Met Asp Ile Gly Ser Tyr Pro His Trp Leu Gln Asp Val Val Gly Thr
 1               5                  10                  15

Val Arg Ala Ala Arg Asp Arg Val Arg Phe His Glu Val Phe Ser Leu
            20                  25                  30

Met Arg Asp Ser Arg Leu Ala Pro Arg Gln Leu Ala Ala Phe Phe Val
            35                  40                  45

Asn Gly Trp Pro Val Val Glu Gln Phe Pro Lys Tyr Met Ser Met Asn
 50                  55                  60

Leu Leu Lys Ala Asn Gly Thr Asn Ser Ser Gly Glu Glu Lys Ala Arg
 65                  70                  75                  80

Arg Tyr Leu Ile Arg Asn Ile Arg Val Glu Leu Asn His Val Glu His
                 85                  90                  95

Trp Val Asn Trp Ala Glu Ala Ser Gly Val Pro Arg Arg Gln Leu Thr
            100                 105                 110

Asp Gly Asp Ser Pro Pro Ala Ala Leu Ala Leu Ser His Trp Cys Trp
            115                 120                 125

Lys Ser Ser Ser Ala Asp Thr Leu Ala Ala Ser Ile Ala Ala Thr Asn
130                 135                 140

Tyr Ala Ile Glu Gly Val Thr Gly Glu Trp Ser Ala Asp Leu Cys Arg

```
            145                 150                 155                 160
Ser Asp Val Tyr Glu Met Gly Phe Pro Glu Ala Val Arg Gly Arg Ala
                    165                 170                 175

Met Arg Trp Leu Arg Leu His Ser Ser Tyr Asp Asp Lys His Pro Trp
                180                 185                 190

Glu Ala Leu Asp Ile Val Ala Thr Ile Leu Gly Gln Ser Pro Ser Thr
            195                 200                 205

Glu Gln Val Arg Asp Val Ala Ala Gly Ile Glu Arg Ser Phe Arg Tyr
        210                 215                 220

Phe Glu Met Ser Leu Ser Cys Cys Leu Asp Ala
225                 230                 235

<210> SEQ ID NO 18
<211> LENGTH: 254
<212> TYPE: PRT
<213> ORGANISM: Burkholderia pseudomallei

<400> SEQUENCE: 18

Met Thr Leu Ser Lys Glu Arg Lys Leu His Ile Pro Phe Glu Arg Asp
1               5                   10                  15

Gly Asp Leu Met Asp Ile Gly Ser Tyr Pro His Trp Leu Gln Asp Val
                20                  25                  30

Val Gly Thr Val Arg Ala Ala Arg Asp Arg Val Arg Phe His Glu Val
            35                  40                  45

Phe Ser Leu Met Arg Asp Gly Arg Leu Ala Pro Arg Gln Leu Ala Ala
        50                  55                  60

Phe Phe Val Asn Gly Trp Pro Val Val Glu Gln Phe Pro Lys Tyr Met
65                  70                  75                  80

Ser Met Asn Leu Leu Lys Ala Asn Gly Thr Asn Ser Ser Gly Glu Glu
                85                  90                  95

Lys Ala Arg Arg Tyr Leu Ile Arg Asn Ile Arg Val Glu Leu Asn His
                100                 105                 110

Val Glu His Trp Val Asn Trp Ala Glu Ala Ser Gly Val Pro Arg Arg
            115                 120                 125

Gln Leu Thr Asp Gly Asp Ser Pro Pro Ala Ala Leu Ala Leu Ser His
        130                 135                 140

Trp Cys Trp Lys Ser Ser Ser Ala Asp Thr Leu Ala Ala Ser Ile Ala
145                 150                 155                 160

Ala Thr Asn Tyr Ala Ile Glu Gly Val Thr Gly Glu Trp Ser Ala Asp
                165                 170                 175

Leu Cys Arg Ser Asp Val Tyr Glu Met Gly Phe Pro Glu Ala Val Arg
                180                 185                 190

Gly Arg Ala Met Arg Trp Leu Arg Leu His Ser Ser Tyr Asp Asp Lys
            195                 200                 205

His Pro Trp Glu Ala Leu Asp Ile Val Ala Thr Ile Leu Gly Gln Ser
        210                 215                 220

Pro Ser Thr Glu Gln Val Arg Asp Val Ala Ala Gly Ile Glu Arg Ser
225                 230                 235                 240

Phe Arg Tyr Phe Glu Met Ser Leu Ser Cys Cys Leu Asp Ala
                245                 250

<210> SEQ ID NO 19
<211> LENGTH: 246
<212> TYPE: PRT
<213> ORGANISM: Burkholderia pseudomallei
```

<400> SEQUENCE: 19

Met His Ile Pro Phe Glu Arg Asp Gly Asp Leu Met Asp Ile Gly Ser
1               5                   10                  15

Tyr Pro His Trp Leu Gln Asp Val Val Gly Thr Val Arg Ala Ala Arg
            20                  25                  30

Asp Arg Val Arg Phe His Glu Val Phe Ser Leu Met Arg Asp Gly Arg
        35                  40                  45

Leu Ala Pro Arg Gln Leu Ala Ala Phe Phe Val Asn Gly Trp Pro Val
    50                  55                  60

Val Glu Gln Phe Pro Lys Tyr Met Ser Met Asn Leu Leu Lys Ala Asn
65                  70                  75                  80

Gly Thr Asn Ser Ser Gly Glu Lys Ala Arg Arg Tyr Leu Ile Arg
                85                  90                  95

Asn Ile Arg Val Glu Leu Asn His Val Glu His Trp Val Asn Trp Ala
            100                 105                 110

Glu Ala Ser Gly Val Pro Arg Arg Gln Leu Thr Asp Gly Asp Ser Pro
        115                 120                 125

Pro Ala Ala Leu Ala Leu Ser His Trp Cys Trp Lys Ser Ser Ala
    130                 135                 140

Asp Thr Leu Ala Ala Ser Ile Ala Ala Thr Asn Tyr Ala Ile Glu Gly
145                 150                 155                 160

Val Thr Gly Glu Trp Ser Ala Asp Leu Cys Arg Ser Asp Val Tyr Glu
                165                 170                 175

Met Gly Phe Pro Glu Ala Val Arg Gly Arg Ala Met Arg Trp Leu Arg
            180                 185                 190

Leu His Ser Ser Tyr Asp Asp Lys His Pro Trp Glu Ala Leu Asp Ile
        195                 200                 205

Val Ala Thr Ile Leu Gly Gln Ser Pro Ser Thr Glu Gln Val Arg Asp
    210                 215                 220

Val Ala Ala Gly Ile Glu Arg Ser Phe Arg Tyr Phe Glu Met Ser Leu
225                 230                 235                 240

Ser Cys Cys Leu Asp Ala
                245

<210> SEQ ID NO 20
<211> LENGTH: 236
<212> TYPE: PRT
<213> ORGANISM: Burkholderia pseudomallei

<400> SEQUENCE: 20

Met Met Asp Ile Gly Ser Tyr Pro His Trp Leu Gln Asp Val Val Gly
1               5                   10                  15

Thr Val Arg Ala Ala Arg Asp Arg Val Arg Phe His Glu Val Phe Ser
            20                  25                  30

Leu Met Arg Asp Gly Arg Leu Ala Pro Arg Gln Leu Ala Ala Phe Phe
        35                  40                  45

Val Asn Gly Trp Pro Val Val Glu Gln Phe Pro Lys Tyr Met Ser Met
    50                  55                  60

Asn Leu Leu Lys Ala Asn Gly Thr Asn Ser Ser Gly Glu Glu Lys Ala
65                  70                  75                  80

Arg Arg Tyr Leu Ile Arg Asn Ile Arg Val Glu Leu Asn His Val Glu
                85                  90                  95

His Trp Val Asn Trp Ala Glu Ala Ser Gly Val Pro Arg Gln Leu
            100                 105                 110

```
Thr Asp Gly Asp Ser Pro Pro Ala Leu Ala Leu Ser His Trp Cys
        115                 120                 125
Trp Lys Ser Ser Ser Ala Asp Thr Leu Ala Ala Ser Ile Ala Ala Thr
130                 135                 140
Asn Tyr Ala Ile Glu Gly Val Thr Gly Glu Trp Ser Ala Asp Leu Cys
145                 150                 155                 160
Arg Ser Asp Val Tyr Glu Met Gly Phe Pro Glu Ala Val Arg Gly Arg
                165                 170                 175
Ala Met Arg Trp Leu Arg Leu His Ser Ser Tyr Asp Asp Lys His Pro
        180                 185                 190
Trp Glu Ala Leu Asp Ile Val Ala Thr Ile Leu Gly Gln Ser Pro Ser
    195                 200                 205
Thr Glu Gln Val Arg Asp Val Ala Ala Gly Ile Glu Arg Ser Phe Arg
210                 215                 220
Tyr Phe Glu Met Ser Leu Ser Cys Cys Leu Asp Ala
225                 230                 235

<210> SEQ ID NO 21
<211> LENGTH: 246
<212> TYPE: PRT
<213> ORGANISM: Burkholderia thailandensis

<400> SEQUENCE: 21

Met His Ile Pro Phe Glu Arg Asp Gly Glu Leu Met Asp Ile Gly Ser
  1               5                  10                  15
Tyr Pro His Trp Leu Gln Asp Val Val Gly Thr Val Arg Ala Ala Arg
                20                  25                  30
Asp Arg Val Arg Phe His Glu Val Phe Ser Leu Met Arg Asp Gly Arg
            35                  40                  45
Leu Ala Pro Arg Gln Leu Ala Ala Phe Val Asn Gly Trp Pro Val
        50                  55                  60
Val Glu Gln Phe Pro Lys Tyr Met Ser Met Asn Leu Leu Lys Ala Asn
 65                  70                  75                  80
Gly Thr Asn Ser Ser Gly Glu Glu Lys Ala Arg Arg Tyr Leu Ile Arg
                85                  90                  95
Asn Ile Arg Val Glu Leu Asn His Val Glu His Trp Val Asn Trp Ala
                100                 105                 110
Glu Ala Ser Gly Val Pro Arg Arg Gln Leu Ile Asp Gly Gly Ser Pro
            115                 120                 125
Pro Ala Ala Leu Ala Leu Ser His Trp Cys Trp Lys Ser Ser Ser Ala
        130                 135                 140
Asp Thr Leu Ala Ala Ser Val Ala Ala Thr Asn Tyr Ala Ile Glu Gly
145                 150                 155                 160
Val Thr Gly Glu Trp Ser Ala Asp Leu Cys Arg Ser Asp Val Tyr Glu
                165                 170                 175
Met Gly Phe Pro Glu Ala Val Arg Gly Arg Ala Met Arg Trp Leu Lys
                180                 185                 190
Leu His Ser Ser Tyr Asp Asp Lys His Pro Trp Glu Ala Leu Asp Ile
            195                 200                 205
Val Ala Thr Ile Leu Gly Gln Ser Pro Ser Thr Glu Gln Val Arg Asp
        210                 215                 220
Val Ala Ala Gly Ile Glu Arg Ser Phe Arg Tyr Phe Glu Met Ser Leu
225                 230                 235                 240
Ser Cys Cys Leu Asp Ala
                245
```

<210> SEQ ID NO 22
<211> LENGTH: 235
<212> TYPE: PRT
<213> ORGANISM: Burkholderia thailandensis

<400> SEQUENCE: 22

Met Asp Ile Gly Ser Tyr Pro His Trp Leu Gln Asp Val Val Gly Thr
1               5                   10                  15

Val Arg Ala Ala Arg Asp Arg Val Arg Phe His Glu Val Phe Ser Leu
            20                  25                  30

Met Arg Asp Gly Arg Leu Ala Pro Arg Gln Leu Ala Ala Phe Phe Val
        35                  40                  45

Asn Gly Trp Pro Val Val Glu Gln Phe Pro Lys Tyr Met Ser Met Asn
    50                  55                  60

Leu Leu Lys Ala Asn Gly Thr Asn Ser Ser Gly Glu Glu Lys Ala Arg
65                  70                  75                  80

Arg Tyr Leu Ile Arg Asn Ile Arg Val Glu Leu Asn His Val Glu His
                85                  90                  95

Trp Val Asn Trp Ala Glu Ala Ser Gly Val Pro Arg Arg Gln Leu Ile
            100                 105                 110

Asp Gly Gly Ser Pro Pro Ala Ala Leu Ala Leu Ser His Trp Cys Trp
        115                 120                 125

Lys Ser Ser Ser Ala Asp Thr Leu Ala Ala Ser Val Ala Ala Thr Asn
    130                 135                 140

Tyr Ala Ile Glu Gly Val Thr Gly Glu Trp Ser Ala Asp Leu Cys Arg
145                 150                 155                 160

Ser Asp Val Tyr Glu Met Gly Phe Pro Glu Ala Val Arg Gly Arg Ala
                165                 170                 175

Met Arg Trp Leu Lys Leu His Ser Ser Tyr Asp Asp Lys His Pro Trp
            180                 185                 190

Glu Ala Leu Asp Ile Val Ala Thr Ile Leu Gly Gln Ser Pro Ser Thr
        195                 200                 205

Glu Gln Val Arg Asp Val Ala Ala Gly Ile Glu Arg Ser Phe Arg Tyr
    210                 215                 220

Phe Glu Met Ser Leu Ser Cys Cys Leu Asp Ala
225                 230                 235

<210> SEQ ID NO 23
<211> LENGTH: 246
<212> TYPE: PRT
<213> ORGANISM: Burkholderia thailandensis

<400> SEQUENCE: 23

Met His Ile Pro Phe Glu Arg Asp Gly Asp Leu Met Asp Ile Gly Ser
1               5                   10                  15

Tyr Pro His Trp Leu Gln Asp Val Val Gly Ala Val Arg Ala Ala Arg
            20                  25                  30

Asp Arg Val Arg Phe His Glu Val Phe Ser Leu Met Arg Asp Gly Arg
        35                  40                  45

Leu Ala Pro Arg Gln Leu Ala Ala Phe Phe Val Asn Gly Trp Pro Val
    50                  55                  60

Val Glu Gln Phe Pro Lys Tyr Met Ser Met Asn Leu Leu Lys Ala Asp
65                  70                  75                  80

Gly Thr Asn Ser Ser Gly Glu Glu Lys Ala Arg Arg Tyr Leu Ile Arg
                85                  90                  95

Asn Ile Arg Val Glu Leu Asn His Val Glu His Trp Val Asn Trp Ala
            100                 105                 110

Glu Ala Ser Gly Val Pro Arg Gln Leu Ile Asp Gly Asp Ser Pro
        115                 120                 125

Pro Ala Ala Leu Ala Leu Ser His Trp Cys Trp Lys Ser Ser Ala
    130                 135                 140

Asp Ser Leu Ala Ala Ser Ile Ala Ala Thr Asn Tyr Ala Ile Glu Gly
145                 150                 155                 160

Val Thr Gly Glu Trp Ser Ala Asp Leu Cys Arg Ser Asp Val Tyr Glu
                165                 170                 175

Met Gly Phe Pro Glu Ala Val Arg Gly Arg Ala Met Arg Trp Leu Lys
                180                 185                 190

Leu His Ser Ser Tyr Asp Asp Lys His Pro Trp Glu Ala Leu Asp Ile
                195                 200                 205

Val Ala Thr Ile Leu Gly Gln Ser Pro Ser Thr Glu Gln Val Arg Asp
            210                 215                 220

Ile Ala Ala Gly Ile Glu Arg Ser Phe Arg Tyr Phe Glu Met Ser Leu
225                 230                 235                 240

Ser Cys Cys Leu Asp Ala
            245

<210> SEQ ID NO 24
<211> LENGTH: 247
<212> TYPE: PRT
<213> ORGANISM: Myxococcus xanthus

<400> SEQUENCE: 24

Met Ser Ser Ala Ala Pro His Arg Tyr Ser Pro Val Leu Thr Leu
1               5                   10                  15

Thr Ala His Pro Arg Trp Leu Glu Ser Met Leu Glu Ser Val Arg Asp
                20                  25                  30

Glu Trp Asn Ala Ala Cys Trp Pro Pro Leu Phe Arg Ala Thr Ala Asp
            35                  40                  45

Gly Gln Arg Pro Pro Leu Arg His Trp Arg Arg Val Leu Ser His Phe
    50                  55                  60

Phe Leu Ile Val Glu Ser Phe Pro Lys Tyr Met Gly Leu Ser Leu Ala
65                  70                  75                  80

Lys Thr Thr Tyr Gly Gln Arg Pro Gly Asp Ala Ser Ala Arg Arg Trp
                85                  90                  95

Leu Leu Gln Asn Leu Gly Val Glu Ala Lys His Ala Glu Trp Phe Ile
            100                 105                 110

Asp Trp Met Arg Gly Ile Gly Leu Ala Pro Glu Asp Val Phe Thr Gln
        115                 120                 125

Arg Pro Leu Pro Glu Val Arg Ala Leu His Glu Phe Leu Leu Asp Thr
    130                 135                 140

Cys Ala His Gly Thr Leu Ala Glu Gly Val Ala Ala Ser Asn Trp Ala
145                 150                 155                 160

Val Glu Gly Ile Thr Gly Val Trp Thr Arg Glu Val Val Glu Pro Phe
                165                 170                 175

Arg Ala Tyr Ala Glu Asp Gly Ala Arg Ile Asp Ala Tyr Ser Met Met
                180                 185                 190

Trp Leu Lys Val His Ala Arg Tyr Asp Asp Gln His Pro Glu Glu Ala
            195                 200                 205

Leu Glu Ile Ile Lys Leu Ser Thr Asp Ala Gly Thr Gly Glu Pro Phe

```
                210                 215                 220
Arg Val Gln Ala Ala Arg Lys Ser Leu Gln Met Tyr Ala Ala Ala
225                 230                 235                 240

Leu His Ala Cys Cys Asn Asp
                245

<210> SEQ ID NO 25
<211> LENGTH: 222
<212> TYPE: PRT
<213> ORGANISM: Myxococcus fulvus

<400> SEQUENCE: 25

Met Leu Glu Ser Leu Arg Glu Asp Trp Asn Thr Ala Cys Trp Pro Pro
1               5                   10                  15

Leu Phe Arg Ala Thr Ala Asp Gly Gln Arg Pro Pro Leu Arg His Trp
            20                  25                  30

Arg Arg Val Leu Ala His Phe Phe Pro Ile Val Glu Ala Phe Pro Lys
        35                  40                  45

Tyr Met Gly Leu Ser Leu Ala Lys Thr Thr Tyr Gly Gln Arg Pro Gly
    50                  55                  60

Asp Ala Ser Ala Arg Arg Trp Leu Leu Gln Asn Leu Gly Val Glu Ala
65                  70                  75                  80

Lys His Ala Glu Trp Phe Ile Asp Trp Met Arg Gly Ile Gly Leu Ala
                85                  90                  95

Pro Glu Asp Val Phe Arg Gln Arg Pro Leu Pro Glu Val Arg Ala Leu
            100                 105                 110

His Glu His Leu Leu Asp Thr Cys Ala Arg Gly Thr Leu Ala Glu Gly
        115                 120                 125

Val Ala Ala Ser Asn Trp Ala Val Glu Gly Ile Thr Gly Val Trp Thr
    130                 135                 140

Arg Glu Val Val Glu Pro Phe Arg Ala Tyr Ala Glu Gly Ala Arg
145                 150                 155                 160

Ile Asp Ala Tyr Ser Met Met Trp Leu Lys Val His Ala Arg Tyr Asp
                165                 170                 175

Asp Gln His Pro Glu Glu Ala Leu Glu Ile Ile Lys Leu Ser Thr Asp
            180                 185                 190

Ala Ser Ser Gly Glu Pro Phe Arg Val Gln Ala Ala Arg Lys Ser
        195                 200                 205

Leu Arg Met Tyr Ala Ala Ala Leu His Ala Cys Cys Arg Asp
    210                 215                 220

<210> SEQ ID NO 26
<211> LENGTH: 258
<212> TYPE: PRT
<213> ORGANISM: Myxococcus stipitatus

<400> SEQUENCE: 26

Met Ser Ser Pro Gly Pro Glu Val Thr Val Pro Thr Phe Thr Ala Ile
1               5                   10                  15

Ala His Arg Tyr Ala Pro Pro Leu Thr Pro Thr Pro His Pro Arg
            20                  25                  30

Trp Val Glu Ser Phe Leu Asp Ala Thr Arg Arg Asp Trp Asp Ala Ala
        35                  40                  45

Cys Trp Pro Pro Leu Phe Arg Asp Thr Ala Asp Gly Leu His Pro Pro
    50                  55                  60

Leu Ser Ser Trp Arg Arg Val Leu Ser Gln Phe Phe Leu Ile Val Glu
```

```
            65                  70                  75                  80
        Ser Phe Pro Lys Tyr Met Gly Leu Ser Leu Ala Lys Thr Thr Tyr Gly
                            85                  90                  95

Gln Ser Pro Gly Asp Ala Ser Ile Arg Arg Trp Leu Gln Asn Leu
                        100                 105                 110

Gly Val Glu Ala Lys His Ala Glu Trp Tyr Ile Asp Trp Val Arg Ala
                        115                 120                 125

Ile Gly Val Ser Pro Glu Ser Leu Phe Arg Leu Arg Pro Leu Pro Ala
                130                 135                 140

Val Gln Ala Leu His Thr His Leu Leu Asp Thr Cys Thr Arg Gly Ser
        145                 150                 155                 160

Leu Ala Glu Gly Val Ala Ala Thr Asn Trp Ala Ile Glu Ser Ile Thr
                        165                 170                 175

Gly Val Trp Thr Arg Glu Val Met Glu Pro Phe Arg Asp Tyr Ala Ala
                    180                 185                 190

Glu Gly Val Arg Val Asp Ala Ala Ser Met Met Trp Leu Lys Ala His
                    195                 200                 205

Ala Arg Tyr Asp Asp Leu His Pro Val Glu Ala Leu Glu Ile Ile Lys
                210                 215                 220

Leu Ser Thr Asp Pro Arg Gly Asp Glu Pro Val Arg Val Leu Ala Ala
        225                 230                 235                 240

Thr Arg Lys Ser Leu Arg Leu Tyr Thr Ala Leu Arg Ala Cys Cys
                        245                 250                 255

Ser Asp

<210> SEQ ID NO 27
<211> LENGTH: 244
<212> TYPE: PRT
<213> ORGANISM: Acinetobacter baylyi

<400> SEQUENCE: 27

Met Ser Ala Leu Leu Glu Gly Thr Asp Leu Lys Ile Thr Pro His Ser
        1               5                   10                  15

Pro Trp Ala Gln Gln Phe Trp Asp Glu Leu Ile Pro Ala Lys Asp Arg
                        20                  25                  30

Val Gly Gln His Pro Leu Phe Gln Asp Met Ala Asn Gly Arg Leu Asn
                    35                  40                  45

Leu Lys Cys Phe Arg Ser Ala Leu Leu Asn Phe Tyr Pro Leu Val Ala
                50                  55                  60

His Phe Pro Ser Tyr Met Ala Leu Ala Leu Ser Lys Ala Thr Asp Phe
        65                  70                  75                  80

Thr Glu Ala Gly Val Thr Glu Thr Arg Asn Trp Leu Ile Gln Asn Ile
                        85                  90                  95

Lys Val Glu Glu Arg His Leu Asn Trp Tyr Arg Asp Trp Ala Gly Gly
                        100                 105                 110

Phe Gly Leu Thr Val Glu Glu Leu Asp Arg Val Arg Pro Pro Val Ala
                    115                 120                 125

Met Asp Ala Val Asn His Phe Leu Trp Asn Ile Asn Thr Lys Gly Ser
                130                 135                 140

Leu Ala Glu Cys Leu Ala Ala Thr Asn Leu Ala Ile Glu Trp Ala Thr
        145                 150                 155                 160

Gly Asp Trp Ser Ile Gln Val Tyr Lys Gly Ile Asn Ala Tyr Ile Asp
                        165                 170                 175

His Pro Glu Val Ser Ile Asn Lys Arg Ser Leu Ala Trp Leu Arg Ala
```

```
            180                 185                 190
His Ala His Tyr Asp Asp Ile His Pro Tyr Glu Ala Met Glu Leu Ile
                195                 200                 205

Lys Arg Leu Gly Glu Gly Lys Pro Glu Ile Gln Glu Lys Ala Phe Gln
    210                 215                 220

Ala Ala Gln Asp Gly Leu Ala Tyr Tyr Glu Leu Ala Leu Asp Glu Cys
225                 230                 235                 240

Tyr Lys His Gln

<210> SEQ ID NO 28
<211> LENGTH: 248
<212> TYPE: PRT
<213> ORGANISM: Acinetobacter baumannii

<400> SEQUENCE: 28

Met Thr Ala Met Asn Gln Tyr Gly Thr Lys Leu Glu Ile Thr Pro His
1               5                   10                  15

Ser Glu Trp Ala Gln Gln Phe Trp Asp Asp Leu Leu Pro Ser Lys Glu
            20                  25                  30

Arg Val Ser Lys His Pro Leu Phe Thr Asp Met Ala Asn Gly Ser Leu
        35                  40                  45

Ser Leu Glu Cys Phe Arg Ser Ala Leu Leu Asn Phe Tyr Pro Leu Val
    50                  55                  60

Ala His Phe Pro Ser Tyr Met Ala Gly Ser Leu Ala Lys Ala Thr Ser
65                  70                  75                  80

Phe Glu Leu Asp Gly Val Thr Glu Thr Arg Asp Trp Leu Ile Gln Asn
                85                  90                  95

Ile Lys Val Glu Glu Arg His Leu Asn Trp Tyr Gln Asp Trp Ala Gly
            100                 105                 110

Gly Phe Gly Leu Thr Val Glu Met Leu Asn Gln Val Lys Pro Pro Val
        115                 120                 125

Ala Met Asn Ala Val Asn His Phe Leu Trp Asp Val Asn Phe Arg Gly
    130                 135                 140

Thr Leu Ala Glu Ser Ile Ala Ala Thr Asn Leu Ala Ile Glu Trp Ala
145                 150                 155                 160

Thr Gly Asp Trp Thr Ile Gln Val Tyr Lys Gly Ile Gln Ala Tyr Thr
                165                 170                 175

Gln His Pro Glu Val Asn Ile Asn Lys Arg Ser Leu Ala Trp Leu Arg
            180                 185                 190

Ala His Ala His Tyr Asp Asp Leu His Pro Tyr Glu Ala Met Glu Leu
        195                 200                 205

Ile Lys Arg Leu Cys Asp Lys Asp Pro Val Leu Gln Gln Lys Ala Phe
    210                 215                 220

Leu Ala Ala Gln Glu Gly Leu Ala Tyr Tyr Glu Leu Ala Leu Asp Glu
225                 230                 235                 240

Cys Tyr Lys Leu Gln His Lys Asn
                245

<210> SEQ ID NO 29
<211> LENGTH: 250
<212> TYPE: PRT
<213> ORGANISM: Acinetobacter baumannii

<400> SEQUENCE: 29

Met Thr Ala Leu Asn Gln Tyr Gly Met Ser Leu Glu Ile Thr Pro His
1               5                   10                  15
```

Asn Gly Trp Ser Gln Arg Phe Trp Glu Asp Leu Leu Pro Val Lys Glu
            20                  25                  30

Arg Val Ser Lys His Pro Phe Phe Thr Glu Met Ala Asn Gly Gly Leu
        35                  40                  45

Ser Leu Glu Ser Phe Arg Tyr Ala Leu Leu Asn Phe Tyr Pro Leu Val
 50                  55                  60

Ala His Phe Pro Ser Tyr Met Ala Gly Ala Leu Ala Lys Ala Thr Ala
65                  70                  75                  80

Phe Ala Glu Pro Gly Val Thr Glu Thr Arg Asp Trp Leu Ile Gln Asn
                85                  90                  95

Ile Lys Val Glu Glu Arg His Leu Gln Trp Tyr Arg Asp Trp Ala Arg
            100                 105                 110

Gly Phe Gly Leu Thr Val Glu Gln Leu Asp Ser Val Arg Pro Pro Ala
        115                 120                 125

Ser Met Asn Ala Val Asn His Phe Leu Trp Asn Val Ser His Arg Gly
130                 135                 140

Asn Leu Ala Glu Cys Leu Ala Ala Thr Asn Leu Ala Ile Glu Trp Ala
145                 150                 155                 160

Thr Gly Asp Trp Ser Ile Gln Val Tyr Lys Gly Ile His Ala Tyr Thr
                165                 170                 175

Asp His Pro Glu Val Thr Ile Asp Lys Arg Ser Leu Ala Trp Leu Arg
            180                 185                 190

Ala His Ala His Tyr Asp Asp Leu His Pro Tyr Glu Ala Met Glu Leu
        195                 200                 205

Ile Lys Arg Leu Cys Asn Glu Arg Pro Asp Trp Gln Gln Lys Ala Phe
210                 215                 220

His Ala Ala Glu Glu Gly Leu Arg Tyr Tyr Glu Leu Ala Leu Asp Asp
225                 230                 235                 240

Cys Tyr Arg Val Gln Leu Gln Ala Ser Ala
                245                 250

<210> SEQ ID NO 30
<211> LENGTH: 250
<212> TYPE: PRT
<213> ORGANISM: Acinetobacter baumannii

<400> SEQUENCE: 30

Met Thr Ala Leu Asn Gln Tyr Gly Met Ser Leu Glu Ile Thr Pro His
 1               5                   10                  15

Asn Gly Trp Ser Gln Arg Phe Trp Glu Asp Leu Leu Pro Val Lys Glu
            20                  25                  30

Arg Val Ser Lys His Pro Phe Phe Thr Glu Met Ala Asn Gly Gly Leu
        35                  40                  45

Ser Leu Glu Ser Phe Arg Tyr Ala Leu Leu Asn Phe Tyr Pro Leu Val
 50                  55                  60

Ala His Phe Pro Ser Tyr Met Ala Gly Ala Leu Ala Lys Ala Thr Ala
65                  70                  75                  80

Phe Ala Glu Pro Gly Val Thr Glu Thr Arg Asp Trp Leu Ile Gln Asn
                85                  90                  95

Ile Lys Val Glu Glu Arg His Leu Gln Trp Tyr Arg Asp Trp Ala Arg
            100                 105                 110

Gly Phe Gly Leu Thr Val Glu Gln Leu Asp Ser Val Arg Pro Pro Ala
        115                 120                 125

Ser Met Asn Ala Val Asn His Phe Leu Trp Asn Met Ser His Arg Gly

```
            130                 135                 140
Asn Leu Ala Glu Cys Leu Ala Ala Thr Asn Leu Ala Ile Glu Trp Ala
145                 150                 155                 160

Thr Gly Asp Trp Ser Ile Gln Val Tyr Lys Gly Ile His Ala Tyr Thr
                165                 170                 175

Asp His Pro Glu Val Thr Ile Asp Lys Arg Ser Leu Ala Trp Leu Arg
                180                 185                 190

Ala His Ala His Tyr Asp Asp Leu His Pro Tyr Glu Ala Met Glu Leu
                195                 200                 205

Ile Lys Arg Leu Cys Asn Glu Arg Pro Asp Trp Gln Gln Lys Ala Phe
                210                 215                 220

His Ala Ala Glu Glu Gly Leu Arg Tyr Tyr Glu Leu Ala Leu Asp Asp
225                 230                 235                 240

Cys Tyr Arg Val Gln Leu Gln Ala Ser Ala
                245                 250

<210> SEQ ID NO 31
<211> LENGTH: 252
<212> TYPE: PRT
<213> ORGANISM: Acinetobacter haemolyticus

<400> SEQUENCE: 31

Met His Arg Asn Asp Cys Tyr Glu Ser Ile Arg Lys Lys Leu Glu Ile
1               5                   10                  15

Thr Ala His Ser Glu Trp Ser Gln Arg Phe Trp Asp Glu Leu Leu Pro
                20                  25                  30

Ala Lys Glu Arg Val Ser Lys His Pro Leu Phe Leu Asp Met Ala Ser
                35                  40                  45

Gly Ser Leu Ser Leu Glu Cys Phe Arg Ser Ala Leu Leu Asn Phe Tyr
50                  55                  60

Pro Leu Val Ala His Phe Pro Ser Tyr Met Ala Gly Thr Leu Ala Lys
65                  70                  75                  80

Ala Thr Ala Phe Ser Leu Ser Gly Val Thr Glu Thr Arg Asp Trp Leu
                85                  90                  95

Ile Gln Asn Ile Lys Val Glu Gly Arg His Leu Thr Tyr Tyr Gln Asp
                100                 105                 110

Trp Ala Gly Gly Phe Gly Leu Thr Val Asp Met Leu Asn Asn Val Arg
                115                 120                 125

Pro Pro Ala Ala Met Asn Ala Val Asn His Phe Leu Trp Ala Val Asn
130                 135                 140

Tyr Arg Gly Ser Leu Ala Glu Ser Ile Ala Ala Thr Asn Leu Ala Ile
145                 150                 155                 160

Glu Trp Ala Thr Gly Asp Trp Ser Ile Gln Val Tyr Lys Gly Val Gln
                165                 170                 175

Ser Tyr Thr Gln Asn Pro Glu Val Thr Ile Asn Lys Arg Ser Leu Ala
                180                 185                 190

Trp Leu Arg Ala His Ala His Tyr Asp Asp Leu His Pro Tyr Glu Ala
                195                 200                 205

Met Glu Leu Ile Lys Arg Leu Cys Asp Gln Asp Pro Val Met Gln Lys
                210                 215                 220

Lys Ala Phe Leu Ala Ala Gln Glu Gly Leu Ala Tyr Tyr Glu Leu Ala
225                 230                 235                 240

Leu Asp Glu Cys Tyr Lys Ile Gln Gln Ala Asn Arg
                245                 250
```

<210> SEQ ID NO 32
<211> LENGTH: 181
<212> TYPE: PRT
<213> ORGANISM: Acinetobacter haemolyticus

<400> SEQUENCE: 32

Met Glu Tyr Asp Trp Ile Lys Ser Tyr Glu Ile Gly Cys Ile Ala Met
1               5                   10                  15

Thr Ala Met Asn Gln Tyr Glu Lys Lys Leu Glu Ile Thr Ala His Ser
            20                  25                  30

Glu Trp Ser Gln Arg Phe Trp Asp Glu Leu Leu Pro Ala Lys Glu Arg
        35                  40                  45

Val Ser Lys His Pro Leu Phe Leu Asp Met Ala Ser Gly Ser Leu Ser
    50                  55                  60

Leu Glu Cys Phe Arg Ser Ala Leu Leu Asn Phe Tyr Pro Leu Val Ala
65                  70                  75                  80

His Phe Pro Ser Tyr Met Ala Gly Thr Leu Ala Lys Ala Thr Ala Phe
                85                  90                  95

Ser Leu Ser Gly Val Thr Glu Thr Arg Asp Trp Leu Ile Gln Asn Ile
            100                 105                 110

Lys Val Glu Glu Arg His Leu Thr Trp Tyr Gln Asp Trp Ala Gly Gly
        115                 120                 125

Phe Gly Leu Thr Val Asp Met Leu Asn Asn Val Arg Pro Pro Ala Ala
    130                 135                 140

Met Asn Ala Val Asn His Phe Leu Trp Asp Val Asn Tyr Arg Gly Ser
145                 150                 155                 160

Leu Ala Glu Ser Ile Ala Ala Thr Asn Leu Ala Ile Glu Trp Ala Thr
                165                 170                 175

Gly Asp Trp Ser Ile
            180

<210> SEQ ID NO 33
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Leu, Ala or Glu
<220> FEATURE:
<221> NAME/KEY: VARIANT
<222> LOCATION: 3
<223> OTHER INFORMATION: Xaa = Asn, Lys or Arg

<400> SEQUENCE: 33

Glu Xaa Xaa His
1

<210> SEQ ID NO 34
<211> LENGTH: 28
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Ala, Pro, Gln or Leu
<220> FEATURE:
<221> NAME/KEY: VARIANT
<222> LOCATION: 2, 3, 4, 6, 24

```
<223> OTHER INFORMATION: Xaa = Any Amino Acid
<220> FEATURE:
<221> NAME/KEY: VARIANT
<222> LOCATION: 5
<223> OTHER INFORMATION: Xaa = Arg or Ala
<220> FEATURE:
<221> NAME/KEY: VARIANT
<222> LOCATION: 7
<223> OTHER INFORMATION: Xaa = Tyr, Phe, Val or Ala
<220> FEATURE:
<221> NAME/KEY: VARIANT
<222> LOCATION: 8
<223> OTHER INFORMATION: Xaa = Leu or Phe
<220> FEATURE:
<221> NAME/KEY: VARIANT
<222> LOCATION: 9
<223> OTHER INFORMATION: Xaa = Ile, Val, Ala or Ser
<220> FEATURE:
<221> NAME/KEY: VARIANT
<222> LOCATION: 10
<223> OTHER INFORMATION: Xaa = Gly, Asn, His or Gln
<220> FEATURE:
<221> NAME/KEY: VARIANT
<222> LOCATION: 11
<223> OTHER INFORMATION: Xaa = Gly or Phe
<220> FEATURE:
<221> NAME/KEY: VARIANT
<222> LOCATION: 12
<223> OTHER INFORMATION: Xaa = Trp, Phe or Tyr
<220> FEATURE:
<221> NAME/KEY: VARIANT
<222> LOCATION: 13
<223> OTHER INFORMATION: Xaa = Pro or Leu
<220> FEATURE:
<221> NAME/KEY: VARIANT
<222> LOCATION: 14
<223> OTHER INFORMATION: Xaa = Val, Ile or Leu
<220> FEATURE:
<221> NAME/KEY: VARIANT
<222> LOCATION: 16
<223> OTHER INFORMATION: Xaa = Glu or Ala
<220> FEATURE:
<221> NAME/KEY: VARIANT
<222> LOCATION: 17
<223> OTHER INFORMATION: Xaa = Gln, Ser or His
<220> FEATURE:
<221> NAME/KEY: VARIANT
<222> LOCATION: 19
<223> OTHER INFORMATION: Xaa = Ala, Ser or Pro
<220> FEATURE:
<221> NAME/KEY: VARIANT
<222> LOCATION: 20
<223> OTHER INFORMATION: Xaa = Leu, Val, Lys or Ser
<220> FEATURE:
<221> NAME/KEY: VARIANT
<222> LOCATION: 23
<223> OTHER INFORMATION: Xaa = Ala, Ser or Gly
<220> FEATURE:
<221> NAME/KEY: VARIANT
<222> LOCATION: 25
<223> OTHER INFORMATION: Xaa = Asn, Ser, Ala or Thr
<220> FEATURE:
<221> NAME/KEY: VARIANT
<222> LOCATION: 27
<223> OTHER INFORMATION: Xaa = Thr or Leu

<400> SEQUENCE: 34

Xaa Xaa Xaa Xaa Xaa Xaa Xaa Xaa Xaa Xaa Xaa Xaa Xaa Xaa Val Xaa
 1               5                   10                  15

Xaa Phe Xaa Xaa Tyr Met Xaa Xaa Xaa Leu Xaa Lys
            20                  25

<210> SEQ ID NO 35
<211> LENGTH: 26
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Glu, Val or Asp
<220> FEATURE:
<221> NAME/KEY: VARIANT
<222> LOCATION: 3
<223> OTHER INFORMATION: Xaa = Asp, Thr, Glu or Ala
<220> FEATURE:
<221> NAME/KEY: VARIANT
<222> LOCATION: 4
<223> OTHER INFORMATION: Xaa = Met, Glu, Lys or Ser
<220> FEATURE:
<221> NAME/KEY: VARIANT
<222> LOCATION: 5
<223> OTHER INFORMATION: Xaa = Ala, Thr or Ile
<220> FEATURE:
<221> NAME/KEY: VARIANT
<222> LOCATION: 7
<223> OTHER INFORMATION: Xaa = Arg, Asn or Asp
<220> FEATURE:
<221> NAME/KEY: VARIANT
<222> LOCATION: 8
<223> OTHER INFORMATION: Xaa = Trp or Tyr
<220> FEATURE:
<221> NAME/KEY: VARIANT
<222> LOCATION: 10
<223> OTHER INFORMATION: Xaa = Met, Ile or Leu
<220> FEATURE:
<221> NAME/KEY: VARIANT
<222> LOCATION: 11
<223> OTHER INFORMATION: Xaa = Arg or Gln
<220> FEATURE:
<221> NAME/KEY: VARIANT
<222> LOCATION: 13
<223> OTHER INFORMATION: Xaa = Ile or Leu
<220> FEATURE:
<221> NAME/KEY: VARIANT
<222> LOCATION: 14
<223> OTHER INFORMATION: Xaa = Arg, Lys or Gly
<220> FEATURE:
<221> NAME/KEY: VARIANT
<222> LOCATION: 17
<223> OTHER INFORMATION: Xaa = Leu, Glu or Ala
<220> FEATURE:
<221> NAME/KEY: VARIANT
<222> LOCATION: 18
<223> OTHER INFORMATION: Xaa = Asn, Arg or Lys
<220> FEATURE:
<221> NAME/KEY: VARIANT
<222> LOCATION: 20
<223> OTHER INFORMATION: Xaa = Ala, Leu or Val
<220> FEATURE:
<221> NAME/KEY: VARIANT
<222> LOCATION: 21, 24
<223> OTHER INFORMATION: Xaa = Any Amino Acid
<220> FEATURE:
<221> NAME/KEY: VARIANT
<222> LOCATION: 22
<223> OTHER INFORMATION: Xaa = Tyr, Trp or His
<220> FEATURE:
<221> NAME/KEY: VARIANT
<222> LOCATION: 23
<223> OTHER INFORMATION: Xaa = Trp, Tyr or Phe
<220> FEATURE:
<221> NAME/KEY: VARIANT
<222> LOCATION: 25
<223> OTHER INFORMATION: Xaa = His, Asn or Asp

<400> SEQUENCE: 35

Gly Xaa Xaa Xaa Xaa Arg Xaa Xaa Leu Xaa Xaa Asn Xaa Xaa Val Glu
 1               5                   10                  15

Xaa Xaa His Xaa Xaa Xaa Xaa Xaa Xaa Trp
            20                  25
```

```
<210> SEQ ID NO 36
<211> LENGTH: 21
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Ile, Ala or Pro
<220> FEATURE:
<221> NAME/KEY: VARIANT
<222> LOCATION: 3
<223> OTHER INFORMATION: Xaa = Val, Ile, Glu or Ala
<220> FEATURE:
<221> NAME/KEY: VARIANT
<222> LOCATION: 4
<223> OTHER INFORMATION: Xaa = Ala, Cys, Ser or Gly
<220> FEATURE:
<221> NAME/KEY: VARIANT
<222> LOCATION: 5
<223> OTHER INFORMATION: Xaa = Ile, Met, Leu or Val
<220> FEATURE:
<221> NAME/KEY: VARIANT
<222> LOCATION: 8
<223> OTHER INFORMATION: Xaa = Thr or Ser
<220> FEATURE:
<221> NAME/KEY: VARIANT
<222> LOCATION: 10
<223> OTHER INFORMATION: Xaa = Tyr, Leu or Trp
<220> FEATURE:
<221> NAME/KEY: VARIANT
<222> LOCATION: 12
<223> OTHER INFORMATION: Xaa = Ile or Val
<220> FEATURE:
<221> NAME/KEY: VARIANT
<222> LOCATION: 14
<223> OTHER INFORMATION: Xaa = Gly, Trp or Ser
<220> FEATURE:
<221> NAME/KEY: VARIANT
<222> LOCATION: 15
<223> OTHER INFORMATION: Xaa = Ala, Val or Ile
<220> FEATURE:
<221> NAME/KEY: VARIANT
<222> LOCATION: 18
<223> OTHER INFORMATION: Xaa = Glu, Asp or Val
<220> FEATURE:
<221> NAME/KEY: VARIANT
<222> LOCATION: 20
<223> OTHER INFORMATION: Xaa = Ser or Thr
<220> FEATURE:
<221> NAME/KEY: VARIANT
<222> LOCATION: 21
<223> OTHER INFORMATION: Xaa = Ala, Ile or Arg

<400> SEQUENCE: 36

Leu Xaa Xaa Xaa Xaa Ala Ala Xaa Asn Xaa Ala Xaa Glu Xaa Xaa Thr
 1               5                  10                  15

Gly Xaa Trp Xaa Xaa
            20

<210> SEQ ID NO 37
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Lys or Arg
<220> FEATURE:
<221> NAME/KEY: VARIANT
<222> LOCATION: 4
<223> OTHER INFORMATION: Xaa = Met, Leu, Ala or Val
```

```
<220> FEATURE:
<221> NAME/KEY: VARIANT
<222> LOCATION: 6
<223> OTHER INFORMATION: Xaa = Ala or Ser
<220> FEATURE:
<221> NAME/KEY: VARIANT
<222> LOCATION: 7
<223> OTHER INFORMATION: Xaa = Gln, His, Ser or Arg
<220> FEATURE:
<221> NAME/KEY: VARIANT
<222> LOCATION: 11
<223> OTHER INFORMATION: Xaa = Any Amino Acid
<220> FEATURE:
<221> NAME/KEY: VARIANT
<222> LOCATION: 14
<223> OTHER INFORMATION: Xaa = Trp, Tyr, Glu or Val
<220> FEATURE:
<221> NAME/KEY: VARIANT
<222> LOCATION: 17
<223> OTHER INFORMATION: Xaa = Leu or Met
<220> FEATURE:
<221> NAME/KEY: VARIANT
<222> LOCATION: 18
<223> OTHER INFORMATION: Xaa = Glu or Asp
<220> FEATURE:
<221> NAME/KEY: VARIANT
<222> LOCATION: 19
<223> OTHER INFORMATION: Xaa = Ile or Leu
<220> FEATURE:
<221> NAME/KEY: VARIANT
<222> LOCATION: 20
<223> OTHER INFORMATION: Xaa = Ile or Val

<400> SEQUENCE: 37

Trp Leu Xaa Xaa His Xaa Xaa Tyr Asp Asp Xaa His Pro Xaa Glu Ala
 1               5                  10                  15

Xaa Xaa Xaa Xaa
            20

<210> SEQ ID NO 38
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Tyr, Cys or Met
<220> FEATURE:
<221> NAME/KEY: VARIANT
<222> LOCATION: 2
<223> OTHER INFORMATION: Xaa = Met, Tyr or Phe
<220> FEATURE:
<221> NAME/KEY: VARIANT
<222> LOCATION: 3
<223> OTHER INFORMATION: Xaa = Tyr, Glu, Ala, Thr or His
<220> FEATURE:
<221> NAME/KEY: VARIANT
<222> LOCATION: 4
<223> OTHER INFORMATION: Xaa = Leu, Met or Ala
<220> FEATURE:
<221> NAME/KEY: VARIANT
<222> LOCATION: 5
<223> OTHER INFORMATION: Xaa = Phe, Ala or Ser
<220> FEATURE:
<221> NAME/KEY: VARIANT
<222> LOCATION: 7
<223> OTHER INFORMATION: Xaa = Glu, Asp, Ser or His
<220> FEATURE:
<221> NAME/KEY: VARIANT
<222> LOCATION: 8
<223> OTHER INFORMATION: Xaa = Arg, Glu, Asp, Cys or Ala

<400> SEQUENCE: 38
```

Xaa Xaa Xaa Xaa Xaa Leu Xaa Xaa Cys
1               5

<210> SEQ ID NO 39
<211> LENGTH: 357
<212> TYPE: PRT
<213> ORGANISM: Pseudomonas protegens

<400> SEQUENCE: 39

Met Gln Gly Ile Ser Ala Ser Pro Glu Arg Met Asn Ala Gln Gln Arg
1               5                   10                  15

Ala Ala His Val Arg Gln Val Val Leu Ala Arg Gly Asp Glu Leu Arg
                20                  25                  30

Arg Arg Phe Pro Leu Leu Arg His Gln Asp Ala Leu Gly Ala Gly Ile
            35                  40                  45

Leu Ala Phe Ala Leu Ser Gly Met Leu Gly Ser Ala Leu Leu Tyr Val
    50                  55                  60

Thr Gly His Leu Ala Trp Trp Ala Cys Leu Leu Leu Asn Ala Phe Phe
65                  70                  75                  80

Ala Ser Leu Thr His Glu Leu Glu His Asp Leu Ile His Ser Met Tyr
                85                  90                  95

Phe Arg Lys Gln Arg Leu Pro His Asn Leu Met Leu Gly Leu Val Trp
            100                 105                 110

Leu Ala Arg Pro Ser Thr Ile Asn Pro Trp Val Arg Arg His Leu His
    115                 120                 125

Leu Asn His His Lys Val Ser Gly Ser Glu Ser Asp Ile Glu Glu Arg
130                 135                 140

Ala Ile Thr Asn Gly Glu Pro Trp Gly Ile Ala Arg Leu Leu Met Val
145                 150                 155                 160

Gly Asp Asn Met Met Ala Ala Phe Ile Arg Leu Leu Arg Ala Pro Gly
                165                 170                 175

Ala Arg Arg Lys Leu Gly Ile Leu Val Arg Thr Leu Ala Val Tyr Ala
            180                 185                 190

Pro Leu Ala Leu Leu His Trp Gly Ala Trp Tyr Val Phe Leu Gly Phe
    195                 200                 205

His Gly Ala Asn Gly Val Ala Ala Leu Leu Gly Ser Pro Ile Gln Trp
210                 215                 220

Ser Gln Asp Thr Ala Ser Leu Met His Tyr Val Asp Ile Ala Val Val
225                 230                 235                 240

Val Ile Ile Gly Pro Asn Val Leu Arg Thr Phe Cys Leu His Phe Val
                245                 250                 255

Ser Ser Asn Met His Tyr Tyr Gly Asp Ile Glu Pro Gly Asn Val Ile
            260                 265                 270

Gln Gln Thr Gln Val Leu Asn Pro Trp Trp Met Trp Pro Leu Gln Ala
    275                 280                 285

Phe Cys Cys Asn Phe Gly Ser Thr His Gly Ile His His Phe Val Val
    290                 295                 300

Arg Glu Pro Phe Tyr Ile Arg Gln Met Thr Ala Ser Val Ala His Lys
305                 310                 315                 320

Val Met Ala Glu Met Gly Val Arg Phe Asn Asp Phe Gly Thr Phe Ala
                325                 330                 335

Arg Ala Asn Arg Phe Thr Arg Gln Glu Arg Glu Ala Met Gln Pro Ala
            340                 345                 350

His Asn Ala Arg Ala
            355

```
<210> SEQ ID NO 40
<211> LENGTH: 352
<212> TYPE: PRT
<213> ORGANISM: Pseudomonas mendocina

<400> SEQUENCE: 40

Met Ser Pro Ser Pro Ala Ser Leu Asn Asp Gln Gln Arg Ala Ala His
1               5                   10                  15

Ile Arg Glu Gln Val Met Ala His Gly Asn Ala Leu Arg Gln Arg Tyr
            20                  25                  30

Pro Ile Leu Gln His Gln Asp Ala Leu Gly Ala Gly Ile Leu Ala Phe
        35                  40                  45

Ala Leu Cys Gly Met Ile Gly Ser Ala Ala Leu Tyr Ile Gly Gly His
50                  55                  60

Leu Pro Trp Trp Ala Cys Leu Leu Asn Ala Phe Phe Ala Ser Leu
65                  70                  75                  80

Thr His Glu Leu Glu His Asp Leu Ile His Ser Met Tyr Phe Arg Lys
                85                  90                  95

Gln Pro Leu Pro His Asn Leu Met Leu Ala Leu Val Trp Leu Ala Arg
            100                 105                 110

Pro Ser Thr Ile Asn Pro Trp Val Arg Arg His Leu His Leu Asn His
        115                 120                 125

His Lys Val Ser Gly Ser Glu Ala Asp Met Glu Glu Arg Ala Ile Thr
130                 135                 140

Asn Gly Glu Pro Trp Gly Ile Ala Arg Leu Leu Met Val Gly Asp Asn
145                 150                 155                 160

Met Met Ser Ser Phe Ile Arg Trp Leu Arg Ala Lys Asn Pro Glu His
                165                 170                 175

Arg Arg Leu Ile Leu Thr Arg Thr Leu Lys Val Tyr Ala Pro Leu Gly
            180                 185                 190

Leu Leu Asn Trp Ala Thr Trp Tyr Leu Phe Leu Gly Phe His Leu Leu
        195                 200                 205

Asp Trp Ala Ala Ala Leu Gly Ala Pro Ile Ala Trp Ser Ala Ser
210                 215                 220

Thr Leu Ser Val Met Gln Val Val Asn Val Ala Val Val Leu Val
225                 230                 235                 240

Gly Pro Asn Val Leu Arg Thr Phe Cys Leu His Phe Val Ser Ser Asn
                245                 250                 255

Met His Tyr Tyr Gly Asp Val Glu Pro Gly Asn Val Ile Gln Gln Thr
            260                 265                 270

Gln Val Leu Asn Pro Trp Trp Leu Trp Pro Leu Gln Ala Phe Cys Phe
        275                 280                 285

Asn Phe Gly Ser Ser His Ala Ile His His Phe Val Val Lys Glu Pro
290                 295                 300

Phe Tyr Ile Arg Gln Leu Thr Val Pro Phe Ala His Arg Val Met Arg
305                 310                 315                 320

Glu Met Gly Val Arg Phe Asn Asp Phe Gly Thr Phe Ala Arg Ala Asn
                325                 330                 335

Arg Trp Thr Arg Arg Ala Arg Thr Gln Gln Glu Arg Ala Ser Thr Ala
            340                 345                 350

<210> SEQ ID NO 41
<211> LENGTH: 338
<212> TYPE: PRT
```

<213> ORGANISM: Glaciecola psychrophila

<400> SEQUENCE: 41

| Met | Gln | Asn | Asn | Gln | Asp | Lys | Gln | Asp | Ile | Lys | Glu | Ile | Val | Ala | Tyr |
| 1 | | | | 5 | | | | | 10 | | | | | 15 | |

| Ile | Lys | Asn | Gln | Glu | Arg | Thr | Leu | Arg | Ser | Asn | His | Pro | Phe | Leu | Ala |
| | | | 20 | | | | | 25 | | | | | 30 | | |

| Gln | Gln | Asn | Ala | Leu | Gly | Leu | Gly | Leu | Leu | Val | Ser | Val | Cys | Gly |
| | | 35 | | | | | 40 | | | | | 45 | | |

| Phe | Thr | Ala | Ala | Gly | Cys | Leu | Tyr | Phe | Tyr | Ala | Val | Ile | Pro | Ala | Trp |
| | 50 | | | | | 55 | | | | | 60 | | | | |

| Cys | Cys | Ile | Ile | Ile | Ala | Ala | Leu | Ser | Ala | Ser | Ile | Ala | His | Glu | Ile |
| 65 | | | | | 70 | | | | | 75 | | | | | 80 |

| Glu | His | Asp | Leu | Ile | His | Gln | Gln | Tyr | Phe | Lys | Ser | Asn | Ser | Ala | Val |
| | | | | 85 | | | | | 90 | | | | | 95 | |

| Tyr | His | Phe | Met | Met | Phe | Met | Val | Trp | Ile | Ile | Arg | Pro | Asn | Thr | Val |
| | | | 100 | | | | | 105 | | | | | 110 | | |

| Asn | Pro | Trp | Tyr | Arg | Lys | Gly | Met | His | Leu | Asn | His | His | Lys | Thr | Ser |
| | | | 115 | | | | | 120 | | | | | 125 | | |

| Gly | Thr | Pro | Gln | Asp | Ile | Glu | Glu | Arg | Leu | Val | Gly | Asn | Gly | Ile | Lys |
| | 130 | | | | | 135 | | | | | 140 | | | | |

| Ser | His | Thr | Leu | Arg | Leu | Leu | Val | Val | Cys | Asp | Gly | Leu | Leu | Gly | Leu |
| 145 | | | | | 150 | | | | | 155 | | | | | 160 |

| Ile | Ile | Arg | Ser | Lys | Gln | Phe | Ser | Arg | Glu | Ile | Lys | Gly | Tyr | Asn | Phe |
| | | | | 165 | | | | | 170 | | | | | 175 | |

| Phe | Asn | Val | Phe | Asn | Ala | Ser | Leu | Pro | Phe | Val | Thr | Val | Tyr | Tyr | Leu |
| | | | 180 | | | | | 185 | | | | | 190 | | |

| Ile | Ile | Tyr | Ile | Phe | Leu | Leu | Phe | His | Gly | Val | Asn | Phe | Ile | Ala | Asp |
| | | | 195 | | | | | 200 | | | | | 205 | | |

| Ser | Ser | Ala | Val | Lys | Leu | Asn | Thr | Pro | Val | Trp | Leu | Val | Ser | Leu | Met |
| | 210 | | | | | 215 | | | | | 220 | | | | |

| Glu | Trp | Val | Asn | Phe | Ala | Met | Val | Val | Trp | Val | Ala | Pro | Asn | Phe | Leu |
| 225 | | | | | 230 | | | | | 235 | | | | | 240 |

| Arg | Ser | Ala | Cys | Leu | Asn | Phe | Ile | Thr | Ser | Ser | Met | His | Tyr | Tyr | Gly |
| | | | | 245 | | | | | 250 | | | | | 255 | |

| Ala | Arg | Phe | Asn | Leu | Leu | Glu | Gln | Thr | Gln | Val | Leu | Asn | His | Trp | Ala |
| | | | 260 | | | | | 265 | | | | | 270 | | |

| Phe | Met | Pro | Phe | Gln | Trp | Phe | Cys | Phe | Asn | Phe | Gly | His | Thr | His | Ser |
| | | 275 | | | | | 280 | | | | | 285 | | | |

| Ile | His | His | Phe | Val | Pro | Asn | Gln | Pro | Phe | Tyr | Ile | Arg | Gln | Ile | Ile |
| | 290 | | | | | 295 | | | | | 300 | | | | |

| Ser | Lys | Gln | Val | Asn | Leu | Leu | Leu | Lys | Asn | Lys | Gly | Val | Lys | Phe | Asn |
| 305 | | | | | 310 | | | | | 315 | | | | | 320 |

| Asp | Leu | Val | Ser | Ile | Phe | Ala | Ala | Asn | His | Tyr | Lys | Lys | Ile | Glu | Arg |
| | | | | 325 | | | | | 330 | | | | | 335 | |

Ser Ser

<210> SEQ ID NO 42
<211> LENGTH: 369
<212> TYPE: PRT
<213> ORGANISM: Burkholderia sp.

<400> SEQUENCE: 42

| Met | Ser | Gln | Pro | Ala | Arg | Thr | Ala | Phe | Arg | Asn | Asp | Ala | Asp | Lys | Val |
| 1 | | | | 5 | | | | | 10 | | | | | 15 | |

Ala Tyr Val Arg Arg Glu Val Asn Ala Ala Ser Asp Ala Ile Arg Ala
            20                  25                  30

Arg Phe Pro Leu Leu Asp Asn Gln Asn Leu Val Gly Ala Thr Val Met
        35                  40                  45

Ala Val Ser Val Ser Ala Met Leu Ala Ile Ala Trp Leu Tyr Ala Arg
50                  55                  60

Gly Ala Ile Ala Trp Tyr Val Ala Leu Pro Leu Ala Ala Phe Val Thr
65                  70                  75                  80

Ser Leu Ile His Glu Leu Glu His Asp Leu Ile His Leu Met Tyr Phe
                85                  90                  95

Lys Lys Thr Pro Trp Ala Tyr His Leu Met Met Ala Leu Cys Trp Leu
            100                 105                 110

Thr Arg Pro Gly Thr Ile Asn Pro Trp Thr Arg Arg Met His Leu
        115                 120                 125

His His His Lys Val Ser Gly Gly Glu Ser Asp Leu Glu Glu Phe Gly
        130                 135                 140

Ile Thr Asn Gly Glu Arg Trp Gly Val Lys Arg Leu Leu Met Ile Ala
145                 150                 155                 160

Asp Gly Met Leu Ala Val Val Leu Arg Pro Thr Ala Met Arg Arg Lys
                165                 170                 175

Val Lys Gln Tyr Val Ala Ala Gln Pro Val Gln Asp Pro Ser Glu Arg
            180                 185                 190

Leu Gln Leu Arg Val Glu Gln Val Ser Ser Tyr Met Pro Val Gly His
        195                 200                 205

Val Tyr Tyr Val Leu Trp His Ala Phe Ile Val Tyr His Val Gly Leu
210                 215                 220

Phe Ala Leu His Ala Phe Gly Phe Pro Val Thr Val Pro Ala Val Val
225                 230                 235                 240

Glu Arg Val Met Ser Val Val Asp Phe Leu Ala Val Val Trp Leu Gly
                245                 250                 255

Pro Asn Phe Val Arg Ser Phe Cys Ile Asn Phe Val Ser Ser Asn Met
            260                 265                 270

His Tyr Phe Gly Asp Ile Asp Ser Arg Asn Val Ile Gln Gln Thr Gln
        275                 280                 285

Val Leu Asn Pro Trp Trp Met Leu Pro Phe Gln Leu Phe Cys Phe Asn
290                 295                 300

Phe Gly Ser Thr His Ala Ile His His Phe Val Val Arg Asp Pro Phe
305                 310                 315                 320

Tyr Ile Arg Gln Leu Thr Ala Arg Thr Ala His Ala Ala Leu Arg Glu
                325                 330                 335

Val Gly Val Arg Phe Asn Asp Val Gly Thr Phe Ala Arg Ala Asn Arg
            340                 345                 350

Trp Ser Gly Tyr Arg Pro Ser Arg Gly Thr Arg Gln Ala Gln Ala Asp
        355                 360                 365

Ala

<210> SEQ ID NO 43
<211> LENGTH: 357
<212> TYPE: PRT
<213> ORGANISM: Pseudomonas fluorescens

<400> SEQUENCE: 43

Met Asp Arg Thr Ser Ala Ser Pro Gln Arg His Asn Ala Ala Gln Arg
1               5                   10                  15

```
Ser Ala His Ile Arg Glu Val Leu Ala Lys Gly Val Glu Leu Arg
        20                  25                  30

Glu Arg Tyr Pro Ile Leu Asn His Gln Asp Ala Leu Gly Ala Gly Ile
            35                  40                  45

Leu Val Phe Ala Leu Ala Gly Met Ile Gly Ser Ala Ala Leu Tyr Val
 50                  55                  60

Thr Gly His Met Ala Trp Trp Ala Cys Leu Leu Asn Ala Phe Phe
 65                  70                  75                  80

Ala Ser Leu Thr His Glu Leu Glu His Asp Leu Ile His Ser Met Tyr
                85                  90                  95

Phe Arg Lys Gln Arg Val Pro His Asn Leu Met Met Gly Leu Val Trp
            100                 105                 110

Leu Ala Arg Pro Ser Thr Ile Asn Pro Trp Ile Arg Arg His Leu His
        115                 120                 125

Leu Asn His His Lys Val Ser Gly Thr Glu Thr Asp Met Glu Glu Arg
130                 135                 140

Ala Ile Thr Asn Gly Glu Pro Trp Gly Phe Ala Arg Leu Leu Met Val
145                 150                 155                 160

Gly Asp Asn Val Met Ser Ala Phe Ile Arg Met Leu Arg Ala Lys Thr
                165                 170                 175

Trp Ala His Lys Phe Ser Ile Ile Lys Arg Thr Leu Lys Val Tyr Ala
            180                 185                 190

Pro Leu Ala Leu Val His Trp Gly Ala Trp Tyr Val Phe Leu Gly Phe
        195                 200                 205

His Ala Ala Asn Gly Ile Ala Tyr Leu Met Gly Ser Pro Ile Glu Trp
    210                 215                 220

Ser Ala Thr Thr Leu Ser Val Met Gln Val Ile Asp Ile Ala Ala Val
225                 230                 235                 240

Val Ile Ile Gly Pro Asn Val Leu Arg Thr Phe Cys Leu His Phe Ile
                245                 250                 255

Ser Ser Asn Met His Tyr Tyr Gly Asp Val Glu Pro Gly Asn Val Leu
            260                 265                 270

Gln Gln Cys Gln Val Leu Asn Pro Trp Trp Leu Trp Pro Leu Gln Ala
        275                 280                 285

Phe Cys Phe Asn Phe Gly Ser Ser His Gly Ile His His Phe Val Val
    290                 295                 300

Lys Glu Pro Phe Tyr Ile Arg Gln Leu Thr Val Pro Val Ala His Lys
305                 310                 315                 320

Val Met Arg Glu Met Gly Val Arg Phe Asn Asp Phe Gly Thr Phe Gly
                325                 330                 335

Arg Ala Asn Arg Phe Val Arg Lys Glu Asn Glu Gly Leu Ala Gly Lys
            340                 345                 350

Ala Ile Glu Val Asn
        355

<210> SEQ ID NO 44
<211> LENGTH: 351
<212> TYPE: PRT
<213> ORGANISM: Acinetobacter baumannii

<400> SEQUENCE: 44

Met Thr Tyr Ile Tyr Lys Asn Pro Ala Gly Met Thr Asp Ser Glu Lys
 1               5                  10                  15

Thr Glu His Ile Lys Lys Ile Val Thr Ala Glu Gly Val Ala Leu Arg
```

```
            20                  25                  30
Lys Arg Tyr Pro Ile Leu Asn His Gln Asn Ala Ile Gly Ala Val

```
Ala Val Ser Val Ser Ala Met Leu Ala Ile Ala Trp Leu Tyr Ala Arg
 50                  55                  60

Gly Ala Ile Ala Trp Tyr Val Ala Leu Pro Leu Ala Ala Phe Ile Thr
 65                  70                  75                  80

Ser Leu Ile His Glu Leu Glu His Asp Leu Ile His Leu Met Tyr Phe
                 85                  90                  95

Lys Lys Thr Pro Trp Ala Tyr His Leu Met Met Ala Leu Cys Trp Leu
            100                 105                 110

Thr Arg Pro Gly Thr Ile Asn Pro Trp Thr Arg Arg Met His Leu
        115                 120                 125

His His His Lys Val Ser Gly Gly Glu Ser Asp Leu Glu Glu Phe Gly
130                 135                 140

Ile Thr Asn Gly Glu Arg Trp Gly Val Lys Arg Leu Leu Met Ile Ala
145                 150                 155                 160

Asp Gly Met Leu Ala Val Val Leu Arg Pro Ala Ala Met Arg Arg Lys
                165                 170                 175

Val Lys Gln Tyr Val Ala Ala Gln Pro Val Gln Asp Pro Ser Glu Arg
            180                 185                 190

Leu Gln Leu Arg Ile Glu Gln Leu Ser Ser Tyr Met Pro Ile Gly His
        195                 200                 205

Leu Tyr Tyr Thr Leu Trp His Ala Phe Ile Val Tyr His Val Gly Leu
210                 215                 220

Phe Ala Leu His Ala Leu Asp Val Ala Val Thr Val Pro Ala Val Val
225                 230                 235                 240

Glu Arg Val Met Ser Val Val Asp Phe Leu Ala Val Val Trp Leu Gly
                245                 250                 255

Pro Asn Phe Val Arg Ser Phe Cys Ile Asn Phe Val Ser Ser Asn Met
            260                 265                 270

His Tyr Phe Gly Asp Ile Asp Ser Arg Asn Val Ile Gln Gln Thr Gln
        275                 280                 285

Val Leu Asn Pro Trp Trp Met Leu Pro Phe Gln Leu Phe Cys Phe Asn
290                 295                 300

Phe Gly Ser Thr His Ala Ile His His Phe Val Val Arg Asp Pro Phe
305                 310                 315                 320

Tyr Ile Arg Gln Leu Thr Ala Arg Ala His Ala Ala Leu Arg Glu
                325                 330                 335

Val Gly Val Arg Phe Asn Asp Val Gly Thr Phe Ala Arg Ala Asn Arg
            340                 345                 350

Trp Gly Gly Tyr Arg Pro Ser Arg Thr His Ala Gln Ala Asp
        355                 360                 365

Ala

<210> SEQ ID NO 46
<211> LENGTH: 357
<212> TYPE: PRT
<213> ORGANISM: Pseudomonas fluorescens

<400> SEQUENCE: 46

Met Gln Gly Ile Ser Ala Ser Pro Glu Arg Met Asn Ala Gln Gln Arg
 1               5                  10                  15

Ala Ala His Val Arg Gln Val Val Leu Ala Arg Gly Asp Glu Leu Arg
                 20                  25                  30

Arg Arg Phe Pro Leu Leu Arg His Gln Asp Ala Leu Gly Ala Gly Ile
             35                  40                  45
```

```
Leu Ala Phe Ala Leu Ser Gly Met Leu Gly Ser Ala Leu Leu Tyr Val
 50                  55                  60

Thr Gly His Leu Ala Trp Trp Ala Cys Leu Leu Leu Asn Ala Phe Phe
 65                  70                  75                  80

Ala Ser Leu Thr His Glu Leu Glu His Asp Leu Ile His Ser Met Tyr
                 85                  90                  95

Phe Arg Lys Gln Arg Leu Pro His Asn Leu Met Leu Gly Leu Val Trp
            100                 105                 110

Leu Ala Arg Pro Ser Thr Ile Asn Pro Trp Val Arg His Leu His
            115                 120                 125

Leu Asn His His Lys Val Ser Gly Ser Glu Ser Asp Ile Glu Glu Arg
        130                 135                 140

Ala Ile Thr Asn Gly Glu Pro Trp Gly Ile Ala Arg Leu Leu Met Val
145                 150                 155                 160

Gly Asp Asn Met Met Ala Ala Phe Ile Arg Leu Leu Arg Ala Pro Gly
                165                 170                 175

Ala Arg Arg Lys Leu Gly Ile Leu Val Arg Thr Leu Ala Val Tyr Ala
            180                 185                 190

Pro Leu Ala Leu Leu His Trp Gly Ala Trp Tyr Val Phe Leu Gly Phe
        195                 200                 205

His Gly Ala Asn Gly Val Ala Ala Leu Leu Gly Ser Pro Ile Gln Trp
    210                 215                 220

Ser Gln Asp Thr Ala Ser Leu Met His Tyr Val Asp Ile Ala Val Val
225                 230                 235                 240

Val Ile Ile Gly Pro Asn Val Leu Arg Thr Phe Cys Leu His Phe Val
                245                 250                 255

Ser Ser Asn Met His Tyr Tyr Gly Asp Ile Glu Pro Gly Asn Val Ile
            260                 265                 270

Gln Gln Thr Gln Val Leu Asn Pro Trp Trp Met Trp Pro Leu Gln Ala
        275                 280                 285

Phe Cys Cys Asn Phe Gly Ser Thr His Gly Ile His His Phe Val Val
    290                 295                 300

Arg Glu Pro Phe Tyr Ile Arg Gln Met Thr Ala Ser Val Ala His Lys
305                 310                 315                 320

Val Met Ala Glu Met Gly Val Arg Phe Asn Asp Phe Gly Thr Phe Ala
                325                 330                 335

Arg Ala Asn Arg Phe Thr Arg Gln Glu Arg Glu Ala Met Gln Pro Ala
            340                 345                 350

His Asn Ala Arg Ala
        355

<210> SEQ ID NO 47
<211> LENGTH: 361
<212> TYPE: PRT
<213> ORGANISM: Nocardia brasiliensis

<400> SEQUENCE: 47

Met Arg Leu Ala Thr Arg Leu Pro Gly Glu Arg Thr Leu Ala Pro Gln
  1               5                  10                  15

Asp Ala Asp Arg Ile Ala Ala Ile Arg Gly Glu Ile Ala Arg Val Gly
                 20                  25                  30

Asp Arg Trp Arg Val Glu His Pro Trp Ile Ala Gly His Gln Asn Thr
             35                  40                  45

Ile Gly Ala Val Ile Phe Leu Gly Ala Val Leu Gly Val Leu Gly Asp
         50                  55                  60
```

```
Ala Ala Leu Tyr Ala Cys Gly Leu Leu Pro Trp Trp Ala Thr Val Leu
 65                  70                  75                  80

Ala Ser Ala Phe Trp Leu Ser Leu Leu His Glu Ile Glu His Asp Leu
                 85                  90                  95

Ile His Ala Met Tyr Phe Arg Thr Asn Lys Trp Val His Asn Ala Met
            100                 105                 110

Leu Ala Gly Val Trp Leu Leu Arg Pro Ser Thr Ile Asn Pro Trp Val
        115                 120                 125

Arg Arg Arg Leu His Leu His His Ala Val Ser Gly Thr Glu Ser
130                 135                 140

Asp Leu Glu Glu Arg Ala Ile Ser Asn Gly Arg Trp Gly His
145                 150                 155                 160

Arg Leu Leu Gly Leu Leu Asp Ser Val Leu Gly Tyr Ala Thr Arg Pro
                165                 170                 175

Phe Arg Met Arg Gly Leu Val Ala Ala Tyr Val Ala Arg Val Ala Arg
            180                 185                 190

Asp Pro Ala Glu Ala Arg Arg Leu Ala Ile Thr Thr Pro Leu Ala Tyr
        195                 200                 205

Phe Pro Leu Ser Ala Met His Tyr Gly Leu Trp Tyr Leu Thr Val Ser
210                 215                 220

Ala His Val Tyr Glu Leu Leu Gly Gly Thr Val Gly Tyr Pro Gly Ala
225                 230                 235                 240

Tyr Arg Ala Leu Asp Ile Leu Ala Val Thr Leu Leu Ala Pro Asn Ala
                245                 250                 255

Ile Arg Thr Phe Cys Leu Tyr Phe Val Ser Ser Asn Leu His Tyr Tyr
            260                 265                 270

Gly Asp Val Glu Pro His Asn Val Leu Gln Gln Thr Gln Val Trp Thr
        275                 280                 285

Ala Arg Trp Leu Trp Pro Val His Ala Leu Cys Phe Asn Phe Gly Gly
290                 295                 300

Thr His Ala Ile His His Phe Val Val Arg Asp Pro Phe Tyr Ile Arg
305                 310                 315                 320

Glu Ala Ile Arg Ala Glu Cys Gln Thr Ile Leu Arg Glu His Gly Val
                325                 330                 335

Arg Phe Asn Asp Phe Gly Thr Phe Arg Arg Ala Asn Arg Phe Gly Leu
            340                 345                 350

Ala Val Pro Pro Gly Ala Val Arg Pro
        355                 360

<210> SEQ ID NO 48
<211> LENGTH: 357
<212> TYPE: PRT
<213> ORGANISM: Pseudomonas brassicacearum

<400> SEQUENCE: 48

Met His Gly Thr Cys Ala Ser Pro Glu Arg Leu Asn Ala Gln Gln Arg
 1               5                  10                  15

Ser Ala His Ile Arg Gln Val Val Leu Ala Arg Gly Glu Glu Leu Arg
                20                  25                  30

Gln Arg Tyr Pro Ile Leu Arg Tyr Gln Asp Ala Leu Gly Ala Gly Ile
            35                  40                  45

Leu Ala Phe Ala Leu Val Gly Met Ile Gly Ser Ala Leu Leu Tyr Leu
        50                  55                  60

Asn Gly His Leu Ala Gly Trp Ala Cys Leu Leu Leu Asn Ala Phe Phe
```

65                  70                  75                  80
Ala Ser Leu Thr His Glu Leu Glu His Asp Leu Ile His Ser Met Tyr
                    85                  90                  95

Phe Arg Lys Gln Arg Leu Pro His Asn Leu Met Met Gly Leu Val Trp
                100                 105                 110

Leu Ala Arg Pro Ser Thr Ile Asn Pro Trp Ile Arg His Leu His
                115                 120                 125

Leu Asn His His Lys Val Ser Gly Ser Glu Ala Asp Met Glu Glu Arg
            130                 135                 140

Ala Ile Thr Asn Gly Glu Pro Trp Gly Leu Ala Arg Leu Leu Met Val
145                 150                 155                 160

Gly Asp Asn Val Met Ser Ala Phe Ile Arg Leu Leu Arg Ala Lys Thr
                    165                 170                 175

Trp Ala His Lys Arg Ser Ile Leu Lys Arg Thr Leu Lys Val Tyr Phe
                180                 185                 190

Pro Leu Ala Leu Leu His Trp Gly Ala Trp Tyr Ala Phe Leu Gly Phe
                195                 200                 205

His Gly Ala Asn Gly Val Ala Ser Leu Leu Gly Thr Ser Val Glu Trp
            210                 215                 220

Ser Ala Thr Thr Leu Ser Val Met His Val Ile Asp Ile Ala Ala Val
225                 230                 235                 240

Val Ile Ile Gly Pro Asn Val Leu Arg Thr Phe Cys Leu His Phe Ile
                    245                 250                 255

Ser Ser Asn Met His Tyr Tyr Gly Asp Ile Glu Pro Gly Asn Val Ile
                260                 265                 270

Gln Gln Thr Gln Val Leu Asn Pro Trp Trp Leu Trp Pro Leu Gln Ala
                275                 280                 285

Phe Cys Phe Asn Phe Gly Ser Ser His Gly Ile His His Phe Val Val
            290                 295                 300

Lys Glu Pro Phe Tyr Ile Arg Gln Leu Thr Val Pro Val Ala His Lys
305                 310                 315                 320

Val Met Arg Glu Met Gly Val Arg Phe Asn Asp Phe Gly Thr Phe Ala
                    325                 330                 335

Arg Ala Asn Arg Phe Val Arg Gln Glu Gly Val Val Arg Glu Ala Gly
                340                 345                 350

Gly Thr Val Arg Val
            355

<210> SEQ ID NO 49
<211> LENGTH: 366
<212> TYPE: PRT
<213> ORGANISM: Leptospira borgpetersenii

<400> SEQUENCE: 49

Met Asn Ser Gln Trp Lys Thr Arg Asn Lys Pro Tyr Lys Val Phe Ser
1               5                   10                  15

Glu Lys Glu Lys Thr Arg Lys Ile Ile Gln Trp Ile Arg Phe Trp Asp
                20                  25                  30

Asp Arg Ile Arg Asn Arg Phe Pro Tyr Leu Ser Lys Tyr Gln Asp Gln
            35                  40                  45

Ile Gly Phe Gly Ile Met Ile Gly Ser Ala Ser Gly Met Ile Leu Phe
        50                  55                  60

Ala Val Leu Tyr Ile Thr Asn Leu Ile Pro Phe Trp Phe Cys Ile Val
65                  70                  75                  80

```
Leu Asn Thr Ile Phe Ala Ser Phe Leu His Glu Ile Glu His Asp Leu
                85                  90                  95

Ile His Asn Leu Tyr Tyr Lys Gly Arg Val Lys Val Gln Asn Phe Met
            100                 105                 110

Leu Trp Val Val Trp Leu Phe Arg Ala Asn Thr Val Asn Pro Trp Phe
        115                 120                 125

Arg Arg Glu Ile His Leu Leu His His Lys Leu Ser Gly Asn Lys Glu
    130                 135                 140

Asp Val Glu Glu Arg Met Ile Gly Asn Gly Val Pro Phe Gly Leu Lys
145                 150                 155                 160

Arg Val Leu Ile Met Ile Asp Gly Asn Leu Ala Leu Ile Leu Gln Gly
                165                 170                 175

Arg Lys Val Ala Lys Asp Ala Tyr Leu Arg Leu Gly Lys Ile Lys Val
            180                 185                 190

Pro Arg Thr Val Gly Leu Tyr Arg Glu Thr Phe Phe Leu Leu Trp Tyr
        195                 200                 205

Ser Phe Leu Ser Val Asn Ala Phe His Ile Leu Asn Val Leu Phe Gly
    210                 215                 220

Asn Pro Ile Ser Glu Pro Ser Phe Leu Glu Thr Asn Arg Ser Val Leu
225                 230                 235                 240

Asn Ser Ala Ala Val Val Tyr Leu Ile Pro Asn Trp Ile Arg Gln Thr
                245                 250                 255

Ser Leu Gln Val Val Ser Ser Asn Met His Tyr Tyr Gly Asn Val Pro
            260                 265                 270

Asn Val Tyr His Gln Thr Gln Val Leu Asn Ser Trp Leu Val Phe Pro
        275                 280                 285

Phe His Leu Phe Cys Phe Asn Phe Gly Ala Thr His Gly Ile His His
    290                 295                 300

Phe Val Val Asn Gln Pro Phe Tyr Leu Arg Gln Trp Val Ala Phe Tyr
305                 310                 315                 320

Val Leu Ser Ala Met Lys Arg Tyr Gly Ile Arg Phe Asn Asp Phe Arg
                325                 330                 335

Ser Met Trp Lys Ser Asn Ser Glu Ser Leu Leu Glu Glu Asn Lys Ile
            340                 345                 350

Asp Phe Ser Lys Met Thr Asn Phe Pro Ile Ser Asn Ser Lys
        355                 360                 365

<210> SEQ ID NO 50
<211> LENGTH: 351
<212> TYPE: PRT
<213> ORGANISM: Acinetobacter sp.

<400> SEQUENCE: 50

Met Thr Tyr Ile Tyr Lys Asn Pro Ala Gly Met Ser Asp Ser Glu Lys
  1               5                  10                  15

Thr Glu His Ile Lys Lys Val Val Thr Ala Glu Gly Val Ala Leu Arg
             20                  25                  30

Lys Arg Tyr Pro Ile Leu Asn His Gln Asn Ala Ile Gly Ala Met Ile
         35                  40                  45

Leu Phe Val Ser Leu Val Gly Met Ile Ala Thr Ala Val Leu Tyr Ile
     50                  55                  60

Asn His Gln Leu Ser Ala Trp Phe Ala Ile Pro Ile Ile Ala Phe Phe
 65                  70                  75                  80

Ala Ser Leu Thr His Glu Leu Glu His Asp Leu Ile His Trp Met Tyr
                 85                  90                  95
```

-continued

Phe Arg Lys Lys Pro Trp Ala His His Leu Met Met Gly Leu Val Trp
            100                 105                 110

Leu Ala Arg Pro Ser Thr Ile Asn Pro Trp Lys Arg Arg Glu Leu His
        115                 120                 125

Phe Asn His His Lys Asn Ser Gly Thr Glu Val Asp Leu Glu Glu Arg
    130                 135                 140

Ala Leu Thr Asn Gly Glu Gln Trp Ser Ile Arg Arg Leu Val Ala Ile
145                 150                 155                 160

Gly Asp Asn Gly Phe Ala Val Leu Leu Arg Ile Ile Ala Ala Ser Asn
                165                 170                 175

Trp Thr Val Arg Lys Val Ile Phe Lys Arg Ala Phe Leu Ala Tyr Phe
            180                 185                 190

Pro Leu Gly Ile Ile His Trp Ser Leu Trp Tyr Ile Phe Leu Gly Phe
        195                 200                 205

His Ala Val Asp Met Val Ala Ser Leu Ala Asn Ala Pro Ile Ala Trp
    210                 215                 220

Ser Ala Thr Thr Leu Asn Val Met His Val Ile Asn Val Leu Thr Val
225                 230                 235                 240

Val Trp Ile Ala Pro Asn Val Leu Arg Thr Phe Cys Leu His Phe Val
                245                 250                 255

Thr Ser Asn Met His Tyr Tyr Gly Asp Val Glu Leu Gly Asn Val Ile
            260                 265                 270

Gln Gln Thr Gln Val Leu Thr Pro Trp Trp Met Met Pro Phe Gln Leu
        275                 280                 285

Phe Cys Phe Asn Phe Gly Ser Thr His Ala Ile His His Phe Val Val
    290                 295                 300

Lys Glu Pro Phe Tyr Ile Arg Gln Met Thr Ala Pro Ile Ala His Lys
305                 310                 315                 320

Val Met Arg Asp Met Gly Val Arg Phe Asn Asp Val Gly Thr Phe Lys
                325                 330                 335

Arg Ala Asn Arg Trp Asn Val Asn Asn Leu Ser Glu Ser Asn Thr
            340                 345                 350

<210> SEQ ID NO 51
<211> LENGTH: 367
<212> TYPE: PRT
<213> ORGANISM: Turneriella parva

<400> SEQUENCE: 51

Met Pro Thr Lys Ile Pro Pro Leu Ser Leu Thr Ala Ala Asp Arg Val
1               5                   10                  15

Asn Arg Ile Ser Arg Ser Ile Arg Met Ala Asp Arg Tyr Leu Arg Arg
            20                  25                  30

His Phe Thr Phe Leu Asn His Gln Asn Leu Ile Gly Phe Ser Ile Trp
        35                  40                  45

Leu Gly Ser Ile Ala Gly Met Ile Gly Met Ala Ala Leu Tyr Tyr Phe
    50                  55                  60

Asp Met Ala Pro Ala Trp Ser Val Ile Leu Val Asn Ala Ile Leu Ala
65                  70                  75                  80

Ser Phe Leu His Glu Leu Glu His Asp Leu Ile His Ser Leu Tyr Phe
                85                  90                  95

Lys Glu Thr Trp Ile Glu Lys Leu Met Met Trp Gly Val Trp Ala Phe
            100                 105                 110

Arg Leu Asn Thr Pro Ser Pro Phe Tyr Arg Lys Lys Ile His Leu Leu

```
            115                 120                 125
His His Lys Glu Ser Gly Gln Phe Ser Asp Ile Glu Glu Gln Met Ile
        130                 135                 140

Gly Asn Gly Met Lys Trp Gly Ile Lys Arg Ile Ile Thr Met Leu Asp
145                 150                 155                 160

Gln Gly Leu Ala Phe Leu Ile Asn Ala Arg Arg Val Gly Lys Thr Ala
                165                 170                 175

Pro Arg Leu Asp Met Lys Glu Met Ala Arg Ala Ala Phe Pro Phe Thr
            180                 185                 190

Tyr Leu Tyr Gln Gly Thr Ser Leu Val Phe Leu Phe Gly Asn Ala Tyr
        195                 200                 205

Leu Leu Ala Met Pro His Val Asp Pro Ala Phe Val Ala Asn Ala Asp
210                 215                 220

Phe Val Gln Leu Met Ala Leu Val Asn Phe Met Ala Val Val Ile Gly
225                 230                 235                 240

Leu Pro Asn Phe Ile Arg Gln Gly Ala Leu Gln Ile Val Ser Ser Ser
                245                 250                 255

Met His Tyr Phe Gly Asp Val Asn Pro Asp Ala Ser Val Gly Leu Leu
            260                 265                 270

Glu Gln Cys Gln Val Met Thr Thr Arg Ser Trp Tyr Met Leu Pro Phe
        275                 280                 285

Gln Leu Phe Cys Phe Asn Phe Gly Ser Thr His Gly Ile His His Phe
        290                 295                 300

Ile Val Asn Gln Pro Phe Tyr Leu Arg Gln Ile Ala Ala Gly Tyr Ser
305                 310                 315                 320

His Ala Ala Met Lys Lys Tyr Gly Val Arg Phe Asp Asp His Gly Ser
                325                 330                 335

Phe Ala Arg Ala Asn Arg Tyr Gly Ser Thr Ala Leu Thr Thr Gly His
            340                 345                 350

Ser Ser Leu Arg Ser Pro Ser Pro Leu Gly Glu Gly Val Gly Gly
        355                 360                 365

<210> SEQ ID NO 52
<211> LENGTH: 357
<212> TYPE: PRT
<213> ORGANISM: Burkholderia pseudomallei

<400> SEQUENCE: 52

Met Asn Lys Thr Leu Arg Phe Lys Asn Asp Ala Glu Lys Val Ala His
1               5                   10                  15

Val Arg Asn Glu Val Asn Ala Ala Ser Asp Ala Leu Arg Ala Lys Tyr
                20                  25                  30

Pro Leu Leu Asp Asn Gln Asn Leu Ile Gly Ala Ala Val Met Ala Leu
            35                  40                  45

Cys Val Ala Thr Leu Ile Gly Ser Ala Tyr Leu Tyr Ala Ile Gly Ala
        50                  55                  60

Ile Ala Trp Tyr Val Ala Leu Pro Ile Ala Thr Leu Ala Thr Ser Leu
65                  70                  75                  80

Ile His Glu Leu Glu His Asp Leu Ile His Leu Met Tyr Phe Lys Lys
                85                  90                  95

Thr Pro Trp Ala Tyr His Ala Met Met Thr Leu Cys Trp Leu Thr Arg
            100                 105                 110

Pro Gly Thr Ile Asn Pro Trp Thr Arg Arg Met His Leu His His
        115                 120                 125
```

```
His Lys Val Ser Gly Gly Glu Ser Asp Leu Glu Glu Tyr Gly Ile Thr
    130                 135                 140

Asn Gly Glu Arg Trp Gly Leu Lys Arg Leu Leu Met Leu Ala Asp Gly
145                 150                 155                 160

Met Leu Ala Val Ala Leu Arg Pro Leu Gly Met Arg Arg Lys Val Leu
                165                 170                 175

Gln Tyr Val Ala Ala Gln Pro Ala Gln Ala Arg Gly Asp Arg Val Arg
            180                 185                 190

Leu Arg Ile Glu Gln Leu Met Ser Tyr Met Pro Ile Gly His Val Tyr
        195                 200                 205

Tyr Val Leu Trp His Ala Phe Ile Ala Tyr His Ala Gly Leu Phe Ala
    210                 215                 220

Leu His Ala Leu Gly Tyr His Pro Ala Val Pro Ala Leu Val Gln Gln
225                 230                 235                 240

Thr Met His Val Val Asp Phe Leu Ala Val Thr Trp Leu Gly Pro Asn
                245                 250                 255

Phe Val Arg Ser Phe Cys Ile Asn Phe Ile Ser Ser Asn Met His Tyr
            260                 265                 270

Tyr Gly Asp Ile Asp Ser Arg Asn Val Val Gln Gln Thr Gln Val Leu
        275                 280                 285

Asn Pro Trp Trp Leu Ile Pro Val Gln Leu Phe Cys Phe Asn Phe Gly
290                 295                 300

Ser Thr His Ala Ile His His Phe Val Val Arg Asp Pro Phe Tyr Ile
305                 310                 315                 320

Arg Gln Leu Thr Ala Lys Arg Ala His Ala Ala Met Arg Ala Val Gly
                325                 330                 335

Val Arg Phe Asn Asp Ile Gly Thr Phe Arg Arg Ala Asn Arg Trp Asn
            340                 345                 350

Glu Thr Arg Ala Ala
        355

<210> SEQ ID NO 53
<211> LENGTH: 357
<212> TYPE: PRT
<213> ORGANISM: Burkholderia thailandensis

<400> SEQUENCE: 53

Met Asn Lys Thr Leu Arg Phe Lys Asn Asp Ala Glu Lys Val Ala Tyr
1               5                   10                  15

Val Arg Asn Glu Val Asn Ala Ala Ser Asp Ala Leu Arg Ala Lys Tyr
            20                  25                  30

Pro Leu Le

Asn Gly Glu Arg Trp Gly Leu Lys Arg Leu Leu Met Leu Ala Asp Gly
145                 150                 155                 160

Met Leu Ala Val Ala Leu Arg Pro Leu Gly Met Arg Lys Val Leu
            165                 170                 175

Gln Tyr Val Ala Ala Gln Pro Ala Gln Glu Arg Gly Asp Arg Val Arg
        180                 185                 190

Leu Arg Ile Glu Gln Leu Met Ser Tyr Met Pro Ile Gly His Val Tyr
        195                 200                 205

Tyr Val Leu Trp His Ala Phe Ile Ala Tyr His Val Gly Leu Leu Ala
        210                 215                 220

Leu His Ala Leu Gly Tyr Gln Pro Asp Val Pro Met Leu Val Gln Gln
225                 230                 235                 240

Ala Met His Val Val Asp Phe Leu Ala Val Thr Trp Leu Gly Pro Asn
            245                 250                 255

Phe Val Arg Ser Phe Cys Ile Asn Phe Ile Ser Ser Asn Met His Tyr
            260                 265                 270

Tyr Gly Asp Ile Asp Ser Arg Asn Val Ile Gln Gln Thr Gln Val Leu
        275                 280                 285

Asn Pro Trp Trp Leu Ile Pro Val Gln Leu Phe Cys Phe Asn Phe Gly
        290                 295                 300

Ser Thr His Ala Ile His His Phe Val Val Arg Asp Pro Phe Tyr Ile
305                 310                 315                 320

Arg Gln Leu Thr Ala Lys Arg Ala His Ala Ala Met Arg Ala Val Gly
            325                 330                 335

Val Arg Phe Asn Asp Ile Gly Thr Phe Arg Arg Ala Asn Arg Trp Asn
        340                 345                 350

Glu Thr Arg Ala Ala
        355

<210> SEQ ID NO 54
<211> LENGTH: 909
<212> TYPE: DNA
<213> ORGANISM: Artificial Sequence
<220> FEATURE:
<223> OTHER INFORMATION: Synthetic Construct

<400> SEQUENCE: 54

```
atgacgaatc tcgaatggaa acctaaaccc aagctgccac aattgctcga tgaccatttt      60
ggcctccatg gcctcgtctt tcgccggact tttgctattc ggtcgtacga agtgggtccc     120
gatcgatcga ccagcatttt ggcggtgatg aaccacatgc aggaagcgac gctcaatcat     180
gcgaaaagcg tggggatcct gggggatggt tttggcacta cactggaaat gtctaaacgc     240
gatttgatgt gggtggtccg ccgcacccat gttgctgtgg agcggtatcc gacgtggggc     300
gataccgtcg aagttgagtg ctggatcggc gcgtctggca ataacggcat gcgccgcgat     360
ttcttggttc gtgattgcaa gactggtgaa attctcacac gctgcacgag cctctcggtg     420
ctgatgaaca cccgcacacg tcgcctgagc actatcccag acgaagtccg tggtgaaatt     480
ggtcctgcat ttattgacaa tgttgcggtt aaggatgatg agattaaaaa actccaaaaa     540
ctgaatgact ccacggctga ctacattcaa ggtggcttga cgccgcgatg gaatgatttg     600
gatgtgaatc aacatgtcaa taatctgaag tatgtcgcat gggtgtttga cggttccg      660 gatagtatct ttgaaagcca tcacatttcg tcttttaccc tcgaataccg gcgggaatgc     720
acccgtgata gcgttttgcg gtccctcacg actgttagcg gaggtagttc cgaagcgggc     780
```

```
ctcgtgtgcg atcatctgct gcagctcgaa ggtggatcgg aagtgctccg tgcgcgaacg    840
gaatggcggc ccaaactgac cgactcgttt cgcggaatca gtgtcattcc agctgaaccc    900
cgggtctag                                                            909
```

```
<210> SEQ ID NO 55
<211> LENGTH: 35
<212> TYPE: DNA
<213> ORGANISM: Artificial Sequence
<220> FEATURE:
<223> OTHER INFORMATION: Synthetic Construct

<400> SEQUENCE: 55
ggtattgagg gtcgcatgat cgacacattc agccg                               35

<210> SEQ ID NO 56
<211> LENGTH: 35
<212> TYPE: DNA
<213> ORGANISM: Artificial Sequence
<220> FEATURE:
<223> OTHER INFORMATION: Synthetic Construct

<400> SEQUENCE: 56
agaggagagt tagagcctca gccttcggcc agtgc                               35

<210> SEQ ID NO 57
<211> LENGTH: 59
<212> TYPE: DNA
<213> ORGANISM: Artificial Sequence
<220> FEATURE:
<223> OTHER INFORMATION: Synthetic Construct

<400> SEQUENCE: 57
ggtattgagg gtcgccttga agtcctcttt cagggaccca tgatcgacac attcagccg     59

<210> SEQ ID NO 58
<211> LENGTH: 35
<212> TYPE: DNA
<213> ORGANISM: Artificial Sequence
<220> FEATURE:
<223> OTHER INFORMATION: Synthetic Construct

<400> SEQUENCE: 58
ggtattgagg gtcgcatgat cgacactttc gagag                               35

<210> SEQ ID NO 59
<211> LENGTH: 35
<212> TYPE: DNA
<213> ORGANISM: Artificial Sequence
<220> FEATURE:
<223> OTHER INFORMATION: Synthetic Construct

<400> SEQUENCE: 59
agaggagagt tagagcccta catttccagt gcggc                               35

<210> SEQ ID NO 60
<211> LENGTH: 35
<212> TYPE: DNA
<213> ORGANISM: Artificial Sequence
<220> FEATURE:
<223> OTHER INFORMATION: Synthetic Construct

<400> SEQUENCE: 60
ggtattgagg gtcgcatgag cgagttcttt gaccg                               35
```

```
<210> SEQ ID NO 61
<211> LENGTH: 35
<212> TYPE: DNA
<213> ORGANISM: Artificial Sequence
<220> FEATURE:
<223> OTHER INFORMATION: Synthetic Construct

<400> SEQUENCE: 61
agaggagagt tagagcccta ctccgcgccg accgc                              35

<210> SEQ ID NO 62
<211> LENGTH: 35
<212> TYPE: DNA
<213> ORGANISM: Artificial Sequence
<220> FEATURE:
<223> OTHER INFORMATION: Synthetic Construct

<400> SEQUENCE: 62
ggtattgagg gtcgcatgtt tgaatcaaac agtta                              35

<210> SEQ ID NO 63
<211> LENGTH: 35
<212> TYPE: DNA
<213> ORGANISM: Artificial Sequence
<220> FEATURE:
<223> OTHER INFORMATION: Synthetic Construct

<400> SEQUENCE: 63
agaggagagt tagagcctta ttgatgttta taaca                              35

<210> SEQ ID NO 64
<211> LENGTH: 35
<212> TYPE: DNA
<213> ORGANISM: Artificial Sequence
<220> FEATURE:
<223> OTHER INFORMATION: Synthetic Construct

<400> SEQUENCE: 64
ggtattgagg gtcgcatgga aatcacaagg atcaa                              35

<210> SEQ ID NO 65
<211> LENGTH: 35
<212> TYPE: DNA
<213> ORGANISM: Artificial Sequence
<220> FEATURE:
<223> OTHER INFORMATION: Synthetic Construct

<400> SEQUENCE: 65
agaggagagt tagagcctca gcccgcagcc aacgc                              35

<210> SEQ ID NO 66
<211> LENGTH: 31
<212> TYPE: DNA
<213> ORGANISM: Artificial Sequence
<220> FEATURE:
<223> OTHER INFORMATION: Synthetic Construct

<400> SEQUENCE: 66
gcaatatccg ggtcgcgctc aatcatgccg a                                  31

<210> SEQ ID NO 67
<211> LENGTH: 31
<212> TYPE: DNA
<213> ORGANISM: Artificial Sequence
<220> FEATURE:
<223> OTHER INFORMATION: Synthetic Construct
```

<400> SEQUENCE: 67
tcggcatgat tgagcgcgac ccggatattg c                                    31

<210> SEQ ID NO 68
<211> LENGTH: 37
<212> TYPE: DNA
<213> ORGANISM: Artificial Sequence
<220> FEATURE:
<223> OTHER INFORMATION: Synthetic Construct

<400> SEQUENCE: 68
cagtaatcgg cagcattgag ctcgacccgg atattgc                              37

<210> SEQ ID NO 69
<211> LENGTH: 37
<212> TYPE: DNA
<213> ORGANISM: Artificial Sequence
<220> FEATURE:
<223> OTHER INFORMATION: Synthetic Construct

<400> SEQUENCE: 69
gcaatatccg ggtcgagctc aatgctgccg attactg                              37

<210> SEQ ID NO 70
<211> LENGTH: 29
<212> TYPE: DNA
<213> ORGANISM: Artificial Sequence
<220> FEATURE:
<223> OTHER INFORMATION: Synthetic Construct

<400> SEQUENCE: 70
ccgtggcccc tgcaatggcg tagttggtg                                       29

<210> SEQ ID NO 71
<211> LENGTH: 29
<212> TYPE: DNA
<213> ORGANISM: Artificial Sequence
<220> FEATURE:
<223> OTHER INFORMATION: Synthetic Construct

<400> SEQUENCE: 71
caccaactac gccattgcag gggccacgg                                       29

<210> SEQ ID NO 72
<211> LENGTH: 34
<212> TYPE: DNA
<213> ORGANISM: Artificial Sequence
<220> FEATURE:
<223> OTHER INFORMATION: Synthetic Construct

<400> SEQUENCE: 72
gaagtggctg aagatggctg cccagtacga cgac                                 34

<210> SEQ ID NO 73
<211> LENGTH: 34
<212> TYPE: DNA
<213> ORGANISM: Artificial Sequence
<220> FEATURE:
<223> OTHER INFORMATION: Synthetic Construct

<400> SEQUENCE: 73
gtcgtcgtac tgggcagcca tcttcagcca cttc                                 34

<210> SEQ ID NO 74
<211> LENGTH: 34

```
<212> TYPE: DNA
<213> ORGANISM: Artificial Sequence
<220> FEATURE:
<223> OTHER INFORMATION: Synthetic Construct

<400> SEQUENCE: 74
tatggatcca aaaaatgatc gacacattca gccg                               34

<210> SEQ ID NO 75
<211> LENGTH: 29
<212> TYPE: DNA
<213> ORGANISM: Artificial Sequence
<220> FEATURE:
<223> OTHER INFORMATION: Synthetic Construct

<400> SEQUENCE: 75
aaagtcgact cagccttcgg ccagtgcca                                     29
```

BIOSYNTHESIS OF 1-UNDECENE AND RELATED TERMINAL OLEFINS

CROSS-REFERENCE(S) TO RELATED APPLICATION

This application claims the benefit of U.S. Provisional Application No. 61/919,680, filed Dec. 20, 2013, which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 677792004540SeqList.txt, date recorded: Dec. 16, 2014, size: 122 KB).

FIELD

The present disclosure relates to the biosynthesis of 1-undecene and related terminal olefins. Specifically, the present disclosure relates to methods of using proteins to produce 1-undecene and related terminal olefins.

BACKGROUND

Surging energy consumption and environmental concerns demand production of chemicals and biofuel through sustainable and renewable approaches. Fatty acid derived fuels and chemicals, such as alkanes and alkenes, are of particular interest to directly replace fossil hydrocarbons (P. P. Peralta-Yahya et al., Nature 488, 320, 2012; R. M. Lennen et al, Curr Opin Biotechnol 24, 1044, 2013). Since the recent discovery of an aldehyde decarbonylase which catalyzes alkane synthesis from fatty acid metabolites (A. Schirmer et al., Science 329, 559, 2010), numerous efforts have been devoted to produce alkanes using engineered microbes from renewable raw materials (Y. J. Choi et al., Nature 502, 571, 2013; T. P. Howard et al., P Natl Acad Sci USA 110, 7636, 2013; C. Andre et al., P Natl Acad Sci USA 110, 3191, 2013). Although routes to bio-hydrocarbons are emerging, a major challenge is to identify biocatalysts which are capable of producing hydrocarbons with desired carbon chain lengths and functionalities (M. K. Akhtar et al., Proc Natl Acad Sci USA, 110, 87, 2013; Y. Qiu et al., Proc Natl Acad Sci USA 109, 14858, 2012).

Medium-chain hydrocarbons are "drop-in" ready fuels with superior properties such as high energy content, low freezing point, easy product recovery, and compatibility with the existing transportation infrastructure. Possessing a derivable terminal functionality (P. S. Coelho et al., Science 339, 307, 2013), aliphatic medium-chain 1-alkenes (MCAEs) show clear advantage over other hydrocarbons as "green" precursors to industrial chemicals such as lubricants and pesticides. MCAEs, also known as medium-chain terminal olefins, are naturally produced in low abundance by diverse species as "volatile organic compounds" (VOCs) with obscure biological functions (S. Schulz et al., Nat Prod Rep 24, 814, 2007).

Despite the high value of MCAEs, nothing is known about the biosynthesis of MCAEs in organisms at either the genetic or biochemical levels. Discovery and characterization of biosynthetic pathway of MCAEs is therefore an indispensable first step towards the bioproduction of MCAEs and MCAE-derived chemicals. There exists a need for the bioproduction of 1-alkenes/terminal olefins from fatty acids.

BRIEF SUMMARY

In one aspect, the present disclosure relates to methods of producing a terminal olefin, the method including: a) contacting a host cell including a recombinant nucleic acid encoding SEQ ID NO: 1 or a homolog thereof with a fatty acid; and b) culturing the host cell under conditions such that a terminal olefin is produced from the fatty acid. In some embodiments, the host cell is a bacterial cell. In some embodiments, the host cell is E. coli. In some embodiments, the host cell is a eukaryotic cell. In some embodiments, the host cell is Saccharomyces cerevisiae. In some embodiments, the host cell is modified to produce excess quantities of free fatty acids as compared to a corresponding unmodified host cell. In some embodiments, the modified host cell has modified beta-oxidation activity, thioesterase activity, and/or acetyl-coA carboxylase activity. In some embodiments that may be combined with any of the preceding embodiments, the homolog includes an amino acid sequence at least 35%, at least 40%, and least 45%, at least 50%, at least 55%, at least 60%, at least 65%, at least 70%, at least 75%, at least 80%, at least 85%, at least 90%, at least 95%, or at least 99% identical to the amino acid sequence of SEQ ID NO: 1. In some embodiments that may be combined with any of the preceding embodiments, the homolog comprises analogous amino acids or conservative substitutions of Glu101, His104, Glu159, and His194 of SEQ ID NO: 1. In some embodiments that may be combined with any of the preceding embodiments, the fatty acid is a C10-C20 fatty acid. In some embodiments, the fatty acid is a C14-C20 fatty acid. In some embodiments that may be combined with any of the preceding embodiments, the fatty acid is a medium chain fatty acid. In some embodiments, the medium chain fatty acid is a C10-C14 fatty acid. In some embodiments, the medium-chain fatty acid is lauric acid. In some embodiments that may be combined with any of the preceding embodiments, the host cell is cultured in an aerobic environment. In some embodiments that may be combined with any of the preceding embodiments, the host cell is cultured in media and the media comprises iron. In some embodiments that may be combined with any of the preceding embodiments, the host cell is cultured in media and the media comprises ascorbic acid. In some embodiments that may be combined with any of the preceding embodiments, the terminal olefin is a C9-C13 terminal olefin. In some embodiments that may be combined with any of the preceding embodiments, the terminal olefin is 1-undecene. In some embodiments that may be combined with any of the preceding embodiments, the yield of the terminal olefin is about 1 µg/mL, about 1.5 µg/mL, about 2 µg/mL, about 2.5 µg/mL, about 3 µg/mL, about 3.5 µg/mL, about 4 µg/mL, about 4.5 µg/mL, about 5 µg/mL, about 5.5 µg/mL, about 6 µg/mL, about 6.5 µg/mL, about 7 µg/mL, about 7.5 µg/mL, about 8 µg/mL, about 8.5 µg/mL, about 9 µg/mL, about 9.5 µg/mL, or about 10 µg/mL or more terminal olefin. In some embodiments that may be combined with any of the preceding embodiments, the method further includes a step of recovering a terminal olefin produced by the host cell.

In another aspect, the present disclosure relates to methods of producing a terminal olefin, the method including: a) contacting a host cell including a recombinant nucleic acid encoding a polypeptide including the amino acid sequence of SEQ ID NO: 33 with a fatty acid; and b) culturing the host cell under conditions such that a terminal olefin is produced from the fatty acid.

In another aspect, the present disclosure relates to methods of producing a terminal olefin, the method including: a) contacting a host cell including a recombinant nucleic acid encoding a polypeptide including the amino acid sequence of SEQ ID NO: 34 with a fatty acid; and b) culturing the host cell under conditions such that a terminal olefin is produced from the fatty acid.

In another aspect, the present disclosure relates to methods of producing a terminal olefin, the method including: a) contacting a host cell including a recombinant nucleic acid encoding a polypeptide including the amino acid sequence of SEQ ID NO: 35 with a fatty acid; and b) culturing the host cell under conditions such that a terminal olefin is produced from the fatty acid.

In another aspect, the present disclosure relates to methods of producing a terminal olefin, the method including: a) contacting a host cell including a recombinant nucleic acid encoding a polypeptide including the amino acid sequence of SEQ ID NO: 36 with a fatty acid; and b) culturing the host cell under conditions such that a terminal olefin is produced from the fatty acid.

In another aspect, the present disclosure relates to methods of producing a terminal olefin, the method including: a) contacting a host cell including a recombinant nucleic acid encoding a polypeptide including the amino acid sequence of SEQ ID NO: 37 with a fatty acid; and b) culturing the host cell under conditions such that a terminal olefin is produced from the fatty acid.

In another aspect, the present disclosure relates to methods of producing a terminal olefin, the method including: a) contacting a host cell including a recombinant nucleic acid encoding a polypeptide including the amino acid sequence of SEQ ID NO: 38 with a fatty acid; and b) culturing the host cell under conditions such that a terminal olefin is produced from the fatty acid.

In another aspect, the present disclosure relates to methods of producing a terminal olefin, the method including: a) contacting a host cell including a recombinant nucleic acid encoding a polypeptide including one or more of the amino acid sequences of SEQ ID NO: 33, SEQ ID NO: 34, SEQ ID NO: 35, SEQ ID NO: 36, SEQ ID NO: 37, and SEQ ID NO: 38 with a fatty acid; and b) culturing the host cell under conditions such that a terminal olefin is produced from the fatty acid. In some embodiments, the host cell is a bacterial cell. In some embodiments, the host cell is $E.\ coli$. In some embodiments, the host cell is a eukaryotic cell. In some embodiments, the host cell is $Saccharomyces\ cerevisiae$. In some embodiments, the host cell is modified to produce excess quantities of free fatty acids as compared to a corresponding unmodified host cell. In some embodiments, the modified host cell has modified beta-oxidation activity, thioesterase activity, and/or acetyl-coA carboxylase activity. In some embodiments that may be combined with any of the preceding embodiments, the fatty acid is a C10-C20 fatty acid. In some embodiments, the fatty acid is a C14-C20 fatty acid. In some embodiments that may be combined with any of the preceding embodiments, the fatty acid is a medium chain fatty acid. In some embodiments, the medium chain fatty acid is a C10-C14 fatty acid. In some embodiments, the medium-chain fatty acid is lauric acid. In some embodiments that may be combined with any of the preceding embodiments, the host cell is cultured in an aerobic environment. In some embodiments that may be combined with any of the preceding embodiments, the host cell is cultured in media and the media comprises iron. In some embodiments that may be combined with any of the preceding embodiments, the host cell is cultured in media and the media comprises ascorbic acid. In some embodiments that may be combined with any of the preceding embodiments, the terminal olefin is a C9-C13 terminal olefin. In some embodiments that may be combined with any of the preceding embodiments, the terminal olefin is 1-undecene. In some embodiments that may be combined with any of the preceding embodiments, the yield of the terminal olefin is about 1 µg/mL, about 1.5 µg/mL, about 2 µg/mL, about 2.5 µg/mL, about 3 µg/mL, about 3.5 µg/mL, about 4 µg/mL, about 4.5 µg/mL, about 5 µg/mL, about 5.5 µg/mL, about 6 µg/mL, about 6.5 µg/mL, about 7 µg/mL, about 7.5 µg/mL, about 8 µg/mL, about 8.5 µg/mL, about 9 µg/mL, about 9.5 µg/mL, or about 10 µg/mL or more terminal olefin. In some embodiments that may be combined with any of the preceding embodiments, the method further includes a step of recovering a terminal olefin produced by the host cell.

In another aspect, the present disclosure relates to methods of producing a terminal olefin, the method including: a) contacting a host cell including a recombinant nucleic acid encoding a non-heme, iron-dependent polypeptide with a fatty acid; and b) culturing the host cell under conditions such that a terminal olefin is produced from the fatty acid.

In another aspect, the present disclosure relates to methods of producing a terminal olefin, the method including: a) contacting a host cell including a recombinant nucleic acid encoding SEQ ID NO: 1 with lauric acid; and b) culturing the host cell under conditions such that 1-undecene is produced from lauric acid.

In another aspect, the present disclosure relates to host cells including a recombinant nucleic acid encoding SEQ ID NO: 1 or a homolog thereof. In some embodiments, the host cell is a bacterial cell. In some embodiments, the host cell is $E.\ coli$. In some embodiments, the host cell is a eukaryotic cell. In some embodiments, the host cell is $Saccharomyces\ cerevisiae$. In some embodiments, the host cell is modified to produce excess quantities of free fatty acids as compared to a corresponding unmodified host cell. In some embodiments, the modified host cell has modified beta-oxidation activity, thioesterase activity, and/or acetyl-coA carboxylase activity. In some embodiments that may be combined with any of the preceding embodiments, the homolog comprises an amino acid sequence at least 35%, at least 40%, and least 45%, at least 50%, at least 55%, at least 60%, at least 65%, at least 70%, at least 75%, at least 80%, at least 85%, at least 90%, at least 95%, or at least 99% identical to the amino acid sequence of SEQ ID NO: 1. In some embodiments that may be combined with any of the preceding embodiments, the homolog comprises analogous amino acids or conservative substitutions of Glu101, His104, Glu159, and His194 of the amino acid sequence of SEQ ID NO: 1. In some embodiments that may be combined with any of the preceding embodiments, the host cell produces terminal olefins from fatty acids.

In one aspect, the present disclosure relates to methods of producing a terminal olefin, the method including: a) contacting a host cell including a recombinant nucleic acid encoding SEQ ID NO: 39 or a homolog thereof with a fatty acid; and b) culturing the host cell under conditions such that a terminal olefin is produced from the fatty acid. In some embodiments, the host cell is a bacterial cell. In some embodiments, the host cell is $E.\ coli$. In some embodiments, the host cell is a eukaryotic cell. In some embodiments, the host cell is $Saccharomyces\ cerevisiae$. In some embodiments, the host cell is modified to produce excess quantities of free fatty acids as compared to a corresponding unmodified host cell. In some embodiments, the modified host cell has modified beta-oxidation activity, thioesterase activity, and/or acetyl-coA carboxylase activity. In some embodiments, the host cell overexpresses UcFatB2 or a homolog thereof. In some embodiments that may be combined with any of the preceding embodiments, the homolog of SEQ ID NO: 39 includes an amino acid sequence at least 35%, at least 40%, and least 45%, at least 50%, at least 55%, at least 60%, at least 65%, at least 70%, at least 75%, at least 80%, at least 85%, at least 90%, at least 95%, or at least 99% identical to the amino acid sequence of SEQ ID NO: 39. In some embodiments that may be combined with any of the preceding embodiments, the fatty acid is a C10-C20 fatty acid. In some embodiments, the fatty acid is a C14-C20 fatty acid. In some embodiments that may be combined with any of the preceding embodiments, the fatty acid is a medium chain fatty acid. In some embodiments, the medium chain fatty acid is a C10-C16 fatty acid. In some embodiments, the medium-chain fatty acid is lauric acid. In some embodiments that may be combined with any of the preceding embodiments, the host cell is cultured in an aerobic environment. In some embodiments that may be combined with any of the preceding embodiments, the terminal olefin is a C9-C13 terminal olefin. In some embodiments that may be combined with any of the preceding embodiments, the terminal olefin is 1-undecene. In some embodiments that may be combined with any of the preceding embodiments, the yield of the terminal olefin is about 1 µg/mL, about 1.5 µg/mL, about 2 µg/mL, about 2.5 µg/mL, about 3 µg/mL, about 3.5 µg/mL, about 4 µg/mL, about 4.5 µg/mL, about 5 µg/mL, about 5.5 µg/mL, about 6 µg/mL, about 6.5 µg/mL, about 7 µg/mL, about 7.5 µg/mL, about 8 µg/mL, about 8.5 µg/mL, about 9 µg/mL, about 9.5 µg/mL, or about 10 µg/mL or more terminal olefin. In some embodiments that may be combined with any of the preceding embodiments, the method further includes a step of recovering a terminal olefin produced by the host cell.

In another aspect, the present disclosure relates to host cells including a recombinant nucleic acid encoding SEQ ID NO: 39 or a homolog thereof. In some embodiments, the host cell is a bacterial cell. In some embodiments, the host cell is *E. coli*. In some embodiments, the host cell is a eukaryotic cell. In some embodiments, the host cell is *Saccharomyces cerevisiae*. In some embodiments, the host cell is modified to produce excess quantities of free fatty acids as compared to a corresponding unmodified host cell. In some embodiments, the modified host cell has modified beta-oxidation activity, thioesterase activity, and/or acetyl-coA carboxylase activity. In some embodiments, the host cell overexpresses UcFatB2 or a homolog thereof. In some embodiments that may be combined with any of the preceding embodiments, the homolog of SEQ ID NO: 39 comprises an amino acid sequence at least 35%, at least 40%, and least 45%, at least 50%, at least 55%, at least 60%, at least 65%, at least 70%, at least 75%, at least 80%, at least 85%, at least 90%, at least 95%, or at least 99% identical to the amino acid sequence of SEQ ID NO: 39. In some embodiments that may be combined with any of the preceding embodiments, the host cell produces terminal olefins from fatty acids.

In another aspect, the present disclosure relates to methods of producing a terminal olefin, the method including: a) contacting a host cell with a fatty acid, wherein the host cell includes: 1) a recombinant nucleic acid encoding SEQ ID NO: 1 or a homolog thereof, and 2) a recombinant nucleic acid encoding SEQ ID NO: 39 or a homolog thereof; and culturing the host cell under conditions such that a terminal olefin is produced from the fatty acid. In some embodiments, the host cell is a bacterial cell. In some embodiments, the host cell is *E. coli*. In some embodiments, the host cell is a eukaryotic cell. In some embodiments, the host cell is *Saccharomyces cerevisiae*. In some embodiments, the host cell is modified to produce excess quantities of free fatty acids as compared to a corresponding unmodified host cell. In some embodiments, the modified host cell has modified beta-oxidation activity, thioesterase activity, and/or acetyl-coA carboxylase activity. In some embodiments, the host cell overexpresses UcFatB2 or a homolog thereof. In some embodiments that may be combined with any of the preceding embodiments, the homolog of either one of SEQ ID NO: 1 or SEQ ID NO: 39 includes an amino acid sequence at least 35%, at least 40%, and least 45%, at least 50%, at least 55%, at least 60%, at least 65%, at least 70%, at least 75%, at least 80%, at least 85%, at least 90%, at least 95%, or at least 99% identical to the amino acid sequence of either one of SEQ ID NO: 1 or SEQ ID NO: 39. In some embodiments that may be combined with any of the preceding embodiments, the fatty acid is a C10-C20 fatty acid. In some embodiments, the fatty acid is a C14-C20 fatty acid. In some embodiments that may be combined with any of the preceding embodiments, the fatty acid is a medium chain fatty acid. In some embodiments, the medium chain fatty acid is a C10-C14 fatty acid. In some embodiments, the medium chain fatty acid is a C10-C16 fatty acid. In some embodiments, the medium-chain fatty acid is lauric acid. In some embodiments that may be combined with any of the preceding embodiments, the host cell is cultured in an aerobic environment. In some embodiments that may be combined with any of the preceding embodiments, the host cell is cultured in media and the media comprises iron. In some embodiments that may be combined with any of the preceding embodiments, the host cell is cultured in media and the media comprises ascorbic acid. In some embodiments that may be combined with any of the preceding embodiments, the terminal olefin is a C9-C13 terminal olefin. In some embodiments that may be combined with any of the preceding embodiments, the terminal olefin is 1-undecene. In some embodiments that may be combined with any of the preceding embodiments, the yield of the terminal olefin is about 1 µg/mL, about 1.5 µg/mL, about 2 µg/mL, about 2.5 µg/mL, about 3 µg/mL, about 3.5 µg/mL, about 4 µg/mL, about 4.5 µg/mL, about 5 µg/mL, about 5.5 µg/mL, about 6 µg/mL, about 6.5 µg/mL, about 7 µg/mL, about 7.5 µg/mL, about 8 µg/mL, about 8.5 µg/mL, about 9 µg/mL, about 9.5 µg/mL, or about 10 µg/mL or more terminal olefin. In some embodiments that may be combined with any of the preceding embodiments, the method further includes a step of recovering a terminal olefin produced by the host cell.

In another aspect, the present disclosure relates to host cells including: 1) a recombinant nucleic acid encoding SEQ ID NO: 1 or a homolog thereof, and 2) a recombinant nucleic acid encoding SEQ ID NO: 39 or a homolog thereof. In some embodiments, the host cell is a bacterial cell. In some embodiments, the host cell is *E. coli*. In some embodiments, the host cell is a eukaryotic cell. In some embodiments, the host cell is *Saccharomyces cerevisiae*. In some embodiments, the host cell is modified to produce excess quantities of free fatty acids as compared to a corresponding unmodified host cell. In some embodiments, the modified host cell has modified beta-oxidation activity, thioesterase activity, and/or acetyl-coA carboxylase activity. In some embodiments, the host cell overexpresses UcFatB2 or a homolog thereof. In some embodiments that may be combined with any of the preceding embodiments, the homolog of either one of SEQ ID NO: 1 or SEQ ID NO: 39 includes an amino acid sequence at least 35%, at least 40%, and least 45%, at least 50%, at least 55%, at least 60%, at least 65%, at least 70%, at least 75%, at least 80%, at least 85%, at least 90%, at least 95%, or at least 99% identical to the amino acid sequence of either one of SEQ ID NO: 1 or SEQ ID NO: 39. In some embodiments that may be combined with any of the preceding embodiments, the homolog of SEQ ID NO: 1 comprises analogous amino acids or conservative substitutions of Glu101, His104, Glu159, and His194 of the amino acid sequence of SEQ ID NO: 1. In some embodiments that may be combined with any of the preceding embodiments, the host cell produces terminal olefins from fatty acids.

DESCRIPTION OF THE FIGURES

The patent or application file contains at least one drawing executed in color. Copies of this patent or patent application publication with color drawings will be provided by the office upon request and payment of the necessary fee.

FIG. 1A-FIG. 1D illustrate that PFL_4321 is responsible for 1-undecene biosynthesis. FIG. 1A illustrates that *Pseudomonas fluorescens* Pf-5 produces 1-undecene. FIG. 1B illustrates that 1-undecene production was observed during the library screening in the *E. coli* EPI300 (fosmid 6F8) carrying PFL_4321. Native *E. coli* EPI300 does not produce 1-undecene. FIG. 1C illustrates that *Pseudomonas aeruginosa* PA14 produces 1-undecene. FIG. 1D illustrates that disruption of the PA14_53120 (PFL_4321 homolog) completely abolished the 1-undecene production in *P. aeruginosa* ΔPA14_53120 mutant.

FIG. 2 illustrates a flow chart for the identification of 1-undecene biosynthetic gene by heterologous expression of the genomic library of *P. fluoresens* Pf-5. In the library screening, three positive fosmid clones, 6F8/6E2/4F3, were identified to be responsible for 1-undecene production in *E. coli*. The 15 kb overlapped region was further trimmed by restriction digestion and narrowed down to two genes, PFL_4320 and PFL_4321. When PFL_4320 and PFL_4321 were separately overexpressed in *E. coli* BL21, PFL_4321 alone, but not PFL_4320, conferred 1-undecene production.

FIG. 4A illustrates the conversion of [1-$^{13}$C]lauric acid to [U-$^{12}$C11]undecene. FIG. 4B illustrates the conversion of [12-$^{13}$C]lauric acid to [11-$^{13}$C]undecene. Reverse panel (bottom panel) in FIG. 4A shows the reference standard of 1-undecene from the NIST spectral database.

FIG. 8A illustrates a proposed 1-undecene biosynthesis catalyzed by PFL_4321 activity. FIG. 8B illustrates Michaelis-Menten plots for PFL_4321 on lauric acid (C12:0), myristic acid (C14:0), and capric acid (C10:0).

FIG. 9A-FIG. 9B illustrates GC-MS analysis of the conversions of capric acid to 1-nonene. Reverse panel (bottom panel) in FIG. 9B illustrates the reference standard of 1-nonene from the NIST spectral database.

FIG. 10A-FIG. 10B illustrates GC-MS analysis of the conversions of myristic acid to 1-tridecene. Reverse panel (bottom panel) in FIG. 10B illustrates the reference standard of 1-tridecene from the NIST spectral database.

FIG. 17A-FIG. 17B illustrates GC-MS analysis of the conversions of 4-methyldodecanoic acid to 3-methylundec-1-ene. Reverse panel (bottom panel) in FIG. 17B illustrates the reference standard of 3-methylundec-1-ene from the NIST spectral database.

FIG. 20A-FIG. 20G illustrates structures of PFL_4321 and a proposed catalytic mechanism. FIG. 20A illustrates overall structure of PFL_4321 with helices in blue and loops in salmon. Iron is shown in black, and DEA is shown in yellow for carbons and red for oxygens. FIG. 20B illustrates substrate binding pocket of PFL_4321. DEA, presented as a ball-and-stick model, is surrounded by a simulated annealing omit map in blue, contoured at 3.0 σ. Pocket-forming residues are displayed as sticks and the hydrophobic residues are colored in orange. FIG. 20C, FIG. 20D, FIG. 20E, and FIG. 20F illustrate weighted electron density maps surrounding the active site of the apo-, DEA- and BHDA-bound structures with $2mF_o$-$DF_c$ (in gray, at 1.8 σ) and $mF_o$-$DF_c$ (green and red, at ±3.0 σ). The distal oxygen atoms of the dioxygen species in FIG. 20E and FIG. 20F are surrounded by the simulated annealing omit maps in green, contoured at 3.0 σ. FIG. 20G illustrates a proposed mechanism for 1-undecene biosynthesis by PFL_4321.

FIG. 21A-FIG. 21D illustrates geometry of the active sites of PFL_4321. FIG. 21A, FIG. 21B, FIG. 21C and FIG. 21D illustrate weighted electron density maps surrounding the active site of the PFL_4321/DEA complex (chain A (FIG. 21A) and chain B (FIG. 21B)) and the active site of the PFL_4321/BHDA complex (chain A (FIG. 21C) and chain B (FIG. 21D)) with $2mF_O$-$DF_C$ (in gray, contoured at 1.0 σ). The simulated annealing electron density maps after omitting the proximal O1 atom are colored in magenta; and after omitting the distal O2 atom are colored in blue. All omit maps are contoured at 4.0 σ. The orientation is approximately equivalent to that shown in the schematic in FIG. 20G.

FIG. 24A illustrates a phylogenetic tree of PFL_4321 and homologs constructed using Minimum Evolution method. FIG. 24B illustrates the total amounts of 1-undecene produced by overexpressing PFL_4321 (*P. fluorescens* Pf-5), PSPTO_1738 (*P. syringae* pv. tomato DC3000), PA14_53120 (*P. aeruginosa* PA14), ACIAD2095 (*Acinetobacter baylyi* ADP1), and Pput_3952 (*P. putida* F1) in E. coli BL21 Star.

FIG. 31A illustrates membrane domain prediction by TMHMM Server v. 2.0. "Inside" and "outside" are with respect to the cell, and the x-axis shows amino acid position of PFL_0203. FIG. 31B illustrates membrane domain prediction by SACS MEMSAT2 Transmembrane Prediction Page.

FIG. 34A illustrates the alignment of amino acid positions 1-175 relative to PFL_0203. FIG. 34B illustrates the alignment of amino acid positions 176-279 relative to PFL_0203. FIG. 34C illustrates the alignment of amino acid positions 280-357 relative to PFL_0203.

DETAILED DESCRIPTION

Figure 3:
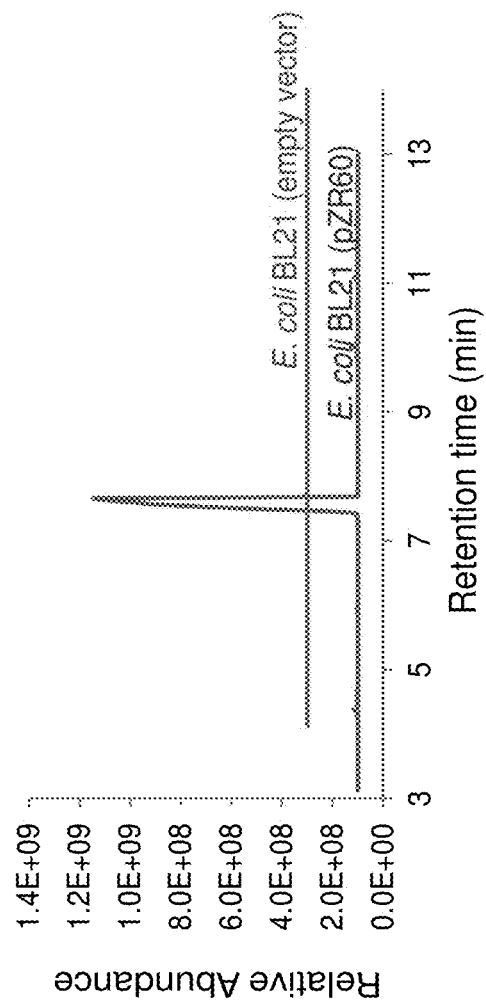
FIG. 3 illustrates the essentiality of PFL_4321 for 1-undecene biosynthesis. *E. coli* BL21 Star (pZR60) expressing PFL_4321 produced ~5 µg/mL 1-undecene, whereas an empty vector control *E. coli* not expressing PFL_4321 did not produce 1-undecene. Headspace GC-MS with extracted ion 55 is shown.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

The present disclosure relates to the biosynthesis of 1-undecene and related terminal olefins. Specifically, the present disclosure relates to methods of using proteins to produce 1-undecene and related terminal olefins.

In particular, the present disclosure is based, at least in part, on Applicant's discovery that an enzyme from *Pseudomonas fluorescens* Pf-5, PFL_4321, converts medium-chain fatty acids (MCFAs, C10-14) into corresponding terminal olefins using an oxygen-activating, non-heme iron dependent mechanism. The X-ray crystal structures of the *Pseudomonas fluorescens* Pf-5 enzyme bound with various substrate analogues show three intermediate stages that define the substrate binding steps and point to a general mechanistic strategy for the non-heme iron enzymes. This enzyme is conserved in pseudomonads and closely-related species with more than 400 homologs identified. Heterologous expressions of several gene homologs in *Escherichia coli* ubiquitously lead to the production and secretion of MCAEs.

Applicants further discovered that the protein PFL_0203 from *Pseduomonas fluorescens* Pf-5 is able to facilitate the conversion of fatty acid substrates into their corresponding terminal olefins. PFL_0203 acts on C10-C16 fatty acid substrates, thus exhibiting some substrate overlap as well as some unique specificity as compared to PFL_4321 as described above. Supplementing culture media with exogenous lauric acid (LA) or co-expressing a codon-optimized UcFatB2 thioesterase with PFL_0203 substantially increased the 1-undecene production titer in *E. coli*. Applicant's findings thus open the road for direct and tailored conversion of renewable raw materials to user-ready fuels and chemical commodities.

Accordingly, Applicant's disclose herein methods of producing a terminal olefin by contacting a fatty acid with a polypeptide that facilitates the production of a terminal olefin from the fatty acid. Various polypeptides, as well as various nucleic acids encoding these polypeptides, for use in the methods of the present disclosure are described herein and will be readily apparent to one of skill in the art in view of the present disclosure. In some embodiments, a polypeptide which facilitates the conversion of a fatty acid into a terminal olefin is expressed in a host cell. In other embodiments, a polypeptide which facilitates the conversion of a fatty acid into a terminal olefin is contacted with a fatty acid in vitro. Various methods of using polypeptides of the present disclosure to produce terminal olefins are described herein and will be readily apparent to one of skill in the art.

Polypeptides of the Disclosure

The present disclosure relates to polypeptides which facilitate the production of terminal olefins using fatty acids as substrates. As used herein, a "polypeptide" is an amino acid sequence including a plurality of consecutive polymerized amino acid residues (e.g., at least about 15 consecutive polymerized amino acid residues). As used herein, "polypeptide" refers to an amino acid sequence, oligopeptide, peptide, protein, or portions thereof, and the terms "polypeptide" and "protein" are used interchangeably.

In some embodiments, a polypeptide for use in the methods of the present disclosure is the polypeptide having the amino acid sequence of SEQ ID NO: 1, which encodes the PFL_4321 protein from *Pseudomonas fluorescens* Pf-5 (also known as *Pseudomonas protegens* Pf-5). PFL_4321 is a protein of 261 amino acids in length that shows modest sequence homology to TenA, the thiaminase II from *Bacillus subtilis* (A. L. Jenkins et al., Bioorg Chem 36, 29, 2008), but the essential catalytic residue cysteine of TenA is missing in PFL_4321.

Sequence alignment of PLF_4321 (SEQ ID NO: 1) and related homologs, as well as protein structural analysis, reveals several regions of conserved sequence motifs that, without wishing to be bound by theory, are thought to contribute to and/or define the active site of the enzyme. Without wishing to be bound by theory, it is thought that the following sequence motif, E101-(L/A/E)-(N/K/R)-H104, is important for enzyme catalytic function. Without wishing to be bound by theory, it is thought that the following sequence motif, (A/P/Q/L)51-X-X-X-(R/A)55-X-(Y/F/V/A)57-(L/F)58-(I/V/A/S)59-(G/N/H/Q)60-(G/F)61-(W/F/Y)62-(P/L)63-(V/I/L)64-V65-(E/A)66-(Q/S/H)67-F68-(A/S/P)69-(L/V/K/S)70-Y71-M72-(A/S/G)73-X-(N/S/A/T)75-L76-(T/L)77-K78, forms an alpha-helix that contributes to the formation of the substrate binding pocket. Without wishing to be bound by theory, it is thought that the following sequence motif, G86-(E/V/D)-(D/T/E/A)-(M/E/K/S)-(A/T/I)-R91-(R/N/D)-(W/Y)-L94-(M/I/L)-(R/Q)-N97-(I/L)-(R/K/G)-V100-E101-(L/E/A)-(N/R/K)-H104-(A/L/V)-X-(Y/W/H)-(W/Y/F)-X-(H/N/D)-W111, forms an alpha-helix that includes two amino acids, E101 and H104, that coordinate to the iron in the catalytic center of the enzyme. Without wishing to be bound by theory, it is thought that the following sequence motif, L147-(I/A/P)-(V/I/E/A)-(A/C/S/G)-(I/M/L/I/V)-A152-A153-(T/S)-N155-(Y/L/W)-A157-(I/V)-E159-(G/W/S)-(A/V/I)-T162-G163-(E/D/V)-W165-(S/T)-(A/I/R), form an alpha-helix that contributes to the formation of the substrate binding pocket, and contains the amino acid residue E159 that may be involved in oxygen binding and/or serve as a proton donor for the regeneration of the enzyme. Without wishing to be bound by theory, it is thought that the following sequence motif, W190-L191-(K/R)-(M/L/A/V)-H194-(A/S)-(Q/H/S/R)-Y197-D198-D199-X-H201-P202-(W/Y/E/V)-E204-A205-(L/M)-(E/D)-(I/L)-(I/V), forms an alpha-helix that includes the amino acid residue H194 that coordinates to the iron in the catalytic center. Without wishing to be bound by theory, it is thought that the following sequence motif, (Y/C/M)235-(M/Y/F)-(Y/E/A/T/H)-(L/M/A)-(F/A/S)-L240-(E/D/S/H)-(R/E/D/C/A)-C243, forms an alpha-helix that contributes to the formation of the substrate binding pocket.

In some embodiments, a polypeptide for use in the methods of the present disclosure is a homolog of the polypeptide having the amino acid sequence of SEQ ID NO: 1. Methods for the identification of polypeptides that are homologs of a polypeptide of interest are well-known to one of skill in the art, as described herein. In some embodiments, polypeptides of the present disclosure include polypeptides containing an amino acid sequence having at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or 100% identity to the amino acid sequence of SEQ ID NO: 1. Polypeptides of the disclosure also include polypeptides having at least 10, at least 12, at least 14, at least 16, at least 18, at least 20, at least 30, at least 40, at least 50, at least 60, at least 70, or at least 80 consecutive amino acids of the amino acid sequence of SEQ ID NO: 1.

Polypeptides that are homologs of SEQ ID NO: 1 may include polypeptides having various amino acid additions, deletions, or substitutions relative to the amino acid sequence of SEQ ID NO: 1. In some embodiments, polypeptides that are homologs of SEQ ID NO: 1 contain non-conservative changes of certain amino acids relative to SEQ ID NO: 1. In some embodiments, polypeptides that are homologs of SEQ ID NO: 1 contain conservative changes of certain amino acids relative to SEQ ID NO: 1, and thus may be referred to as conservatively modified variants. A conservatively modified variant may include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). A modification of an amino acid to produce a chemically similar amino acid may be referred to as an analogous amino acid.

Polypeptides that are homologs of SEQ ID NO: 1 may contain a conservative amino acid substitution at one or more positions corresponding to positions of the amino acid sequence of SEQ ID NO: 1. In some embodiments, the homolog contains a conservative amino acid substitution at a position corresponding to Glu101 of SEQ ID NO: 1. In some embodiments, the homolog contains a conservative amino acid substitution at a position corresponding to His104 of SEQ ID NO: 1. In some embodiments, the homolog contains a conservative amino acid substitution at a position corresponding to Glu159 of SEQ ID NO: 1. In some embodiments, the homolog contains a conservative amino acid substitution at a position corresponding to His194 of SEQ ID NO: 1. The homolog may contain various combinations of one or more conservative amino acid substitutions at a position corresponding to Glu101, His104, Glu159, and His194 of SEQ ID NO: 1. In some embodiments, the homolog contains conservative amino acid substitutions at a position corresponding to all four of Glu101, His104, Glu159, and His194 of SEQ ID NO: 1.

In some embodiments, a homolog of SEQ ID NO: 1 for use in the methods of the present disclosure is the polypeptide having the amino acid sequence of SEQ ID NO: 2, which encodes the Pput_3952 protein from *P. putida* F1. In some embodiments, a homolog of SEQ ID NO: 1 for use in the methods of the present disclosure is the polypeptide having the amino acid sequence of SEQ ID NO: 3, which encodes the PA14_53120 protein from *P. aeruginosa* PA14. In some embodiments, a homolog of SEQ ID NO: 1 for use in the methods of the present disclosure is the polypeptide having the amino acid sequence of SEQ ID NO: 4, which encodes the ACIAD2095 protein from *Acinetobacter baylyi* ADP1. In some embodiments, a homolog of SEQ ID NO: 1 for use in the methods of the present disclosure is the polypeptide having the amino acid sequence of SEQ ID NO: 5, which encodes the PSPTO_1738 protein from *P. syringae* pv. tomato DC3000.

In some embodiments, a polypeptide for use in the methods of the present disclosure is a homolog of the polypeptide having the amino acid sequence of any one of SEQ ID NO: 2, SEQ ID NO: 3, SEQ ID NO: 4, and/or SEQ ID NO: 5. In some embodiments, polypeptides of the present disclosure include polypeptides containing an amino acid sequence having at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or 100% identity to the amino acid sequence of any one of SEQ ID NO: 2, SEQ ID NO: 3, SEQ ID NO: 4, and/or SEQ ID NO: 5. Polypeptides of the disclosure also include polypeptides having at least 10, at least 12, at least 14, at least 16, at least 18, at least 20, at least 30, at least 40, at least 50, at least 60, at least 70, or at least 80 consecutive amino acids of the amino acid sequence of any one of SEQ ID NO: 2, SEQ ID NO: 3, SEQ ID NO: 4, and/or SEQ ID NO: 5.

In other embodiments, a polypeptide for use in the methods of the present disclosure is a polypeptide having the amino acid sequence of any one of SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, and/or SEQ ID NO: 32. In some embodiments, a polypeptide for use in the methods of the present disclosure is a homolog of the polypeptide having the amino acid sequence of any one of SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, and/or SEQ ID NO: 32. In some embodiments, polypeptides of the present disclosure include polypeptides containing an amino acid sequence having at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or 100% identity to the amino acid sequence of any one of SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, and/or SEQ ID NO: 32. Polypeptides of the disclosure also include polypeptides having at least 10, at least 12, at least 14, at least 16, at least 18, at least 20, at least 30, at least 40, at least 50, at least 60, at least 70, or at least 80 consecutive amino acids of the amino acid sequence of any one of SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, and/or SEQ ID NO: 32.

In some embodiments, a polypeptide for use in the methods of the present disclosure includes, for example, a polypeptide having a E-(L/A/E)-(N/K/R)-H motif, which is set forth herein as SEQ ID NO: 33. In some embodiments, a polypeptide for use in the methods of the present disclosure includes, for example, a polypeptide having a (A/P/Q/L)-X-X-X-(R/A)-X-(Y/F/V/A)-(L/F)-(I/V/A/S)-(G/N/H/Q)-(G/F)-(W/F/Y)-(P/L)-(V/I/L)-V-(E/A)-(Q/S/H)-F-(A/S/P)-(L/V/K/S)-Y-M-(A/S/G)-X-(N/S/A/T)-L-(T/L)-K motif, which is set forth herein as SEQ ID NO: 34. In some embodiments, a polypeptide for use in the methods of the present disclosure includes, for example, a polypeptide having a G-(E/V/D)-(D/T/E/A)-(M/E/K/S)-(A/T/I)-R-(R/N/D)-(W/Y)-L-(M/I/L)-(R/Q)-N-(I/L)-(R/K/G)-V-E-(L/E/A)-(N/R/K)-H-(A/L/V)-X-(Y/W/H)-(W/Y/F)-X-(H/N/D)-W motif, which is set forth herein as SEQ ID NO: 35. In some embodiments, a polypeptide for use in the methods of the present disclosure includes, for example, a polypeptide having a L-(I/A/P)-(V/I/E/A)-(A/C/S/G)-(I/M/L/I/V)-A-A-(T/S)-N-(Y/L/W)-A-(I/V)-E-(G/W/S)-(A/V/I)-T-G-(E/D/V)-W-(S/T)-(A/I/R) motif, which is set forth herein as SEQ ID NO: 36. In some embodiments, a polypeptide for use in the methods of the present disclosure includes, for example, a polypeptide having a W-L-(K/R)-(M/L/A/V)-H-(A/S)-(Q/H/S/R)-Y-D-D-X-H-P-(W/Y/E/V)-E-A-(L/M)-(E/D)-(I/L)-(I/V) motif, which is set forth herein as SEQ ID NO: 37. In some embodiments, a polypeptide for use in the methods of the present disclosure includes, for example, a polypeptide having a (Y/C/M)-(M/Y/F)-(Y/E/A/T/H)-(L/M/A)-(F/A/S)-L-(E/D/S/H)-(R/E/D/C/A)-C motif, which is set forth herein as SEQ ID NO: 38. In some embodiments, a polypeptide for use in the methods of the present disclosure includes the amino acid sequence from one or more of any one of the amino acid sequences set forth in SEQ ID NO: 33, SEQ ID NO: 34, SEQ ID NO: 35, SEQ ID NO: 36, SEQ ID NO: 37, and/or SEQ ID NO: 38. In some embodiments, a polypeptide for use in the methods of the present disclosure includes each of the amino acid sequences as set forth in SEQ ID NO: 33, SEQ ID NO: 34, SEQ ID NO: 35, SEQ ID NO: 36, SEQ ID NO: 37, and SEQ ID NO: 38.

Polypeptides having non-heme, iron-dependent activity may also be used in the methods of the present disclosure. Non-heme, iron-dependent proteins may include enzymes that require the presence of iron (Fe) to enhance or facilitate proper catalytic function. Exemplary non-heme, iron-dependent proteins include, for example, PFL_4321 (SEQ ID NO: 1). Suitable non-heme, iron-dependent proteins are those proteins that are capable of facilitating the production of terminal olefins from fatty acid substrates.

In some embodiments, a polypeptide for use in the methods of the present disclosure is the polypeptide having the amino acid sequence of SEQ ID NO: 39, which encodes the PFL_0203 protein from *Pseudomonas fluorescens* Pf-5 (also known as *Pseudomonas protegens* Pf-5). PFL_0203 is annotated as a hypothetical protein, and sequence analysis suggests that this is a membrane-associated protein.

Polypeptides that are homologs of SEQ ID NO: 39 may also be used in the methods and compositions described herein. Polypeptides that are homologs of SEQ ID NO: 39 may include polypeptides having various amino acid additions, deletions, or substitutions relative to the amino acid sequence of SEQ ID NO: 39. In some embodiments, polypeptides that are homologs of SEQ ID NO: 39 contain non-conservative changes of certain amino acids relative to SEQ ID NO: 39. In some embodiments, polypeptides that are homologs of SEQ ID NO: 39 contain conservative changes of certain amino acids relative to SEQ ID NO: 39, and thus may be referred to as conservatively modified variants. In some embodiments, polypeptides of the present disclosure include polypeptides containing an amino acid sequence having at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or 100% identity to the amino acid sequence of any one of SEQ ID NO: 39-SEQ ID NO: 53. Polypeptides of the disclosure also include polypeptides having at least 10, at least 12, at least 14, at least 16, at least 18, at least 20, at least 30, at least 40, at least 50, at least 60, at least 70, or at least 80 consecutive amino acids of the amino acid sequence of any one of SEQ ID NO: 39-SEQ ID NO: 53.

In other embodiments, a polypeptide for use in the methods of the present disclosure is a polypeptide having the amino acid sequence of any one of SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, and/or SEQ ID NO: 53.

In some embodiments, a polypeptide for use in the methods of the present disclosure is a homolog of the polypeptide having the amino acid sequence of any one of SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, and/or SEQ ID NO: 53. In some embodiments, polypeptides of the present disclosure include polypeptides containing an amino acid sequence having at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or 100% identity to the amino acid sequence of any one of SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, and/or SEQ ID NO: 53. Polypeptides of the disclosure also include polypeptides having at least 10, at least 12, at least 14, at least 16, at least 18, at least 20, at least 30, at least 40, at least 50, at least 60, at least 70, or at least 80 consecutive amino acids of the amino acid sequence of any one of SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, and/or SEQ ID NO: 53.

In some embodiments, a polypeptide for use in the methods of the present disclosure is the polypeptide encoded by nucleic acid sequence of SEQ ID NO: 54. SEQ ID NO: 54 encodes a codon-optimized UcFatB2 polypeptide. Without wishing to be bound by theory, it is thought that this protein acts to increase the concentration of intracellular fatty acids in cells.

Polynucleotides Encoding Polypeptides

The present disclosure further relates to polynucleotides that encode polypeptides of the present disclosure. Polynucleotides that encode a polypeptide are also referred to herein as "genes." For example, polynucleotides encoding, for example, any one of the amino acid sequences of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, and/or SEQ ID NO: 53, as well as homologs and/or fragments thereof, as described herein are provided. Methods for determining the relationship between a polypeptide and a polynucleotide that encodes the polypeptide are well-known to one of skill in the art. Similarly, methods of determining the polypeptide sequence encoded by a polynucleotide sequence are well-known to one of skill in the art.

As used herein, the terms "polynucleotide," nucleic acid sequence," "nucleic acid," and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing non-nucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog, and inter-nucleotide modifications. As used herein, the symbols for nucleotides and polynucleotides are those recommended by the IUPAC-IUB Commission of Biochemical Nomenclature.

Sequences of the polynucleotides of the present disclosure may be prepared by various suitable methods known in the art, including, for example, direct chemical synthesis or cloning. For direct chemical synthesis, formation of a polymer of nucleic acids typically involves sequential addition of 3'-blocked and 5'-blocked nucleotide monomers to the terminal 5'-hydroxyl group of a growing nucleotide chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. Such methodology is known to those of ordinary skill in the art and is described in the pertinent texts and literature (e.g., in Matteucci et al., (1980) Tetrahedron Lett 21:719-722; U.S. Pat. Nos. 4,500,707; 5,436,327; and 5,700,637). In addition, the desired sequences may be isolated from natural sources by splitting DNA using appropriate restriction enzymes, separating the fragments using gel electrophoresis, and thereafter, recovering the desired polynucleotide sequence from the gel via techniques known to those of ordinary skill in the art, such as utilization of polymerase chain reactions (PCR; e.g., U.S. Pat. No. 4,683,195).

In some embodiments, polynucleotides encoding polypeptides of the disclosure are recombinant. "Recombinant nucleic acid" or "heterologous nucleic acid" or "recombinant polynucleotide" may refer to a polymer of nucleic acids where the sequence of nucleic acids is foreign to (i.e., not naturally found in) a given host cell, where the sequence may be naturally found in a given host cell, but in an unnatural (e.g., greater than expected) amount; or where the sequence of nucleic acids contains two or more subsequences that are not found in the same relationship to each other in nature. For example, a recombinant nucleic acid sequence may have two or more sequences from unrelated genes arranged to make a new functional nucleic acid. Specifically, the present disclosure describes the introduction of an expression vector into a host cell, where the expression vector contains a nucleic acid sequence coding for a protein that is not normally found in a host cell or contains a nucleic acid coding for a protein that is normally found in a cell but is under the control of different regulatory sequences. With reference to the host cell's genome, then, the nucleic acid sequence that codes for the protein is recombinant. A protein that is referred to as recombinant generally implies that it is encoded by a recombinant nucleic acid sequence in the host cell.

A "recombinant" polypeptide, protein, or enzyme of the present disclosure, is a polypeptide, protein, or enzyme that is encoded by a "recombinant nucleic acid" or "heterologous nucleic acid" or "recombinant polynucleotide."

In some embodiments, the polynucleotides encoding the polypeptides in the host cell may be heterologous to the host cell or these genes may be endogenous to the host cell but are operatively linked to heterologous promoters and/or control regions which result in the higher expression of the gene(s) in the host cell. In certain embodiments, the host cell does not naturally produce the desired proteins, and contains heterologous nucleic acid constructs capable of expressing one or more genes necessary for producing those molecules.

The nucleic acids employed in the methods and compositions described herein may be codon optimized relative to a parental template for expression in a particular host cell. Cells differ in their usage of particular codons, and codon bias corresponds to relative abundance of particular tRNAs in a given cell type. By altering codons in a sequence so that they are tailored to match with the relative abundance of corresponding tRNAs, it is possible to increase expression of a product (e.g. a polypeptide) from a nucleic acid. Similarly, it is possible to decrease expression by deliberately choosing codons corresponding to rare tRNAs. Thus, codon optimization/deoptimization can provide control over nucleic acid expression in a particular cell type (e.g. bacterial cell, mammalian cell, etc.). Methods of codon optimizing a nucleic acid for tailored expression in a particular cell type are well-known to those of skill in the art.

Methods of Identifying Sequence Similarity

As described above, various polypeptides having similar sequences to the polypeptides used in the methods and compositions of the present disclosure may also be used herein. Various methods are known to those of skill in the art for identifying similar (e.g. homologs, orthologs, paralogs, etc.) polypeptide and/or polynucleotide sequences, including phylogenetic methods, sequence similarity analysis, and hybridization methods.

Phylogenetic trees may be created for a gene family by using a program such as CLUSTAL (Thompson et al. Nucleic Acids Res. 22: 4673-4680 (1994); Higgins et al. *Methods Enzymol* 266: 383-402 (1996)) or MEGA (Tamura et al. *Mol. Biol. & Evo.* 24:1596-1599 (2007)). Once an initial tree for genes from one species is created, potential orthologous sequences can be placed in the phylogenetic tree and their relationships to genes from the species of interest can be determined. Evolutionary relationships may also be inferred using the Neighbor-Joining method (Saitou and Nei, *Mol. Biol. & Evo.* 4:406-425 (1987)). Homologous sequences may also be identified by a reciprocal BLAST strategy. Evolutionary distances may be computed using the Poisson correction method (Zuckerkandl and Pauling, pp. 97-166 in *Evolving Genes and Proteins*, edited by V. Bryson and H. J. Vogel. Academic Press, New York (1965)).

In addition, evolutionary information may be used to predict gene function. Functional predictions of genes can be greatly improved by focusing on how genes became similar in sequence (i.e. by evolutionary processes) rather than on the sequence similarity itself (Eisen, *Genome Res.* 8: 163-167 (1998)). Many specific examples exist in which gene function has been shown to correlate well with gene phylogeny (Eisen, *Genome Res.* 8: 163-167 (1998)).

When a group of related sequences are analyzed using a phylogenetic program such as CLUSTAL, closely related sequences typically cluster together or in the same clade (a group of similar genes). Groups of similar genes can also be identified with pair-wise BLAST analysis (Feng and Doolittle, *J. Mol. Evol.* 25: 351-360 (1987)). Analysis of groups of similar genes with similar function that fall within one clade can yield sub-sequences that are particular to the clade. These sub-sequences, known as consensus sequences, can not only be used to define the sequences within each clade, but define the functions of these genes; genes within a clade may contain paralogous sequences, or orthologous sequences that share the same function (see also, for example, Mount, Bioinformatics: Sequence and Genome Analysis Cold Spring Harbor Laboratory Press, Cold Spring Harbor, N.Y., page 543 (2001)).

To find sequences that are homologous to a reference sequence, BLAST nucleotide searches can be performed with the BLASTN program, score=100, wordlength=12, to obtain nucleotide sequences homologous to a nucleotide sequence encoding a protein of the disclosure. BLAST protein searches can be performed with the BLASTX program, score=50, wordlength=3, to obtain amino acid sequences homologous to a protein or polypeptide of the disclosure. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, or PSI-BLAST, the default parameters of the respective programs (e.g., BLASTN for nucleotide sequences, BLASTX for proteins) can be used.

Methods for the alignment of sequences and for the analysis of similarity and identity of polypeptide and polynucleotide sequences are well-known in the art.

As used herein "sequence identity" refers to the percentage of residues that are identical in the same positions in the sequences being analyzed. As used herein "sequence similarity" refers to the percentage of residues that have similar biophysical/biochemical characteristics in the same positions (e.g. charge, size, hydrophobicity) in the sequences being analyzed.

Methods of alignment of sequences for comparison are well-known in the art, including manual alignment and computer assisted sequence alignment and analysis. This latter approach is a preferred approach in the present disclosure, due to the increased throughput afforded by computer assisted methods. As noted below, a variety of computer programs for performing sequence alignment are available, or can be produced by one of skill.

The determination of percent sequence identity and/or similarity between any two sequences can be accomplished using a mathematical algorithm. Examples of such mathematical algorithms are the algorithm of Myers and Miller, CABIOS 4:11-17 (1988); the local homology algorithm of Smith et al., Adv. Appl. Math. 2:482 (1981); the homology alignment algorithm of Needleman and Wunsch, *J. Mol. Biol.* 48:443-453 (1970); the search-for-similarity-method of Pearson and Lipman, *Proc. Natl. Acad. Sci.* 85:2444-2448 (1988); the algorithm of Karlin and Altschul, *Proc. Natl. Acad. Sci. USA* 87:2264-2268 (1990), modified as in Karlin and Altschul, *Proc. Natl. Acad. Sci. USA* 90:5873-5877 (1993).

Computer implementations of these mathematical algorithms can be utilized for comparison of sequences to determine sequence identity and/or similarity. Such implementations include, for example: CLUSTAL in the PC/Gene program (available from Intelligenetics, Mountain View, Calif.); the AlignX program, version10.3.0 (Invitrogen, Carlsbad, Calif.) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. *Gene* 73:237-244 (1988); Higgins et al. *CABIOS* 5:151-153 (1989); Corpet et al., *Nucleic Acids Res.* 16:10881-90 (1988); Huang et al. *CABIOS* 8:155-65 (1992); and Pearson et al., *Meth. Mol. Biol.* 24:307-331 (1994). The BLAST programs of Altschul et al. *J. Mol. Biol.* 215:403-410 (1990) are based on the algorithm of Karlin and Altschul (1990) supra.

Polynucleotides homologous to a reference sequence can be identified by hybridization to each other under stringent or under highly stringent conditions. Single stranded polynucleotides hybridize when they associate based on a variety of well characterized physical-chemical forces, such as hydrogen bonding, solvent exclusion, base stacking and the like. The stringency of a hybridization reflects the degree of sequence identity of the nucleic acids involved, such that the higher the stringency, the more similar are the two polynucleotide strands. Stringency is influenced by a variety of factors, including temperature, salt concentration and composition, organic and non-organic additives, solvents, etc. present in both the hybridization and wash solutions and incubations (and number thereof), as described in more detail in references cited below (e.g., Sambrook et al., Molecular Cloning: A Laboratory Manual, 2nd Ed., Vol. 1-3, Cold Spring Harbor Laboratory, Cold Spring Harbor, N.Y. ("Sambrook") (1989); Berger and Kimmel, Guide to Molecular Cloning Techniques, Methods in Enzymology, vol. 152 Academic Press, Inc., San Diego, Calif. ("Berger and Kimmel") (1987); and Anderson and Young, "Quantitative Filter Hybridisation." In: Hames and Higgins, ed., Nucleic Acid Hybridisation, A Practical Approach. Oxford, TRL Press, 73-111 (1985)).

Encompassed by the disclosure are polynucleotide sequences that are capable of hybridizing to the disclosed polynucleotide sequences and fragments thereof under various conditions of stringency (see, for example, Wahl and Berger, *Methods Enzymol.* 152: 399-407 (1987); and Kimmel, *Methods Enzymo.* 152: 507-511, (1987)). Full length cDNA, homologs, orthologs, and paralogs of polynucleotides of the present disclosure may be identified and isolated using well-known polynucleotide hybridization methods.

With regard to hybridization, conditions that are highly stringent, and means for achieving them, are well known in the art. See, for example, Sambrook et al. (1989) (supra); Berger and Kimmel (1987) pp. 467-469 (supra); and Anderson and Young (1985)(supra).

Hybridization experiments are generally conducted in a buffer of pH between 6.8 to 7.4, although the rate of hybridization is nearly independent of pH at ionic strengths likely to be used in the hybridization buffer (Anderson and Young (1985)(supra)). In addition, one or more of the following may be used to reduce non-specific hybridization: sonicated salmon sperm DNA or another non-complementary DNA, bovine serum albumin, sodium pyrophosphate, sodium dodecylsulfate (SDS), polyvinyl-pyrrolidone, ficoll and Denhardt's solution. Dextran sulfate and polyethylene glycol 6000 act to exclude DNA from solution, thus raising the effective probe DNA concentration and the hybridization signal within a given unit of time. In some instances, conditions of even greater stringency may be desirable or required to reduce non-specific and/or background hybridization. These conditions may be created with the use of higher temperature, lower ionic strength and higher concentration of a denaturing agent such as formamide.

Stringency conditions can be adjusted to screen for moderately similar fragments such as homologous sequences from distantly related organisms, or to highly similar fragments such as genes that duplicate functional enzymes from closely related organisms. The stringency can be adjusted either during the hybridization step or in the post-hybridization washes. Salt concentration, formamide concentration, hybridization temperature and probe lengths are variables that can be used to alter stringency. As a general guideline, high stringency is typically performed at $T_m-5°$ C. to $T_m-20°$ C., moderate stringency at $T_m-20°$ C. to $T_m-35°$ C. and low stringency at $T_m-35°$ C. to $T_m-50°$ C. for duplex >150 base pairs. Hybridization may be performed at low to moderate stringency (25-50° C. below $T_m$), followed by post-hybridization washes at increasing stringencies. Maximum rates of hybridization in solution are determined empirically to occur at $T_m-25°$ C. for DNA-DNA duplex and $T_m-15°$ C. for RNA-DNA duplex. Optionally, the degree of dissociation may be assessed after each wash step to determine the need for subsequent, higher stringency wash steps.

High stringency conditions may be used to select for nucleic acid sequences with high degrees of identity to the disclosed sequences. An example of stringent hybridization conditions obtained in a filter-based method such as a Southern or northern blot for hybridization of complementary nucleic acids that have more than 100 complementary residues is about 5° C. to 20° C. lower than the thermal melting point ($T_m$) for the specific sequence at a defined ionic strength and pH.

Hybridization and wash conditions that may be used to bind and remove polynucleotides with less than the desired homology to the nucleic acid sequences or their complements that encode the present polypeptides include, for example: 6×SSC and 1% SDS at 65° C.; 50% formamide, 4×SSC at 42° C.; 0.5×SSC to 2.0×SSC, 0.1% SDS at 50° C. to 65° C.; or 0.1×SSC to 2×SSC, 0.1% SDS at 50° C.-65° C.; with a first wash step of, for example, 10 minutes at about 42° C. with about 20% (v/v) formamide in 0.1×SSC, and with, for example, a subsequent wash step with 0.2×SSC and 0.1% SDS at 65° C. for 10, 20 or 30 minutes.

For identification of less closely related homologs, wash steps may be performed at a lower temperature, e.g., 50° C. An example of a low stringency wash step employs a solution and conditions of at least 25° C. in 30 mM NaCl, 3 mM trisodium citrate, and 0.1% SDS over 30 min. Greater stringency may be obtained at 42° C. in 15 mM NaCl, with 1.5 mM trisodium citrate, and 0.1% SDS over 30 min. Wash procedures will generally employ at least two final wash steps. Additional variations on these conditions will be readily apparent to those skilled in the art (see, for example, US Patent Application No. 20010010913).

If desired, one may employ wash steps of even greater stringency, including conditions of 65° C.-68° C. in a solution of 15 mM NaCl, 1.5 mM trisodium citrate, and 0.1% SDS, or about 0.2×SSC, 0.1% SDS at 65° C. and washing twice, each wash step of 10, 20 or 30 min in duration, or about 0.1×SSC, 0.1% SDS at 65° C. and washing twice for 10, 20 or 30 min. Hybridization stringency may be increased further by using the same conditions as in the hybridization steps, with the wash temperature raised about 3° C. to about 5° C., and stringency may be increased even further by using the same conditions except the wash temperature is raised about 6° C. to about 9° C.

Polynucleotide probes may be prepared with any suitable label, including a fluorescent label, a colorimetric label, a radioactive label, or the like. Labeled hybridization probes for detecting related polynucleotide sequences may be produced, for example, by oligolabeling, nick translation, end-labeling, or PCR amplification using a labeled nucleotide.
Vectors for Delivering and Expressing Polypeptides of the Disclosure Each polynucleotide of the present disclosure may be incorporated into an expression vector. "Expression vector" or "vector" refers to a compound and/or composition that transduces, transforms, or infects a host cell, thereby causing the cell to express polynucleotides and/or proteins other than those native to the cell, or in a manner not native to the cell. An "expression vector" contains a sequence of polynucleotides (ordinarily RNA or DNA) to be expressed by the host cell. Optionally, the expression vector also includes materials to aid in achieving entry of the polynucleotide into the host cell, such as a virus, liposome, protein coating, or the like. The expression vectors contemplated for use in the present disclosure include those into which a polynucleotide sequence can be inserted, along with any preferred or required operational elements. Further, the expression vector must be one that can be transferred into a host cell and replicated therein. Preferred expression vectors are plasmids, particularly those with restriction sites that have been well-documented and that contain the operational elements preferred or required for transcription of the polynucleotide sequence. Such plasmids, as well as other expression vectors, are well-known in the art.

Incorporation of the individual polynucleotides may be accomplished through known methods that include, for example, the use of restriction enzymes (such as BamHI, EcoRI, HhaI, XhoI, XmaI, and so forth) to cleave specific sites in the expression vector, e.g., plasmid. The restriction enzyme produces single stranded ends that may be annealed to a polynucleotide having, or synthesized to have, a terminus with a sequence complementary to the ends of the cleaved expression vector. Annealing is performed using an appropriate enzyme, e.g., DNA ligase. As will be appreciated by those of ordinary skill in the art, both the expression vector and the desired polynucleotide are often cleaved with the same restriction enzyme, thereby assuring that the ends of the expression vector and the ends of the polynucleotide are complementary to each other. In addition, DNA linkers may be used to facilitate linking of polynucleotide sequences into an expression vector.

A series of individual polynucleotides can also be combined by utilizing methods that are known in the art (e.g., U.S. Pat. No. 4,683,195). For example, each of the desired polynucleotides can be initially generated in a separate PCR. Thereafter, specific primers are designed such that the ends of the PCR products contain complementary sequences. When the PCR products are mixed, denatured, and reannealed, the strands having the matching sequences at their 3' ends overlap and can act as primers for each other. Extension of this overlap by DNA polymerase produces a molecule in which the original sequences are "spliced" together. In this way, a series of individual polynucleotides may be "spliced" together and subsequently transduced into a host cell simultaneously. Thus, expression of each of the plurality of polynucleotides is affected.

Individual polynucleotides, or "spliced" polynucleotides, are then incorporated into an expression vector. The present disclosure is not limited with respect to the process by which the polynucleotide is incorporated into the expression vector. Those of ordinary skill in the art are familiar with the necessary steps for incorporating a polynucleotide into an expression vector. A typical expression vector contains the desired polynucleotide preceded by one or more regulatory regions, along with a ribosome binding site, e.g., a nucleotide sequence that is 3-9 nucleotides in length and located 3-11 nucleotides upstream of the initiation codon in E. coli. See Shine and Dalgarno (1975) Nature 254(5495):34-38 and Steitz (1979) Biological Regulation and Development (ed. Goldberger, R. F.), 1:349-399 (Plenum, New York).

The term "operably linked" as used herein refers to a configuration in which a control sequence is placed at an appropriate position relative to the coding sequence of the DNA sequence or polynucleotide such that the control sequence directs the expression of a polypeptide.

Regulatory regions include, for example, those regions that contain a promoter and an operator. A promoter is operably linked to the desired polynucleotide, thereby initiating transcription of the polynucleotide via an RNA polymerase enzyme. An operator is a sequence of polynucleotides adjacent to the promoter, which contains a protein-binding domain where a repressor protein can bind. In the absence of a repressor protein, transcription initiates through the promoter. When present, the repressor protein specific to the protein-binding domain of the operator binds to the operator, thereby inhibiting transcription. In this way, control of transcription is accomplished, based upon the particular regulatory regions used and the presence or absence of the corresponding repressor protein. Examples include lactose promoters (LacI repressor protein changes conformation when contacted with lactose, thereby preventing the LacI repressor protein from binding to the operator) and tryptophan promoters (when complexed with tryptophan, TrpR repressor protein has a conformation that binds the operator; in the absence of tryptophan, the TrpR repressor protein has a conformation that does not bind to the operator). Another example is the tac promoter (see de Boer et al., (1983) Proc Natl Acad Sci USA 80(1):21-25).

Methods of producing host cells of the disclosure may include the introduction or transfer of the expression vectors containing recombinant nucleic acids of the disclosure into the host cell. Such methods for transferring expression vectors into host cells are well-known to those of ordinary skill in the art. For example, one method for transforming cells with an expression vector involves a calcium chloride treatment where the expression vector is introduced via a calcium precipitate. Other salts, e.g., calcium phosphate, may also be used following a similar procedure. In addition, electroporation (i.e., the application of current to increase the permeability of cells to nucleic acid sequences) may be used to transfect the host cell. Cells also may be transformed through the use of spheroplasts (Schweizer, M, Proc. Natl. Acad. Sci., 78: 5086-5090 (1981). Also, microinjection of the nucleic acid sequences provides the ability to transfect host cells. Other means, such as lipid complexes, liposomes, and dendrimers, may also be employed. Those of ordinary skill in the art can transfect a host cell with a desired sequence using these or other methods.

In some cases, cells are prepared as protoplasts or spheroplasts prior to transformation. Protoplasts or spheroplasts may be prepared, for example, by treating a cell having a cell wall with enzymes to degrade the cell wall. Fungal cells may be treated, for example, with chitinase.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host, is integrated into the genome and replicated together with the chromosome(s) into which it has been integrated. Furthermore, a single vector or plasmid or two or more vectors or plasmids that together contain the total DNA to be introduced into the genome of the host, or a transposon may be used.

The vectors preferably contain one or more selectable markers which permit easy selection of transformed host cells. A selectable marker is a gene the product of which provides, for example, biocide or viral resistance, resistance to heavy metals, prototrophy to auxotrophs, and the like. Selection of bacterial cells may be based upon antimicrobial resistance that has been conferred by genes such as the amp, gpt, neo, and hyg genes.

Selectable markers for use in fungal host cells may include, for example, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Suitable markers for *S. cerevisiae* hosts are, for example, ADE2, HIS3, LEU2, LYS2, MET3, TRP1, and URA3.

The vectors may contain an element(s) that permits integration of the vector into the host's genome or autonomous replication of the vector in the cell independent of the genome.

For integration into the host genome, the vector may rely on the gene's sequence or any other element of the vector for integration of the vector into the genome by homologous or nonhomologous recombination. Alternatively, the vector may contain additional nucleotide sequences for directing integration by homologous recombination into the genome of the host. The additional nucleotide sequences enable the vector to be integrated into the host genome at a precise location(s) in the chromosome(s). To increase the likelihood of integration at a precise location, the integrational elements should contain a sufficient number of nucleic acids, such as 100 to 10,000 base pairs, 400 to 10,000 base pairs, or 800 to 10,000 base pairs, which are highly homologous with the corresponding target sequence to enhance the probability of homologous recombination. The integrational elements may be any sequence that is homologous with the target sequence in the genome of the host. Furthermore, the integrational elements may be non-encoding or encoding nucleotide sequences. On the other hand, the vector may be integrated into the genome of the host by non-homologous recombination.

For autonomous replication, the vector may further contain an origin of replication enabling the vector to replicate autonomously in the host in question. The origin of replication may be any plasmid replicator mediating autonomous replication which functions in a cell. The term "origin of replication" or "plasmid replicator" is defined herein as a sequence that enables a plasmid or vector to replicate in vivo.

Various promoters for regulation of expression of a recombinant nucleic acid of the disclosure in a vector are well-known in the art and include, for example, constitutive promoters and inducible promoters. Promoters are described, for example, in Sambrook, et al. Molecular Cloning: A Laboratory Manual, 3rd edition, Cold Spring Harbor Laboratory Press, (2001). Promoter can be viral, bacterial, fungal, mammalian, or plant promoters. Additionally, promoters can be constitutive promoters, inducible promoters, environmentally regulated promoters, or developmentally regulated promoters. Examples of suitable promoters for regulating recombinant nucleic acid of the disclosure are well-known in the art. In some embodiments, expression of a recombinant polypeptide of the disclosure is under the control of a heterologous promoter. In some preferred embodiments, the promoter is a T7 promoter or a variation thereof.

More than one copy of a gene may be inserted into the host to increase production of the gene product. An increase in the copy number of the gene can be obtained by integrating at least one additional copy of the gene into the host genome or by including an amplifiable selectable marker gene with the nucleotide sequence where cells containing amplified copies of the selectable marker gene, and thereby additional copies of the gene, can be selected for by cultivating the cells in the presence of the appropriate selectable agent.

The procedures used to ligate the elements described above to construct the recombinant expression vectors of the present disclosure are well-known to one skilled in the art (see, e.g., Sambrook et al., 1989, supra). When only a single expression vector is used (without the addition of an intermediate), the vector will contain all of the nucleic acid sequences necessary.

Once a polypeptide of the present disclosure is expressed and produced in a host cell, the polypeptide may be purified to produce a substantially isolated polypeptide. Methods of isolation and purification of proteins are well-known in the art and are described herein. For example, recombinant polypeptides containing an affinity tag may be affinity purified from the host cell to yield an isolated polypeptide. Isolated polypeptides of the present disclosure may be used, for example, in various in vitro assays according to the methods of the present disclosure.

An expression vector which is configured to produce a polypeptide of the present disclosure may produce the polypeptide without the use of a host cell. For example, an in vitro transcription and in vitro translation system may be used to produce the polypeptide using the expression vector. The expression vector is preferably linearized prior to in vitro transcription. Methods of in vitro transcription and translation are well-known in the art, as are methods of purifying translated proteins from such in vitro systems.

Host Cells of the Disclosure

Host cells of the present disclosure are capable of producing a terminal olefin from a fatty acid substrate. Host cells of the disclosure produce a polypeptide of the disclosure and may be cultured under conditions such that the polypeptide facilitates the production of a terminal olefin from a fatty acid.

"Host cell" may refer to a living biological cell that can be manipulated to alter, for example, the activity of one or more polypeptides in the cell. For example, host cells may be transformed via insertion of recombinant DNA or RNA. Such recombinant DNA or RNA can be in an expression vector. Further, host cells may be subject to mutagenesis to induce mutations in polypeptide-encoding polynucleotides. Host cells that have been genetically modified are recombinant host cells.

The host cells of the present disclosure may be genetically modified. For example, recombinant nucleic acids may have been introduced into the host cells or the host cells may have mutations introduced into endogenous and/or exogenous polynucleotides, and as such the genetically modified host cells do not occur in nature. A suitable host cell may be, for example, one that is capable of expressing one or more nucleic acid constructs for different functions such as, for example, recombinant protein expression.

In some embodiments, host cells contain a recombinant nucleic acid of the present disclosure. In some embodiments, host cells of the present disclosure contain a recombinant nucleic acid encoding SEQ ID NO: 1. In some embodiments, host cells of the present disclosure contain a recombinant nucleic acid encoding a homolog or fragment of SEQ ID NO: 1 such as, for example, any one of SEQ ID NO: 2, SEQ ID NO: 3, SEQ ID NO: 4, SEQ ID NO: 5, and/or any one of SEQ ID NO: 6-SEQ ID NO: 32. When the recombinant nucleotide is expressed in the host to produce a polypeptide such as, for example, the polypeptide encoded by SEQ ID NO: 1, the recombinant polypeptide may facilitate the production of terminal olefins from fatty acids when the host cell has been contacted with a fatty acid.

In some embodiments, host cells of the present disclosure contain a recombinant nucleic acid encoding SEQ ID NO: 39, or a homolog thereof (e.g. any one of SEQ ID NO: 40-SEQ ID NO: 53). In some embodiments, host cells of the present disclosure contain a recombinant nucleic acid encoding SEQ ID NO: 1, or a homolog thereof (e.g. any one of SEQ ID NO: 2-SEQ ID NO: 32), and a recombinant nucleic acid encoding SEQ ID NO: 39, or a homolog thereof (e.g. any one of SEQ ID NO: 40-SEQ ID NO: 53). In some embodiments, host cells of the present disclosure contain a recombinant nucleic acid encoding a protein including the amino acid sequence of any one of SEQ ID NO: 33-38, and a recombinant nucleic acid encoding SEQ ID NO: 39, or a homolog thereof (e.g. any one of SEQ ID NO: 40-SEQ ID NO: 53).

Source of Host Cells

Host cells of the present disclosure may include or be derived from a variety of sources readily apparent to those skilled in the art. Host cells of the present disclosure may be prokaryotic such as, for example, an organism from the kingdom Eubacteria, which includes species of bacteria. In some embodiments, a prokaryotic host cell may include, for example, a cell from the bacterium *E. coli* (Dien, B. S. et al., 2003; Yomano, L. P. et al., 1998; Moniruzzaman et al., 1996), *Bacillus subtilis* (Susana Romero et al., 2007), *Zymomonas mobilis* (B. S. Dien et al., 2003; Weuster Botz, 1993; Alterthum and Ingram, 1989), *Thermoanaerobacterium saccharolyticum* (Marietta Smith, 2009), or *Klebsiella oxytoca* (Dien, B. S. et al., 2003; Zhou et al., 2001; Brooks and Ingram, 1995). In other embodiments, the prokaryotic host cells are *Carboxydocella* sp. (Dominik et al., 2007), *Corynebacterium glutamicum* (Masayuki Inui, et al., 2004), Enterobacteriaceae (Ingram et al., 1995), *Erwinia chrysanthemi* (Zhou and Ingram, 2000; Zhou et al., 2001), *Lactobacillus* sp. (McCaskey, T. A., et al., 1994), *Pediococcus acidilactici* (Zhou, S. et al., 2003), *Rhodopseudomonas capsulata* (X. Y. Shi et al., 2004), *Streptococcus lactis* (J. C. Tang et al., 1988), *Vibrio furnissii* (L. P. Wackett, 2010), *Vibrio furnissii* M1 (Park et al., 2001), *Caldicellulosiruptor saccharolyticus* (Z. Kadar et al., 2004), or *Xanthomonas campestris* (S. T. Yang et al., 1987). In other embodiments, the host cells are cyanobacteria. Additional examples of bacterial host cells may include, for example, those species assigned to the *Escherichia, Enterobacter, Azotobacter, Erwinia, Bacillus, Pseudomonas, Klebsiella, Proteus, Salmonella, Serratia, Shigella, Rhizobia, Vitreoscilla, Synechococcus, Synechocystis*, and *Paracoccus* taxonomical classes.

Host cells of the present disclosure may also be eukaryotic and may include, for example, fungal, plant, insect and mammalian cells. In some embodiments, the host cell is from a fungal strain. Fungi may include, for example, the phyla Ascomycota, Basidiomycota, Chytridiomycota, and Zygomycota as well as the Oomycota and all mitosporic fungi. In some embodiments, the host cell is from yeast such as, for example, *Saccharomyces cerevisiae*.

In other embodiments, the host cell is from yeast such as, for example, a *Candida, Hansenula, Issatchenkia, Kluyveromyces, Pichia, Saccharomyces, Schizosaccharomyces,* or *Yarrowia* strain. In other embodiments, the yeast host is a *Saccharomyces carlsbergensis* (Todkar, 2010), *Saccharomyces cerevisiae* (Duarte et al., 2009), *Saccharomyces diastaticus, Saccharomyces douglasii, Saccharomyces kluyveri, Saccharomyces norbensis, Saccharomyces monacensis* (GB-Analysts Reports, 2008), *Saccharomyces bayanus* (Kristen Publicover, 2010), *Saccharomyces pastorianus* (Nakao et al., 2007), *Saccharomyces pombe* (Mousdale, 2008), or *Saccharomyces oviformis* strain. In yet other embodiments, the yeast host is *Kluyveromyces lactis* (O. W. Merten, 2001), *Kluyveromyces fragilis* (Pestal et al., 2006; Siso, 1996), *Kluyveromyces marxiamus* (K. Kourkoutas et al., 2008), *Pichia stipitis* (Almeida et al., 2008), *Candida shehatae* (Ayhan Demirbas, 2003), or *Candida tropicalis* (Jamai et al., 2006). In other embodiments, the yeast host may be *Yarrowia lipolytica* (Biryukova E. N., 2009), Brettanomyces custersii (Spindler D. D. et al., 1992), or *Zygosaccharomyces roux* (Chaabane et al., 2006).

In some embodiments, the host cell may be, for example, any one of *Acinetobacter baumannii, A. baumannii, A. baumannii, Acinetobacter haemolyticus* ATCC 19194, *A. haemolyticus, Acinetobacter baylyi, A. baylyi, Burkholderia mallei, B. mallei* ATCC 23344, *B. mallei* PRL-20, *Burkholderia pseudomallei* K96243, *Burkholderia pseudomallei, Burkholderia pseudomallei* 406e, *Burkholderia thailandensis* E264, *B. thailandensis* MSMB121, *B. thailandensis* MSMB43, *Myxococcus xanthus* DK 1622, *Myxococcus fulvus* HW-1, *Myxococcus stipitatus* DSM 14675, *Pseudomonas aeruginosa* PA-14, *P. aeruginosa* PAO1, *P. aeruginosa* M18, *Pseudomonas putida* F1, *P. putida* KT2440, *P. putida* S16, *Pseudomonas fluorescens* Pf-5, *P. fluorescens* Pf0-1, *P. fluorescens* F113, *Pseudomonas syringae* Cit7, *Pseudomonas syringae* pv. *phaseolicola* 1448A, *Pseudomonas syringae* pv. tomato DC3000, and *Pseudomonas syringae* pv. *syringae* B728.

Host cells of the present disclosure may also include, for example, host cells that produce excess quantities of free fatty acids. Host cells of the present disclosure that produce excess quantities of free fatty acids may be modified to produce excess quantities of free fatty acids as compared to a corresponding unmodified host cell. The modification may be, for example, genetic modification. Where the modification is a genetic modification, a corresponding unmodified host cell may be, for example, a host cell that lacks the same genetic modification facilitating the production of excess quantities of free fatty acids in the modified host cell.

Host cells that produce excess quantities of free fatty acids, as well as methods of making such host cells, are known in the art. In some embodiments, beta-oxidation has been eliminated in the host cell, which leads to reduced utilization of fatty acids. Elimination of beta-oxidation in a host cell such as, for example, *E. coli*, may be accomplished via a ΔfadD deletion, or deletion of a homolog of fadD. In some embodiments, the host cell is engineered to encourage production of fatty acids from precursors. This may be accomplished, for example, by the overexpression of one or more thioesterases such as, for example, TesA' and FatB1, from *Cinnamomum camphorum*. In some embodiments, the host cell is engineered to encourage production of malonyl-coA, which is involved in elongating fatty acid chains. This may be accomplished, for example, by the overexpression of an acetyl-coA carboxylase (ACC) such as, for example, acetyl-coA carboxylase (ACC) from *E. coli*. In some embodiments, the host cell is engineered to limit the fatty acid yield to shorter chain fatty acids in the C12-C14 range.

This may be accomplished, for example, by the overexpression of the thioesterase from *Umbellularia californica* (UcTE) (Lennen et al., Trends in Cell Biology 30:12, pp. 659-667, 2012). In some embodiments, the host cell is engineered for reverse beta-oxidation. Host cells such as, for example, *E. coli*, may be engineered for reverse beta-oxidation by, for example, reducing or eliminating the activity of the fadR, atoC(c), crp, arcA, adhE, pta, frdA, fucO, yqhD, and fadD genes or homologs thereof, as well as overexpressing FadBA and at least one thioesterase from the group including TesA TesB, FadM, and YciA, or homologs thereof. The particular thioesterase overexpressed may impact the chain length distribution of the final products (Dellomonaco et al., Nature 475, pp. 355-359, 2011). In some embodiments, host cells of the present disclosure overexpress a FatB2 protein from *Umbellularia californica*, which may be codon-optomized (e.g. UcFatB2 encoded by SEQ ID NO: 54).

Various other host cells that produce excess quantities of free fatty acids are known in the art. For example, the *E. coli* strains S001-pJT208, 5002-pJT208, GAS2-strains, and fadD-deleted GAS2 strains are exemplary organisms that produce excess quantities of free fatty acids (Torella, J. P et al., PNAS, 2013; Choi, Y J et al., Nature, 2013). Additional examples of host cells that produce excess quantities of free fatty acids, as well as methods of producing such host cells, will be apparent to one of skill in the art.

Exemplary fatty acid accumulating organisms that are suitable as a source of host cells include *Rhodococcus* (such as *Rhodococcus* sp. PD600), oleaginous yeast, *Pseudomonas putida* (such as *P. putida* F1 and *P. putida* KT2440), and *Pseudomonas fluorescens* (such as *P. fluorescens* Pf-5 and *P. fluorescens* Pf0-1).

Additional host cells suitable for use in the methods of the present disclosure will be readily apparent to one of skill in the art in view of the present disclosure.

Methods of Producing Terminal Olefins

The methods of the present disclosure relate to the use of polypeptides which facilitate the production of terminal olefins from fatty acids as substrates. In some embodiments, a polypeptide which facilitates the conversion of a fatty acid into a terminal olefin is expressed in a host cell. In other embodiments, a polypeptide which facilitates the conversion of a fatty acid into a terminal olefin is contacted with a fatty acid in vitro.

Conditions for Host Cells

In some embodiments, the methods of the present disclosure include contacting a host cell containing a recombinant polypeptide of the disclosure such as, for example, SEQ ID NO: 1 and/or SEQ ID NO: 39, or homologs thereof, with a fatty acid, and culturing the host cell under conditions such that a terminal olefin is produced from the fatty acid.

Standard methods of culturing organisms such as, for example, bacteria and yeast, are well-known in the art and are described herein. For example, host cells may be cultured in a standard growth media under standard temperature and pressure conditions, and in an aerobic environment. Standard growth media for various host cells are commercially available and well-known in the art, as are standard conditions for growing various host cells. Suitable conditions for facilitating the production of terminal olefins from fatty acids by host cells are described herein and will be readily apparent to one of skill in the art in view of the present disclosure. In an exemplary embodiment, *E. coli* cells transformed to express and produce SEQ ID NO: 1 may be cultured in LB medium at 37° C. in the presence of a fatty acid to produce a terminal olefin.

In some embodiments, various compounds and/or reagents may be added to the growth medium of a host cell that produces a recombinant polypeptide of the disclosure to enhance or facilitate the production of terminal olefins from fatty acids. In some embodiments, the culture medium may be supplemented with iron (Fe) or a source of iron. In some embodiments, the culture medium may be supplemented with ascorbic acid. The culture media may be supplemented with combinations of various compounds and/or reagents, such as, for example, a source of iron, ascorbic acid, and/or cysteine.

In Vitro Assays

In some embodiments, the methods of the present disclosure include contacting a fatty acid with a recombinant polypeptide of the disclosure such as, for example, SEQ ID NO: 1 or homologs thereof, and/or SEQ ID NO: 39 or homologs thereof, and incubating the fatty acid under conditions such that a terminal olefin is produced from the fatty acid.

Standard methods of performing in vitro enzymatic assays are well-known in the art and are described herein. In an exemplary embodiment, a polypeptide of the present disclosure is expressed in a host cell and substantially purified. The substantially purified polypeptide may be added to an in vitro assay platform, such, for example, as a well of a 96-well plate, where the well contains a fatty acid, such as lauric acid. The purified polypeptide and the fatty acid may be incubated together for a period of time to allow production of a terminal olefin from the fatty acid.

In some embodiments, various compounds and/or reagents may be added to the in vitro platform containing a polypeptide of the disclosure and a fatty acid to enhance or facilitate the production of terminal olefins from fatty acids. In some embodiments, the platform may be supplemented with iron (Fe) or a source of iron. In some embodiments, the platform may be supplemented with ascorbic acid. The platform may be supplemented with combinations of various compounds and/or reagents, such as, for example, a source of iron, ascorbic acid, and/or cysteine.

Fatty Acids

The methods of the present disclosure relate to conversion of fatty acids into terminal olefins by polypeptides. Fatty acids may be endogenously produced by host cells, or they may be exogenously added to the growth culture of host cells as supplemental fatty acids. In in vitro assays, fatty acids may be added to the in vitro platform such as, for example, a 96-well plate or other suitable platform for carrying out an enzymatic reaction.

Various fatty acids are well-known in the art and may be used in the methods of the present disclosure as substrates for the production of terminal olefins. In some embodiments, the fatty acid is a medium-chain fatty acid. In some embodiments, the fatty acid is a C10-14 fatty acid. In some embodiments, the fatty acid is a C10-C16 fatty acid. In some embodiments, the fatty acid is a C14-C20 fatty acid. In some embodiments, the fatty acid is a C10-C20 fatty acid. The species of fatty acid substrate used in the methods of the present disclosure is a determinant of the species of terminal olefin produced from fatty acid. In some embodiments where the fatty acid is a medium chain fatty acid, the medium-chain fatty acid is a C10-C14 fatty acid. In some embodiments where the fatty acid is a medium-chain fatty acid, the medium-chain fatty acid used to produce a terminal olefin by a polypeptide of the present disclosure is lauric acid. Other suitable medium-chain fatty acids may include, for example, myristic acid, capric acid, 11-bromoundecanoic acid, 12-bromododecanoic acid, 10-undecynoic acid, 11-aminoundecanoic acid, 12-aminododecanoic, 11-methyldodecanoic acid, 4-methyldodecanoic acid, and hydroxydodecanoic acid. Additional suitable fatty acids that may be used in the methods of the present disclosure will be readily apparent to one of skill in the art in view of the present disclosure.

Terminal Olefins

The methods of the present disclosure relate to the production of terminal olefins by polypeptides where fatty acids are used as substrates. The species of terminal olefin produced by the methods of the present disclosure is a function of the species of fatty acid used as the substrate. In some embodiments, the terminal olefin produced by the methods of the present disclosure is a C9-C13 terminal olefin. In some embodiments, the terminal olefin produced is 1-undecene. Other terminal olefins that may be produced from the methods of the present disclosure may include, for example, 1-nonene, 1-tridecene, 10-bromodec-1-ene, 11-bromoundec-1-ene, dec-1-en-9-yne, 11-aminoundec-1-ene, 10-methylundec-1-ene, 3-methylundec-1-ene, and 1-undecanal. Additional terminal olefins that may be produced by the methods of the present disclosure will be readily apparent to one of skill in the art in view of the present disclosure. In general, the methods of the present disclosure result in a species of fatty acid being converted into its corresponding "minus-1-carbon" 1-alkene, or "M-1 carbon" 1-alkene.

In some embodiments, after a terminal olefin has been produced from a fatty acid substrate, a recovery step may be performed to recover the terminal olefin from the host cell, the growth medium, or the in vitro assay platform. Methods for the recovery of terminal olefins may include, for example, the use of organosolvents or evaporation techniques to trap volatile hydrocarbons. Additional methods of recovering hydrocarbons, such as terminal olefins, are well-known in the art.

Terminal olefins that have been recovered from a host cell may be referred to as substantially purified terminal olefins. A substantially purified terminal olefin generally refers to a terminal olefin that is substantially free of contaminating agents (e.g. cellular material and other culture medium components) from the culture medium source where the terminal olefin is produced by the host cell. For example, a substantially purified terminal olefin may be in association with less than 30%, 20%, 10%, and more preferably 5% or less (by weight) contaminating agents. A composition containing a substantially purified terminal olefin preparation may include, for example, a composition where culture medium (and associated contaminating agents) represents less than about 20%, sometimes less than about 10%, and often less than about 5% of the volume of the terminal olefin preparation.

The yield of the terminal olefin may be, for example, about 1 µg/mL, about 1.5 µg/mL, about 2 µg/mL, about 2.5 µg/mL, about 3 µg/mL, about 3.5 µg/mL, about 4 µg/mL, about 4.5 µg/mL, about 5 µg/mL, about 5.5 µg/mL, about 6 µg/mL, about 6.5 µg/mL, about 7 µg/mL, about 7.5 µg/mL, about 8 µg/mL, about 8.5 µg/mL, about 9 µg/mL, about 9.5 µg/mL, about 10 µg/mL, about 11 µg/mL, about 12 µg/mL, about 13 µg/mL, about 14 µg/mL, about 15 µg/mL, about 16 µg/mL, about 17 µg/mL, about 18 µg/mL, about 19 µg/mL, about 20 µg/mL, about 21 µg/mL, about 22 µg/mL, about 23 µg/mL, about 24 µg/mL, about 25 µg/mL, about 26 µg/mL, about 27 µg/mL, about 28 µg/mL, about 29 µg/mL, or about 30 µg/mL or more terminal olefin.

EXAMPLES

The following Examples are offered for illustrative purposes and to aid one of skill in better understanding the various embodiments of the disclosure. The following examples are not intended to limit the scope of the present disclosure in any way.

Example 1: Microbial Biosynthesis of Medium-Chain 1-Alkenes

This Example demonstrates the use of a single enzyme from *Pseduomonas fluorescens* Pf-5 to convert medium-chain fatty acids into their corresponding terminal olefins using an oxygen-activating, non-heme iron dependent mechanism. This enzyme, PFL_4321, is conserved in pseudomonads and closely-related species with more than 400 enzyme homologs identified. Heterologous expression of selected homologs in *Escherichia coli* ubiquitously leads to the production and secretion of medium-chain 1-alkenes. These findings open the road for tailored conversion of renewable raw materials to fuels and chemical commodities.

Materials and Methods

Bacterial Strains, Plasmids, and Instruments

*E. coli* Top10 and *E. coli* BL21 Gold (DE3) were purchased from Invitrogen. *Pseudomonas fluorescens* Pf-5, *P. aeruginosa* PAO-1, *P. aeruginosa* PA14, *P. syringae* pv. *syringae* B301D, *P. syringae* pv. *syringae* B728a, *P. putida* F1, *P. putida* ATCC 17633, *P. putida* S12, and *Acinetobacter baylyi* ADP1 were obtained from the American Type Culture Collection. *Pseudomonas syringae* TLP2, *P. syringae* Cit7, and *P. syringae* pv. tomato DC3000 were obtained from Prof. Steven Lindow of UC Berkeley. *P. aeruginosa* PA14 transposon insertion mutants were purchased from Massachusetts General Hospital (Boston, Mass.).

Media and chemicals were purchased from Difco, Sigma-Aldrich, and EMD Chemicals. Oligonucleotide primers were synthesized by Elim Biopharm, and PCR was performed with Phusion High-Fidelity PCR Master Mix (NEB). Cloning was performed using the Xa/LIC Cloning Kit (Novagen), Zero Blunt PCR Cloning Kit (Invitrogen), or restriction enzymes from NEB. Recombinant plasmid DNA was purified with a QIAprep kit (Qiagen). DNA sequencing was performed at Quintara Biosciences (Albany, Calif.). Site-directed mutagenesis was performed by using the QuikChange Site-Directed Mutagenesis Kit (Agilent). SDS-PAGE gels and nickel-nitrilotriacetic acid agarose (Ni-NTA) superflow resin were purchased from Biorad and Qiagen, respectively. Protein samples were concentrated using the 10 kDa cutoff Amicon Ultra-15 Centrifugal Filter Units (Millipore). DNA and protein concentrations were determined by a Nanodrop 1000 spectrophotometer (Thermo Scientific).

Typical GC-MS analysis was conducted on a Varian CP-3800 instrument equipped with a Varian 320-MS using a Varian factorFOUR capillary column (30 m, 0.25 mm, DF=0.25). Carbon dioxide analysis was performed with a gastight syringe (Hamilton) and Agilent 5975C GCMS system equipped with Agilent Technologies J&W HP-PLOT Q column (30 m, 0.32 mm, 20.00 µm).

Bacterial Growth and Hydrocarbon Analysis

*E. coli*, *P. aeruginosa* PAO-1, and *P. aeruginosa* PA14 strains were grown in 5 mL of LB medium overnight at 37° C., while all the other *Pseudomonas* and *Acinetobacter* strains were grown at 30° C. For 1-undecene production, 50 µL of seed culture was used to inoculate 5 mL of LB medium supplemented with 100 µM of lauric acid. The culture was shaken in a sealed 20 mL headspace vial (Agilent certified) containing a stir bar at 30° C. for 36 hr. After incubation, an SPME fiber (30 µm polydimethylsiloxane, Supelco, Sigma-Aldrich Group, Bellefonte, Pa.) was manually inserted into the headspace vial and incubated at 25° C. for 12.5 min. GC-MS analysis was conducted on a Varian CP-3800 instrument equipped with a Varian 320-MS. The analytes were desorbed from the fiber at 280° C. in a splitless injector equipped with a 78.5 mm×6.5 mm×0.75 mm liner (Sigma), and developed on a Varian factorFOUR capillary column (30 m×0.25 mm, DF=0.25) using helium as the carrier gas (1 mL/min) and the following temperature gradient: initial 50° C. for 3 min, ramped at 10° C./min to 130° C., ramped at 30° C./min to 300° C., and then held for 5 min. The mass spectrometer was operated in electron ionization mode with automatically tuned parameters; the acquired mass range was 15-250. The signals of the 1-alkenes were identified and quantified by comparison with authentic samples (MP Biomedicals), which were diluted in ethyl acetate, added to 5 mL of culture medium in a sealed headspace vial, and sampled by the same SPME-GCMS method as described above.

Identification of the Undecene Biosynthetic Gene

Molecular biology procedures and DNA manipulations were carried out according to standard protocols. The fosmid genomic library of *P. fluorescens* Pf-5 was constructed using a pCC2Fos CopyControl library kit following the manufacturer's protocol (Epicentre Biotechnologies) (FIG. 2). The host used for library construction was *E. coli* EPI300. 10 individual colonies were combined to inoculate 500 µL of LB with chloramphenicol (25 µg/mL) in each well of the 96 deepwell plates (Nunc), and 6 plates were generated from a library of ~6000 fosmids. To screen the library, 30 µL of seed culture from each tens-of-clones was used to inoculate 3 mL of LB with chloramphenicol (25 µg/mL) and CopyControl Fosmid Autoinduction Solution (Epicentre Biotechnologies), and the culture was shaken in a sealed 20-mL headspace vial containing a stir bar (Agilent certified) at 30° C. for 36 hr. The headspace volatiles were sampled by the SPME GC-MS method mentioned above to screen for 1-undecene-producing cultures. Positive tens-of-clones were sub-cultured, and another round of screening was performed to identify single 1-undecene-producing clones. Three fosmids: 6F8, 6E2, and 4F3, were sequenced to reveal a 15-kb overlapping region.

The overlapping insertion region of 6F8 was digested with HindIII/XbaI and ligated into pCR-Blunt vector to give pZR52 (FIG. 2). After *E. coli* EPI300 (pZR52) was confirmed to produce 1-undecene, pZR52 was digested with BglII/HindIII or BglII/XbaI and ligated into pCR-Blunt to yield pZR56 or pZR57, respectively. pZR56 and pZR57 were subsequently introduced into *E. coli* TOP10 (Invitrogen) to examine 1-undecene production as mentioned above. As *E. coli* EPI300 (pZR57) but not *E. coli* EPI300 (pZR56) produced 1-undecene, pZR57 was further digested with SmaI/XbaI to give pZR59, which conferred 1-undecene production in *E. coli* TOP10 (pZR59). PFL_4321 was PCR-amplified by using pZR60-F/R as primers (Table 1) and pZR59 as template, and cloned into pET-30Xa-LIC under a T7 promoter to yield pZR60.

TABLE 1

Primers Used in this Study

| Primer Name | Sequence | SEQ ID NO: |
|---|---|---|
| pZR60-F | GGTATTGAGGGTCGCATGATCGACACATTCAGCCG | 55 |
| pZR60-R | AGAGGAGAGTTAGAGCCTCAGCCTTCGGCCAGTGC | 56 |
| pZR60-F_HRV3C* | GGTATTGAGGGTCGC<u>CTTGAAGTCCTCTTTCAGGGACCC</u>ATGATCGACACATTCAGCCG | 57 |
| pZR80_F | GGTATTGAGGGTCGCATGATCGACACTTTCGAGAG | 58 |
| pZR80_R | AGAGGAGAGTTAGAGCCCTACATTTCCAGTGCGGC | 59 |
| pZR95_F | GGTATTGAGGGTCGCA TGAGCGAGTTCTTTGACCG | 60 |
| pZR95_R | AGAGGAGAGTTAGAGCC CTACTCCGCGCCGACCGC | 61 |
| pZR96_F | GGTATTGAGGGTCGCATGTTTGAATCAAACAGTTA | 62 |
| pZR96_R | AGAGGAGAGTTAGAGCCTTATTGATGTTTATAACA | 63 |
| pZR97_F | GGTATTGAGGGTCGCA TGGAAATCACAAGGATCAA | 64 |
| pZR97_R | AGAGGAGAGTTAGAGCC TCAGCCCGCAGCCAACGC | 65 |
| pZR60_E101A_F | GCAATATCCGGGTCGCGCTCAATCATGCCGA | 66 |
| pZR60_E101A_R | TCGGCATGATTGAGCGCGACCCGGATATTGC | 67 |
| pZR60_H104A_F | CAGTAATCGGCAGCATTGAGCTCGACCCGGATATTGC | 68 |
| pZR60_H104A_R | GCAATATCCGGGTCGAGCTCAATGCTGCCGATTACTG | 69 |
| pZR60_E159A_F | CCGTGGCCCCTGCAATGGCGTAGTTGGTG | 70 |
| pZR60_E159A_R | CACCAACTACGCCATTGCAGGGGCCACGG | 71 |
| pZR60_H194A_F | GAAGTGGCTGAAGATGGCTGCCCAGTACGACGAC | 72 |
| pZR60_H194A_R | GTCGTCGTACTGGGCAGCCATCTTCAGCCACTTC | 73 |
| pESC-und-F | TATGGATCCAAAAAATGATCGACACATTCAGCCG | 74 |
| pESC-und-R | AAAGTCGACTCAGCCTTCGGCCAGTGCCA | 75 |

*the human rhinovirus 3C proteinase site is underlined

All of the plasmid constructs were confirmed by DNA sequencing. pZR60 was introduced into E. coli BL21 Gold (DE3), which was grown at 37° C. in 30 mL of LB medium supplemented with 50 μg/mL kanamycin. Once the $OD_{600}$ reached 0.4, a 5 mL aliquot was transferred into the headspace vial and induced with 0.1 mM of isopropyl-β-D-thiogalactopyranoside (IPTG) at 16° C. for 16 hr. 1-Undecene production was detected by using the SPME-GCMS method. PFL_4320 was also overexpressed in E. coli BL21, but failed to enable the 1-undecene production.

Overexpression and Purification of Undecene Biosynthetic Enzymes

To overexpress PFL_4321 for enzymatic analysis, E. coli BL21 Gold (DE3, pZR60) was grown in 1 L of LB medium with 50 μg/mL kanamycin until $OD_{600}$ 0.6, harvested, and lysed as mentioned below. The insoluble fraction was removed by centrifugation, and the soluble proteins were incubated with 1 mL of Ni-NTA beads (Qiagen) on a nutator at 4° C. for 1 hr. The proteins were then loaded onto a gravity flow column, washed with washing buffer (50 mM imidazole, 20 mM Tris, 300 mM NaCl, pH 8.5), and eluted with eluting buffer (250 mM imidazole, 20 mM Tris, 300 mM NaCl, pH 8.5). Purified proteins were exchanged into 20 mM Tris (pH 8.5) and 300 mM NaCl using Amicon Centrifugal Filter Units, flash frozen in liquid nitrogen, and preserved at −80° C.

To overexpress PFL_4321 for X-ray crystallization, the gene was PCR-amplified by using pZR60-F_HRV3C/pZR60-R as primers (Table 1) and pZR59 as template, and cloned into pET-30Xa-LIC under a T7 promoter to yield pZR60_HRV3C. E. coli BL21 Gold (DE3, pZR60_HRV3c) was grown in 1 L of Terrific Broth medium (24 g/L yeast extract, 12 g/L tryptone, and 10 g/L NaCl, pH 7.4) containing 6 mL of glycerol and 50 μg/mL kanamycin to an $OD_{600}$ of 1.0-1.2. The culture was cooled on ice for 10 min, induced with 0.1 mM of IPTG, and grown at 180 rpm and 25° C. for 12 hr. The cells were spun down and resuspended in 70 mL of lysis buffer (50 mM Tris, pH 8.5, 300 mM NaCl, 50 mM imidazole, and Sigma® protease inhibitor cocktail), and lysed on ice by homogenization using a Emulsiflex-C3 homogenizer. The soluble proteins were collected by centrifugation at 20,000 g and 4° C. for 1 hr, and the supernatant was loaded onto a 5-mL Ni-affinity HisTrap HP column (GE Healthcare). The recombinant PFL_4321 was eluted with a gradient of 50-300 mM imidazole in 20 mM Tris (pH 8.5) and 300 mM NaCl, and the imidazole was thoroughly removed by passing the eluent through a Hiprep 26/10 desalting column (GE Healthcare). 100 mg of His-tagged PFL_4321 was digested with 0.5 mg of human rhinovirus 3C proteinase (QB3 Macrolab, UC Berkeley) at 4° C. for 20 hr. The digested mixture was loaded onto a 5-mL Ni-affinity HisTrap HP column (GE Healthcare). The flow-through was collected, added with 0.85 M ammonium sulfate, and loaded onto a Resource PHE column (GE Healthcare) equilibrated with 1 M ammonium sulfate and 20 mM Tris pH 8.0 at room temperature. Bound PFL_4321 was eluted with a gradient of 850-0 mM ammonium sulfate and 20 mM Tris over 50 column volumes, and concentrated in 10 mM Tris, 100 mM NaCl, and 200 mM ammonium sulfate with Amicon® Ultra filters for crystallization.

Detection of Carbon Dioxide

A 9.5 mL of reaction mixture contains 50 mM MES buffer (pH 6.2), 300 mM NaCl, 100 μM $(NH_4)_2Fe(SO_4)_2$, 1 mM ascorbic acid, 100 μM lauric acid, and 10 μM enzyme. The reaction was performed in a 10-ml sealed headspace vial (Agilent), initiated by adding the enzyme, and incubated at 30° C. for 1 hr. 100 μL of the headspace gas was acquired using a gastight syringe (Hamilton) and injected into Agilent 5975C GCMS system equipped with an Agilent Technologies J&W HP-PLOT Q column (30 m, 0.32 mm, 20.00 μm). Injector temperature was set at 120° C., and helium was used as the carrier gas at a flow-rate of 3 mL/min. The temperature gradient was as follows: initial 40° C. for 5 min, ramped at 30° C./min to 240° C., and then held for 1 min. The mass spectrometer was operated in electron ionization mode with automatically tuned parameters, and the acquired mass range was m/z=15-200. The $CO_2$ signal was identified by the same retention time as the authentic sample prepared with dry-ice, and $^{13}CO_2$ was quantified by extracting m/z=45.

In Vitro Anaerobic Enzymatic Assays

All of the reagents were bubbled with nitrogen gas and equilibrated in the anaerobic chamber overnight before use. E. coli BL21 Gold (DE3, pZR60_HRV3c) was grown, harvested, and lysed as mentioned above. The insoluble fraction was removed by centrifugation, and the soluble proteins were incubated with 1 mL of Ni-NTA beads (Qiagen) on a nutator at 4° C. for 1 hr. The proteins were then moved into the anaerobic chamber, loaded onto a gravity flow column, washed with washing buffer (50 mM imidazole, 20 mM Tris, 300 mM NaCl, pH 8.5), and eluted with eluting buffer (300 mM imidazole, 20 mM Tris, 300 mM NaCl, pH 8.5). Purified proteins were exchanged into 20 mM Tris (pH 8.5) and 300 mM NaCl by passing through a desalting column (GE Disposable PD-10), and then concentrated using Amicon Centrifugal Filter Units. The protein solution was equilibrated in the anaerobic chamber on a Thermomixer at 4° C. overnight.

Glucose oxidase and catalase powder (Sigma) were dissolved in 20 mM Tris (pH 8.5) in the anaerobic chamber to make stock solutions at 100 U/mL and 6,000 U/mL, respectively. 1 mL of reaction mixture contains 50 mM MES buffer (pH 6.2), 300 mM NaCl, 100 μM $(NH_4)_2Fe(SO_4)_2$, 1 mM ascorbic acid, 100 μM lauric acid, 2 U/mL glucose oxidase, 120 U/mL catalase, 15 mM glucose, and 10 μM PFL_4321. The reaction was initiated by adding PFL_4321, incubated for 1 min, and quenched with 1 mL of 5 M NaOH in a sealed headspace vial. The control group lacked glucose oxidase and was performed in the presence of ambient oxygen. SPME-GCMS detection of 1-undecene was performed as described as above.

Enzymatic Assays

A typical condition is as follows: 1 mL of reaction mixture contains 50 mM MES buffer (pH 6.2), 300 mM NaCl, 100 μM $(NH_4)_2Fe(SO_4)_2$, 1 mM ascorbic acid, 100 μM fatty acid substrate or analogs, and 10 μM enzyme. The reaction was performed in a sealed headspace vial at 30° C., initiated by adding lauric acid and quenched by injecting equal volume of 5 M NaOH. 1-Undecene production was analyzed and quantified by using the SPME-GCMS method. To determine the kinetic parameters of PFL_4321 on lauric acid, initial velocities at 1, 10, 20, 50, 100, and 150 μM of lauric acid were measured (25 mM lauric acid solution was prepared by adding 0.5% tergitol and heating at 65° C. for 10 min). The reactions were quenched at 2, 4, 6, 8, and 10 seconds, and the acquired turnover rates were fit to the Michaelis-Menten equation using GraphPad Prism to obtain $k_{cat}$ and $K_m$. The $k_{cat}$ and $K_m$ of myristic acid and capric acid were determined similarly.

Site-Directed Mutagenesis of PFL_4321

$Glu_{101}$, $His_{104}$, $Glu_{159}$, and $His_{194}$ in PFL_4321 were all mutated to Ala using the QuikChange Site-Directed Mutagenesis Kit (Agilent) following the manufacturer's protocol and using primers pZR60_E101A_F/R, pZR60_H104A_F/R, pZR60_E159A_F/R, and pZR60_H194A_F/R, respectively (Table 1). Mutations were verified by DNA sequencing.

Crystallization of PFL_4321

Purified PFL_4321 was incubated with 0.1 mM $(NH_4)_2Fe(SO_4)_2$ for 10 min, then buffer-exchanged into 10 mM Tris (pH 8.5), 100 mM NaCl, and 0.2 M $(NH_4)_2SO_4$ and concentrated to 10 mg/mL. PFL_4321 crystals were grown at room temperature using the hanging-drop vapor diffusion method in 0.1M MES, 1.8 M $(NH_4)_2SO_4$, 0.2 mM $(NH_4)_2Fe(SO_4)_2$, pH 6.5-7.0. To obtain ligand bound structures, PFL_4321 was incubated with 2.5 mM DEA or BHDA on ice for 15 min before crystallization. X-ray diffraction data were collected at beamline 8.3.1 at the Advanced Light Source (ALS) at Lawrence Berkeley National Laboratory. The initial phases were obtained by the molecular replacement method using search models of PSPTO1738 (PDB entry: 3OQL). The structure models were iteratively built with COOT (P. Emsley et al., Acta Crystallogr D Biol Crystallogr 60, 2126, 2004), and refined with Phenix (P. D. Adams et al., Acta Crystallogr D Biol Crystallogr 58, 1948, 2002), and REFMAC5 (G. Murshudov et al., Acta Crystallogr D Biol Crystallogr 53, 240, 1997). Table 2 summarizes the statistics of data collection and refinement. The O—O bond lengths of the dioxygen species in 2,3-dodecenoic acid- and β-hydroxydodecanoic acid-bound proteins were refined without restraints on bond length. Simulated annealing omit maps were calculated with Phenix. Structural figures were prepared with the molecular visualization software PyMol (http://www.pymol.org).

TABLE 2

Crystallization data collection and refinement statistics

|  | APO | DEA-bound | BHDA-bound |
|---|---|---|---|
| Data collection |  |  |  |
| Space group | C222 (21) | P2221 (17) | P2221 (17) |
| Cell dimensions |  |  |  |
| a, b, c (Å) | 141.38, 218.44, 67.31 | 67.48, 74.16, 142.50 | 67.41, 73.99, 142.51 |
| α, β, γ (°) | 90.00, 90.00, 90.00 | 90.00, 90.00, 90.00 | 90.00, 90.00, 90.00 |
| Resolution (Å) | 58.55-1.90 (1.94-1.90)* | 71.25-1.80 (1.84-1.80) | 73.99-1.70 (1.73-1.70) |
| CC(1/2) | 0.995 (0.169) | 0.996 (0.205) | 0.999 (0.425) |
| $R_{merge}$ | 0.12 (1.63) | 0.17 (2.28) | 0.085 (1.256) |

TABLE 2-continued

Crystallization data collection and refinement statistics

| | APO | DEA-bound | BHDA-bound |
|---|---|---|---|
| $I/\sigma$ | 9.7 (1.7) | 8.1 (0.6) | 14.5 (1.1) |
| Completeness (%) | 99.9 (99.9) | 97.0 (94.9) | 95.8 (70.9) |
| Redundancy | 4.4 (4.3) | 6.7 (4.9) | 8.4 (5.1) |
| Refinement | | | |
| Resolution (Å) | 54.67-1.90 (1.97-1.90) | 71.35-1.8 (1.86-1.80) | 65.75-1.70 (1.76-1.70) |
| No. reflections | 72,082 (8,157) | 63,640 (6,049) | 75,678 (5662) |
| $R_{work}/R_{free}$ | 0.143/0.194 (0.315/0.357) | 0.161/0.229 (0.321/0.368) | 0.137/0.185 (0.306/0.301) |
| No. atoms | | | |
| Protein | 4201 | 4170 | 4182 |
| Ligand/ion | 95 | 90 | 76 |
| Water | 558 | 497 | 564 |
| B-factors | | | |
| Protein | 34.40 | 33.70 | 29.90 |
| Ligand/ion | 55.30 | 60.90 | 52.30 |
| Water | 46.60 | 43.60 | 42.70 |
| R.m.s. deviations | | | |
| Bond lengths (Å) | 0.021 | 0.011 | 0.011 |
| Bond angles (°) | 2.00 | 1.33 | 1.30 |
| Ramachandran | | | |
| Favored (%) | 98 | 98 | 99 |
| Allowed (%) | 2 | 2 | 2 |
| Outlier (%) | 0 | 0 | 0 |

*Values in parentheses are for the highest-resolution shell.

Small Scale 1-Alkene Production in *E. coli*

PSPTO_1738 (*P. syringae* pv. tomato DC3000), PA14_53120 (*P. aeruginosa* PA14), ACIAD2095 (*Acinetobacter baylyi* ADP1), and Pput_3952 (*P. putida* F1) were PCR-amplified by using pZR80-F/R, pZR95-F/R, pZR96-F/R, and pZR97-F/R as primers (Table 1) and their corresponding genomic DNA as templates, and cloned into pET-30Xa-LIC under a T7 promoter to yield pZR80, pZR95-97. All of the expression constructs were confirmed by DNA sequencing and introduced into *E. coli* BL21 Star for 1-undecene production. A starter *E. coli* culture was grown overnight in 5 mL of LB medium at 37° C. and 250 rpm, and 0.3 mL was used to inoculate 30 mL of LB medium supplemented with 0.5% glycerol and 50 µg/mL kanamycin, which was shaken at 37° C. until the $OD_{600}$ reached 0.6. A 3 mL aliquot was transferred into a culture tube with a loose cap, 300 µL octane was added, and the culture was induced with 0.1 mM IPTG at 30° C. for 24 hr. The octane layer was skimmed from the culture, centrifuged to remove the remaining medium, and dehydrated by adding magnesium sulfate anhydrate. 1 µL of extract was injected with a split ratio 10:1. The GCMS development method was identical to that mentioned above except that the initial 4.5 min was not recorded to avoid the solvent peak. A standard curve of 1-undecene was generated by extracting known amounts of 1-undecene from the culture media using the same way described herein.

Small-Scale 1-Alkene Production in *S. cerevisiae*

PFL_4321 was PCR-amplified by using pESC-und-F/-R as primers (Table 1) and pZR59 as template, digested with BamH1/Sal1, and ligated into the pESC-URA vector to yield pESC-PFL_4321. *S. cerevisiae* was then transformed with pESC-PFL_4321 using the lithium acetate method outlined in the pESC-URA manual (Stratagene). Transformants were selected by resistance to Geneticin. The cultures were grown in yeast-peptone media supplemented with 1% galactose in headspace GC vials at 30° C. for 36 hr before SPME-GCMS analysis.

Phylogenetic Analysis

MEGA 5.2 was applied for the sequence alignment and molecular evolutionary analysis of 1-undecene biosynthetic enzymes. The consensus phylogenetic tree was constructed using the Neighbor-Joining method tested with Bootstrap with 1000 replications. Representative enzymes used in the tree construction were shown as follows: YP_001713821 (*Acinetobacter baumannii* 6013150), WP_000126118 (*A. baumannii* ATCC17978), and WP_009512776 (*A. baumannii* WC-323); WP_004639121 (*Acinetobacter haemolyticus* ATCC 19194) and WP_005090558 (*A. haemolyticus* NIPH 261); YP_046725 (*Acinetobacter baylyi* ADP1) and WP_004927551 (*A. baylyi* DSM 14961); YP_990704 (*Burkholderia mallei* SAVP1), YP_338554 (*B. mallei* ATCC 23344), and WP_004206269 (*B. mallei* PRL-20); YP_112319 (*Burkholderia pseudomallei* K96243), YP_001064242 (*Burkholderia pseudomallei* 1026b), and WP_004523249 (*Burkholderia pseudomallei* 406e); YP_440524 (*Burkholderia thailandensis* E264), YP_007921242 (*B. thailandensis* MSMB121), and WP_006028320 (*B. thailandensis* MSMB43); YP_629506 (*Myxococcus xanthus* DK 1622); YP_004663502 (*Myxococcus fulvus* HW-1); YP_007358297 (*Myxococcus stipitatus* DSM 14675); YP_792415 (*Pseudomonas aeruginosa* PA-14), NP_249553 (*P. aeruginosa* PAO1), and YP_005976761 (*P. aeruginosa* M18); YP_001269260 (*Pseudomonas putida* F1), NP_743918 (*P. putida* KT2440), and YP_004700858 (*P. putida* S16); YP_261413 (*Pseudomonas fluorescens* Pf-5), YP_349813 (*P. fluorescens* Pf0-1), and YP_005207048 (*P. fluorescens* F113); WP_003369700 (*Pseudomonas syringae* Cit7), YP_275816 (*Pseudomonas syringae* pv. *phaseolicola* 1448A), NP_791563 (*Pseudomonas syringae* pv. tomato DC3000), and YP_236724 (*Pseudomonas syringae* pv. *syringae* B728).

Kinetic Parameters of PFL_4321

To acquire the kinetic parameters of PFL_4321 on 11-aminoundecanoic acid and 12-aminododecanoic acid, initial velocities at 25, 50, 100, 150, 200, 250, 500, and 700 µM were measured. 50 µl of aliquots of the reaction were quenched at 1, 1.5, 2, 2.5, 3, 3.5, 4, 4.5, 5, 5.5, and 6 minutes by adding 100 µl of acetonitrile. Denatured enzymes were removed by centrifugation at 15,000 g for 20 min. LC-HRMS analysis was carried out on an Agilent Technologies 6520 Accurate-Mass Q-TOF LC-MS instrument equipped with an Agilent Eclipse Plus C18 column (3.5 µm, 4.6×100 mm). 10 µL of the solution was injected into LC-HRMS and a linear gradient of 55 to 95% $CH_3CN$ (vol/vol) over 15 min in $H_2O$ with 0.1% (vol/vol) formic acid at a flow rate of 0.5 mL/min was used for analysis. The exact masses of aminoundec-1-ene and aminodec-1-ene were extracted, and the peaks were integrated and compared with the standard compounds.

Results

Medium-chain 1-alkenes, such as 1-undecene, were reported as one of the signature VOCs produced by selected *Pseudomonas* species (J. M. Zechman et al., Can J Microbiol 31, 232, 1985). Medium-chain 1-alkene production by various *Pseudomonas* strains having published genomes was assessed to facilitate the identification of biosynthetic genes. The headspace of bacterial culture was subjected to a solid phase microextraction (SPME)—gas chromatography mass spectrometry (GCMS) analysis that allows efficient extraction and sensitive detection of VOCs. Results are presented in FIG. 1 and Table 3 below.

TABLE 3

Occurrence of 1-undecene productions from selected strains with fully sequenced genomes

| Strain | 1-undecene previously reported | 1-undecene observed in this study |
|---|---|---|
| *Pseudomonas fluorescens* Pf-5 | N.A. | Yes |
| *P. aeruginosa* PAO-1 | N.A. | Yes |
| *P. aeruginosa* PA14 | N.A. | Yes |
| *P. syringae* pv. *syringae* B301D | N.A. | Yes |
| *P. syringae* pv. *syringae* B728a | N.A. | Yes |
| *P. syringae* TLP2 | N.A. | Yes |
| *P. syringae* Cit7 | N.A. | Yes |
| *P. syringae* pv. Tomato DC3000 | N.A. | Yes |
| *P. putida* F1 | N.A. | Yes |
| *P. putida* ATCC 17633 | No | Yes |
| *P. putida* S12 | N.A. | Yes |
| *Acinetobacter baylyi* ADP1 | N.A. | Yes |
| *E. coli* EPI300 | N.A. | No |
| *E. coli* BL21 | N.A. | No |

All the tested strains accumulated 5-200 ng/mL of 1-undecene in headspace, including previously documented nonproducer *P. putida* (J. M. Zechman et al., Can J Microbiol 31, 232, 1985), suggesting a conserved biosynthetic pathway for 1-undecene in pseudomonads. Although enzymes such as a P450 fatty acid decarboxylase or a multi-domain polyketide synthase are known to catalyze terminal olefin biosynthesis (M. A. Rude et al., Appl Environ Microb 77, 1718, 2011; D. Mendez-Perez et al., Appl Environ Microb 77, 4264, 2011; L. Gu et al., J Am Chem Soc 131, 16033, 2009), they recognize long-chain fatty acyl substrates (>C18) and appear not to be involved in 1-undecene biosynthesis in pseudomonads based on bioinformatics analysis.

To find gene(s) that are responsible for 1-undecene biosynthesis, a genome mining approach was employed by heterologously expressing genes from *P. fluorescens* Pf-5 in *E. coli*, a 1-undecene nonproducer, followed by phenotype screening (FIG. 2). One single gene, PFL_4321, was demonstrated to be essential and sufficient to confer 1-undecene production in *E. coli* (FIG. 1 and FIG. 3). PFL_4321 encodes a small hypothetical protein (261 amino acids) that shows modest sequence homology to TenA, the thiaminase II from *Bacillus subtilis* (A. L. Jenkins et al., Bioorg Chem 36, 29, 2008), but the essential catalytic residue cysteine of TenA is missing in PFL_4321. To confirm the function of this gene in 1-undecene biosynthesis, the ΔPA14_53120 mutant of *P. aeruginosa* PA14 that bears a transposon insertion in the gene PA14_53120 homologous to PFL_4321 was examined (N. T. Liberati et al., P Natl Acad Sci USA 103, 2833, 2006). This gene disruption completely abolished the 1-undecene production in *P. aeruginosa* UCBPP-PA14 (FIG. 1D), confirming the necessity of this gene in 1-undecene biosynthesis in *P. aeruginosa*.

Figure 4B:
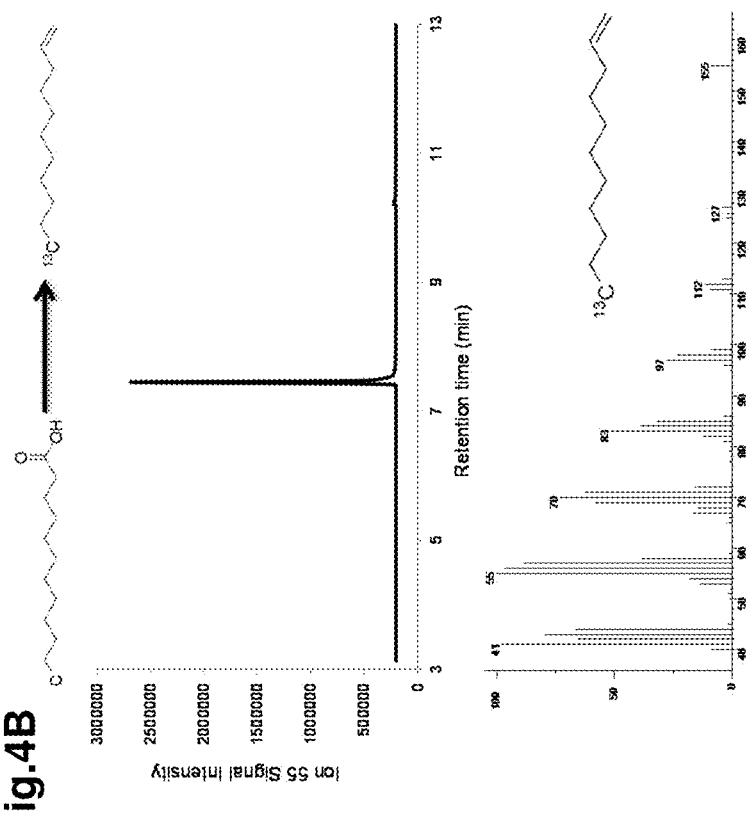
FIG. 4A-FIG. 4B illustrate GC-MS analysis results of in vitro enzymatic assays with the purified recombinant PFL_4321 enzyme.
Figure 4A:
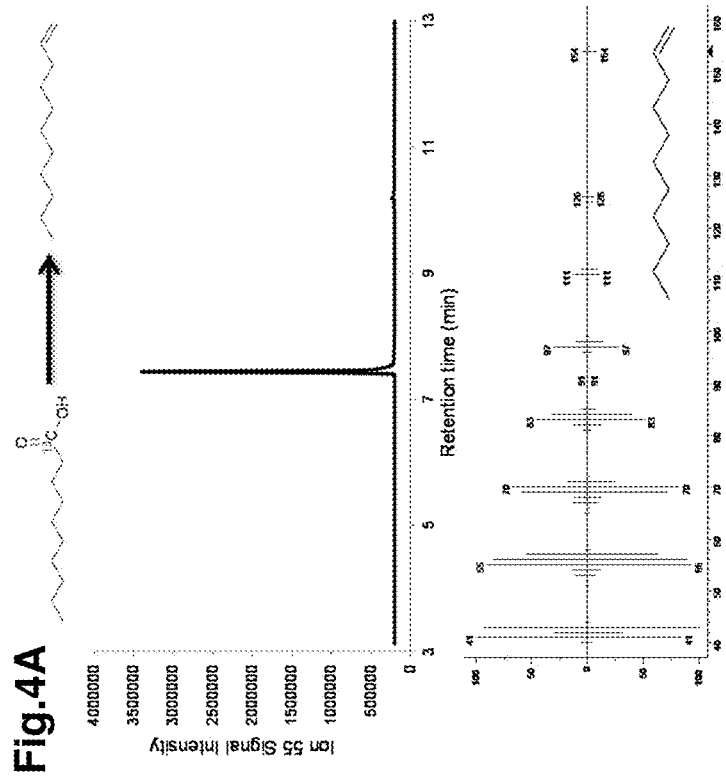

To biochemically characterize PFL_4321, in vitro enzymatic assays were performed with the recombinant enzyme purified from *E. coli*. Feeding [12-$^{13}$C]lauric acid and [1-$^{13}$C]lauric acid to the microbial 1-undecene producers resulted in the production of [11-$^{13}$C]undecene and [U-$^{12}$C11]undecene respectively (FIG. 4A and FIG. 4B), implying that lauric acid is the 1-undecene biosynthetic precursor and the terminal carboxylic acid moiety is removed during 1-undecene formation.

Figure 5:
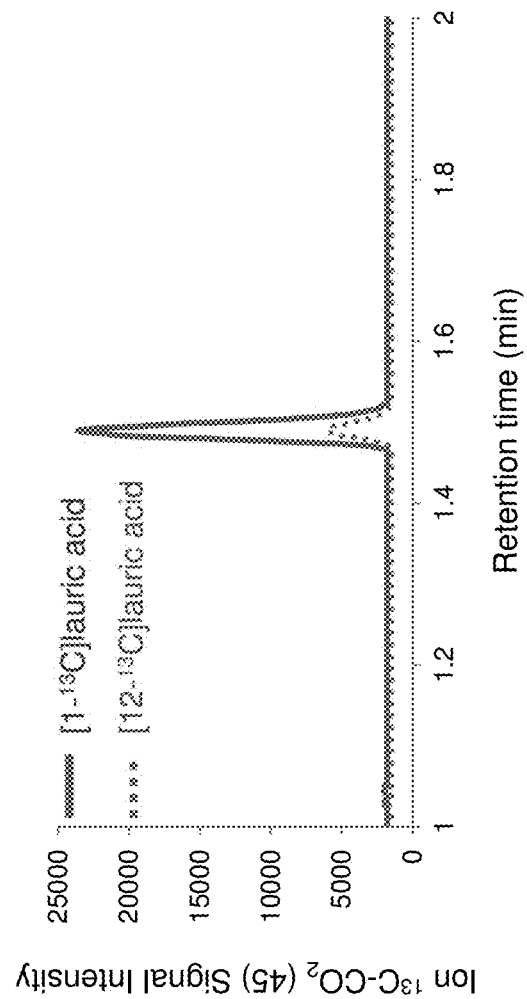
FIG. 5 illustrates GC-MS detection of in vitro $^{13}C$—$CO_2$ formation by PFL_4321 activity. [12-$^{13}$C]lauric acid was used as the negative control to show the natural abundance of $^{13}C$—$CO_2$.
Figure 6:
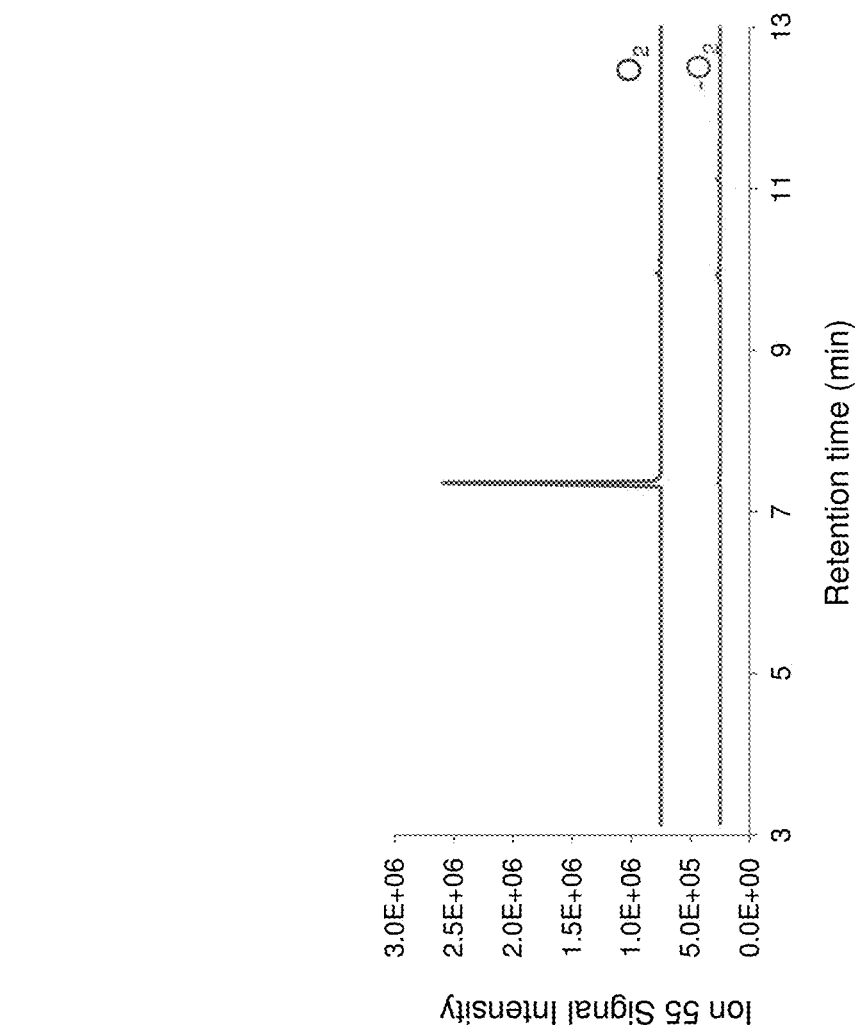
FIG. 6 illustrates GC-MS detection of 1-undecene production by PFL_4321 in the aerobic/anaerobic assays. The anaerobic assay was performed by using the anaerobically purified enzyme and degassed reagents, adding glucose oxidase/glucose/catalase, and conducting the experiment in an anaerobic chamber with ppm $O_2$<0.7. The control aerobic assay was performed by using a similar reaction mixture under ambient air conditions and omitting glucose oxidase.

Additional in vitro assays were performed with PFL_4321 using lauric acid, its esters, or thioesters as potential substrates. None of them were converted to 1-undecene; however, 1-undecene was detected upon the addition of *E. coli* crude extract to the mixture of PFL_4321 protein and lauric acid, suggesting that factors enabling 1-undecene production are present in the *E. coli* crude extract, and free lauric acid is the substrate for enzymatic catalysis. Surprisingly, this reaction can be quenched by the addition of ethylenediaminetetraacetic acid (EDTA), a chelating agent, indicating the necessity of a metal ion. PFL_4321 was incubated with lauric acid in the presence of various metal ions, including $Fe^{2+}$, $Fe^{3+}$, $Mg^{2+}$, $Ca^{2+}$, $Mn^{2+}$, $Co^{2+}$, $Ni^{2+}$, $Cu^{2+}$, and $Zn^{2+}$. Only $Fe^{2+}$, but not any other ion, elicited the 1-undecene production, suggesting that PFL_4321 is a non-heme iron (II)-dependent enzyme. Using [1-$^{13}$C]lauric acid as the substrate, the formation of [$^{13}$C]$CO_2$ was detected (FIG. 5), confirming that PFL_4321 catalyzes the production of 1-undecene from lauric acid through oxidative decarboxylation, analogous to the reaction promoted by the P450 long-chain fatty acid decarboxylase (M. A. Rude et al., Appl Environ Microb 77, 1718, 2011). Since no additional oxidant was introduced into the in vitro system, without wishing to be bound by theory, it was proposed that molecular oxygen served as the oxidant of the reaction, which was supported by the observation that the 1-undecene production was decreased by more than 150-fold in the anaerobic enzymatic assays (FIG. 6).

Figure 7:
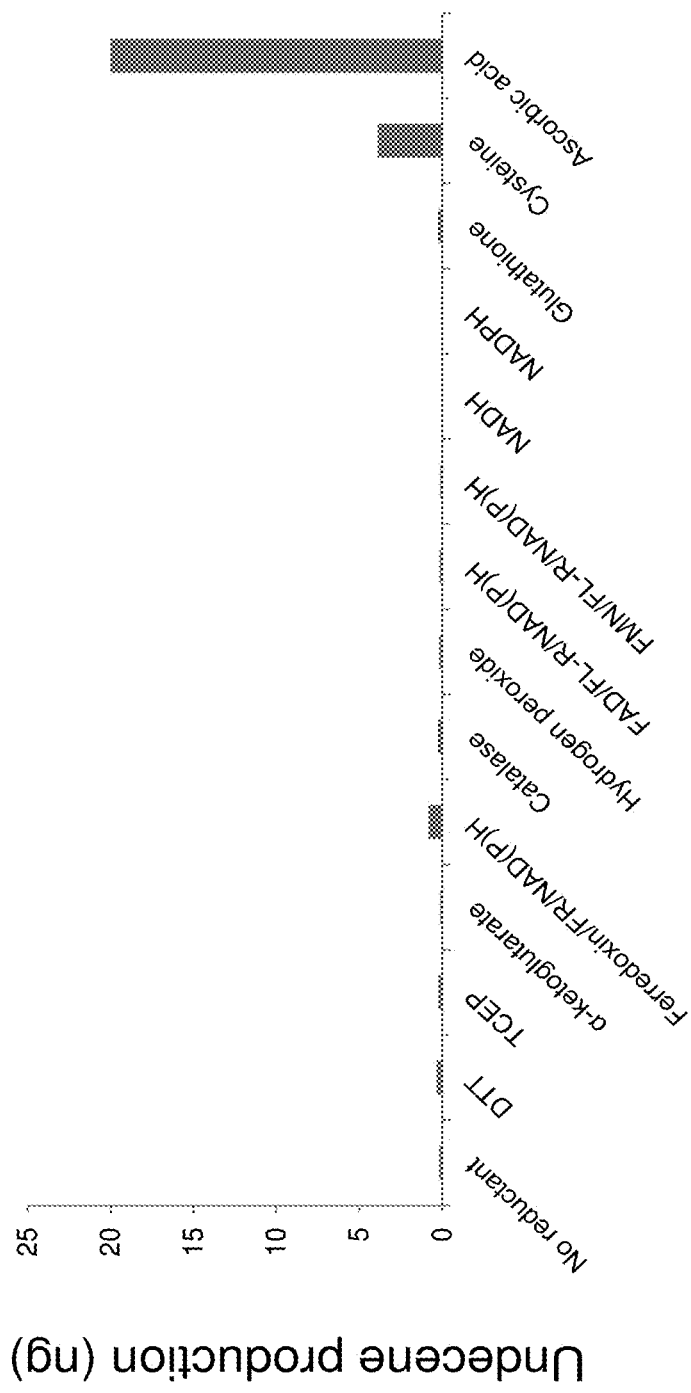
FIG. 7 illustrates a comparison of 1-undecene production by using various reductive cofactors/cosubstrates under iron-limited conditions. 2.5 mL of reaction mixture contains 100 µM MES (pH 6.1), 300 mM NaCl, 50 µM lauric acid, 5 µM PFL_4321, 0.1 µM $(NH_4)_2Fe(SO_4)_2$, and 1 mM reductive cofactor. When needed, 40 µM FAD, FMN, ferredoxin, or phenazine, and 20 µM flavin reductase (FL-R) or ferredoxin reductase (FR) were added.
Figure 8A:
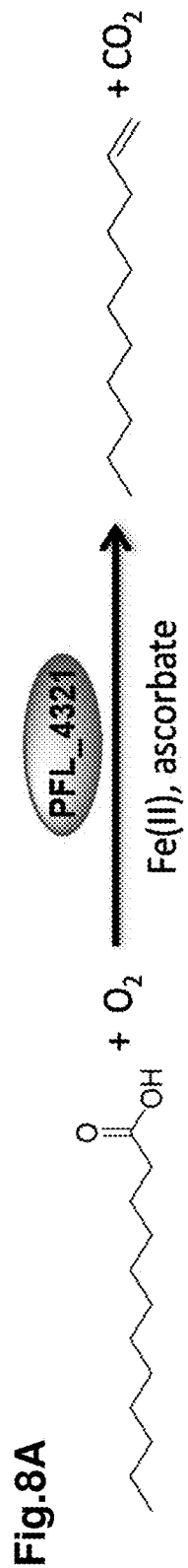
FIG. 8A-FIG. 8B illustrates PFL_4321 activity.
Figure 8B:
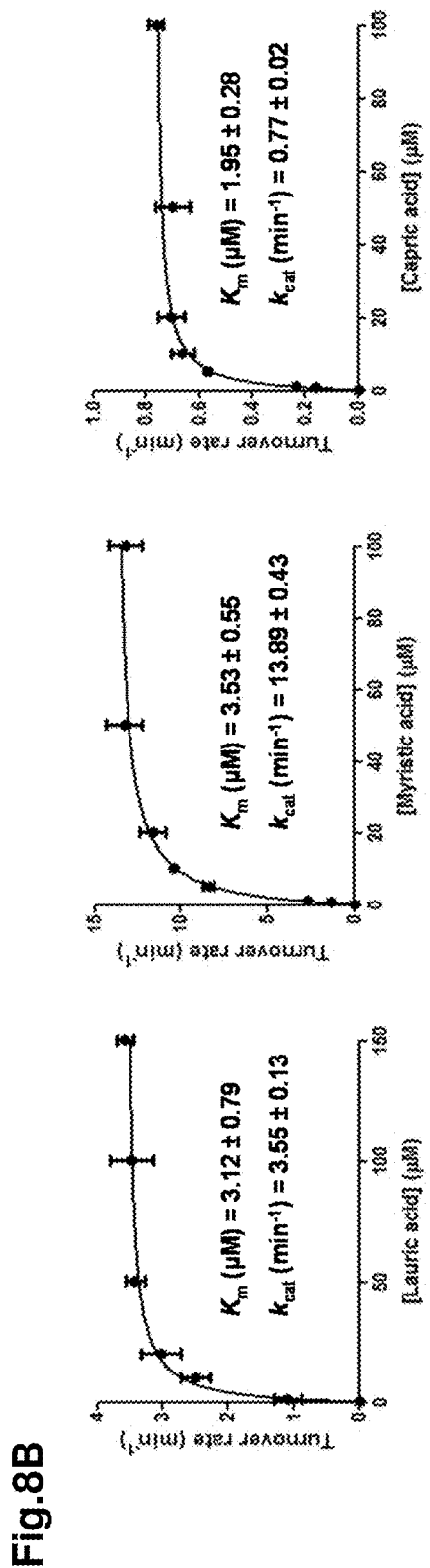
Figure 11A:
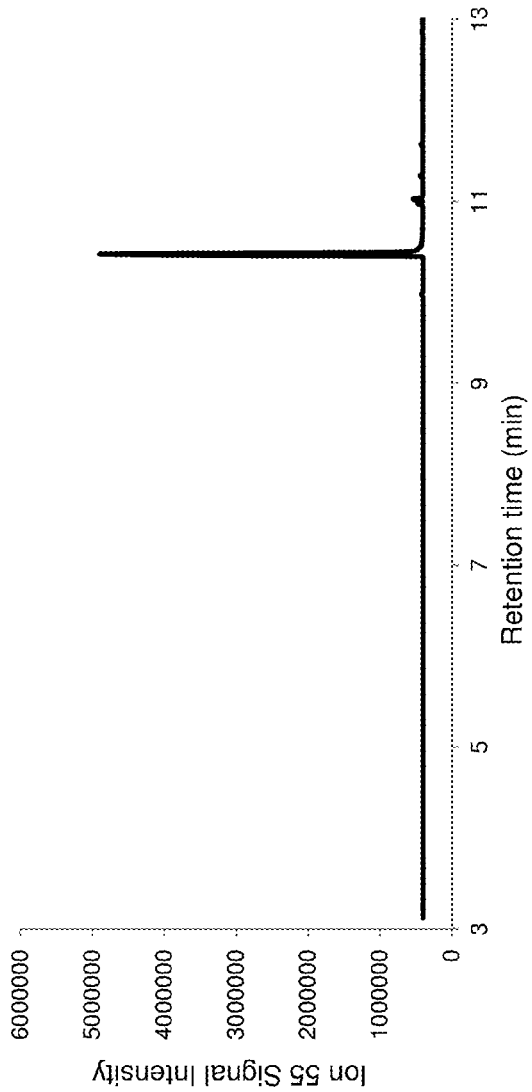
FIG. 11A-FIG. 11B illustrates GC-MS analysis of the conversions of 11-bromoundecanoic acid to 10-bromodec-1-ene. Reverse panel (bottom panel) in FIG. 11B illustrates the reference standard of 10-bromodec-1-ene acid from the NIST spectral database.
Figure 11B:
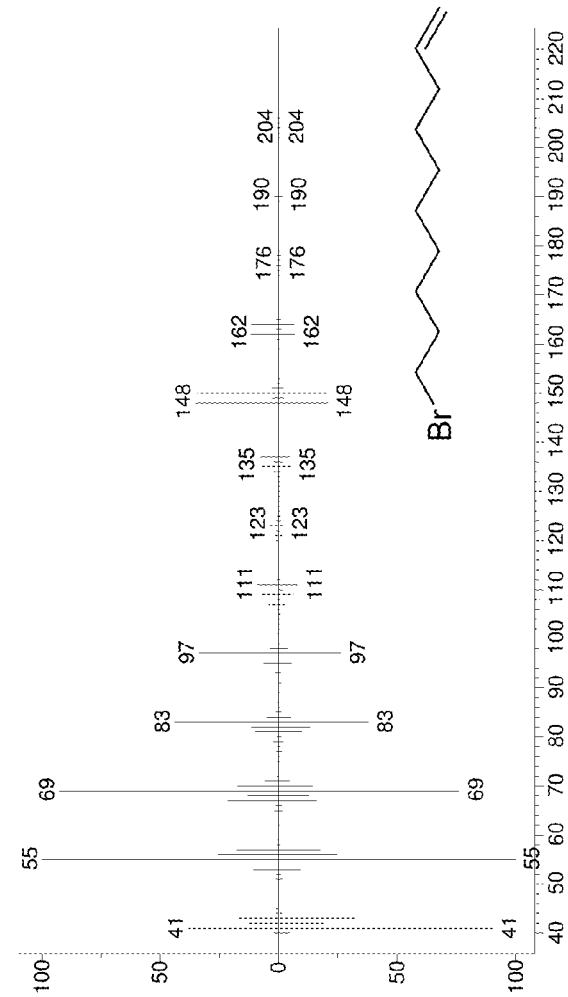
Figures 12A, 12B:
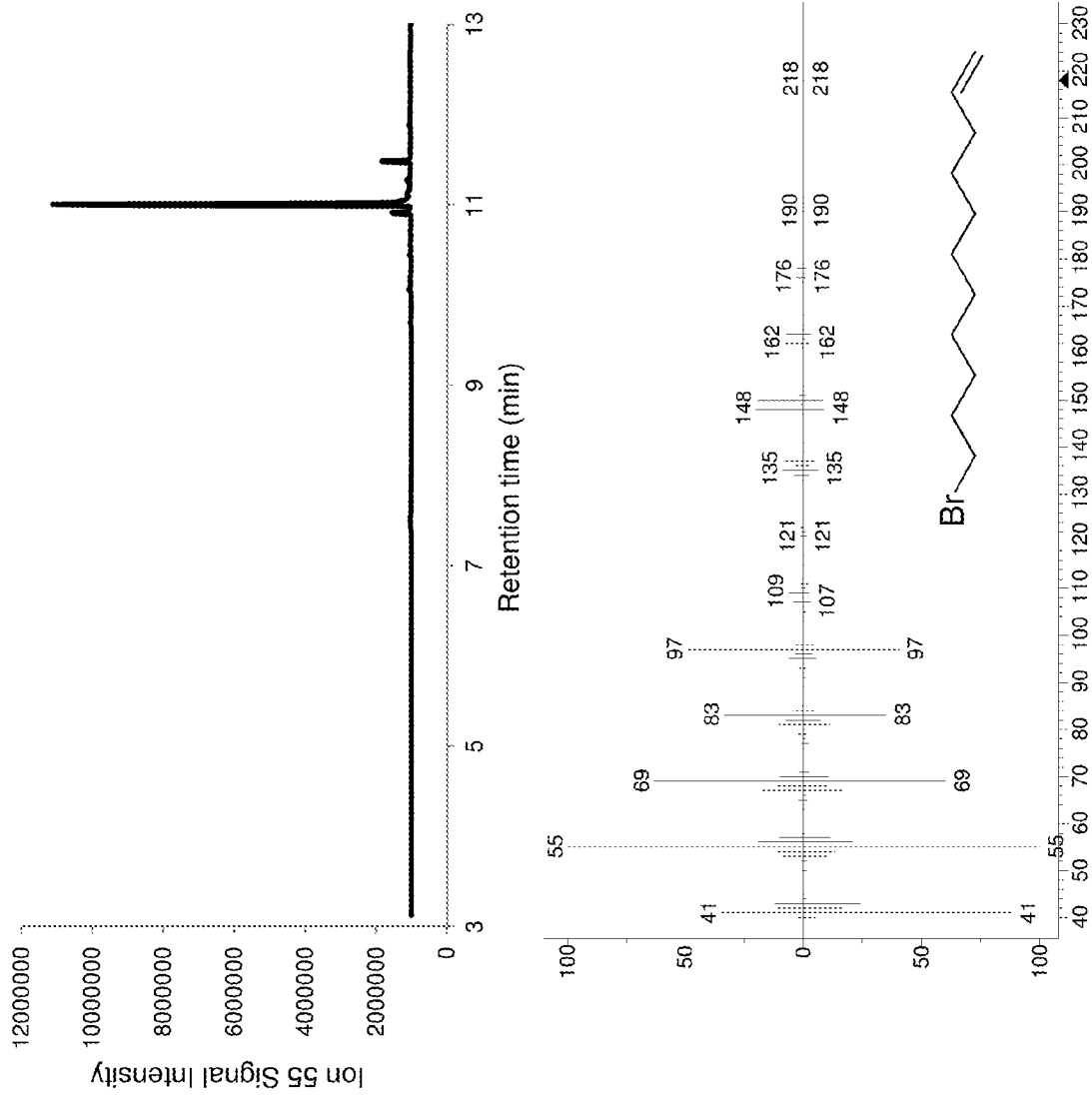
FIG. 12A-FIG. 12B illustrates GC-MS analysis of the conversions of 12-bromododecanoic acid to 11-bromoundec-1-ene. Reverse panel (bottom panel) in FIG. 12B illustrates the reference standard of 11-bromoundec-1-ene from the NIST spectral database.
Figure 13A:
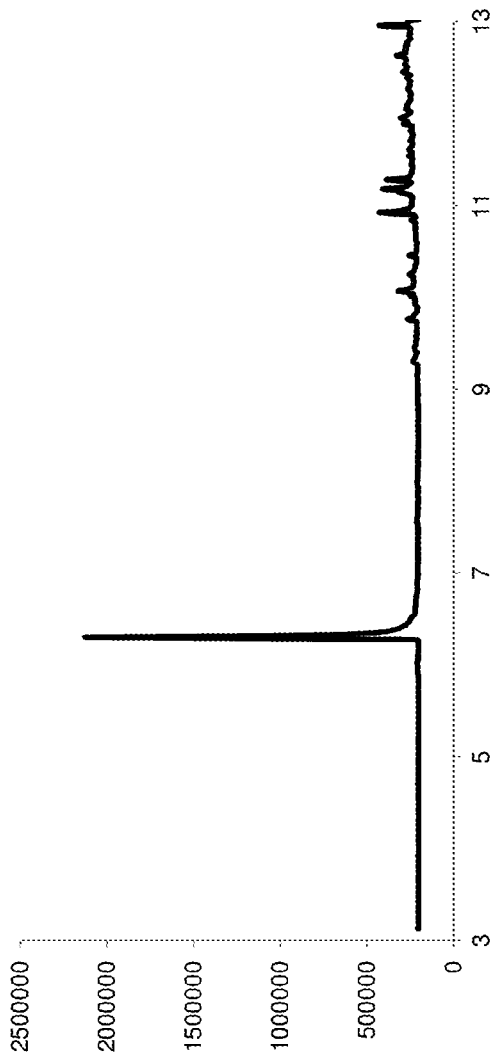
FIG. 13A-FIG. 13B illustrates GC-MS analysis of the conversions of 10-undecynoic acid to dec-1-en-9-yne.
Figure 13B:
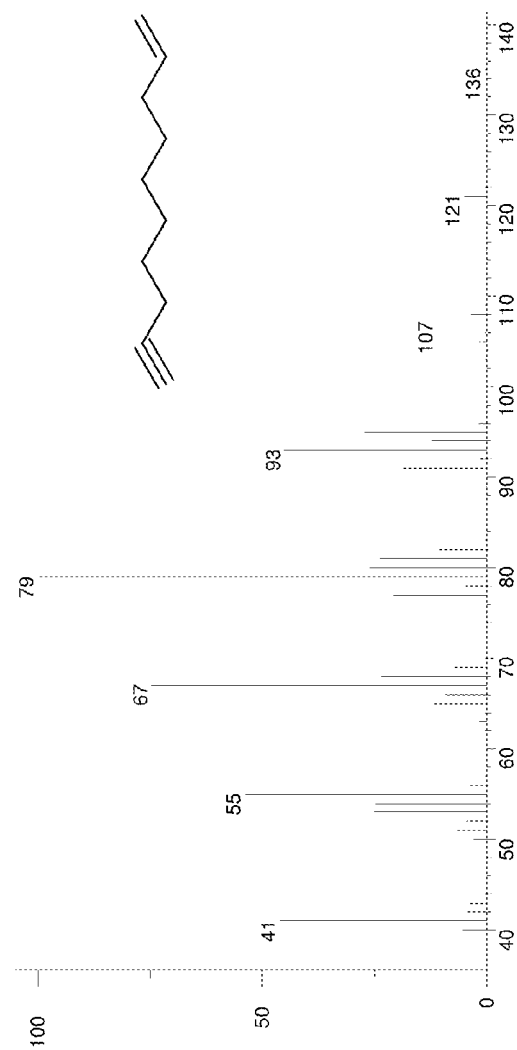
Figure 14:
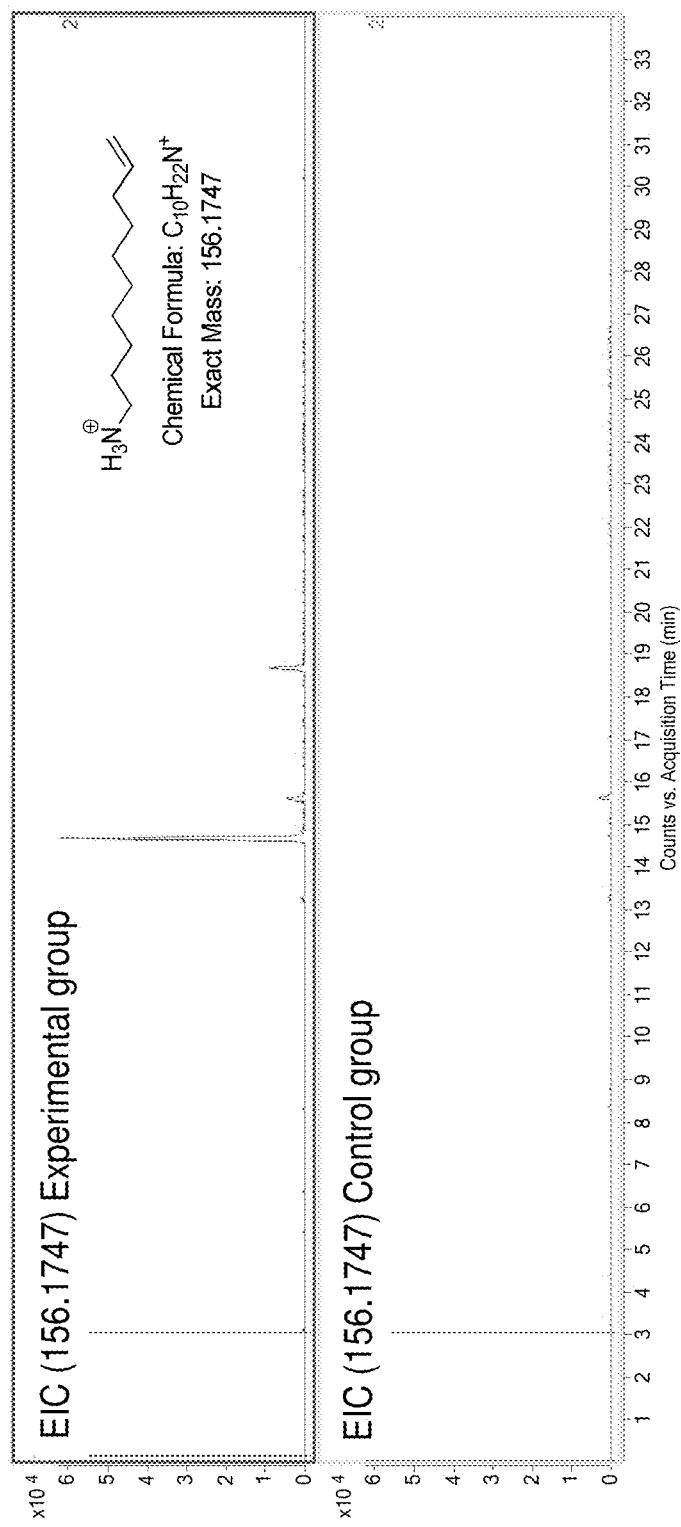
FIG. 14 illustrates extracted ion chromatograms from LC-HRMS analysis showing the conversion of 11-aminoundecanoic acid to 10-amino-dec-1-ene catalyzed by PFL_4321. PFL_4321 was omitted from the control group. The calculated mass with 10 ppm mass error tolerance was used.
Figure 15:
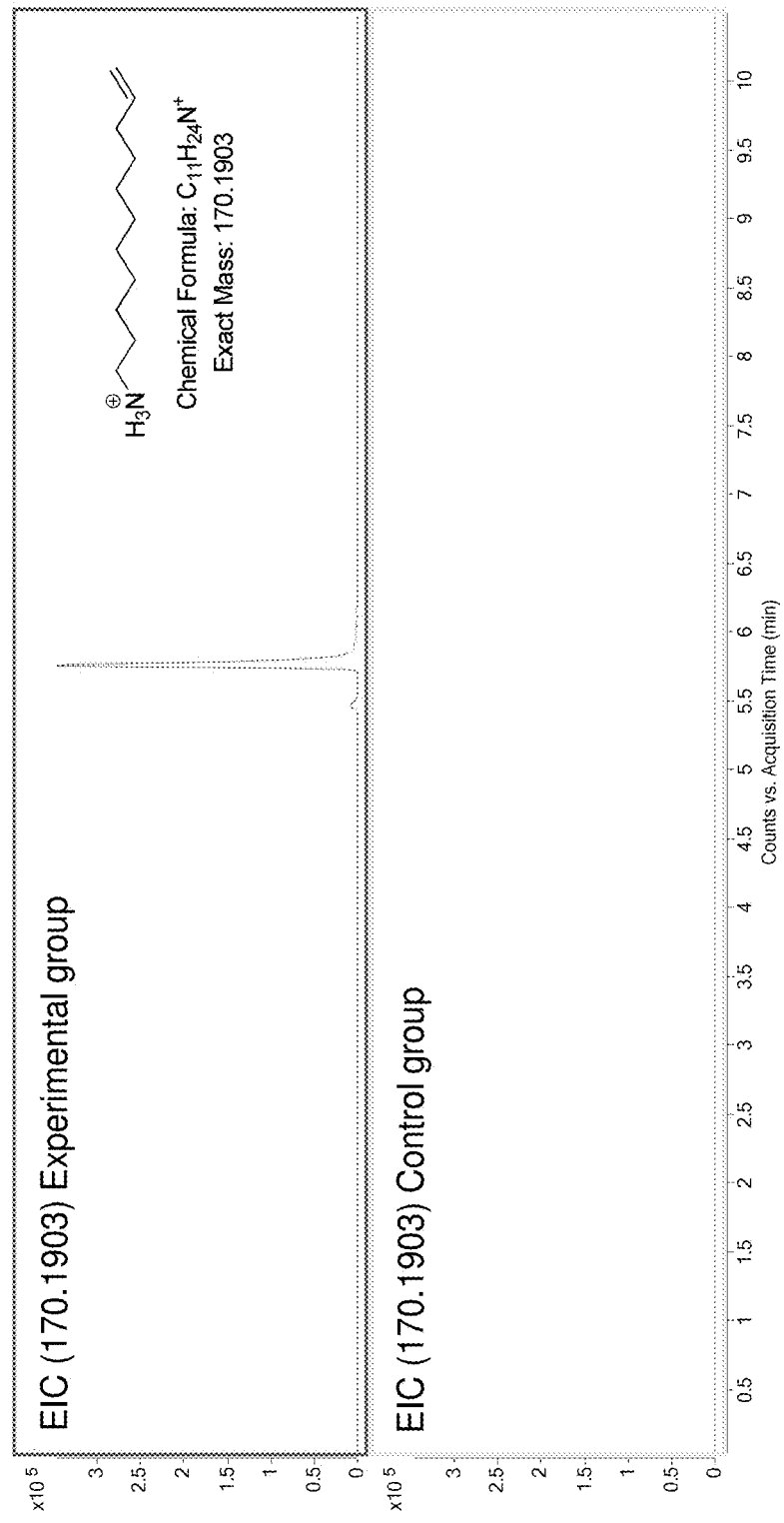
FIG. 15 illustrates extracted ion chromatograms from LC-HRMS analysis of the conversions of 12-aminododecanoic acid to 11-aminoundec-1-ene catalyzed by PFL_4321. PFL_4321 was omitted from the control group. The calculated mass with 10 ppm mass error tolerance was used.

A survey was conducted to identify the possible reductive cofactor/cosubstrates according to the well-studied oxygen-activating iron-dependent oxygenases, including but not limited to α-ketoglutarate, ascorbic acid, glutathione, cysteine, nicotinamides, flavins, ferredoxin (F. H. Vaillancourt et al., Nature 436, 1191, 2005; W. C. Chang et al., Nature 496, 114, 2013; L. M. Mirica et al., J Am Chem Soc 130, 8122, 2008; P. C. Bruijnincx et al., Chem Soc Rev 37, 2716, 2008). Under iron-limiting conditions, ascorbic acid significantly increased the yield of 1-undecene; cysteine had a modest effect; and none of other reagents exhibited a significant effect (FIG. 7). Accordingly, ascorbic acid was included in all of the following in vitro assays and the kinetic parameters of PFL_4321 toward lauric acid (C12) were determined (FIG. 8).

Figure 16A:
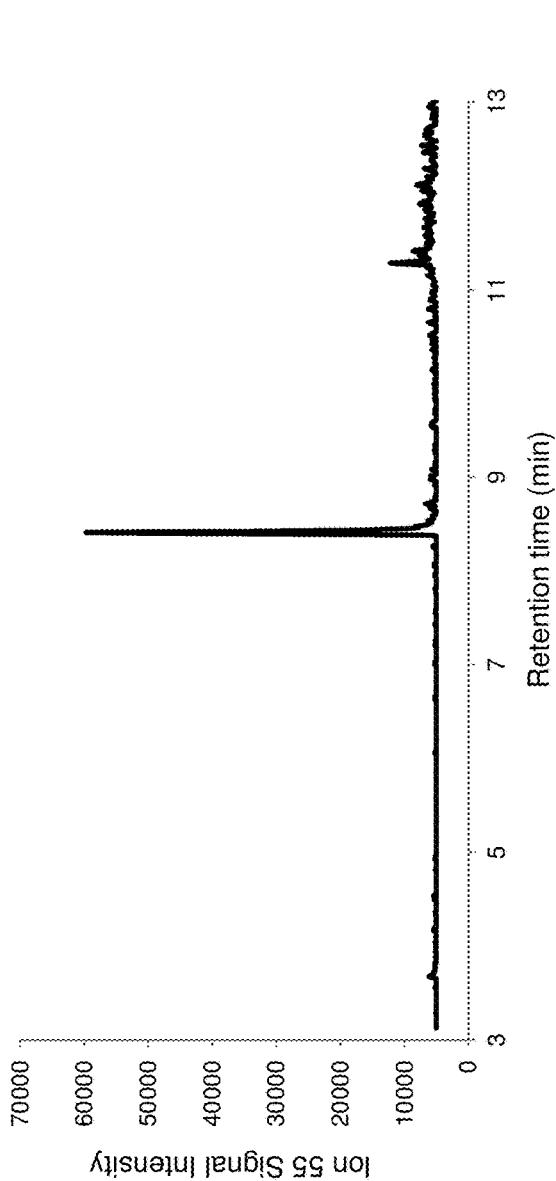
FIG. 16A-FIG. 16B illustrates GC-MS analysis of the conversions of 11-methyldodecanoic acid to 10-methylundec-1-ene. Reverse panel (bottom panel) in FIG. 16B illustrates the reference standard of 10-methylundec-1-ene from the NIST spectral database.
Figure 16B:
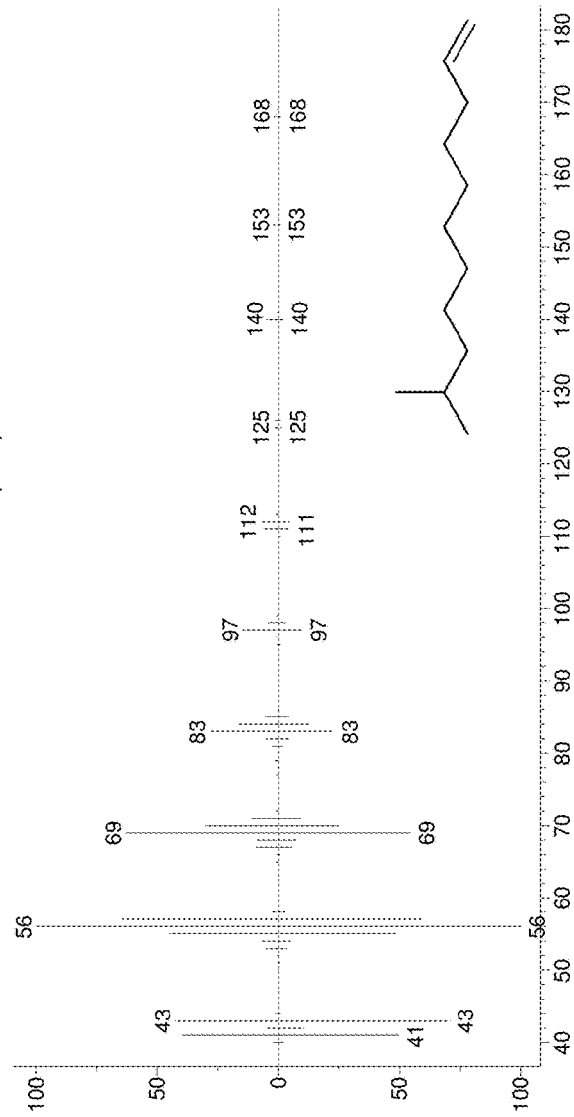
Figures 18A, 18B:
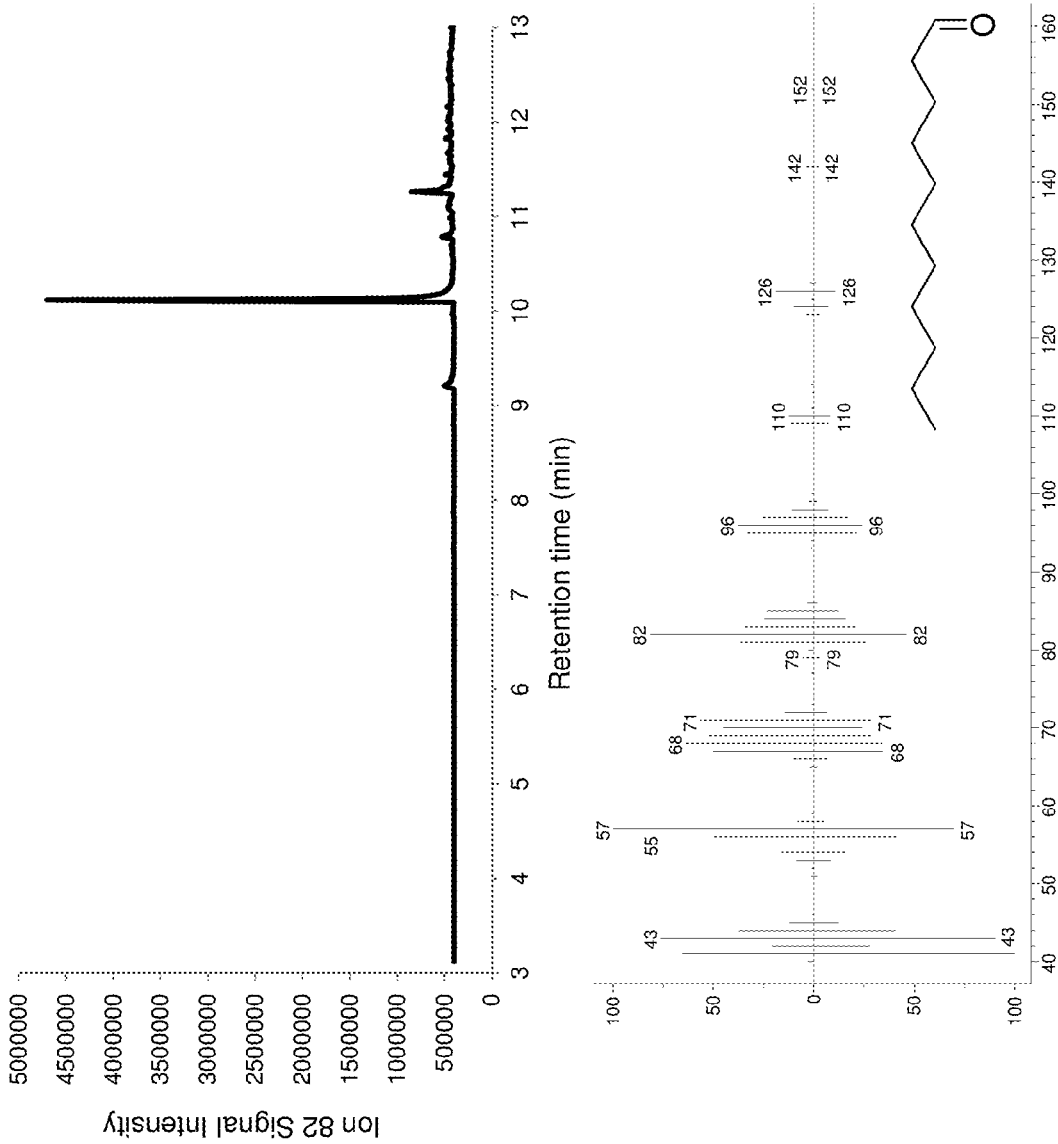
FIG. 18A-FIG. 18B illustrates GC-MS analysis of the conversions of α-hydroxylauric acid to 1-undecanal. Reverse panel (bottom panel) in FIG. 18B illustrates the reference standard of 1-undecanal from the NIST spectral database.
Figure 19:
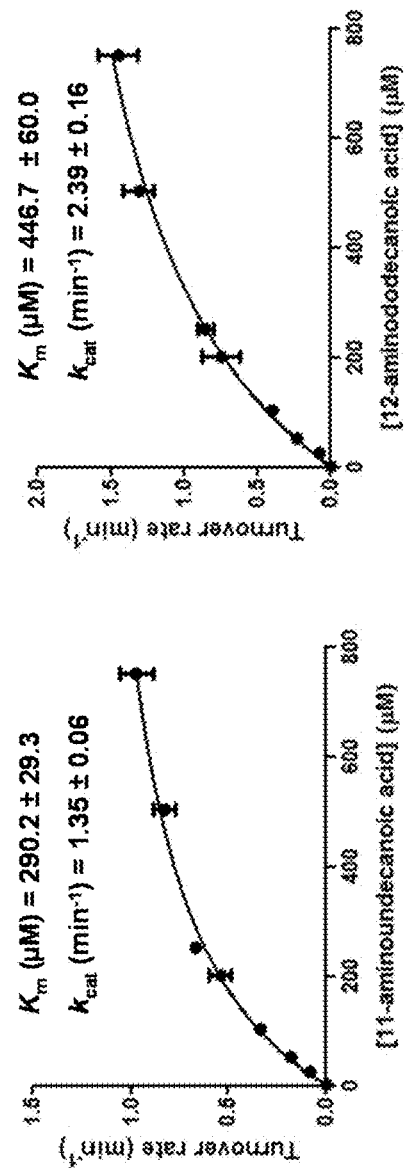
FIG. 19 illustrates Michaelis-Menten plots for PFL_4321 on 11-aminoundecanoic acid and 12-aminododecanoic acid.

In addition to using lauric acid as a substrate, PFL_4321 converted myristic acid (C14) and capric acid (C10) to their corresponding "[M-1] carbon" 1-alkenes (FIG. 8, FIG. 9, and FIG. 10), but failed to act on palmitic acid (C16) or caprylic acid (C8), indicating that the substrate binding pocket accepts a range of medium-chain length fatty acid substrates. Additionally, PFL_4321 catalyzed the conversion of 11-bromoundecanoic acid, 12-bromododecanoic acid, 10-undecynoic acid, 11-aminoundecanoic acid, and 12-aminododecanoic acid to form their corresponding minus-1-carbon 1-alkene, implying a wide spectrum of functionality tolerance on the ω-carbon (FIG. 11, FIG. 12, FIG. 13, FIG. 14, FIG. 15, and FIG. 19). Branched fatty acids such as 11-methyl- and 4-methyldodecanoic acid were also converted to their corresponding terminal olefins, showing the potential of developing this enzyme into a useful biocatalyst (FIG. 16 and FIG. 17). Interestingly, PFL_4321 transformed α-hydroxydodecanoic acid to 1-undecanal (FIG. 18), but exhibited no activity toward 2,3-dodecenoic acid (DEA) and β-hydroxydodecanoic acid (BHDA), suggesting that the β-carbon of lauric acid, rather than the α-carbon, is the site of activation during enzymatic catalysis.

Figures 22A, 22B:
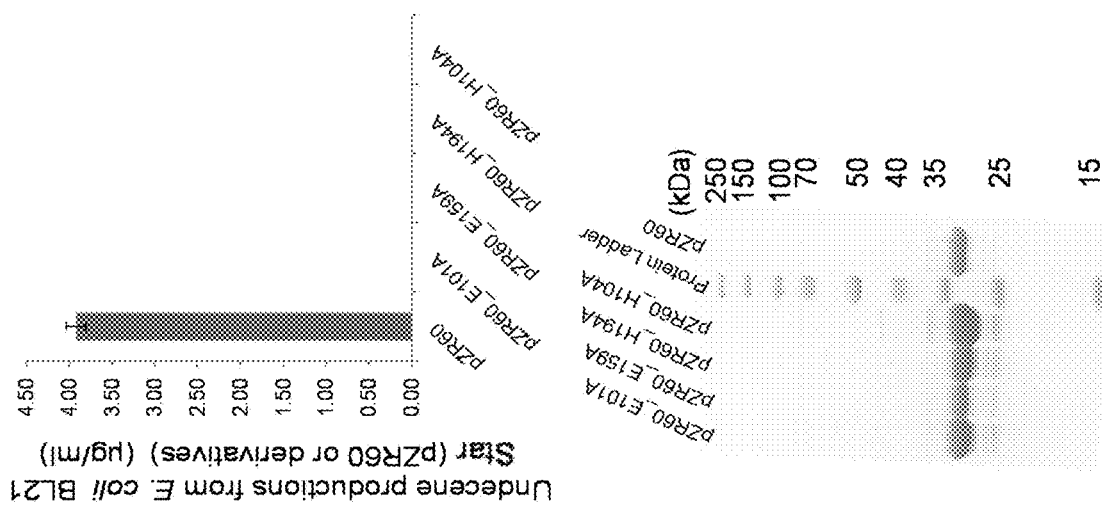
FIG. 22A illustrates a comparison of 1-undecene productions of E. coli BL21 (pZR60) and E. coli BL21 (pZR60 derivatives bearing point mutations on PFL_4321).
FIG. 22B illustrates that the point-mutation proteins are soluble.

To understand the molecular basis of catalysis and the substrate recognition mechanism, the crystal structures of PFL_4321 in its apo form and in complex with two substrate analogues, either DEA or BHDA, were determined with resolutions ranging from 1.7 to 1.9 Å (FIG. 20, FIG. 21, and Table 2). The active site of PFL_4321 contains a single iron center in an octahedral configuration with three sites of coordination from the enzyme side chains of $Glu_{101}$, $His_{104}$, $His_{194}$, and three variable sites of coordination, two facing the pocket and one exposed to exterior. The three variable sites are coordinated by oxygen atoms from the substrate analogues, solvents such as water or glycerol, or $O_2$. The critical roles of the $His_{194}$-$His_{104}$-$Glu_{101}$ residues were confirmed by site-directed mutagenesis, which resulted in an over 1000-fold drop in 1-undecene production (FIG. 22). The substrate analogues DEA or BHDA reside in a deep hydrophobic pocket that extends from the surface to the center of the enzyme (FIG. 20A and FIG. 20B). The depth of the pocket limits the length of the fatty acid substrate to an approximately 14-carbon chain, consistent with the in vitro biochemical results. Whereas the apo-structure represents the resting state of the active site with three iron coordination positions occupied by solvent molecules (one from water and two from glycerol) (FIG. 20C), co-crystallization with the substrate analogues DEA and BHDA seemed to trap the enzyme in different oxygen activation steps of the catalytic cycle. In crystals with DEA-bound enzymes, two different intermediates are present in the crystallographic asymmetric unit. One subunit contains a water molecule coordinated to the iron, demonstrating an intermediate stage with a bound fatty acid substrate prior to $O_2$ binding (FIG. 20D). In the other subunit, a diatomic molecule, assigned as molecular oxygen, replaces the water and occupies the iron coordination site opposite to the carboxyl oxygen of the fatty acid substrate in an end-on fashion (FIG. 20E). Dioxygen also appears in the BHDA-bound structure, which differs from the DEA-bound structures by the coordination of the β-hydroxyl group opposite to $His_{104}$ (FIG. 20F). The refined distance between the oxygen atoms in the BHDA-bound structure converges to 1.45 Å, suggesting the presence of a peroxide species, although this assignment is tentative due to the limit of resolution of 1.7 Å. The β-hydroxyl oxygen of BHDA is positioned only 2.45 Å from the distal oxygen atom (FIG. 21), implying a possible β-hydrogen abstraction from the native substrate lauric acid during the catalytic cycle.

Figure 23A:
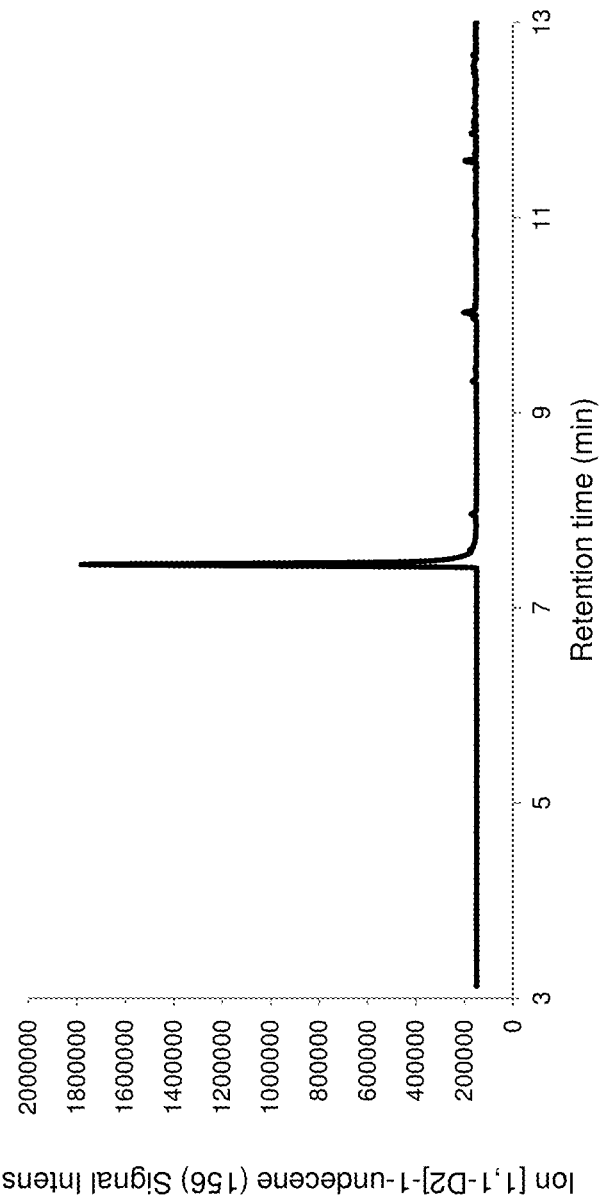
FIG. 23A-FIG. 23B illustrates GC-MS analysis of the conversions of [2,2-D2]lauric acid to [1,1-D2]undecene.
Figure 23B:
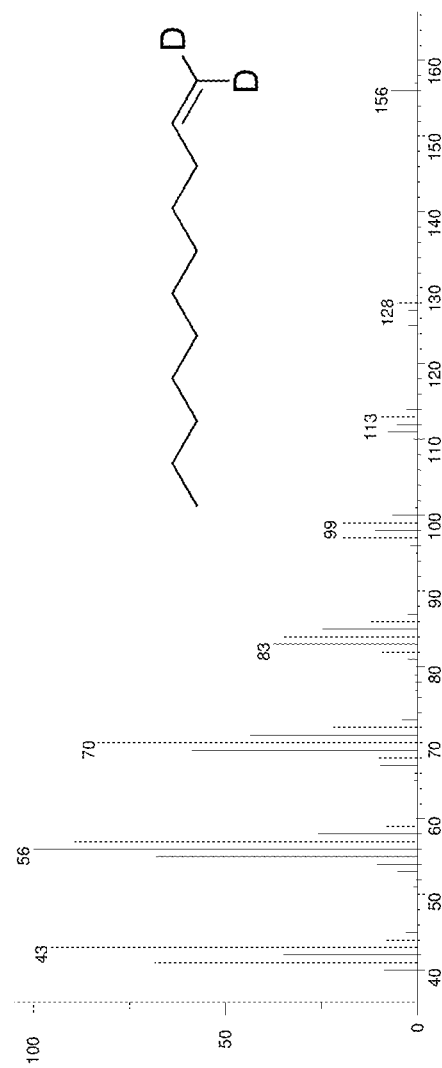

Based on the biochemical and structural characterization of PFL_4321, and without wishing to be bound by theory, an $O_2$-activating, non-heme Fe(II) dependent mechanism for the oxidative decarboxylation of lauric acid was postulated (FIG. 20G). First, lauric acid binds to the ferrous iron of the enzyme through its carboxylate moiety and organizes the iron center to coordinate molecular oxygen. This sequential binding is similar to that in many other non-heme iron enzymes, such as naphthalene dioxygenase and superoxide reductase (W. C. Chang et al., Nature 496, 114, 2013; P. C. Bruijnincx et al., Chem Soc Rev 37, 2716, 2008; A. Karlsson et al., Science 299, 1039, 2003; G. Katona et al., Science 316, 449, 2007; J. H. Jeoung et al., Proc Natl Acad Sci USA 110, 12625, 2013; W. A. van der Donk et al., Curr Opin Struct Biol 20, 673, 2010). Then, $O_2$ binds, generating a superoxo-Fe(III) species that likely abstracts the β-hydrogen of lauric acid. β-hydrogen abstraction is in agreement with the activity of PFL_4321 on the α- and β-substituted lauric acid analogues mentioned above, and it was further confirmed by enzymatic assays with the substrate [α,α-D2] (lauric acid which led to the production of 1-undecene retaining both deuterium atoms (FIG. 23). Subsequent single electron transfer at the stage of a highly reactive radical intermediate leads to the formation of 1-undecene, $CO_2$, and a possible Fe(II)-O—OH species that can be reduced back to the ferrous state to regenerate the active form of the enzyme. The residue $Glu_{159}$ might be involved in oxygen binding and/or serve as a proton donor, and its critical role was confirmed by the mutagenesis study (FIG. 22).

Figure 24B:
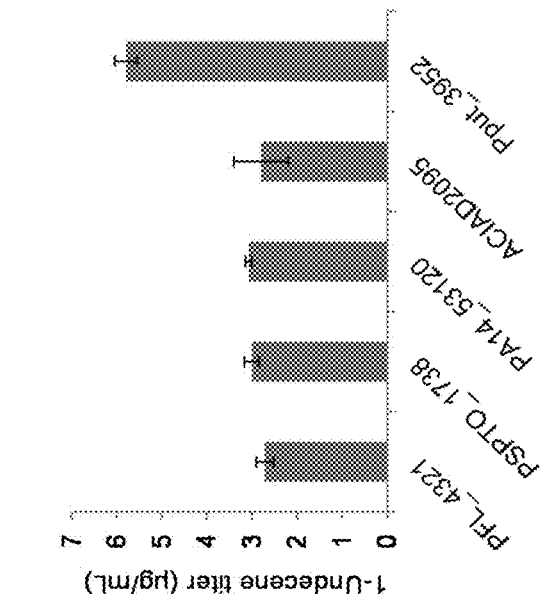
FIG. 24A-FIG. 24B illustrates the activities of PFL_4321 homologs.
Figure 24A:
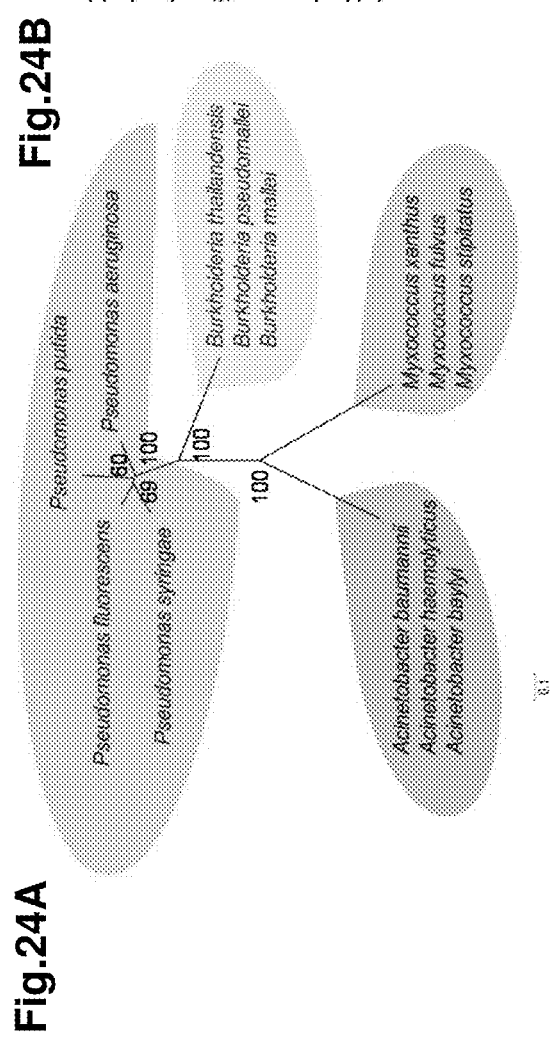
Figure 25:
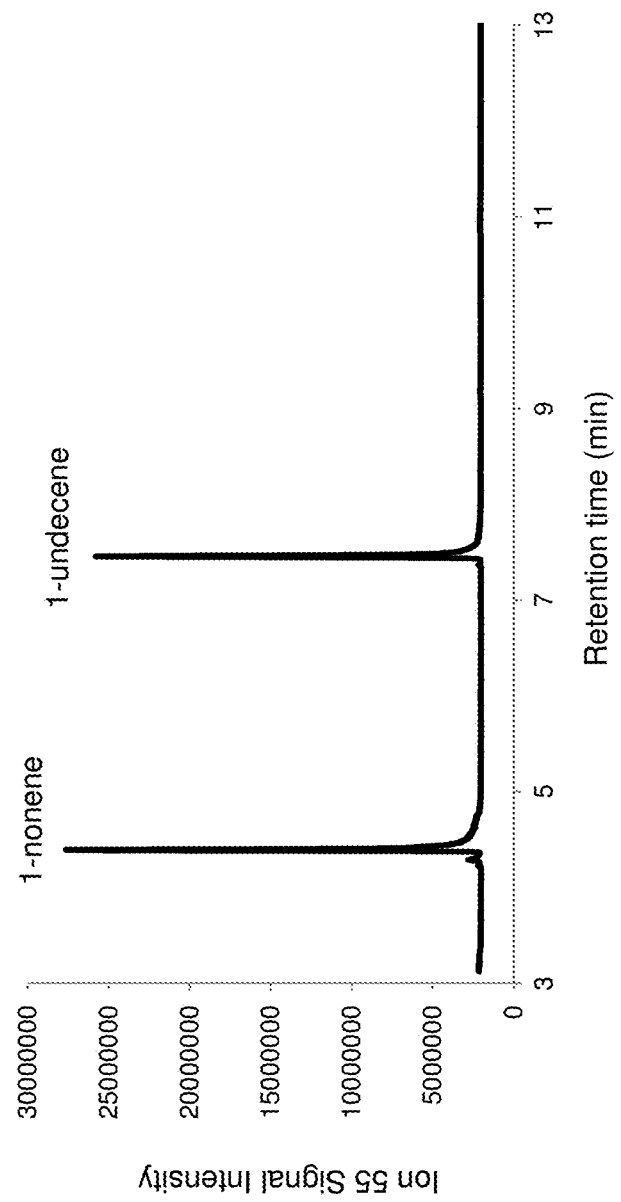
FIG. 25 illustrates GC-MS analysis of 1-undecene and nonene productions from *Saccharomyces cerevisiae* S288c (pESC_URA_PFL_4321). *Saccharomyces cerevisiae* S288c (pESC_URA_PFL_4321) was cultured in YPD media in sealed headspace vial at 30° C. for 36 hours before sampling using SPME-GCMS method.

Phylogenetic analysis revealed that PFL_4321 is ubiquitous in all of the sequenced *Pseudomonas* species and several other closely-related species, including species from *Acinetobacter*, *Burkholderia*, and *Myxococcus* genera, with a total of more than 400 homologs identified from published genomes (FIG. 24A). This is consistent with the initial screening results that all of the identified 1-undecene natural producers contain a gene homologous to PFL_4321, while the confirmed 1-undecene non-producers such as *E. coli* do not have a PFL_4321 homolog in their genomes. To further probe the activity of PFL_4321 homologs in the biosynthesis of 1-undecene, four additional PFL_4321 homologs from various *Pseudomonas* and *Acinetobacter* species were heterologously expressed. The overexpression of all gene candidates in *E. coli* conferred 1-undecene production, confirming the proposed function of these genes (FIG. 24B). The production titer of 1-undecene exceeded 5 μg/mL in *E. coli* in these initial efforts, suggesting that this family of enzymes are highly efficient in converting medium-chain free fatty acids into medium-chain 1-alkenes, since little free lauric acid is produced by *E. coli* (J. P. Torella et al., Proc Natl Acad Sci USA 110, 11290, 2013; R. M. Lennen et al., Trends Biotechnol 30, 659, 2012). Furthermore, PFL_4321 is functional in eukaryotic hosts such as *Saccharomyces cerevisiae*, in which the expression of PFL_4321 led to the production of 1-undecene and 1-nonene in comparable amounts (FIG. 25). The different product profiles of medium-chain 1-alkenes in yeast compared to those of *E. coli* reflect the different free fatty acid pools in these two model organisms.

Functions of this family of non-heme iron enzymes described herein substantially broaden the enzymatic reaction inventory to transform fatty acid precursors. By introducing a derivable terminal double bond on a medium-chain carbon backbone, the microbial production of medium-chain 1-alkenes could fundamentally revolutionize the current industrial practice of hydrocarbon production. This work serves as a basis for establishing bioprocesses for the production of fatty acid-derived chemicals and fuels from renewable resources.

Example 2: Additional Characterization of Medium-Chain 1-Alkene Production Mediated by PFL_4321

This Example provides additional characterization of the PFL_4321 protein presented in Example 1 and its role in facilitating the production of medium-chain 1-alkenes using fatty acid substrates.

Materials and Methods

Expression and Purification of PFL_4321 for In Vitro Assays

Unless otherwise noted, PFL_4321 was expressed in *E. coli* and purified for use in in vitro enzymatic assays as described in Example 1. General experimental protocols for in vitro assays not described in additional detail below were performed as described in Example 1.

Reconstitution of Holo-PFL_4321 In Vitro

The apo-PFL_4321 was rendered anoxic on a vacuum line by 5 cycles of evacuation and $N_2$ purge. To prevent reaction of the Fe(II) center with $O_2$, all subsequent manipulations to obtain PFL_4321-Fe(II) were carried out anaerobically with stringently deoxygenated solutions. 1 mM of PFL_4321 was incubated with 1 mM of $(NH_4)_2Fe(SO_4)_2$ and 1 mM DTT for 30 min in the anaerobic chamber before desalting on the GE Disposable PD-10 columns equilibrated in 10 mM Tris (8.5), 100 mM NaCl, and 200 mM $(NH_4)_2SO_4$. The desalted enzyme solution was analyzed by ICP-MS (Perkin Elmer Optima 5300 DV), and the iron concentration was fitted to the calibration curve obtained using four standard solutions (Sigma-Aldrich) in the range 10-1000 μg/L. For in vitro enzymatic assays, the desalted PFL_4321-Fe(II) was immediately used in the enzymatic reaction to achieve maximum activity.

Stoichiometry Determination in Single-Turnover Reactions

To investigate 1-undecene formation and the $O_2$ consumption, 0.5 mL of reaction mixture was prepared to contain 50 mM MES buffer (pH 6.2), 300 mM NaCl, 45 μM PFL_4321-Fe(II), and 500 μM LA (25 mM stock solution of LA sodium salt was prepared in 2% tergitol; tergitol is not required for <150 μM of LA). MES buffer (pH 6.2) was selected to reach slightly higher enzymatic activity than other buffers such as Bis-Tris (pH 6.0-7.0), Tris (pH 7.5-8.5), MOPS (pH 6.5-7.5), and HEPES (pH 6.8-8.0). The reaction was performed in a sealed headspace vial, initiated by adding PFL_4321 at room temperature and quenched by injecting equal volume of 5 M NaOH. 1-undecene production was analyzed and quantified using the SPME-GCMS method. The correlations of total 1-undecene produced and enzyme used were further determined varying PFL_4321 concentrations (40-1000 μM), and similar single turnover reactions were obtained in all assays (~0.7-0.8 molecule of 1-undecene per molecule of PFL_4321-Fe(II)). $O_2$ concentration was measured in a sealed reaction chamber (0.5 mL) with an integrated oxygen electrode unit (Oxygraph Plus System, Hansatech Instruments, UK). For the control group, LA was omitted from the reaction mixture.

$H_2O_2$ Detection

For the detection of $H_2O_2$, the enzymatic reaction was conducted by using the oxygen electrode unit as mentioned above. After the concentration of $O_2$ reached equilibrium, 120 U/mL of catalase was added to the reaction chamber. No rapid increase in the $O_2$ concentration was observed, suggesting that $H_2O_2$ was not present in the reaction mixture. Additionally, production of $H_2O_2$ was not readily detected using Amplex® Red Hydrogen Peroxide/Peroxidase Assay Kit. 250 μL of reaction mixture contained 50 mM MES buffer (pH 6.2), 200 mM $(NH_4)_2SO_4$, 500 μM PFL_4321-Fe(II), and 1 mM LA. The reaction mixture was subjected to centrifugation using Amicon® Ultra filters (3 kD cutoff) and 50 μL of flowthrough was added to 50 μL of the Amplex® Red Hydrogen Peroxide working solution, incubated for an hour at room temperature in the dark, and examined with excitation/emission maxima=570/585 nm for fluorescence as instructed. The positive controls contained 50 mM MES buffer (pH 6.2), 200 mM $(NH_4)_2SO_4$, 500 μM $(NH_4)_2Fe(SO_4)_2$, 500 μM LA, and various amounts of standard $H_2O_2$ either provided by the same kit or Sigma. The positive controls showed that this coupled assay had a sensitivity of 1 μM for $H_2O_2$ in the original reaction mixture of PFL_4321.

Enzyme Recycling Experiments

To recycle the PFL_4321, 1 mL of the oxygenated buffer solution (50 mM MES, pH 6.2, 100 mM NaCl) was mixed with 1 mL of an $O_2$-free solution containing 50 mM MES buffer (pH 6.2), 100 mM NaCl, 200 μM PFL_4321, 1 mM $(NH_4)_2Fe(SO_4)_2$, 2 mM LA, so that the final mixture contained 50 mM MES buffer (pH 6.2), 100 mM NaCl, 100 μM PFL_4321, 0.5 mM $(NH_4)_2Fe(SO_4)_2$, and 1 mM LA. This original reaction was quenched by adding 10-fold excess of EDTA to iron. The mixture was desalted on a GE Disposable PD-10 column and incubated at 4° C. on a nutator for two hours to completely remove the residual 1-undecene in the solution. The recycled apo-PFL_4321 was concentrated by using Centrifugal Filter Units (Millipore) and subjected to a second enzymatic assay that contained 50 mM MES buffer (pH 6.2), 100 mM NaCl, 100 μM PFL_4321, 0.5 mM $(NH_4)_2Fe(SO_4)_2$, and 1 mM LA. To initiate the reaction, 100 μL of the oxygenated buffer solution (50 mM MES, pH 6.2, 100 mM NaCl) was mixed with 100 μL of an $O_2$-free solution containing 50 mM MES buffer (pH 6.2), 100 mM NaCl, 200 μM PFL_4321, 1 mM $(NH_4)_2Fe(SO_4)_2$, 2 mM LA. The control group was set up under similar conditions except that the original apo-PFL_4321 which had not been used for any enzymatic reactions was used. The experimental group containing recycled PFL_4321 produced 80% of the 1-undecene compared with the control group that contained the original PFL_4321. When EDTA was omitted, the desalted recycled PFL_4321 failed to catalyze the reaction to produce 1-undecene.

Initial Production Rate Determination

Figure 29A:
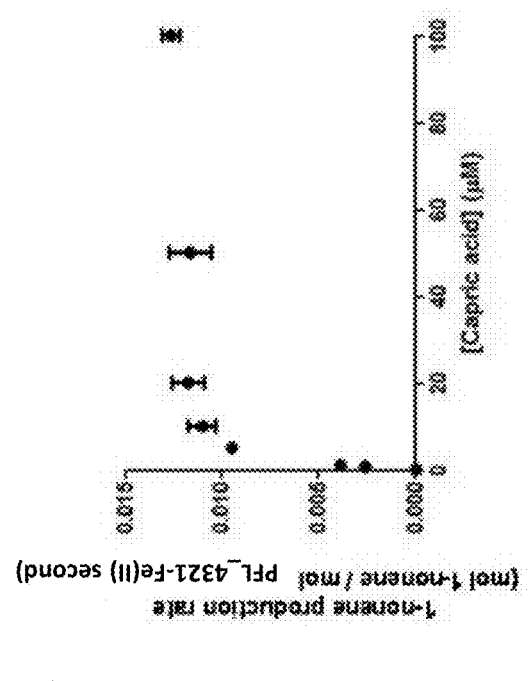
FIG. 29A-FIG. 29C illustrates measurements of the initial production rates of 1-alkenes by PFL_4321 at varying substrate concentrations. Substrates presented are lauric acid (LA) (FIG. 29A), capric acid (FIG. 29B), and myristic acid (FIG. 29C). Error bars represent standard deviations from at least three independently performed experiments.
Figure 29B:
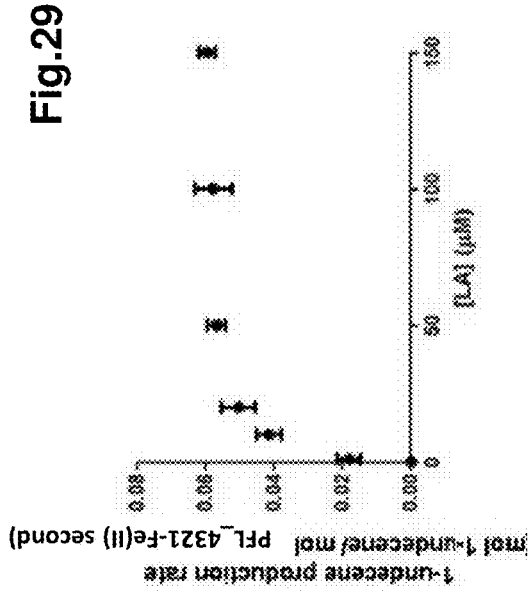
Figure 29C:
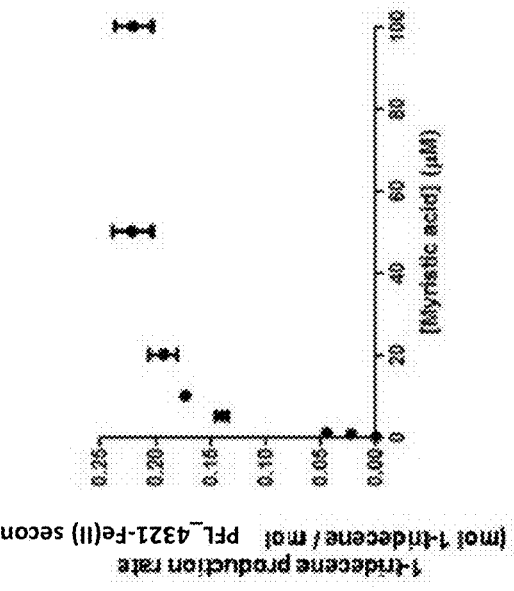

To determine the initial rates of 1-alkene production under the single turnover conditions, the $O_2$-saturated buffer solution (50 mM MES, pH 6.2, 100 mM NaCl) was mixed with an equal volume of an $O_2$-free solution containing 50 mM MES buffer (pH 6.2), 100 mM NaCl, 200 μM $(NH_4)_2Fe(SO_4)_2$, 0.2-20 μM PFL_4321, and various concentrations of substrate (2-300 μM), so that the final mixture contained 50 mM MES buffer (pH 6.2), 100 mM NaCl, 0.1-10 μM PFL_4321, 100 μM $(NH_4)_2Fe(SO_4)_2$, and various concentrations of substrate (1-150 μM). The reactions were carried out in sealed GC vials and quenched by injecting 1 M NaOH at 2, 4, 6, 8, 10, 20, 30, 40, 50, 60 seconds. The productions of 1-alkenes were analyzed by SPME-GCMS analysis. The acquired 1-alkene production rates were plotted against fatty acid concentrations as shown in FIG. 29.

Reductive Co-Substrate Screening

To survey the possible reductive co-substrates, the oxygenated buffer solution (50 mM MES, pH 6.2, 100 mM NaCl) was mixed with an equal volume of an $O_2$-free solution containing 50 mM MES buffer (pH 6.2), 100 mM NaCl, 200 µM PFL_4321, 200 µM $(NH_4)_2Fe(SO_4)_2$, 2 mM LA, and 4 mM of the reductive co-substrate, so that the final mixture contained 50 mM MES buffer (pH 6.2), 100 mM NaCl, 100 µM PFL_4321, 100 µM $(NH_4)_2Fe(SO_4)_2$, 1 mM LA, and 2 mM of the reductive co-substrate. The reaction was carried out in a sealed GC vial due to the semi-volatility of 1-undecene. For the chlorite dismutase coupled assay, 2 µM of chlorite dismutase (Dassama L M K, et al., *Biochemistry-Us* 51(8):1607-1616) was included in the mixture, and 1 mM of sodium chlorite was injected through the septa four times every 20 min. 2 mM of reductive co-substrate was added with the following exceptions: 40 µM FAD or FMN was coupled with 20 µM Flavin reductase (AsuE2 (Rui Z et al., 2013, Chem Biol 20(7):879-887)) and 2 mM NAD(P)H; 40 µM ferredoxin was coupled with 20 µM ferredoxin reductase and 2 mM NAD(P)H; 40 µM of pyrroloquinoline quinone was coupled with 2 mM of cysteine (Ouchi A et al., 2009, *J Agric Food Chem* 57(2):450-456); and 40 µM phenazine methosulfate was coupled with 2 mM NADH (Eser B E et al., 2011, *Biochemistry-Us* 50(49):10743-10750).

Test of $H_2O_2$ as a Possible Substrate

To examine whether the $H_2O_2/Fe^{3+}$ or the $H_2O_2/Fe^{2+}$ system provides for the PFL_4321 activity, anaerobic enzymatic reactions in the glove box were performed. The deoxygenated reaction mixture contained 50 mM MES buffer (pH 6.2), 100 mM NaCl, 100 µM PFL_4321, 100 µM either $FeCl_3$ or $(NH_4)_2Fe(SO_4)_2$, 1 mM LA, and various amount of $H_2O_2$ (100, 200, 500, 1000, 5000 µM), and 1-undecene production was analyzed. The aerobic reaction was carried out under similar conditions except that the $O_2$ was provided by mixing with the equal volume of $O_2$-saturated buffer solution (50 mM MES, pH 6.2, 100 mM NaCl).

Results

Various assays investigating the role of PFL_4321 (also referred to as undA) in the production of medium-chain 1-alkenes using fatty acid substrates were performed as described in Example 1. Additional assays were performed to build upon these initial investigations as described in the present Example.

Biochemical Analysis

Figure 26:
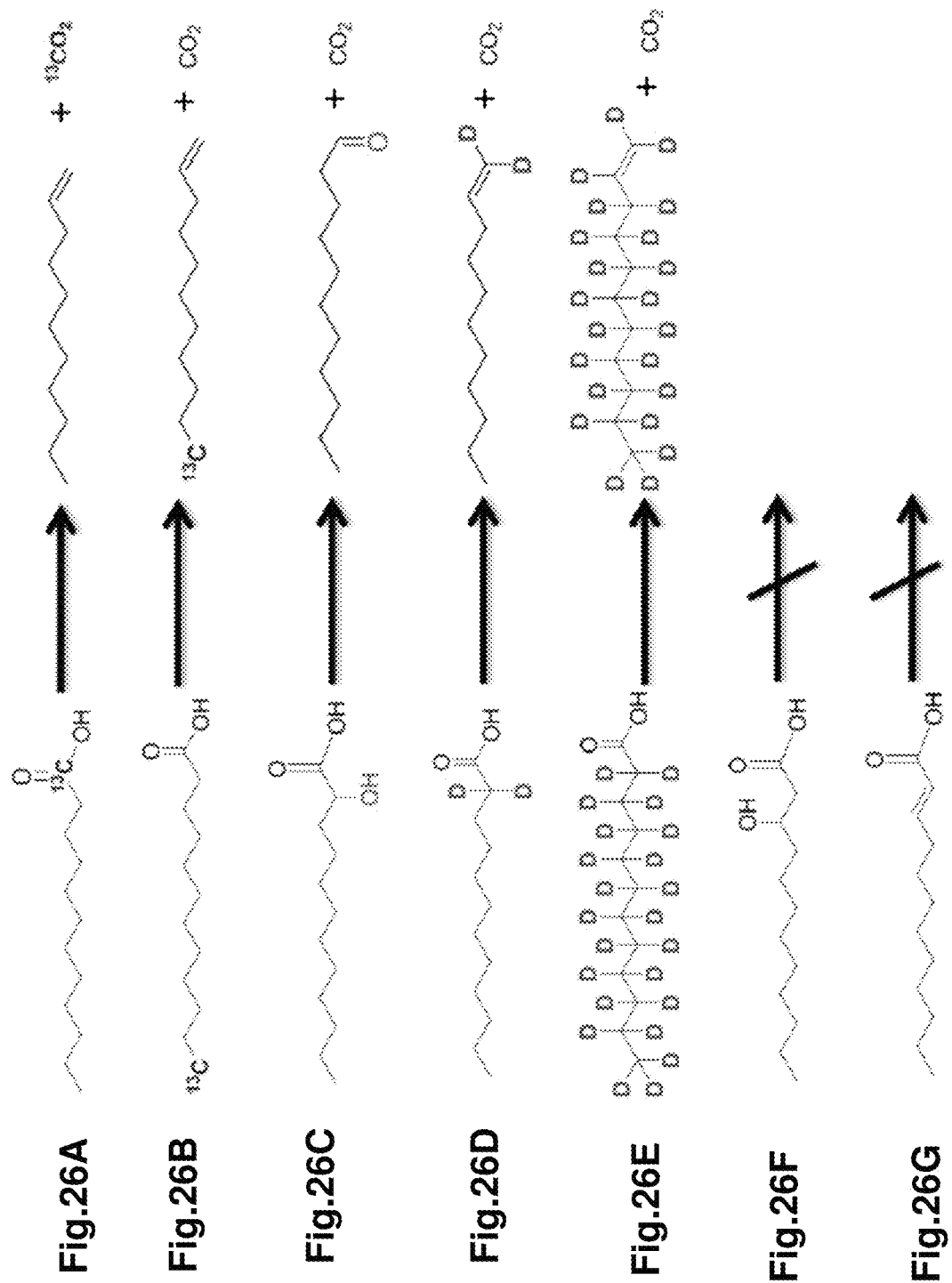
FIG. 26A-FIG. 26G illustrates PFL_4321 activity toward selected substrates. Substrates shown are as follows: [$1$-$^{13}$C] lauric acid (FIG. 26A); [$12$-$^{13}$C]lauric acid (FIG. 26B); α-hydroxydodecanoic acid (AHDA) (FIG. 26C); [α,α-D2] lauric acid (FIG. 26D); [D23]lauric acid (FIG. 26E); β-hydroxydodecanoic acid (BHDA) (FIG. 26F); 2,3-dodecenoic acid (DEA) (FIG. 26G).
Figure 27:
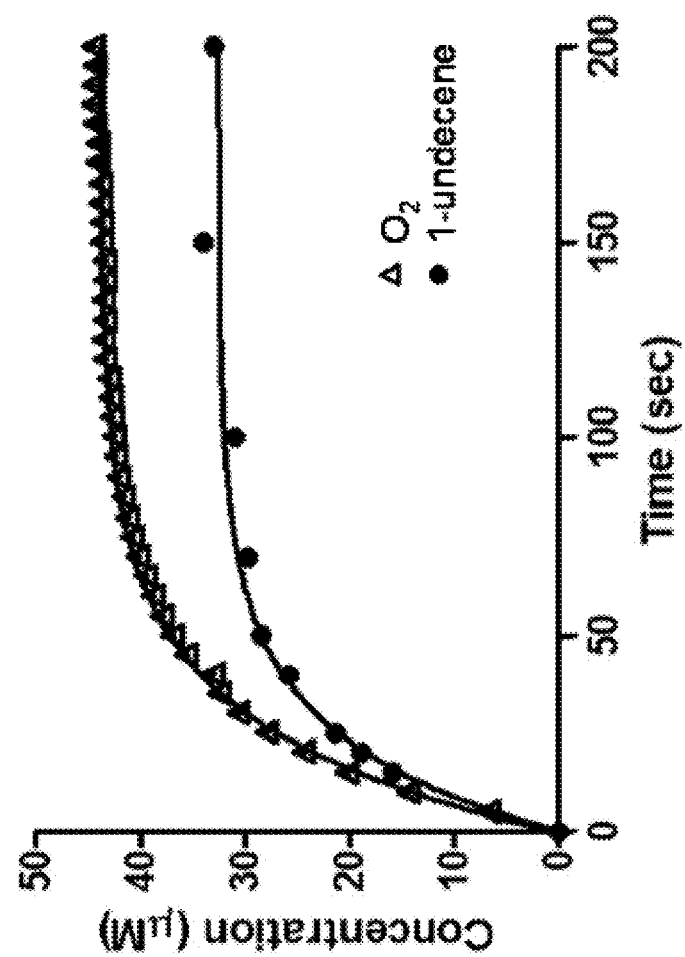
FIG. 27 illustrates the requirement for $O_2$ for PFL_4321 activity. This in vitro assay with PFL_4321 shows the consumption of dissolved oxygen (Δ) detected by the oxygen electrode in relation with the formation of 1-undecene (•) measured by SPME-GCMS in a typical reaction mixture containing 50 mM MES buffer (pH 6.2), 300 mM NaCl, 45 μM holo-PFL_4321, and 500 μM LA.

After reconstituting the activity of PFL_4321 in vitro, detailed biochemical analyses of this enzyme were performed. The iron content of PFL_4321 after anaerobic reconstitution of purified apo-PFL_4321 with $Fe^{2+}$ was determined to be 82% by inductively coupled plasma mass spectrometry (ICP-MS). Using [1-$^{13}$C]lauric acid as a substrate, formation of [$^{13}$C]$CO_2$ was detected (FIG. 5 and FIG. 26), confirming that PFL_4321 catalyzes production of 1-undecene from LA through oxidative decarboxylation. Since the in vitro aerobic reaction mixture contained only desalted PFL_4321-Fe(II) and LA with no additional oxidant/reductant, it was reasoned that molecular oxygen served as the oxidant of the reaction, which was supported by the observations that 1-undecene production was nearly abolished in anaerobic enzymatic assays, and that $O_2$ was consumed in aerobic assays (FIG. 6 and FIG. 27). The measured stoichiometry of the reaction showed that one molecule of PFL_4321-Fe(II) consumed approximately one equivalent of $O_2$ to produce close to one equivalent of 1-undecene (FIG. 27). $O_2$ was presumably reduced to hydrogen peroxide or water by PFL_4321. Without wishing to be bound by theory, it is proposed that $H_2O$ was a likely end product since no production of $H_2O_2$ was detected in the PFL_4321 assays by two independent sensitive analytical methods, and the addition of catalase to the reaction system had no detectable effect.

Initially, only single turnover reactions were obtained in the PFL_4321 in vitro assays, probably due to an electron imbalance, where two electrons are donated by one molecule of LA while four electrons are required to reduce one molecule of $O_2$ to water. Without wishing to be bound by theory, it is thought that this electron imbalance stalls the enzyme, presumably with an inactive oxidized iron species. This hypothesis is supported by a PFL_4321 recycling experiment in which apo-PFL_4321 recycled after the single turnover reaction maintained over 80% activity upon reconstitution with fresh $Fe^{2+}$.

Figure 28:
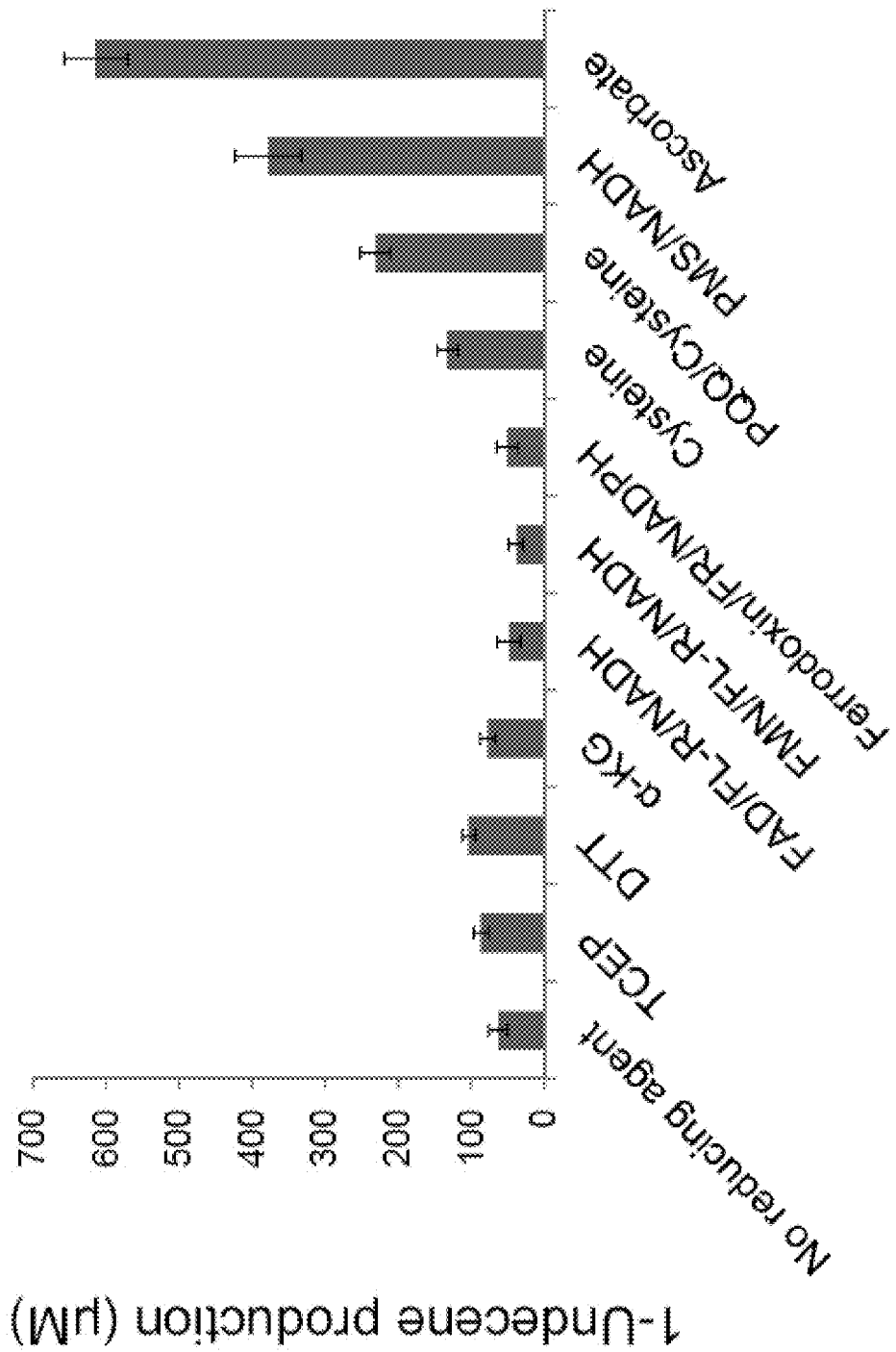
FIG. 28 illustrates a comparison of 1-undecene production by using various reductive cofactors/cosubstrates in the presence of excessive $O_2$ provided by the coupled chloride dismutase reaction. The reaction mixture contains 100 μM MES (pH 6.1), 300 mM NaCl, 1 mM lauric acid (dissolved in 0.5% tergitol), 100 μM PFL_4321, 100 μM $(NH_4)_2Fe(SO_4)_2$, 2 μM chlorite dismutase, 4 mM sodium chlorite, and 2 mM reductive cofactor/co-substrates. When needed, 40 μM FAD, FMN, ferredoxin, PQQ, or PMS, and 20 μM flavin reductase (FL-R) or ferredoxin reductase (FR) were added. 1-undecene production was analyzed after reacting for 100 min. Error bars represent standard deviations from at least three independently performed experiments.

Next, a group of possible reductive co-substrates based on those used by well-studied oxygen-activating iron-dependent oxygenases was surveyed (F. H. Vaillancourt et al., Nature 436, 1191, 2005; W. C. Chang et al., Nature 496, 114, 2013; L. M. Mirica et al., J Am Chem Soc 130, 8122, 2008; P. C. Bruijnincx et al., Chem Soc Rev 37, 2716, 2008). These reductive co-substrates included α-ketoglutarate (α-KG), ascorbic acid, glutathione, cysteine, dithiothreitol (DTT), tris(2-carboxyethyl)phosphine (TCEP), nicotinamides, flavins, ferredoxin, tetrahydropterin, phenazine methosulfate (PMS)/NADH, and PQQ/cysteine. Initially, none of the tested reducing systems promoted 1-undecene production over the stoichiometric amount of one turnover. Without wishing to be bound by theory, it was suspected that the limiting factor was likely the consumption of dissolved $O_2$ by both the enzymatic reaction and some of the tested reducing agents in the sealed vial without replenishment. Indeed, through coupling with the chlorite dismutase reaction to generate $O_2$ in situ (Dassama L M K, et al., 2012, *Biochemistry-Us* 51(8):1607-1616), it was found that ascorbate allowed for multiple turnovers for PFL_4321 in vitro, but the rate (four turnovers per hour) was much slower than the initial rate of 1-undecene production under the single turnover condition [0.06±0.002 mol 1-undecene/(mol PFL_4321-Fe(II) second)] (FIG. 28 and FIG. 29). Other electron donors such as PMS/NADH and PQQ/cysteine also allowed for multiple turnovers, although the resulting rates and yields were lower than when ascorbate was the reductant (FIG. 28).

Since HppE, a long recognized non-heme iron (II) oxidase was recently characterized to be a peroxidase (Wang C, et al., 2013, *Science* 342(6161):991-995), the possibility that $H_2O_2$, rather than $O_2$, could be the real substrate for PFL_4321 was tested. The reduction of $H_2O_2$ to water requires only two electrons, matching the two-electron requirement for the overall conversion of LA to 1-undecene. However, in the presence of $H_2O_2$, no 1-undecene was formed in anaerobic reactions with either PFL_4321-Fe(III) or PFL_4321-Fe(II). In the presence of both $H_2O_2$ and $O_2$, no 1-undecene was formed with PFL_4321-Fe(III), further confirming the requirement of Fe(II) for the activity of PFL_4321. In addition, $H_2O_2$ did not promote the 1-undecene formation in the reaction containing $O_2$ and PFL_4321-Fe(II), indicating that $H_2O_2$ is not the substrate for PFL_4321. These results are consistent with the observations that addition of dithionite to reduce $O_2$ to $H_2O_2$ in situ inhibited 1-undecene production by PFL_4321, but the addition of dithionite increased the rate of HppE up to 1000 times (Wang C, et al., 2013, *Science* 342(6161):991-995).

Figure 30A:
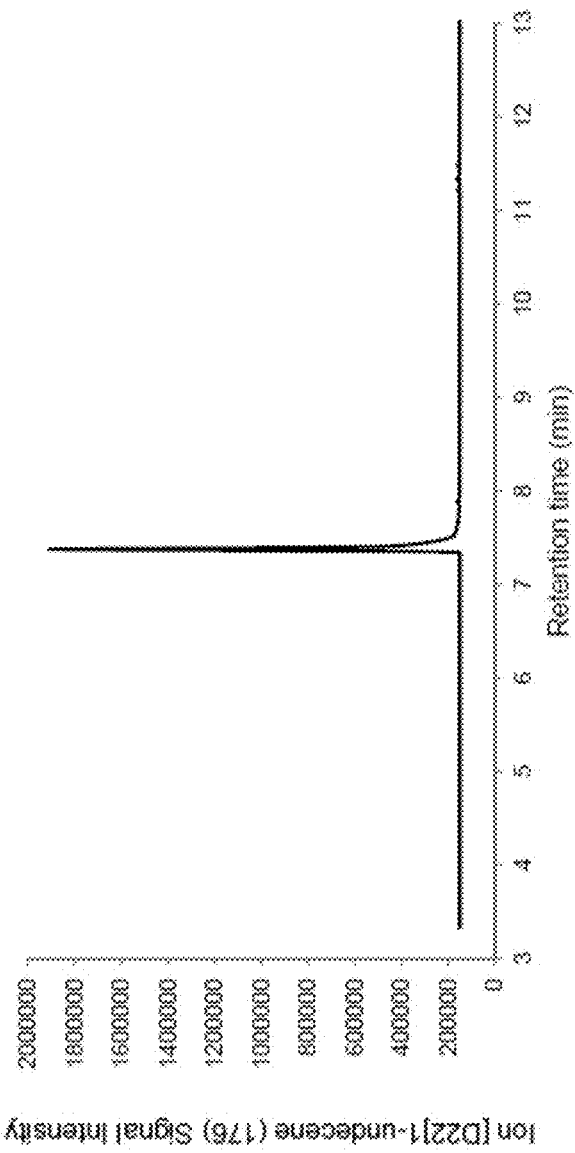
FIG. 30A-FIG. 30B illustrates GC-MS analysis of the conversion of [D23]lauric acid to [D22]1-undecene.
Figure 30B:
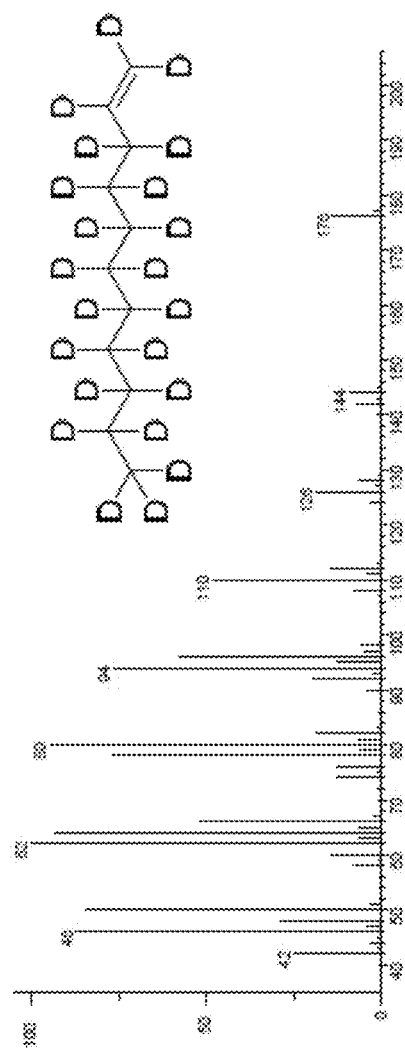

Further, as described in Example 1, in addition to LA (C12:0), PFL_4321 converted myristic acid (C14:0) and capric acid (C10:0) to their corresponding "[M-1]-carbon" 1-alkenes, and the initial rates of 1-alkene production at varying substrate concentrations were further measured (FIG. 29). PFL_4321 failed to act on palmitic acid (C16:0) or caprylic acid (C8:0), indicating that the substrate binding pocket of the enzyme accepts a range of medium-chain length fatty acid substrates. Interestingly, PFL_4321 transformed AHDA to 1-undecanal, but exhibited no activity toward DEA and BHDA (FIG. 26), suggesting that the β-carbon of LA, rather than the α-carbon, is the site of activation during enzymatic catalysis. This is further confirmed by the PFL_4321 assay with [α,α-D2]lauric acid, which led to the production of 1-undecene retaining both deuterium atoms (FIG. 23), and the PFL_4321 assay with [D23]lauric acid, which led to the production of [D22]1-undecene (FIG. 26 and FIG. 30).

Discussion

In summary, the data presented in this Example and in Example 1 demonstrate that Applicants have revealed the genetic basis and molecular mechanism for biosynthesis of 1-undecene, a ubiquitous hydrocarbon metabolite of *Pseudomonas*. In these investigations, it was found that a new family of non-heme oxidases that convert medium-chain fatty acids (C10-C14) into the corresponding terminal olefins use an oxygen-activating, non-heme iron-dependent mechanism. Both biochemical and structural analyses suggest an unusual mechanism of β-hydrogen abstraction by a "less reactive" iron center during fatty acid activation. It is notable that without strain optimization, overexpression of PFL_4321 homologs in *E. coli* produced 1-undecene at a titer over 25-fold higher than the best titer in *Pseudomonas* (FIG. 24B). These results expand the scarce enzyme inventory for the transformation of fatty acid precursors to hydrocarbons (R. M. Lennen et al, Curr Opin Biotechnol 24, 1044, 2013), and establish a platform for producing medium-chain 1-alkenes, useful as fuels and chemical building blocks, from renewable resources.

Example 3: Identification of PFL_0203 as a Membrane-Bound Medium-Chain 1-Alkene Formation Enzyme This Example demonstrates that the protein PFL_0203 from *Pseduomonas fluorescens* Pf-5 is able to facilitate the conversion of fatty acid substrates into their corresponding terminal olefins. PFL_0203 acts on C10-C16 fatty acid substrates, thus exhibiting some substrate overlap as well as some unique specificity as compared to PFL_4321 as described in Examples 1 and 2. Supplementing culture media with exogenous lauric acid (LA) or co-expressing a codon-optimized UcFatB2 thioesterase with PFL_0203 substantially increased the 1-undecene production titer in *E. coli*. These findings further establish methods for tailored conversion of renewable raw materials to fuels and chemical commodities.

Introduction

From Example 1, a library screening technique was used to identify potential proteins from *Pseudomonas fluorescens* Pf-5 involved in the biosynthesis of 1-undecene, which led to the identification of PFL_4321 as an enzyme involved in facilitating the production of medium-chain 1-alkenes using fatty acid substrates. In that particular screen, segments of the *P. fluorescens* Pf-5 genome were heterologously expressed in *E. coli* and the resultant transformants were monitored for the production of 1-undecene; a compound that *E. coli* does not naturally produce. Although PFL_4321 was successfully identified from this screen, it was recognized that the intracellular concentration of free fatty acids in *E. coli* is actually fairly limited. In view of this, it was considered possible that this screen may not have identified 1-undecene biosynthetic enzymes that prefer and/or require a higher free fatty acid concentration than is endogenously present in *E. coli* in order to facilitate significant production of 1-undecene. Accordingly, Applicants performed an additional screen in an attempt to identify additional 1-undecene biosynthetic enzymes. The results of this screen are presented in this Example.

Materials and Methods

Unless otherwise noted, all experiments with PFL_0203 as described herein were performed using similar assays, procedures, and techniques as used in a given corresponding experiment as described in Example 1.

Computational Tools

The structure of PFL_0203 was computationally analyzed using the TMHMM Server v. 2.0 program (http://www.cbs.dtu.dk/services/TMHMM-2.0/) and the SACS MEMSAT2 Transmembrane Prediction Page program (http://www.sacs.ucsf.edu/cgi-bin/memsat.py).

Cell Fractionation Assay

*E. coli* BL21 expressing PFL_0203 (pZR74) was grown until OD 0.6, induced with 0.1 mM IPTG, and cultured at 16° C. overnight. The cells were then harvested and lysed by sonication. The membrane fraction was separated from the soluble protein fraction by centrifugation at 20,000 g. Either the membrane fraction or the soluble protein fraction was mixed with 1 mM LA, 50 mM MES (pH 6.2), and 1 mM ferrous iron. The SPME-GCMS analysis of 1-undecene was as described in Examples 1 and 2.

Co-Expression with UcFatB2

*E. coli* cell lines were constructed where UcFatB2 was co-expressed with either PFL_4321 or PFL_0203. UcFatB2 was expressed under the control of the T7 promoter on pJT208, a pET based vector. The pJT208 vector housing codon-optimized UcFatB2, as well as the sequence of the codon-optomized UcFatB2 itself, were previously described and used herein (Torella et al., 2013).

Results

Identification of PFL_0203

A library screen analogous to that described in Example 1 was performed, except that the screen was modified by supplementing the culture media with 200 μM exogenous lauric acid. In this modified screen, the fosmid clone designated as 5B5 was found to produce 1-undecene only in the presence of exogenous lauric acid. Without wishing to be bound by theory, it is thought that fosmid clone 5B5 was not identified in the screen described in Example 1 because the culture media was not supplemented with exogenous lauric acid.

To identify the specific gene(s) responsible for the 1-undecene production, the cosmid clone 5B5 was trimmed down to a 10 gene-containing clone (pZR66) that still allowed for the production of 1-undecene in the *E. coli* host. However, further attempts to narrow down the genes all resulted in the abolishment of 1-undecene production. Without wishing to be bound by theory, it is thought that the 10 gene-containing clone (pZR66) contains one or more genes that encode putative transcriptional regulators of the true gene(s) present in the clone that is responsible for facilitating the production of 1-undecene. In addition to the putative transcriptional regulators, the 10 candidate genes present on the clone include several genes related to sulfate metabolism, as well as one hypothetical gene, PFL_0203.

To investigate whether PFL_0203 was facilitating the production of 1-undecene, this gene was individually expressed in *E. coli* and the cells were monitored for 1-undecene production. Exogenous lauric acid was added to the culture media, consistent with the library screening conditions. Surprisingly, individual heterologous expression of PFL_0203 (also referred to as undB) in *E. coli* resulted in the production 1-undecene, indicating that PFL_0203 alone can elicit the production of 1-undecene in this host. For comparison, PFL_4321 (See Examples 1 and 2) was also expressed in *E. coli* under these conditions, and PFL_0203 produced a higher titer of 1-undecene than PFL_4321 when exogenous lauric acid was added to the culture media. In a related experiment, *E. coli* housing either PFL_4321 or PFL_0203 were cultured under conditions where exogenous lauric acid was not added to the culture media (no feeding). Consistent with the results obtained with the above-mentioned screening conditions used to identify PFL_0203, the production of 1-undecene by *E. coli* heterologously expressing this gene was greatly decreased in the absence of exogenous lauric acid in the culture media. These results are presented in Table 4 below.

TABLE 4

1-undecene production in *E. coli* overexpressing PFL_4321 or PFL_0203

|  | No feeding (1-undecene μg/mL) | Feeding with LA (1-undecene μg/mL) |
| --- | --- | --- |
| BL21 (PFL_4321) | 4 | 7 |
| BL21 (PFL_0203) | 0.01 | 20 |

Structural Analysis of PFL_0203

Figure 31B:
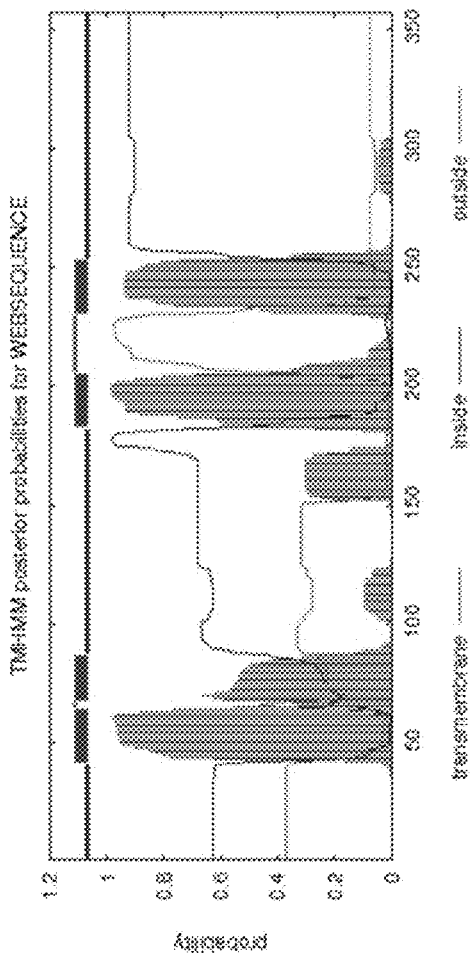
FIG. 31A-FIG. 31B illustrates predicted membrane domains of PFL_0203.
Figure 31A:
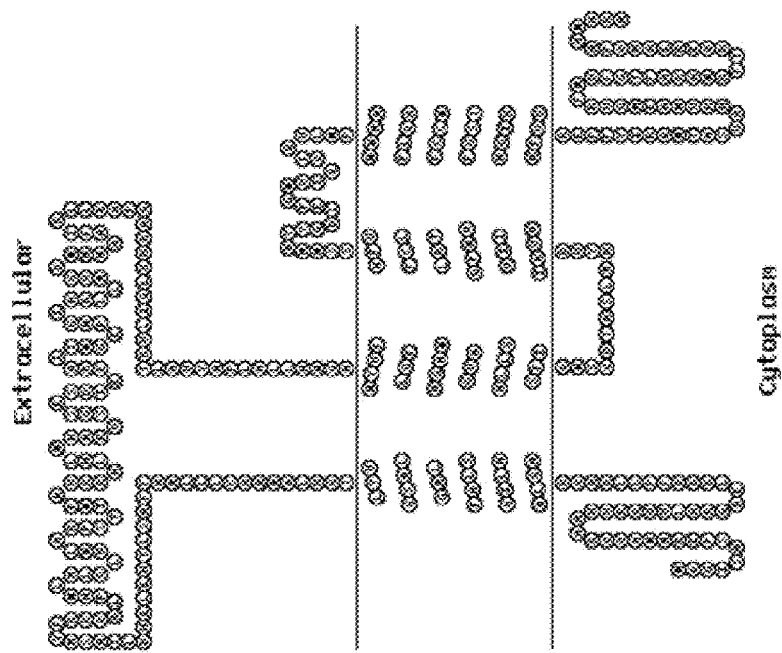

In an attempt to gain insight into the mode of action by which PFL_0203 confers 1-undecene production, various computational tools were used to analyze this protein. The Pfam database categorizes PFL_0203 into the fatty acid desaturase family that removes two hydrogen atoms from fatty acids to create a double bond. However, without wishing to be bound by theory, it is not thought that PFL_0203 functions as a fatty acid desaturase enzyme, as explained in more detail below. Further, both the TMHMM Server v. 2.0 and SACS MEMSAT2 computational tools predict that PFL_0203 is a cell membrane-associated protein (FIG. 31A and FIG. 31B).

Membrane Association of PFL_0203

The computationally predicted membrane association of PFL_0203 was further explored. In a first experiment, *E. coli* BL21 expressing PFL_0203 was cultured and the cells were lysed to separate the membrane fraction from the soluble protein fraction. The ability of each fraction to facilitate 1-undecene production was then analyzed in vitro. As can be seen in Table 5, only the membrane fraction could facilitate production of 1-undecene. These results suggested that PFL_0203 was a membrane-associated protein.

TABLE 5

Analysis of 1-undecene production by cellular fraction

| Cell fraction | 1-undecene production |
| --- | --- |
| Membrane fraction | Yes |
| Soluble protein fraction | Not detectable |

Further confirming the above result, recombinant PFL_0203 was found to be retained in the membrane fraction during protein purification, and was also tightly attached to some other membrane proteins. These co-eluted unknown proteins were separated from PFL_0203 by Sodium Dodecyl Sulfate Polyacrylamide Gel Electrophoresis (SDS-PAGE), extracted, and identified to be a ubiquinone oxidase and an NADH dehydrogenase. In an additional in vitro experiment, mixing the purified PFL_0203 with the *E. coli* crude extract and exogenous lauric acid resulted in 1-undecene production, and control experiments showed that the production of 1-undecene was dependent on both PFL_0203 and the crude extract.

Substrate Specificity of PFL_0203

The fatty acid substrate specificity of PFL_0203 was investigated in a series of in vitro experiments. From these assays, it was found that PFL_0203 converted C10-C16 fatty acids into their corresponding [M-1] 1-alkenes, but failed to act on C8 or C18 fatty acids. Thus, PFL_4321 and PFL_0203 share some overlap in suitable substrates; PFL_4321 is able to act on C10-C14 fatty acid substrates, and PFL_0203 is able to act on C10-C16 fatty acid substrates. These results are presented below in Table 6.

TABLE 6

In vitro activity of PFL_4321 and PFL_0203 toward fatty acids with various chain lengths

|  | C8:0 | C10:0 | C12:0 | C14:0 | C16:0 |
| --- | --- | --- | --- | --- | --- |
| PFL_4321 | x | ✓ | ✓ | ✓ | x |
| PFL_0203 | x | trace | ✓ | ✓ | trace |

(✓) indicates production of the corresponding 1-alkene from the indicated substrate,
(x) indicates failure to produce the corresponding 1-alkene from the indicated substrate Co-Expression of PFL_0203 and UcFatB2

Figure 32:
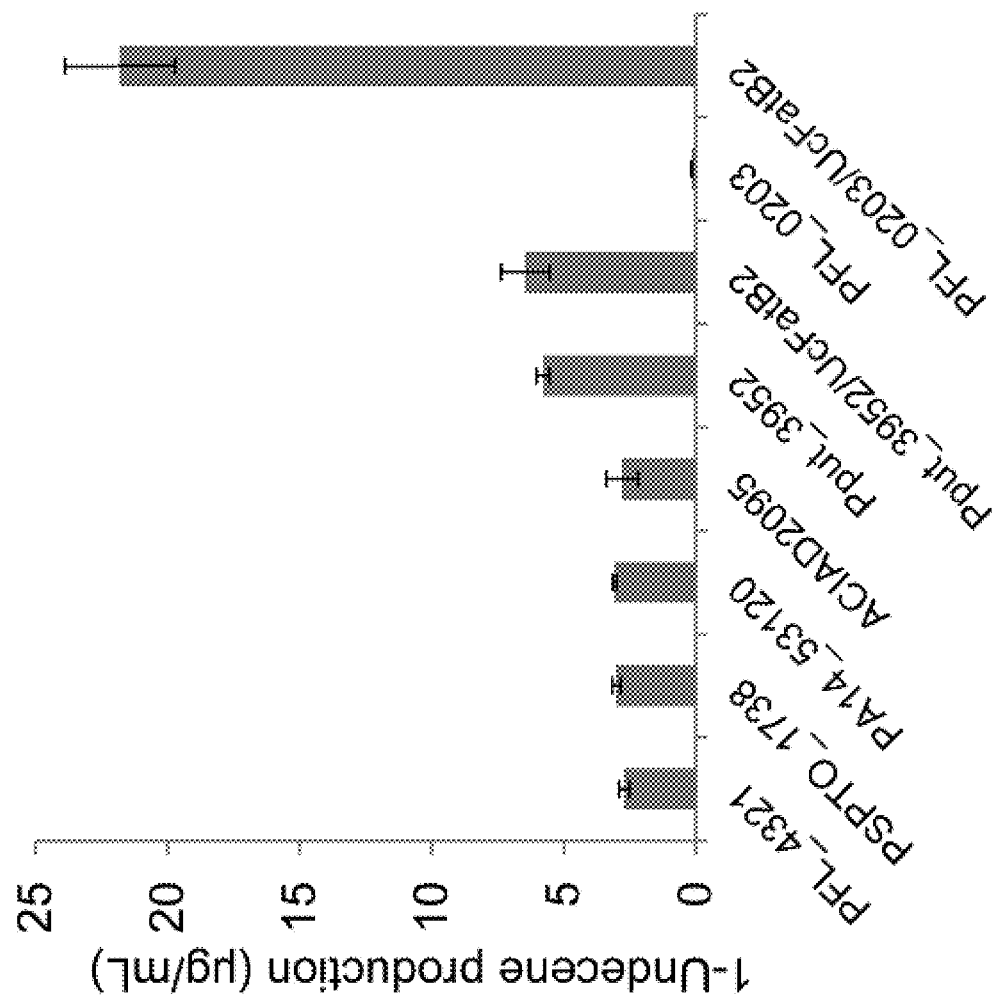
FIG. 32 illustrates the production titers of extracellular 1-undecene by overexpressing PFL_4321 (*P. fluorescens* Pf-5), PFL_0203 (*P. fluorescens* Pf-5), PSPTO_1738 (*P. syringae* pv. tomato DC3000), PA14_53120 (*P. aeruginosa* PA14), ACIAD2095 (*Acinetobacter baylyi* ADP1), and Pput_3952 (*P. putida* F1) in conjunction with or without UcFatB2 as indicated in E. coli.

Overexpression of PFL_0203 in *E. coli* led to the production of 1-undecene at a low titer of ~0.2 μg/mL after one-day of shake flask culture in LB media without exogenous lauric acid. As described above, addition of exogenous lauric acid to the culture media greatly increased 1-undecene production by PFL_0203. However, Applicants also sought to explore other methods of increasing 1-undecene titers in *E. coli* hosts expressing recombinant PFL_0203. To this end, a codon-optimized UcFatB2 gene was co-expressed in *E. coli* along with PFL_0203. Without wishing to be bound by theory, it is thought that UcFatB2 acts to generate endogenous intracellular lauric acid. Interestingly, co-expression of both PFL_0203 and UcFatB2, a medium-chain specific thioesterase, increased the titer of 1-undecene to over 20 μg/mL in *E. coli* without adding exogenous lauric acid to the culture media (FIG. 32). This result further suggests that PFL_0203 prefers C12:0 free acid to its CoA or other thioester form. UcFatB2 was also co-expressed with PFL_4321 in *E. coli*, but this co-expression had a less dramatic impact on 1-undecene production than was observed when co-expressing UcFatB2 and PFL_0203. These results are summarized in Table 7 below.

TABLE 7

1-undecene production in various cell genotypes

|  | No feeding (1-undecene μg/mL) | Feeding with LA (1-undecene μg/mL) |
| --- | --- | --- |
| BL21 (PFL_4321) | 4 | 7 |
| BL21 (PFL_0203) | 0.01 | 20 |
| BL21 (PFL_4321/UcFatB2) | 7 | 7 |
| BL21 (PFL_0203/UcFatB2) | 20 | 20 |

Phylogenetic Analysis of PFL_0203

Figure 33:
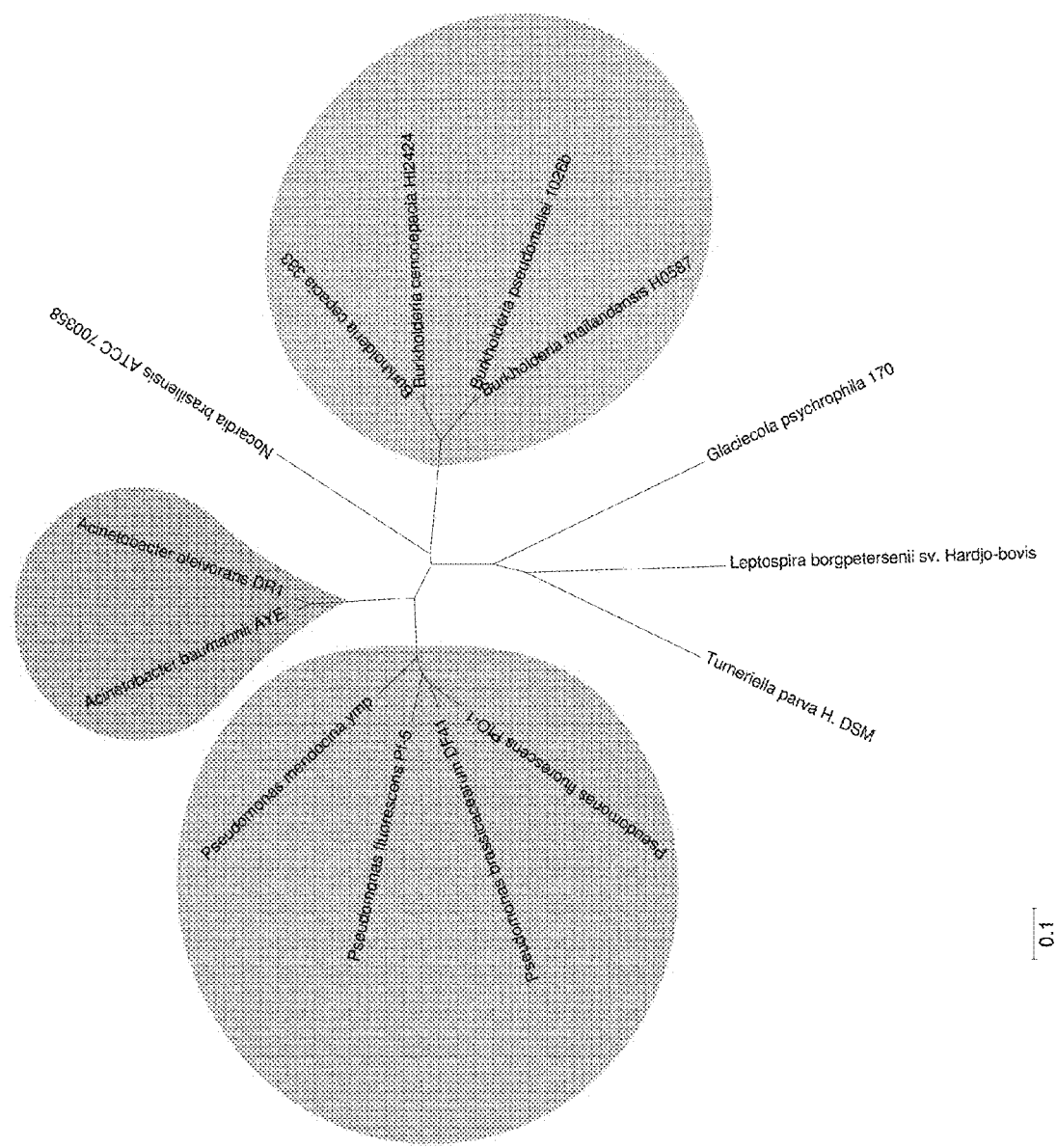
FIG. 33 illustrates a phylogenetic tree (neighbor joining algorithm) of PFL_0203.
Figure 34A:
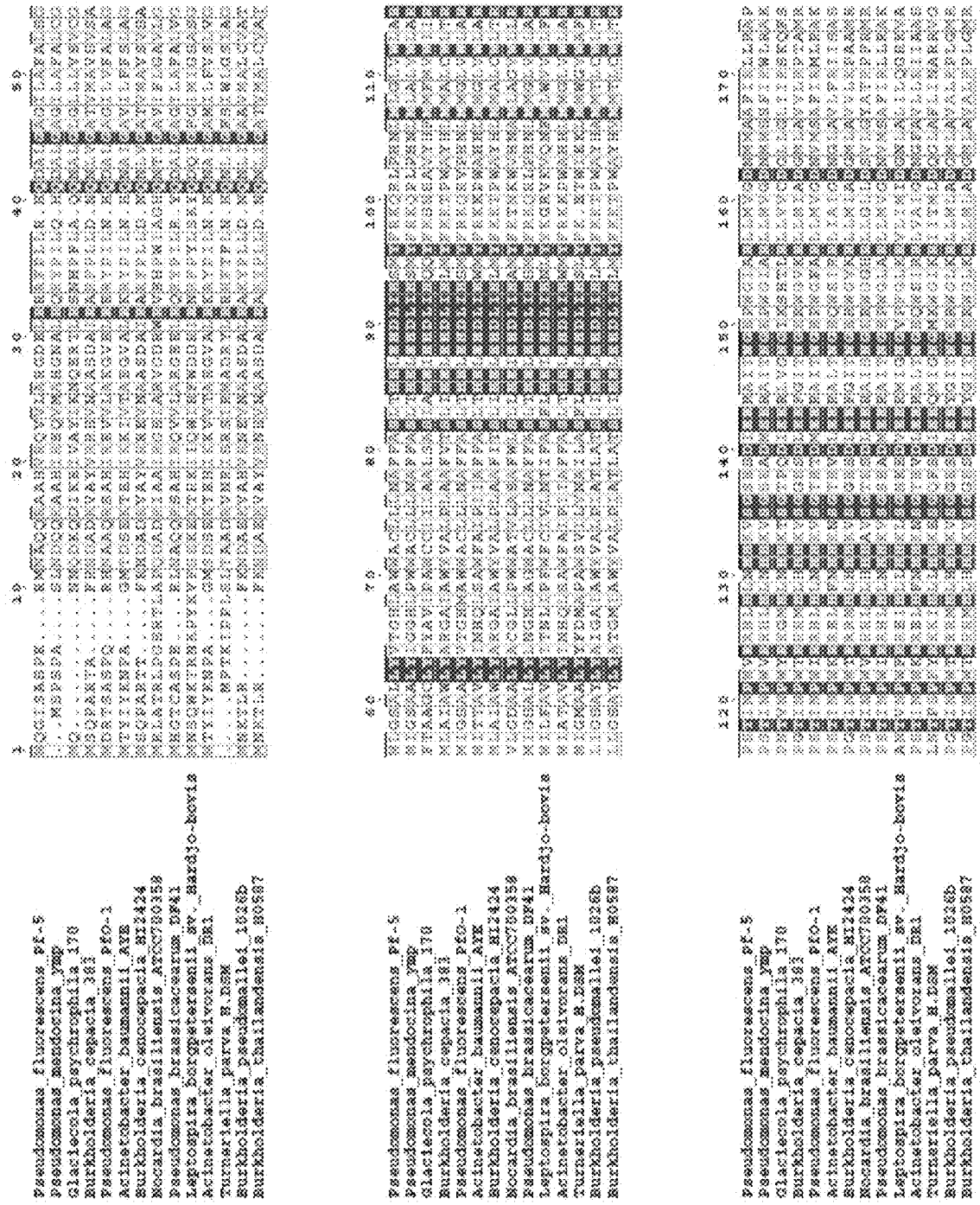
FIG. 34A-FIG. 34C illustrates an amino acid sequence alignment of PFL_0203 and related homologs.
Figure 34B:
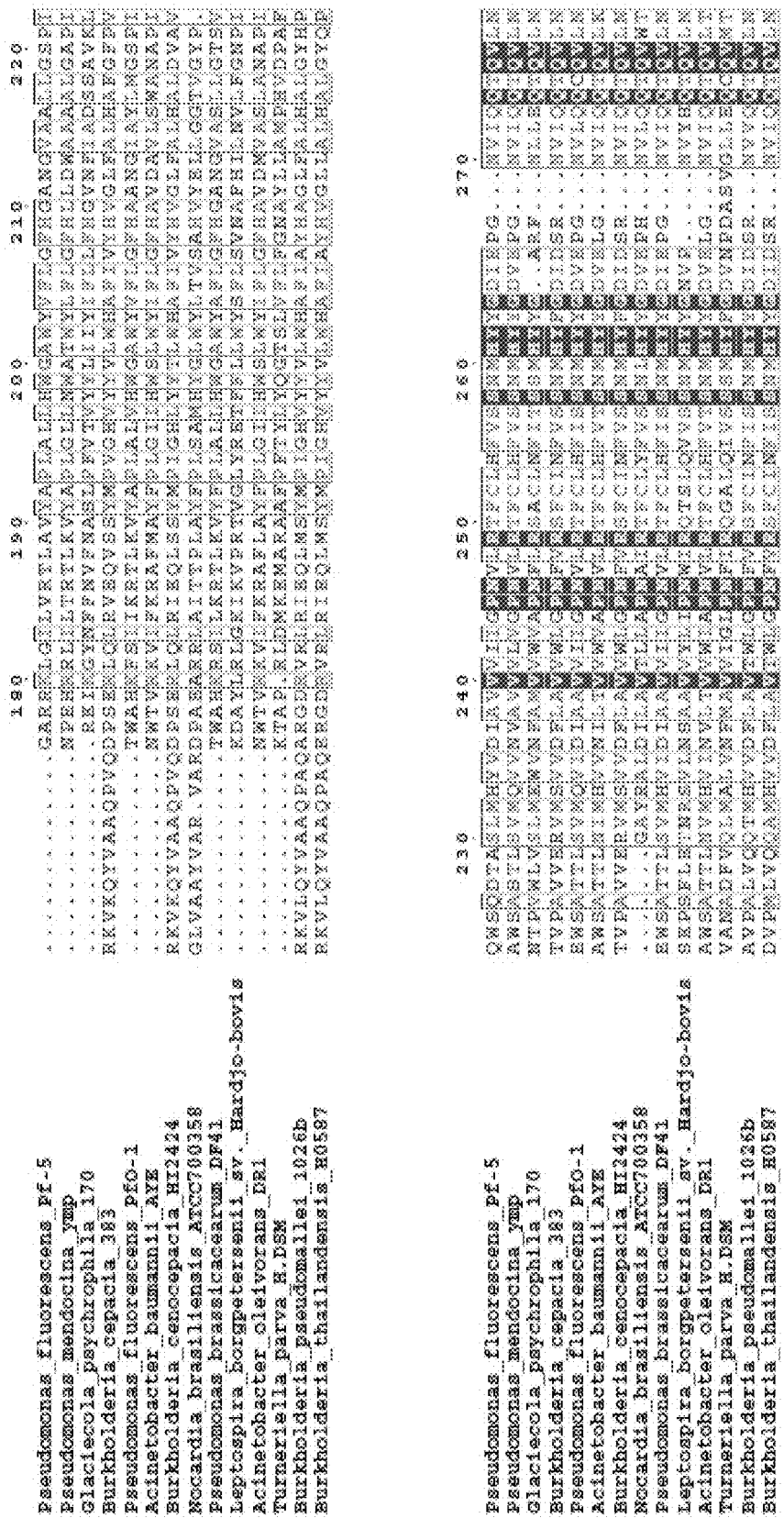
Figure 34C:
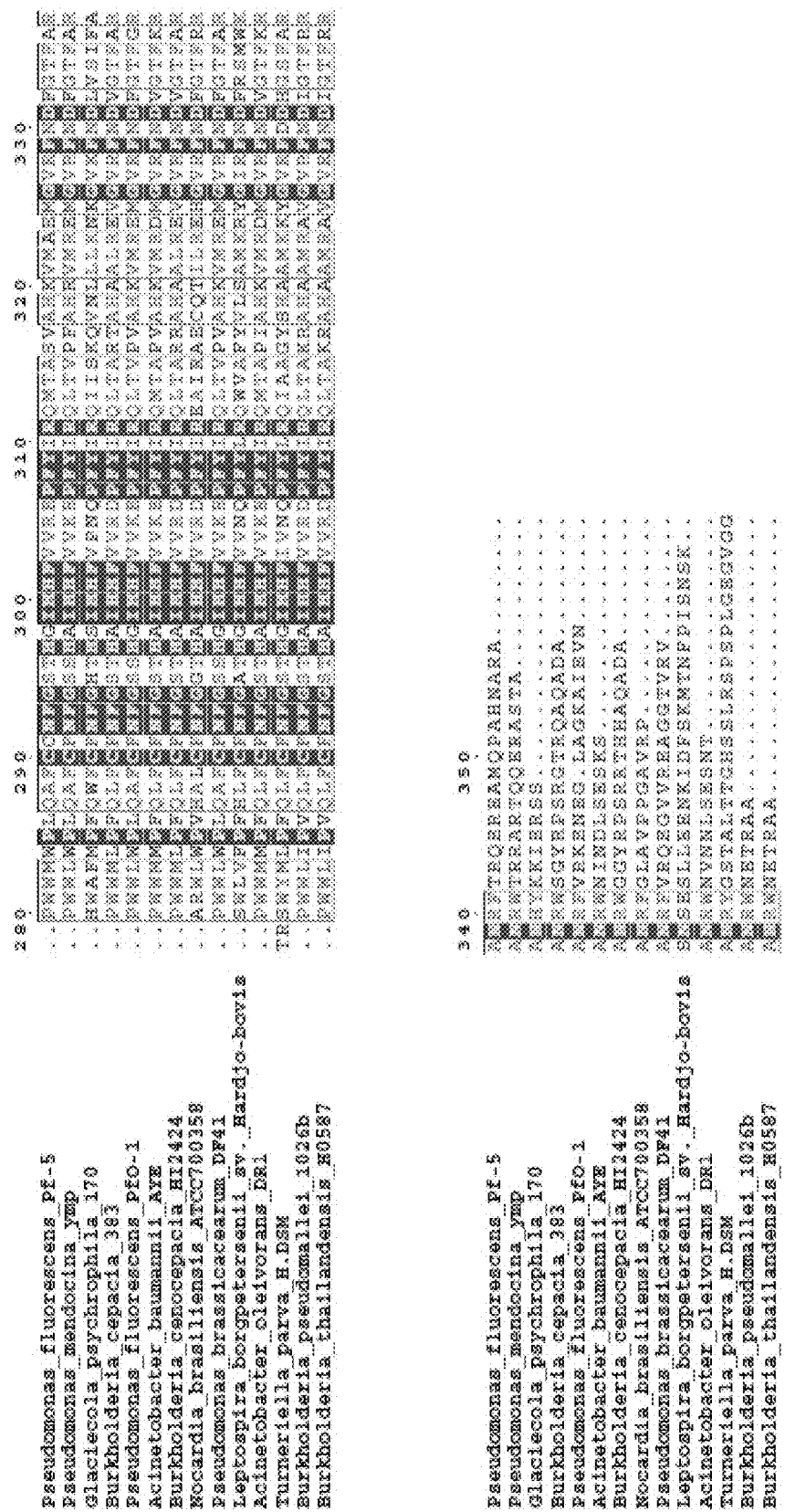

Based on sequence homology analysis, PFL_0203 is present in several *Pseudomonas* strains such as *P. fluorescens, mendocina,* and *brassicacearum,* but is absent from many widely-spread *Pseudomonas* strains such as *P. aerugi-* nosa, putida, and many *syringae* strains (FIG. 33). Aside from other *Pseudomonas* species, PFL_0203 has homologs in other species as well. An amino acid alignment of PFL_0203 and related homologs is presented in FIG. 34A-FIG. 34C. Without wishing to be bound by theory, although it is thought the PFL_0203 is not a fatty acid desaturase, the identification of a Pfam-predicted fatty acid desaturase domain in this protein is interesting given that the protein does indeed act on fatty acid substrates.

Summary

In summary, Applicants have identified an additional protein, PFL_0203, that facilitates the production of 1-undecene and related terminal olefins using fatty acid substrates. As described above, PFL_4321 is able to act on C10-C14 fatty acid substrates, while PFL_0203 is able to act on C10-C16 fatty acid substrates to produce corresponding [M-1] 1-alkenes. The results described herein indicate that both PFL_4321 and PFL_0203 may be simultaneously co-expressed in a single host cell to increase the range of suitable free fatty acids (FFAs) to be converted into terminal olefins.

REFERENCES

P. P. Peralta-Yahya, F. Zhang, S. B. del Cardayre, J. D. Keasling, Microbial engineering for the production of advanced biofuels. Nature 488, 320 (Aug. 16, 2012).

R. M. Lennen, B. F. Pfleger, Microbial production of fatty acid-derived fuels and chemicals. Curr Opin Biotechnol 24, 1044 (December, 2013).

A. Schirmer, M. A. Rude, X. Li, E. Popova, S. B. del Cardayre, Microbial biosynthesis of alkanes. Science 329, 559 (Jul. 30, 2010).

Y. J. Choi, S. Y. Lee, Microbial production of short-chain alkanes. Nature 502, 571 (Oct. 24, 2013).

T. P. Howard et al., Synthesis of customized petroleum-replica fuel molecules by targeted modification of free fatty acid pools in *Escherichia coli*. P Natl Acad Sci USA 110, 7636 (May 7, 2013).

C. Andre, S. W. Kim, X. H. Yu, J. Shanklin, Fusing catalase to an alkane-producing enzyme maintains enzymatic activity by converting the inhibitory byproduct H2O2 to the cosubstrate O2. P Natl Acad Sci USA 110, 3191 (Feb. 19, 2013).

M. K. Akhtar, N. J. Turner, P. R. Jones, Carboxylic acid reductase is a versatile enzyme for the conversion of fatty acids into fuels and chemical commodities. Proc Natl Acad Sci USA 110, 87 (Jan. 2, 2013).

Y. Qiu et al., An insect-specific P450 oxidative decarbonylase for cuticular hydrocarbon biosynthesis. Proc Natl Acad Sci USA 109, 14858 (Sep. 11, 2012).

P. S. Coelho, E. M. Brustad, A. Kannan, F. H. Arnold, Olefin cyclopropanation via carbene transfer catalyzed by engineered cytochrome P450 enzymes. Science 339, 307 (Jan. 18, 2013).

S. Schulz, J. S. Dickschat, Bacterial volatiles: the smell of small organisms. Nat Prod Rep 24, 814 (2007).

J. M. Zechman, J. N. Labows, Volatiles of *Pseudomonas aeruginosa* and related species by automated headspace concentration—gas chromatography. Can J Microbiol 31, 232 (1985).

M. A. Rude et al., Terminal Olefin (1-Alkene) Biosynthesis by a Novel P450 Fatty Acid Decarboxylase from *Jeotgalicoccus* Species. Appl Environ Microb 77, 1718 (March, 2011).

D. Mendez-Perez, M. B. Begemann, B. F. Pfleger, Modular synthase-encoding gene involved in alpha-olefin biosynthesis in *Synechococcus* sp. strain PCC 7002. Appl Environ Microb 77, 4264 (June, 2011).

L. Gu et al., Polyketide decarboxylative chain termination preceded by o-sulfonation in curacin a biosynthesis. J Am Chem Soc 131, 16033 (Nov. 11, 2009).

A. L. Jenkins, Y. Zhang, S. E. Ealick, T. P. Begley, Mutagenesis studies on TenA: a thiamin salvage enzyme from *Bacillus subtilis*. Bioorg Chem 36, 29 (February, 2008).

N. T. Liberati et al., An ordered, nonredundant library of *Pseudomonas aeruginosa* strain PA14 transposon insertion mutants. P Natl Acad Sci USA 103, 2833 (Feb. 21, 2006).

F. H. Vaillancourt, E. Yeh, D. A. Vosburg, S. E. O'Connor, C. T. Walsh, Cryptic chlorination by a non-haem iron enzyme during cyclopropyl amino acid biosynthesis. Nature 436, 1191 (Aug. 25, 2005).

W. C. Chang et al., Mechanistic studies of an unprecedented enzyme-catalysed 1,2-phosphono-migration reaction. Nature 496, 114 (Apr. 4, 2013).

L. M. Mirica, K. P. McCusker, J. W. Munos, H. W. Liu, J. P. Klinman, 18O kinetic isotope effects in non-heme iron enzymes: probing the nature of Fe/O2 intermediates. J Am Chem Soc 130, 8122 (Jul. 2, 2008).

P. C. Bruijnincx, G. van Koten, R. J. Klein Gebbink, Mononuclear non-heme iron enzymes with the 2-His-1-carboxylate facial triad: recent developments in enzymology and modeling studies. Chem Soc Rev 37, 2716 (December, 2008).

A. Karlsson et al., Crystal structure of naphthalene dioxygenase: side-on binding of dioxygen to iron. Science 299, 1039 (Feb. 14, 2003).

G. Katona et al., Raman-assisted crystallography reveals end-on peroxide intermediates in a nonheme iron enzyme. Science 316, 449 (Apr. 20, 2007).

J. H. Jeoung, M. Bommer, T. Y. Lin, H. Dobbek, Visualizing the substrate-, superoxo-, alkylperoxo-, and product-bound states at the nonheme Fe(II) site of homogentisate dioxygenase. Proc Natl Acad Sci USA 110, 12625 (Jul. 30, 2013).

W. A. van der Donk, C. Krebs, J. M. Bollinger, Jr., Substrate activation by iron superoxo intermediates. Curr Opin Struct Biol 20, 673 (December, 2010).

J. P. Torella et al., Tailored fatty acid synthesis via dynamic control of fatty acid elongation. Proc Natl Acad Sci USA 110, 11290 (Jul. 9, 2013).

R. M. Lennen, B. F. Pfleger, Engineering *Escherichia coli* to synthesize free fatty acids. Trends Biotechnol 30, 659 (December, 2012).

P. Emsley, K. Cowtan, Coot: model-building tools for molecular graphics. Acta Crystallogr D Biol Crystallogr 60, 2126 (December, 2004).

P. D. Adams et al., PHENIX: building new software for automated crystallographic structure determination. Acta Crystallogr D Biol Crystallogr 58, 1948 (November, 2002).

G. Murshudov, A. Vagin, E. Dodson, Refinement of macromolecular structures by the maximum-likelihood method. Acta Crystallogr D Biol Crystallogr 53, 240 (May 1, 1997, 1997).

Ray S, Rao P V C, Choudary N V (2012) Poly-alpha-olefin-based synthetic lubricants: a short review on various synthetic routes. *Lubr Sci* 24(1):23-44.

Moiseenkov A M, Schaub B, Margot C, Schlosser M (1985) A New Stereoselective Synthesis of (Z)-9-Tricosene, the Sex Attractant of the Common Housefly. *Tetrahedron Lett* 26(3):305-306.

Kai M, et al. (2009) Bacterial volatiles and their action potential. *Appl Microbiol Biotechnol* 81(6):1001-1012.

Labows J N, McGinley K J, Webster G F, Leyden J J (1980) Headspace analysis of volatile metabolites of *Pseudomonas aeruginosa* and related species by gas chromatography-mass spectrometry. *J Clin Microbiol* 12(4):521-526.

Graham J E (2013) Bacterial volatiles and diagnosis of respiratory infections. *Adv Appl Microbiol* 82:29-52.

Bos L D, Sterk P J, Schultz M J (2013) Volatile metabolites of pathogens: a systematic review. *PLoS Pathog* 9(5):e1003311.

Belcher J, et al. (2014) Structure and biochemical properties of the alkene producing cytochrome P450 OleTJE (CYP152L1) from the *Jeotgalicoccus* sp. 8456 bacterium. *J Biol Chem* 289(10):6535-6550.

Dassama L M K, et al. (2012) O-2-Evolving Chlorite Dismutase as a Tool for Studying O-2-Utilizing Enzymes. *Biochemistry-Us* 51(8):1607-1616.

Wang C, et al. (2013) Evidence that the Fosfomycin-Producing Epoxidase, HppE, Is a Non-Heme-Iron Peroxidase. *Science* 342(6161):991-995.

Rocklin A M, Kato K, Liu H W, Que L, Jr., Lipscomb J D (2004) Mechanistic studies of 1-aminocyclopropane-1-carboxylic acid oxidase: single turnover reaction. *J Biol Inorg Chem* 9(2):171-182.

Mirica L M, Klinman J P (2008) The nature of O2 activation by the ethylene-forming enzyme 1-aminocyclopropane-1-carboxylic acid oxidase. *Proc Natl Acad Sci USA* 105 (6):1814-1819.

Smirnoff N (2011) Vitamin C: The Metabolism and Functions of Ascorbic Acid in Plants. *Adv Bot Res* 59:107-177.

Bremus C, Herrmann U, Bringer-Meyer S, Sahm H (2006) The use of microorganisms in L-ascorbic acid production. *J Biotechnol* 124(1):196-205.

Myllyla R, Kuutti-Savolainen E R, Kivirikko K I (1978) The role of ascorbate in the prolyl hydroxylase reaction. *Biochem Biophys Res Commun* 83(2):441-448.

Clifton I J, et al. (2006) Structural studies on 2-oxoglutarate oxygenases and related double-stranded beta-helix fold proteins. *J Inorg Biochem* 100(4):644-669.

Costas M, Mehn M P, Jensen M P, Que L (2004) Dioxygen activation at mononuclear nonheme iron active sites: Enzymes, models, and intermediates. *Chem Rev* 104(2):939-986.

Puistola U, Turpeenniemi-Hujanen T M, Myllyla R, Kivirikko K I (1980) Studies on the lysyl hydroxylase reaction. I. Initial velocity kinetics and related aspects. *Biochim Biophys Acta* 611(1):40-50.

Belcher J, et al. (2014) Structure and biochemical properties of the alkene producing cytochrome P450 OleTJE (CYP152L1) from the *Jeotgalicoccus* sp. 8456 bacterium. *J Biol Chem*.

Hengge R (2009) Principles of c-di-GMP signalling in bacteria. *Nat Rev Microbiol* 7(4):263-273.

An S, Wu J, Zhang L H (2010) Modulation of *Pseudomonas aeruginosa* biofilm dispersal by a cyclic-Di-GMP phosphodiesterase with a putative hypoxia-sensing domain. *Appl Environ Microb* 76(24):8160-8173.

Newell P D, Yoshioka S, Hvorecny K L, Monds R D, O'Toole G A (2011) Systematic Analysis of Diguanylate Cyclases That Promote Biofilm Formation by *Pseudomonas fluorescens* Pf0-1. *J Bacteriol* 193(18):4685-4698.

Blom D, et al. (2011) Production of plant growth modulating volatiles is widespread among rhizosphere bacteria and strongly depends on culture conditions. *Environ Microbiol* 13(11):3047-3058.

Rui Z, Sandy M, Jung B, Zhang W (2013) Tandem enzymatic oxygenations in biosynthesis of epoxyquinone pharmacophore of manumycin-type metabolites. *Chem Biol* 20(7):879-887.

Ouchi A, Nakano M, Nagaoka S, Mukai K (2009) Kinetic study of the antioxidant activity of pyrroloquinolinequinol (PQQH(2), a reduced form of pyrroloquinolinequinone) in micellar solution. *J Agric Food Chem* 57(2):450-456.

Eser B E, Das D, Han J, Jones P R, Marsh E N (2011) Oxygen-independent alkane formation by nonheme iron-dependent cyanobacterial aldehyde decarbonylase: investigation of kinetics and requirement for an external electron donor. *Biochemistry-Us* 50(49):10743-10750.

Battye T G, Kontogiannis L, Johnson O, Powell H R, Leslie A G (2011) iMOSFLM: a new graphical interface for diffraction-image processing with MOSFLM. *Acta Crystallogr D Biol Crystallogr* 67(Pt 4):271-281.

Winn M D, et al. (2011) Overview of the CCP4 suite and current developments. *Acta Crystallogr D Biol Crystallogr* 67(Pt 4):235-242.

Karplus P A, Diederichs K (2012) Linking crystallographic model and data quality. *Science* 336(6084):1030-1033.

Particular Embodiments

1. A method of producing a terminal olefin, the method comprising:
    a) contacting a host cell comprising a recombinant nucleic acid encoding SEQ ID NO: 1 or a homolog thereof with a fatty acid; and
    b) culturing the host cell under conditions such that a terminal olefin is produced from the fatty acid.
2. The method of claim 1, wherein the host cell is a bacterial cell.
3. The method of claim 2, wherein the host cell is *E. coli*.
4. The method of claim 1, wherein the host cell is a eukaryotic cell.
5. The method of claim 4, wherein the host cell is *Saccharomyces cerevisiae*.
6. The method of claim 1, wherein the host cell is modified to produce excess quantities of free fatty acids as compared to a corresponding unmodified host cell.
7. The method of claim 6, wherein the modified host cell has modified beta-oxidation activity, thioesterase activity, and/or acetyl-coA carboxylase activity.
8. The method of any one of claims 1-7, wherein the homolog comprises an amino acid sequence at least 35%, at least 40%, and least 45%, at least 50%, at least 55%, at least 60%, at least 65%, at least 70%, at least 75%, at least 80%, at least 85%, at least 90%, at least 95%, or at least 99% identical to the amino acid sequence of SEQ ID NO: 1.
9. The method of any one of claims 1-8, wherein the homolog comprises analogous amino acids or conservative substitutions of Glu101, His104, Glu159, and His194 of SEQ ID NO: 1.
10. The method of any one of claims 1-9, wherein the fatty acid is a C10-C20 fatty acid.
11. The method of claim 10, wherein the fatty acid is a C14-C20 fatty acid.
12. The method of any one of claims 1-9, wherein the fatty acid is a medium chain fatty acid.
13. The method of claim 12, wherein the medium chain fatty acid is a C10-C14 fatty acid.
14. The method of claim 13, wherein the medium-chain fatty acid is lauric acid.

15. The method of any one of claims 1-14, wherein the host cell is cultured in an aerobic environment.
16. The method of any one of claims 1-15, wherein the host cell is cultured in media and the media comprises iron.
17. The method of any one of claims 1-16, wherein the host cell is cultured in media and the media comprises ascorbic acid.
18. The method of any one of claims 1-17, wherein the terminal olefin is a C9-C13 terminal olefin.
19. The method of any one of claims 1-18, wherein the terminal olefin is 1-undecene.
20. The method of any one of claims 1-19, wherein the yield of the terminal olefin is about 1 µg/mL, about 1.5 µg/mL, about 2 µg/mL, about 2.5 µg/mL, about 3 µg/mL, about 3.5 µg/mL, about 4 µg/mL, about 4.5 µg/mL, about 5 µg/mL, about 5.5 µg/mL, about 6 µg/mL, about 6.5 µg/mL, about 7 µg/mL, about 7.5 µg/mL, about 8 µg/mL, about 8.5 µg/mL, about 9 µg/mL, about 9.5 µg/mL, or about 10 µg/mL or more terminal olefin.
21. The method of any one of claims 1-20, further comprising a step of recovering a terminal olefin produced by the host cell.
22. A method of producing a terminal olefin, the method comprising:
    a) contacting a host cell comprising a recombinant nucleic acid encoding a polypeptide comprising the amino acid sequence of SEQ ID NO: 33 with a fatty acid; and
    b) culturing the host cell under conditions such that a terminal olefin is produced from the fatty acid.
23. A method of producing a terminal olefin, the method comprising:
    a) contacting a host cell comprising a recombinant nucleic acid encoding a polypeptide comprising the amino acid sequence of SEQ ID NO: 34 with a fatty acid; and
    b) culturing the host cell under conditions such that a terminal olefin is produced from the fatty acid.
24. A method of producing a terminal olefin, the method comprising:
    a) contacting a host cell comprising a recombinant nucleic acid encoding a polypeptide comprising the amino acid sequence of SEQ ID NO: 35 with a fatty acid; and
    b) culturing the host cell under conditions such that a terminal olefin is produced from the fatty acid.
25. A method of producing a terminal olefin, the method comprising:
    a) contacting a host cell comprising a recombinant nucleic acid encoding a polypeptide comprising the amino acid sequence of SEQ ID NO: 36 with a fatty acid; and
    b) culturing the host cell under conditions such that a terminal olefin is produced from the fatty acid.
26. A method of producing a terminal olefin, the method comprising:
    a) contacting a host cell comprising a recombinant nucleic acid encoding a polypeptide comprising the amino acid sequence of SEQ ID NO: 37 with a fatty acid; and
    b) culturing the host cell under conditions such that a terminal olefin is produced from the fatty acid.
27. A method of producing a terminal olefin, the method comprising:
    a) contacting a host cell comprising a recombinant nucleic acid encoding a polypeptide comprising the amino acid sequence of SEQ ID NO: 38 with a fatty acid; and
    b) culturing the host cell under conditions such that a terminal olefin is produced from the fatty acid.
28. A method of producing a terminal olefin, the method comprising:
    a) contacting a host cell comprising a recombinant nucleic acid encoding a polypeptide comprising one or more of the amino acid sequences of SEQ ID NO: 33, SEQ ID NO: 34, SEQ ID NO: 35, SEQ ID NO: 36, SEQ ID NO: 37, and SEQ ID NO: 38 with a fatty acid; and
    b) culturing the host cell under conditions such that a terminal olefin is produced from the fatty acid.
29. A method of producing terminal olefins, the method comprising:
    a) contacting a host cell comprising a recombinant nucleic acid encoding a non-heme, iron-dependent polypeptide with a fatty acid; and
    b) culturing the host cell under conditions such that a terminal olefin is produced from the fatty acid.
30. A method of producing 1-undecene, the method comprising:
    a) contacting a host cell comprising a recombinant nucleic acid encoding SEQ ID NO: 1 with lauric acid; and
    b) culturing the host cell under conditions such that 1-undecene is produced from lauric acid.
31. A host cell comprising a recombinant nucleic acid encoding SEQ ID NO: 1 or a homolog thereof.
32. The host cell of claim 31, wherein the host cell is a bacterial cell.
33. The host cell of claim 32, wherein the host cell is *E. coli*.
34. The host cell of claim 31, wherein the host cell is a eukaryotic cell.
35. The host cell of claim 34, wherein the host cell is *Saccharomyces cerevisiae*.
36. The host cell of claim 31, wherein the host cell is modified to produce excess quantities of free fatty acids as compared to a corresponding unmodified host cell.
37. The host cell of claim 36, wherein the modified host cell has modified beta-oxidation activity, thioesterase activity, and/or acetyl-coA carboxylase activity.
38. The host cell of any one of claims 31-37, wherein the homolog comprises an amino acid sequence at least 35%, at least 40%, and least 45%, at least 50%, at least 55%, at least 60%, at least 65%, at least 70%, at least 75%, at least 80%, at least 85%, at least 90%, at least 95%, or at least 99% identical to the amino acid sequence of SEQ ID NO: 1.
39. The host cell of any one of claims 31-38, wherein the homolog comprises analogous amino acids or conservative substitutions of Glu101, His104, Glu159, and His194 of the amino acid sequence of SEQ ID NO: 1.
40. The host cell of any one of claims 31-39, wherein the host cell produces terminal olefins from fatty acids.
41. A method of producing a terminal olefin, the method comprising:
    a) contacting a host cell comprising a recombinant nucleic acid encoding SEQ ID NO: 39 or a homolog thereof with a fatty acid; and
    b) culturing the host cell under conditions such that a terminal olefin is produced from the fatty acid.

42. The method of claim 41, wherein the host cell is a bacterial cell.
43. The method of claim 42, wherein the host cell is *E. coli*.
44. The method of claim 41, wherein the host cell is a eukaryotic cell.
45. The method of claim 44, wherein the host cell is *Saccharomyces cerevisiae*.
46. The method of claim 41, wherein the host cell is modified to produce excess quantities of free fatty acids as compared to a corresponding unmodified host cell.
47. The method of claim 46, wherein the modified host cell has modified beta-oxidation activity, thioesterase activity, and/or acetyl-coA carboxylase activity.
48. The method of claim 47, wherein the host cell overexpresses UcFatB2 or a homolog thereof.
49. The method of any one of claims 41-48, wherein the homolog of SEQ ID NO: 39 comprises an amino acid sequence at least 35%, at least 40%, and least 45%, at least 50%, at least 55%, at least 60%, at least 65%, at least 70%, at least 75%, at least 80%, at least 85%, at least 90%, at least 95%, or at least 99% identical to the amino acid sequence of SEQ ID NO: 39.
50. The method of any one of claims 41-49, wherein the fatty acid is a C10-C20 fatty acid. 51. The method of claim 50, wherein the fatty acid is a C14-C20 fatty acid.
52. The method of any one of claims 41-49, wherein the fatty acid is a medium chain fatty acid.
53. The method of claim 52, wherein the medium chain fatty acid is a C10-C16 fatty acid.
54. The method of claim 53, wherein the medium-chain fatty acid is lauric acid.
55. The method of any one of claims 41-54, wherein the host cell is cultured in an aerobic environment.
56. The method of any one of claims 41-55, wherein the terminal olefin is a C9-C13 terminal olefin.
57. The method of any one of claims 41-56, wherein the terminal olefin is 1-undecene.
58. The method of any one of claims 41-57, wherein the yield of the terminal olefin is about 1 µg/mL, about 1.5 µg/mL, about 2 µg/mL, about 2.5 µg/mL, about 3 µg/mL, about 3.5 µg/mL, about 4 µg/mL, about 4.5 µg/mL, about 5 µg/mL, about 5.5 µg/mL, about 6 µg/mL, about 6.5 µg/mL, about 7 µg/mL, about 7.5 µg/mL, about 8 µg/mL, about 8.5 µg/mL, about 9 µg/mL, about 9.5 µg/mL, or about 10 µg/mL or more terminal olefin.
59. The method of any one of claims 41-58, further comprising a step of recovering a terminal olefin produced by the host cell.
60. A host cell comprising a recombinant nucleic acid encoding SEQ ID NO: 39 or a homolog thereof.
61. The host cell of claim 60, wherein the host cell is a bacterial cell.
62. The host cell of claim 61, wherein the host cell is *E. coli*.
63. The host cell of claim 60, wherein the host cell is a eukaryotic cell.
64. The host cell of claim 64, wherein the host cell is *Saccharomyces cerevisiae*.
65. The host cell of claim 60, wherein the host cell is modified to produce excess quantities of free fatty acids as compared to a corresponding unmodified host cell.
66. The host cell of claim 65, wherein the modified host cell has modified beta-oxidation activity, thioesterase activity, and/or acetyl-coA carboxylase activity.
67. The host cell of claim 66, wherein the host cell overexpresses UcFatB2 or a homolog thereof.
68. The host cell of any one of claims 60-67, wherein the homolog of SEQ ID NO: 39 comprises an amino acid sequence at least 35%, at least 40%, and least 45%, at least 50%, at least 55%, at least 60%, at least 65%, at least 70%, at least 75%, at least 80%, at least 85%, at least 90%, at least 95%, or at least 99% identical to the amino acid sequence of SEQ ID NO: 39.
69. The host cell of any one of claims 60-68, wherein the host cell produces terminal olefins from fatty acids.
70. A method of producing a terminal olefin, the method comprising:
    a) contacting a host cell with a fatty acid, wherein the host cell comprises:
        a recombinant nucleic acid encoding SEQ ID NO: 1 or a homolog thereof, and
        a recombinant nucleic acid encoding SEQ ID NO: 39 or a homolog thereof; and
    b) culturing the host cell under conditions such that a terminal olefin is produced from the fatty acid.
71. A host cell comprising:
    a recombinant nucleic acid encoding SEQ ID NO: 1 or a homolog thereof, and
    a recombinant nucleic acid encoding SEQ ID NO: 39 or a homolog thereof.

What is claimed is:

1. A method of producing a terminal olefin, the method comprising:
   a) contacting a cell expressing a *Pseudomonas, Acinetobacter, Burkholderia,* or *Myxococcus* UndA with a fatty acid, wherein the UndA is a non-heme oxidase heterologous to the cell or endogenous to the cell and operatively linked to a heterologous promoter, and
   b) culturing the cell under conditions such that the UndA catalyzes conversion of the fatty acid to the terminal olefin.

2. The method of claim 1, wherein:
   the *Pseudomonas* is *Pseudomonas aeruginosa, Pseudomonas putida, Pseudomonas fluorescens,* or *Pseudomonas Syringae;*
   the *Acinetobacter* is *Acinetobacter baumannii, Acinetobacter haemolyticus* or *Acinetobacter baylyi;*
   the *Burkholderia* is *Burkholderia mallei, Burkholderia pseudomallei* or *Burkholderia thailandensis;* and
   the *Myxococcus* is *Myxococcus xanthus, Myxococcus fulvus,* or *Myxococcus stipitatus.*

3. The method of claim 1, wherein the UndA is:
   *Pseudomonas aeruginosa* UndA and has the amino acid sequence of SEQ ID NO:03, SEQ ID NO:08 or SEQ ID NO:09;
   *Pseudomonas putida* UndA and has the amino acid sequence SEQ ID NO:02, SEQ ID NO:10, or SEQ ID NO:11;
   *Pseudomonas fluorescens* UndA and has the amino acid sequence SEQ ID NO:01, SEQ ID NO:06 or SEQ ID NO:07;
   *Pseudomonas Syringae* UndA and has the amino acid sequence SEQ ID NO:05, SEQ ID NO:12, SEQ ID NO:13 or SEQ ID NO:14;
   *Acinetobacter baumannii* UndA and has the amino acid sequence of SEQ ID NO:28, SEQ ID NO:29 or SEQ ID NO:30;
   *Acinetobacter haemolyticus* and the UndA has the amino acid sequence of SEQ ID NO:31 or SEQ ID NO:32;
   *Acinetobacter baylyi* UndA and has the amino acid sequence of SEQ ID NO:04 or SEQ ID NO:27;
   *Burkholderia mallei* UndA and has the amino acid sequence of SEQ ID NO:15, SEQ ID NO:16 or SEQ ID NO:17;
   *Burkholderia pseudomallei* UndA and has the amino acid sequence of SEQ ID NO:18, SEQ ID NO:19 or SEQ ID NO:20;
   *Burkholderia thailandensis* UndA and has the amino acid sequence of SEQ ID NO:21, SEQ ID NO:22 or SEQ ID NO:23;
   *Myxococcus xanthus* UndA and has the amino acid sequence of SEQ ID NO:24;
   *Myxococcus fulvus* UndA and has the amino acid sequence of SEQ ID NO:25; or
   *Myxococcus stipitatus* UndA and has the amino acid sequence of SEQ ID NO:26.

4. The method of claim 1, wherein the UndA is:
   *Pseudomonas aeruginosa* UndA and has the amino acid sequence of SEQ ID NO:03;
   *Pseudomonas putida* UndA and has the amino acid sequence SEQ ID NO:02;
   *Pseudomonas fluorescens* UndA and has the amino acid sequence SEQ ID NO:01;
   *Pseudomonas Syringae* UndA and has the amino acid sequence SEQ ID NO:05; or
   *Acinetobacter baylyi* UndA and has the amino acid sequence of SEQ ID NO:04.

5. The method of claim 1, wherein the UndA is:
   *Pseudomonas fluorescens* UndA and has the amino acid sequence SEQ ID NO:01.

6. The method of claim 1, wherein the fatty acid is a C10-C14 fatty acid, and the terminal olefin is a C9-C13 terminal olefin.

7. The method of claim 2, wherein the fatty acid is a C10-C14 fatty acid, and the terminal olefin is a C9-C13 terminal olefin.

8. The method of claim 3, wherein the fatty acid is a C10-C14 fatty acid, and the terminal olefin is a C9-C13 terminal olefin.

9. The method of claim 1, wherein the host cell is a bacterial cell that is *E. coli.*

10. The method of claim 2, wherein the host cell is a bacterial cell that is *E. coli.*

11. The method of claim 3, wherein the host cell is a bacterial cell that is *E. coli.*

12. The method of claim 1, wherein the host cell is a eukaryotic cell that is *Saccharomyces cerevisiae.*

13. The method of claim 2, wherein the host cell is a eukaryotic cell that is *Saccharomyces cerevisiae.*

14. The method of claim 3, wherein the host cell is a eukaryotic cell that is *Saccharomyces cerevisiae.*

15. The method of claim 1, further comprising a step of recovering the terminal olefin produced by the cell.

16. The method of claim 2, further comprising a step of recovering the terminal olefin produced by the cell.

17. The method of claim 3, further comprising a step of recovering the terminal olefin produced by the cell.

18. The method of claim 6, further comprising a step of recovering the terminal olefin produced by the cell.

19. The method of claim 7, further comprising a step of recovering the terminal olefin produced by the cell.

20. The method of claim 8, further comprising a step of recovering the terminal olefin produced by the cell.

* * * * *